US012522845B2

(12) United States Patent
Esteves

(10) Patent No.: US 12,522,845 B2
(45) Date of Patent: *Jan. 13, 2026

(54) AAV VECTORS ENCODING NF1 AND USES THEREOF

(71) Applicant: University of Massachusetts, Westborough, MA (US)

(72) Inventor: Miguel Sena Esteves, Westford, MA (US)

(73) Assignee: University of Massachusetts, Westborough, MA (US)

(*) Notice: Subject to any disclaimer, the term of this patent is extended or adjusted under 35 U.S.C. 154(b) by 695 days.

This patent is subject to a terminal disclaimer.

(21) Appl. No.: 17/847,291

(22) Filed: Jun. 23, 2022

(65) Prior Publication Data

US 2023/0002787 A1 Jan. 5, 2023

Related U.S. Application Data

(63) Continuation of application No. 17/483,115, filed on Sep. 23, 2021, now Pat. No. 11,401,531.

(60) Provisional application No. 63/082,513, filed on Sep. 24, 2020.

(51) Int. Cl.

| | |
|---|---|
| ***C12N 15/86*** | (2006.01) |
| ***A61P 35/00*** | (2006.01) |
| ***C07K 14/47*** | (2006.01) |
| *A61K 48/00* | (2006.01) |

(52) U.S. Cl.

CPC .............. *C12N 15/86* (2013.01); *A61P 35/00* (2018.01); *C07K 14/4705* (2013.01); *A61K 48/00* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 11,401,531 | B2 | 8/2022 | Esteves |
| 2003/0138772 | A1 | 7/2003 | Gao et al. |
| 2008/0250514 | A1 | 10/2008 | Tsunoda et al. |
| 2010/0092965 | A1 | 4/2010 | Seshagiri et al. |
| 2010/0210830 | A1 | 8/2010 | Massie et al. |
| 2015/0252432 | A1 | 9/2015 | Lee et al. |
| 2019/0153050 | A1 | 5/2019 | Boye et al. |

FOREIGN PATENT DOCUMENTS

| | | | |
|---|---|---|---|
| WO | WO 1994/028009 | A1 | 12/1994 |
| WO | WO 2008/061213 | A2 | 5/2008 |
| WO | WO 2020/101878 | A2 | 5/2020 |

OTHER PUBLICATIONS

International Search Report and Written Opinion for Application No. PCT/US2021/051667, mailed Dec. 27, 2021.

[No Author Listed], Arabidopsis thaliana transmembrane protein, putative (DUF707) (AT1G13000), mRNA. NCBI Ref Sequence No. NM_001035957.3. Feb. 14, 2019. 3 pages.

[No Author Listed], *Homo sapiens* neurofibromin 1 (NF1), transcript variant 1, mRNA. Feb. 13, 2022. NCBI Ref Sequence No. NM_001042492.3. 11 pages.

Bai et al., Feasibility of using NF1-GRD and AAV for gene replacement therapy in NF1-associated tumors. Gene Ther. Jun. 2019;26(6):277-286. doi: 10.1038/s41434-019-0080-9. Epub May 24, 2019.

Baudou et al., Can the Cognitive Phenotype in Neurofibromatosis Type 1 (NF1) Be Explained by Neuroimaging? A Review. Front Neurol. Jan. 14, 2020;10:1373. doi: 10.3389/fneur.2019.01373.

Cooper et al., The Human Gene Mutation Database. The Institute of Medical Genetics in Cardiff. Accessed on Mar. 2, 2022 at http://www.hgmd.cf.ac.uk/ac/index.php. 2007. 2 pages.

D'angelo et al., A novel bipartite phospholipid-binding module in the neurofibromatosis type 1 protein. EMBO Rep. Feb. 2006;7(2):174-9. doi: 10.1038/sj.embor.7400602.

De Luca et al., Deletions of NF1 gene and exons detected by multiplex ligation-dependent probe amplification. J Med Genet. Dec. 2007;44(12):800-8. doi: 10.1136/jmg.2007.053785.

Hiatt et al., Neurofibromin GTPase-activating protein-related domains restore normal growth in Nf1−/− cells. J Biol Chem. Mar. 9, 2001;276(10):7240-5. doi: 10.1074/jbc.M009202200. Epub Nov. 15, 2000.

Hoyng et al., Gene delivery to rat and human Schwann cells and nerve segments: a comparison of AAV 1-9 and lentiviral vectors. Gene Ther. Oct. 2015;22(10):767-80. doi: 10.1038/gt.2015.47. Epub May 4, 2015. PMID: 25938190.

Johnson et al., Neurofibromin can inhibit Ras-dependent growth by a mechanism independent of its GTPase-accelerating function. Mol Cell Biol. Jan. 1994;14(1):641-5. doi: 10.1128/mcb.14.1.641-645. 1994.

Keng et al., Conditional Inactivation of Pten with EGFR Overexpression in Schwann Cells Models Sporadic MPNST. Sarcoma. 2012;2012:620834. doi: 10.1155/2012/620834. Epub Dec. 18, 2012. PMID: 23319880; PMCID: PMC3539440.

Li et al., Somatic mutations in the neurofibromatosis 1 gene in human tumors. Cell. Apr. 17, 1992;69(2):275-81. doi: 10.1016/0092-8674(92)90408-5.

Martin et al., The GAP-related domain of the neurofibromatosis type 1 gene product interacts with ras p21. Cell. Nov. 16, 1990;63(4):843-9. doi: 10.1016/0092-8674(90)90150-d.

Plantier et al., A factor VIII minigene comprising the truncated intron I of factor IX highly improves the in vitro production of factor VIII. Thromb Haemost. Aug. 2001;86(2):596-603.

(Continued)

*Primary Examiner* — Robert M Kelly

(74) *Attorney, Agent, or Firm* — Wolf, Greenfield & Sacks, P.C.

(57) ABSTRACT

Aspects of the disclosure relate to compositions and methods of treating certain genetic disease (e.g., Neurofibromatosis type I) by delivering functional neurofibromin 1(NF1) protein (e.g., mini-NF1 protein and/or full-length NF1 protein) to target cell (e.g., cells and/or tissue of a subject). The disclosure is based, in part, on isolated nucleic acids (e.g., rAAV vectors) and rAAVs engineered to express a functional NF1 protein (e.g., mini-NF1 protein and/or full-length NF1 protein) or variants thereof.

13 Claims, 13 Drawing Sheets

Specification includes a Sequence Listing.

(56) References Cited

OTHER PUBLICATIONS

Singh et al., 733. Approaches for Gene Therapy of Neurofibromatosis Type 1 (NF1) Using Mini-NF1 and Trans Splicing Dual Adeno-Associated Virus (AAV) Vectors. Mol Ther. Apr. 28, 2020:28(4S1):322-323.
Singh et al., 733. Approaches for Gene Therapy of Neurofibromatosis Type 1 (NF1) Using Mini-NF1 and Trans Splicing Dual Adeno-Associated Virus (AAV) Vectors. Poster Presentation. Am Soc Gene Cell Ther. No date. 4 pages.
Thomas et al., Reconstitution of the NF1 GAP-related domain in NF1-deficient human Schwann cells. Biochem Biophys Res Commun. Sep. 29, 2006;348(3):971-80. doi: 10.1016/j.bbrc.2006.07.159. Epub Aug. 2, 2006.
Welti et al., The sec 14 homology module of neurofibromin binds cellular glycerophospholipids: mass spectrometry and structure of a lipid complex. J Mol Biol. Feb. 16, 2007;366(2):551-62. doi: 10.1016/j.jmb.2006.11.055. Epub Nov. 18, 2006.
Wu-Chou et al., Genetic diagnosis of neurofibromatosis type 1: targeted next- generation sequencing with Multiple Ligation-Dependent Probe Amplification analysis. J Biomed Sci. Oct. 5, 2018;25(1):72. doi: 10.1186/s12929-018-0474-9.
Xiao et al., Rescue of the albino phenotype by introducing a functional tyrosinase minigene into Kunming albino mice. World J Gastroenterol. Jan. 14, 2007;13(2):244-9. doi: 10.3748/wjg.v13.i2.244.
Yang et al., The investigation for potential modifier genes in patients with neurofibromatosis type 1 based on next-generation sequencing. Onco Targets Ther. Feb. 21, 2018;11:919-932. doi: 10.2147/OTT.S156998.
Extended European Search Report for Application No. 21873397.0, mailed Sep. 10, 2024.
International Preliminary Report on Patentability for Application No. PCT/US2021/051667, mailed Apr. 6, 2023.
No Author Listed, Genbank Submission; NCBI, Accession No. NM_000267.3; *Homo sapiens* neurofibromin 1 (NF1), transcript variant 2, mRNA. Sep. 7, 2020.
Anshuman et al., 733. Approaches for Gene Therapy of Neurofibromatosis Type 1(NF1) Using Mini-NF1 and Trans Splicing Dual Adeno-Associated Virus (AAV) Vectors. Molecular Therapy. Apr. 28, 2020; 28(4s1): 324.
Cui et al., NF1, Neurofibromin and Gene Therapy: Prospects of Next-Generation Therapy. Curr Gene Ther. 2020;20(2):100-108. doi: 10.2174/1566523220666200806111451.

AAV VECTORS ENCODING NF1 AND USES THEREOF

RELATED APPLICATIONS

This application is a continuation of U.S. application Ser. No. 17/483,115, filed Sep. 23, 2021, which claims the benefit under 35 U.S.C. 119(e) of the filing date of U.S. provisional application Ser. No. 63/082,513, filed Sep. 24, 2020, the entire contents of which are incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 17, 2022, is named U012070146US02-SEQ-LJG and is 230,487 bytes in size.

BACKGROUND OF INVENTION

Neurofibromatosis type I (NF1) is caused by sporadic or inherited germline mutations in the NF1 gene. Sporadic loss of the remaining wild-type allele is associated with skin lesions and benign neurofibromas, which develop along peripheral nerves. Malignant complications include optic pathway gliomas and malignant peripheral nerve sheath tumors (MPNST). In addition, NF1 haploinsufficiency can cause cognitive deficits and NF1 deficiency plays an important supporting role in tumor formation. However, the NF1 coding sequence is 8,540 bp, far exceeding the packaging capacity of recombinant AAV vectors, rendering gene therapy to correct NF1 gene mutation difficult.

SUMMARY OF INVENTION

The present disclosure relates to compositions and methods of treating certain genetic disease (e.g., Neurofibromatosis type I) by delivering functional neurofibromin 1(NF1) protein (e.g., mini-NF1 protein and/or full-length NF1 protein) to target cell (e.g., cells and/or tissue of a subject). The disclosure is based, in part, on isolated nucleic acids (e.g., rAAV vectors) and rAAVs engineered to express a functional NF1 protein (e.g., mini-NF1 protein and/or full-length NF1 protein) or variants thereof.

In some aspects, the present disclosure provides an isolated nucleic acid comprising a transgene, wherein the transgene comprises a nucleotide sequence encoding a mini-neurofibromin (mini-NF1) protein.

In some embodiments, the transgene further comprises a promoter operably linked to the nucleotide sequence encoding the mini-NF1 protein. In some embodiments, the promoter is a constitutive promoter, an inducible promoter, or a minimal promoter. In some embodiments, the promoter is a chicken β-actin (CBA) promoter, or a CAG promoter. In some embodiments, the minimal promoter is a short Mecp2 promoter, a mini-CMV promoter, or a Jet promoter.

In some embodiments, the mini-NF1 protein comprises a GTPase-activating protein (GAP)-related domain (GRD). In some embodiments, the nucleotide sequence encoding the mini-NF is codon optimized. In some embodiments, the mini-NF comprises the amino acid sequence of SEQ ID NO: 1. In some embodiments, the nucleotide sequence encoding the mini-NF comprises a nucleotide sequence at least 80% identical to SEQ ID NO: 2.

In some embodiments, the mini-NF1 comprises a GTPase-activating protein (GAP)-related domain (GRD) and a CRAL-TRIO domain. In some embodiments, the mini-NF comprises the amino acid sequence of SEQ ID NO: 3. In some embodiments, the nucleotide sequence encoding the mini-NF is codon optimized. In some embodiments, the nucleotide sequence encoding the mini-NF comprises a nucleotide sequence at least 80% identical to SEQ ID NO: 4.

In some embodiments, the mini-NF1 comprises a GTPase-activating protein (GAP)-related domain (GRD), a CRAL-TRIO domain and a bipartite phospholipid binding domain. In some embodiments, the mini-NF comprises the amino acid sequence of SEQ ID NO: 5. In some embodiments, the nucleotide sequence encoding the mini-NF is codon optimized. In some embodiments, the nucleotide sequence encoding the mini-NF comprises a nucleotide sequence at least 80% identical to SEQ ID NO: 6.

In some embodiments, the transgene further comprises a nucleotide sequence encoding a tag operably linked to the promoter. In some embodiments, the tag is a hemagglutinin (HA) tag.

In some embodiments, the transgene is flanked by adeno-associated virus (AAV) inverted terminal repeats (ITRs). In some embodiments, the ITRs are adeno-associated virus ITRs of a serotype selected from the group consisting of AAV1 ITR, AAV2 ITR, AAV3 ITR, AAV4 ITR, AAV5 ITR, and AAV6 ITR. In some embodiments, the ITRs are AAV2 ITR.

In some embodiments, the transgene further comprises a polyadenylation signal.

In some aspects, the present disclosure provides an 5' isolated nucleic acid flanked by adeno-associated virus (AAV) inverted terminal repeats (ITRs), wherein the isolated nucleic acid comprises, from 5' to 3', a promoter operably linked to a nucleotide sequence encoding a first portion of NF1 protein, and a nucleotide sequence encoding a splice donor of an intron.

In some embodiments, the nucleotide sequence encoding the first portion of NF1 protein comprises exons 1-31 of an NF1 gene. In some embodiments, the nucleotide sequence encoding the first portion of NF1 protein comprises the nucleotide sequence of SEQ ID NO: 11.

In some embodiments, the promoter is a constitutive promoter, an inducible promoter, or a minimal promoter. In some embodiments, the promoter is a chicken β-actin (CBA) promoter, or a CAG promoter. In some embodiments, the minimal promoter is a short Mecp2 promoter, a mini-CMV promoter, or a Jet promoter.

In some embodiments, the ITRs are adeno-associated virus ITRs of a serotype selected from the group consisting of AAV1 ITR, AAV2 ITR, AAV3 ITR, AAV4 ITR, AAV5 ITR, and AAV6 ITR. In some embodiments, the ITRs are AAV2 ITR.

In some embodiments, the intron is a human dysferlin intron. In some embodiments, the nucleotide sequence encoding the splicing donor comprises the nucleotide sequence of SEQ ID NO: 18.

In some aspects, the present disclosure also provides an 3' isolated nucleic acid flanked by adeno-associated virus (AAV) inverted terminal repeats (ITRs), wherein the isolated nucleic acid comprises, from 5' to 3', a nucleotide sequence encoding a splice acceptor of an intron, and a nucleotide sequence encoding a second portion of NF1 protein. In some embodiments, the isolated nucleic acid further comprises a polyadenylation signal positioned between the nucleotide sequence encoding second portion of NF1 protein and the 3' ITR. In some embodiments, the polyadenylation signal is an SV40 polyadenylation signal.

In some embodiments, the nucleotide sequence encoding the second portion of NF1 protein comprises exons 32-61 of an NF1 gene. In some embodiments, the nucleotide sequence encoding the second portion of NF1 protein comprises the nucleotide sequence of SEQ ID NO: 14.

In some embodiments, the ITRs are adeno-associated virus ITRs of a serotype selected from the group consisting of AAV1 ITR, AAV2 ITR, AAV3 ITR, AAV4 ITR, AAV5 ITR, and AAV6 ITR. In some embodiments, the ITRs are AAV2 ITR.

In some embodiments, the intron is a human dysferlin intron. In some embodiments, the nucleotide sequence encoding the splicing acceptor comprises the nucleotide sequence of SEQ ID NO: 19.

In some aspects, the present disclosure also provides a vector comprising the isolated nucleic acid, the 5' isolated nucleic acid, or the 3' isolated nucleic acid as described herein. In some embodiments, the vector is a plasmid DNA, or closed-ended DNA, or lipid/DNA nanoparticle, or a viral vector. In some embodiments, the viral vector is an adeno-associated virus (AAV) vector, adenoviral (Ad) vector, lentiviral vector, retroviral vector, or Baculovirus vector. In some embodiments, the vector comprises a nucleic acid sequence of any one of SEQ ID NO: 7-19, 12, or 15.

In some aspects, the present disclosure provides a recombinant adeno-associated virus (rAAV) comprising: (i) the isolated nucleic acid encoding any of the mini-NF1 protein; and (ii)

an AAV capsid protein.

In some aspects, the present disclosure also provides a 5' recombinant adeno-associated virus (rAAV) comprising: (i) the 5' isolated nucleic acid encoding the first portion of full-length NF1 protein; and (ii) an AAV capsid protein.

In some aspects, the present disclosure also provides a 3' recombinant adeno-associated virus (rAAV) comprising: (i) the 3' isolated nucleic acid encoding the second portion of full-length NF1 protein; and (ii) an AAV capsid protein.

In some embodiments, the capsid protein is of a serotype selected from AAV1, AAV2, AAV3, AAV4, AAV5, AAV6, AAV7, AAV8, AAV9 and a variant thereof. In some embodiments, the capsid protein is AAV9, AAV-DJ, AAV-Anc80, AAV-PHP.B, or AAV. PHP.eB, or AAVrh10.

In some embodiments, the capsid protein has tropism for Schwann cells, peripheral neurons, optic nerve glioma cells, or cells in the central nervous system.

In some aspects, the present disclosure provides a neurofibromin (NF1) expression system comprising: the 5'rAAV; and the 3' rAAV as described herein for delivering a full-length NF1 protein to a target cell.

In some aspects, the present disclosure provides a host cell comprising the isolated nucleic acid, the 5' isolated nucleic acid, the 3' isolated nucleic acid, the vector, the rAAV, the 5' rAAV, the 3' rAAV, or the NF1 expression system as described herein.

In some aspects, the present disclosure provides a pharmaceutical composition comprising the isolated nucleic acid, the 5' isolated nucleic acid, the 3' isolated nucleic acid, the vector, the rAAV, the 5' rAAV, the 3' rAAV, the NF1 expression system, or the host cell as described herein. In some embodiments, the pharmaceutical composition further comprises a pharmaceutically acceptable carrier.

In some aspects, the present disclosure also provides a method for inhibiting Ras activity in a cell, the method comprising delivering to the cell the isolated nucleic acid, the rAAV, the NF1 expression system, or the pharmaceutical composition as described herein.

In some aspects, the present disclosure also provides a method for inhibiting Ras activity in a subject in need thereof, the method comprising administering to the subject the isolated nucleic acid, the rAAV, the NF1 expression system, or the pharmaceutical composition as described herein.

In some aspects, the present disclosure also provides a method for preventing or treating an NF1-associated disease in a subject in need thereof, the method comprising administering to the subject the isolated nucleic acid, the rAAV, the NF1 expression system, or the pharmaceutical composition as described herein.

In some aspects, the present disclosure also provides a method for preventing or treating an Neurofibromatosis type I in a subject in need thereof, the method comprising administering to the subject the isolated nucleic acid, the rAAV, the NF1 expression system, or the pharmaceutical composition as described herein.

In some aspects, the present disclosure also provides a method for preventing or treating a cognitive dysfunction associated with NF1 in a subject in need thereof, the method comprising administering to the subject the isolated nucleic acid, the rAAV, the NF1 expression system, or the pharmaceutical composition as described herein.

In some embodiments, the subject comprises one or more mutation in NF1 gene. In some embodiments, the NF1-associated disease or Neurofibromatosis type I comprises skin lesions, benign tumor, malignant tumor, and/or cognitive impairment. In some embodiments, the benign tumor is a benign neurofibroma. In some embodiments, the malignant tumor is optic pathway gliomas or malignant peripheral nerve sheath tumors (MPNST).

In some embodiments, the subject is a human. In some embodiments, the subject is a non-human mammal. In some embodiments, the non-human mammal is mouse, rat, cat, dog, sheep, rabbit, horse, cow, goat, pig, guinea pig, hamster, chicken, turkey, or a non-human primate. In some embodiments, the administration is systemic administration or local administration. In some embodiments, the systemic administration is intravenous injection, intramuscular injection, or subcutaneous injection. In some embodiments, the local administration is intratumoral injection, intracranial injection, nerve injection, cerebral spinal fluid (CSF) injection via cerebral lateral ventricles, cisterna *magna* (CM) injection, intrathecal (IT) injection, or intracerebroventricular injection. In some embodiments, the local administration is intrathecal (IT) injection. In some embodiments, the local administration is intracerebroventricular injection. In some embodiments, the administration results in delivery of a neurofibromin (NF1) protein in Schwann cells, peripheral nerve cells, or optic nerve cells. In some embodiments, the administration results in delivery of a neurofibromin (NF1) protein in any cells or areas in the CNS that is appropriate for the isolated nucleic acids and methods disclosed herein.

In some embodiments, the present disclosure provides a dual vector system. In some embodiments, the dual vector system comprises a 5' recombinant adeno-associated virus (rAAV) comprising a 5' isolated nucleic acid flanked by adeno-associated virus (AAV) inverted terminal repeats (ITRs), wherein the isolated nucleic acid comprises, from 5' to 3', a promoter operably linked to a nucleotide sequence encoding a first portion of NF1 protein, a nucleotide sequence encoding a splice donor of an intron, and an AAV capsid protein. In some embodiments, the dual vector system comprises a 3' rAAV comprising a 3' isolated nucleic acid flanked by adeno-associated virus (AAV) inverted terminal repeats (ITRs), wherein the isolated nucleic acid comprises, from 5' to 3', a nucleotide sequence encoding a splice acceptor of an intron, a nucleotide sequence encoding a second portion of NF1 protein and an AAV capsid protein.

In some embodiments, the administration of the isolated nucleic acid, the rAAV, the NF1 expression system, or the pharmaceutical composition as described herein results in reduction of tumor burden.

BRIEF DESCRIPTION OF DRAWINGS

FIG. 1A shows schematic illustrations of full-length NF1 genes and mini-NF1 genes. Full length NF1 with some domains identified for comparison with the mini-NF1 genes NF1-GAP_M, NF1-GAP_MCT and NF1-GAP_MLB. FIG. 1B shows AAV vector backbone with cytomegalovirus enhancer/chicken beta actin promoter (CMV enhancer/CB promoter) driving expression of mini-NF1 genes fused to an HA tag at the C-terminus. FIG. 1C is the rAAV vector map encoding mini-NF1 having the GRD (SEQ ID NO: 7). FIG. 1D is the rAAV vector map encoding mini-NF1 having the GRD and CRAL-TRIO domain (SEQ ID NO: 8). FIG. 1E is the rAAV vector map encoding mini-NF1 having the GRD, CRAL-TRIO domain, and the bipartite phospholipid binding domain (SEQ ID NO: 9). FIG. 1F shows western blot analysis of mini-NF1 protein expression at 72 hours post-infection of HEK293T cells at $3\times10^5$ vg/cell.

FIG. 2A shows the dual AAV-NF1 vector system: The AAV-MeCP2p-5'NF1-intron vector carries NF1 exons 1-31 under the mouse Mecp2 229-bp promoter followed by a splice donor (SD) and part of an intron; The AAV-intron.3NF1 carries part of an intron with a splice acceptor (SA) followed by NF1 exons 32-61 and an SV40 polyadenylation signal (pA). All cassettes flanked by AAV2 inverted terminal repeats (ITR). FIG. 2B is a schematic illustration that shows, upon dual infection of target cells, full length NF1 mRNA will be generated by trans-splicing across ITR elements in concatemerized AAV genomes. FIG. 2C shows trans-splicing dual AAV vector constructs. In 5' AAV vector consists of a small ubiquitous promoter, 5' sequence of NF1 cDNA and splice donor (SD) signal from NF1 intronic sequences. The 3' AAV vector consists of splice acceptor (SA) also from NF1 intronic sequences, 3' sequence of NF1 cDNA and HA-tag before the ploy A signal from SV40. Two parts of the transgene are delivered to the same cell and concatemerization of the right side ITR of the 5' vector and left side ITR of the 3' vector reconstitutes the full-length gene. After transcription, splicing leads to the removal of the ITR structure formed at the middle, which in-turn restores the mature RNA of the transgene.

FIG. 2D shows the 5' AAV vector map encoding the first portion of NF1 protein. FIG. 2E shows the 3' AAV vector map encoding the first portion of NF1 protein. FIG. 2F shows western blot analysis of HA-tagged full length NF1 expression in HEK293T cells at 72 hrs post-transduction with each AAV vector alone, or in combination at $3\times10^5$ vg/cell.

FIG. 3A shows human ST267 and ST642 were transduced with increasing doses of AAV-DJ.GFP-NLS vector and GFP expression analyzed at 72 hours post-transduction. FIG. 3B shows western blot analysis of NF1 expression and impact on Ras pathway activity indirectly assessed by changes in pERK1/2 levels. Cells were transduced at $3\times10^5$ vg/cell and protein expression analyzed at 72 hours post-transduction. Antigens detected in each blot are shown on the left size. The approximate size of the detected bands is shown in KDa on the right side of the blots. The identity of samples 1-6 is shown on the bottom. FIG. 3C shows cell proliferation assays conducted in MPNST cells (STS26T and 5462) treated with different AAV vectors encoding mini-NF1 genes, trans-splicing dual AAV vectors and GFP-NLS packaged with DJ capsid.

FIG. 4A shows MRIs of mice before and after intrathecal injection of AAV-mini NF1 vector. Mouse No. 613 was a male mouse and mouse No. 003 was a female mouse that were treated with $1\times10^{12}$ vg AAV-PHP.eB-GAP_MLB-HA (mini-NF1). FIG. 4B shows MRIs of mice before and after intrathecal injection of dual-AAV-NF1 vectors. Both mice No. 001 and No. 002 were female mice that were treated with $1\times10^{12}$ vg dual-AAV(5'NF1+3'NF1-HA).

DETAILED DESCRIPTION OF INVENTION

Figure 1A:
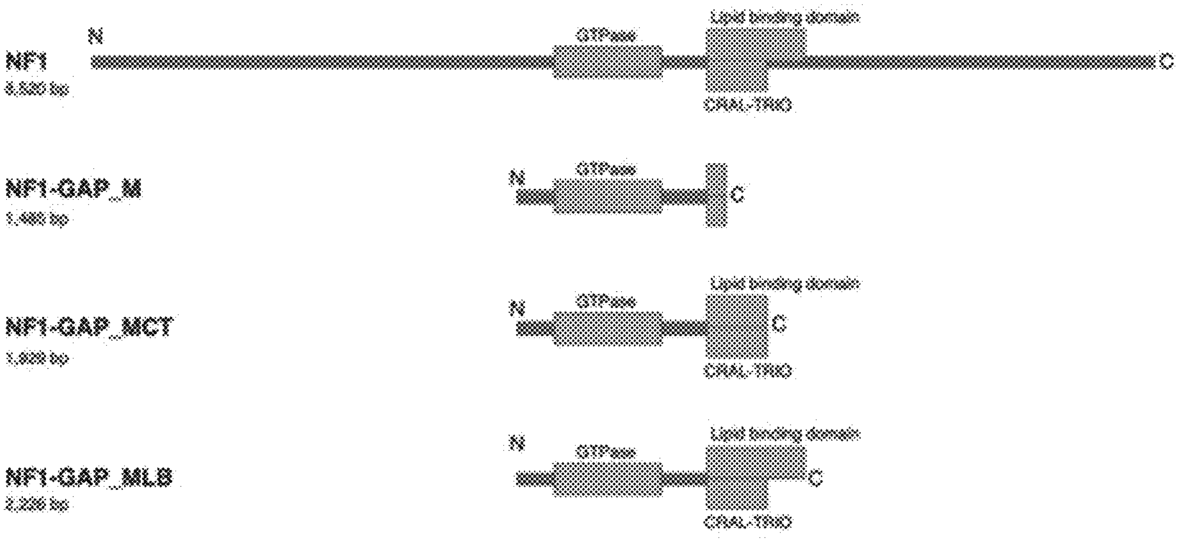
FIGS. 1A-1F show AAV vector system for mini-NF1 expression.

The present disclosure relates to compositions and methods of treating certain genetic disease (e.g., Neurofibromatosis type I) by delivering functional neurofibromin 1(NF1) protein (e.g., mini-NF1 protein and/or full-length NF1 protein) to target cell (e.g., cells and/or tissue of a subject). The disclosure is based, in part, on isolated nucleic acids (e.g., rAAV vectors) and rAAVs engineered to express a functional NF1 protein (e.g., mini-NF1 protein and/or full-length NF1 protein) or variants thereof.

Isolated Nucleic Acid

In some aspects, the disclosure relates to compositions and methods useful for treating certain genetic diseases, for example Neurofibromatosis type I and/or conditions associated thereof. Neurofibromatosis type I is caused by sporadic or inherited germline mutations in the Neurofibromin 1 gene (NF1 gene). Sporadic loss of the remaining wild-type NF1 allele is associated with skin lesions and benign neurofibromas, which develop along peripheral nerves. Malignant complications include conditions such as optic pathway gliomas and malignant peripheral nerve sheath tumors (MPNST). In addition, NF1 haploinsufficiency can cause cognitive deficits in Neurofibromatosis type I patients. NF1 deficiency plays an important supporting role in tumor formation. The NF1 protein is a GTPase-activating protein (GAP) that inactivates Ras through activation of GTP to GDP hydrolysis. Loss of NF1 GAP function leaves Ras in the activated state (Ras-GTP) with resulting over-activation of this signaling pathway (RAF-MEK-ERK) (see, e.g., Johnson et al., Neurofibromin 1 inhibits Ras-dependent growth by a mechanism independent of its GTPase-accelerating function, *Mol Cell Biol.* 1994 January; 14(1): 641-645). Ras activation stimulates cell growth and formation of benign tumors which may progress to malignancies (e.g., MPNSTs and optic gliomas). NF1 patients may also show cognitive deficits, suggesting that NF1 plays an important role in normal neuronal function. Reconstitution of normal NF1 function (e.g., by rAAV mediated gene therapy) is capable of repressing RAS over-activation and treating Neurofibromatosis type I and associated conditions. However, the NF1 coding sequence is 8,540 bp, far exceeding the packaging capacity of recombinant AAV vectors. In some embodiments, an NF1 protein coding sequence comprises the nucleic acid sequence set forth in NCBI Reference Sequence Accession Number NM_001042492.3 (SEQ ID NO: 16), or splice variants thereof generated by incorporation of exons 9a, 23a, or 48a. In some embodiments, an NF1 gene encodes a protein having the amino acid sequence set forth in NCBI Reference Sequence Accession Number NP_001035957.1 (SEQ ID NO: 17), or protein isoforms with additional amino acids resulting from incorporation of exons 9a, 23a, and 48a in the NF1 mRNA. In some embodiments, a wild-type full-length NF1 coding sequence comprises 61 exons.

Accordingly, the disclosure is based, in part, on isolated nucleic acids and gene therapy vectors, such as viral (e.g., rAAV) vectors, comprising a transgene, which comprises one or more nucleotide sequence encoding a therapeutic gene product, such as a functional neurofibromin 1 (NF1) protein (e.g., mini-NF1 protein and/or full-length NF1 protein). In some embodiment, the nucleotide sequence encoding the mini-NF1 protein is within the packaging capacity of recombinant AAV vectors. In some embodiments, the full-length NF1 protein is delivered by a dual AAV vector system.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

(i) NF1 Minigenes

In some aspects, the disclosure relates to isolated nucleic acids comprising a transgene (e.g., a minigene) encoding a functional NF1 protein, such as a mini-NF1 protein (e.g., a gene product expressed from a NF1 gene or a portion thereof, such as an NF1 minigene). As used herein, "minigene" refers to an isolated nucleic acid sequence encoding a recombinant peptide or protein where one or more non-essential elements of the corresponding gene encoding the naturally-occurring peptide or protein have been removed and where the peptide or protein encoded by the minigene retains function of the corresponding naturally-occurring peptide or protein. A "therapeutic minigene" refers to a minigene encoding a peptide or protein useful for treatment of a genetic disease, for example dystrophin, dysferlin, Factor VIII, Amyloid precursor protein (APP), Tyrosinase (Tyr), NF1, etc. Minigenes are known in the art and are described, for example by Karpati and Acsadi (1994) Clin Invest Med 17(5):499-509; Plantier et al. (2001) Thromb Haemost. 86(2):596-603; and Xiao et al. (2007) World J. Gastroenterol. 13(2):244-9. In some embodiments, a minigene does not comprise the sequence of the corresponding naturally-occurring peptide or protein.

Generally, an isolated nucleic acid encoding a minigene (e.g., a therapeutic minigene, such as an NF1 minigene) is between about 10% and about 99% (e.g., about 10%, about 15%, about 20%, about 25%, about 30%, about 40% about 50%, about 60%, about 70%, about 75%, about 80%, about 90%, about 99%, etc.) truncated with respect to a nucleic acid sequence encoding the corresponding naturally-occurring wild-type NF1 protein (e.g., SEQ ID NO: 17). The truncations may be continuous (e.g., single, continuous truncation of amino acid residues) or discontinuous (e.g., two or more truncations of amino acids, for example truncation of two or more domains, that are separated by one or more peptides). For example, in some embodiments, a minigene encoding a mini-NF1 protein is truncated (e.g., comprises about less than 95%, less than 90%, less than 80%, less than 70%, less than 60%, less than 50%, less than 40%, less than 30%, less than 20%, or less than 10% of the wild type nucleic acid sequence encoding NF1) compared to a wild-type NF1 coding sequence(e.g., SEQ ID NO: 16). In some embodiments, a nucleotide sequence encoding a mini-NF1 protein (e.g., a mini-NF1 protein) comprises a start codon (e.g., the nucleic acid sequence ATG) prior to the nucleic acid sequence encoding the mini-NF1 protein. In some embodiments, the nucleic acid encoding any of the NF1-minigene described herein are codon optimized for expression in a target cell (e.g., human cell).

In some embodiments, an NF1 minigene comprises a GTPase-activating protein (GAP)-related domain (GRD) of the wildtype NF1 protein. The GRD of NF1 protein has been shown to be responsible for GAP activity and represents a functionally defined segment of NF1 protein (see, e.g., Li, Y. et al. (1992) Somatic mutations in the neurofibromatosis 1 gene in human tumors. Cell, 69, 275-281). In some embodiments, the mini-NF1 comprising the GRD domain of NF1 protein is capable of acting as a GTPase activating protein (GAP) on Ras. In some embodiments, the mini-NF1 comprises (or consists of) an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 1 or 20.

An exemplary amino acid sequence of a mini-NF1 protein comprising a GRD domain is set forth in SEQ ID NO: 1:

```
MEAKSQLFLKYFTLFMNLLNDCSEVEDESAQTGGRKRGMSRRLASLRHCTVLAMSNLLNANVDS

GLMHSIGLGYHKDLQTRATFMEVLTKILQQGTEFDTLAETVLADRFERLVELVTMMGDQGELPI

AMALANVVPCSQWDELARVLVTLFDSRHLLYQLLWNMFSKEVELADSMQTLFRGNSLASKIMTF
```

-continued

CFKVYGATYLQKLLDPLLRIVITSSDWQHVSFEVDPTRLEPSESLEENQRNLLQMTEKFFHAII

SSSSEFPPQLRSVCHCLYQATCHSLLNKATVKEKKENKKSVVSQRFPQNSIGAVGSAMFLRFIN

PAIVSPYEAGILDKKPPPRIERGLKLMSKILQSIANHVLFTKEEHMRPFNDFVKSNFDAARRFF

LDIASDCPTSDAVNHSLSFISDGNVLALHRLLWNNQEKIGQYLSSNRDHKAVGRRPFDKMATLL

AYLGPPEHKPVADTHWSSLNLTSSKFEEFMTRHQVHEKEEFKALKTL

An exemplary amino acid sequence of a mini-NF1 protein comprising a GRD domain with an HA tag (bold) is set forth in SEQ ID NO: 20:

MEAKSQLFLKYFTLFMNLLNDCSEVEDESAQTGGRKRGMSRRLASLRHCTVLAMSNLLNANVDS

GLMHSIGLGYHKDLQTRATFMEVLTKILQQGTEFDTLAETVLADRFERLVELVTMMGDQGELPI

AMALANVVPCSQWDELARVLVTLFDSRHLLYQLLWNMFSKEVELADSMQTLFRGNSLASKIMTF

CFKVYGATYLQKLLDPLLRIVITSSDWQHVSFEVDPTRLEPSESLEENQRNLLQMTEKFFHAII

SSSSEFPPQLRSVCHCLYQATCHSLLNKATVKEKKENKKSVVSQRFPQNSIGAVGSAMFLRFIN

PAIVSPYEAGILDKKPPPRIERGLKLMSKILQSIANHVLFTKEEHMRPFNDFVKSNFDAARRFF

LDIASDCPTSDAVNHSLSFISDGNVLALHRLLWNNQEKIGQYLSSNRDHKAVGRRPFDKMATLL

AYLGPPEHKPVADTHWSSLNLTSSKFEEFMTRHQVHEKEEFKALKTLYPYDVPDYA

In some embodiments, the nucleotide sequence encoding the mini-NF1 protein (e.g., mini-NF1 protein having the GRD domain of the wild-type NF1 protein) comprises a nucleotide sequence at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 2 or 21.

An exemplary nucleotide sequence encoding a mini-NF1 having an NF1 GRD is set forth in SEQ ID NO: 2:

ATGGAAGCCAAGAGCCAGCTGTTTCTGAAATACTTTACCCTGTTTATGAA

TCTGCTGAACGACTGTAGTGAGGTGGAGGACGAGAGTGCCCAGACCGGCG

GCAGGAAGAGAGGCATGTCTAGGAGACTGGCCAGCCTGAGGCACTGCACA

GTGCTGGCCATGTCCAACCTGCTGAACGCCAATGTGGACTCCGGCCTGAT

GCACTCTATCGGCCTGGGCTACCACAAGGATCTGCAGACCCGCGCCACAT

TCATGGAGGTGCTGACCAAGATCCTGCAGCAGGGCACCGAGTTTGACACA

CTGGCCGAGACCGTGCTGGCAGATAGGTTCGAGCGCCTGGTGGAGCTGGT

GACAATGATGGGCGACCAGGGAGAGCTGCCTATCGCAATGGCACTGGCCA

ACGTGGTGCCATGCAGCCAGTGGGACGAGCTGGCCAGGGTGCTGGTGACC

CTGTTTGATTCCAGACACCTGCTGTACCAGCTGCTGTGGAACATGTTCTC

TAAGGAGGTGGAGCTGGCCGACAGCATGCAGACACTGTTTAGGGGCAATT

CCCTGGCCTCTAAGATCATGACCTTCTGTTTTAAGGTGTACGGCGCCACA

TATCTGCAGAAGCTGCTGGATCCACTGCTGAGAATCGTGATCACCAGCTC

CGACTGGCAGCACGTGTCCTTCGAGGTGGATCCTACACGGCTGGAGCCAA

GCGAGTCCCTGGAGGAGAACCAGCGCAATCTGCTGCAGATGACCGAGAAG

TTCTTTCACGCCATCATCTCTAGCTCCTCTGAGTTTCCCCCTCAGCTGCG

GTCCGTGTGCCACTGTCTGTACCAGGCCACCTGCCACTCTCTGCTGAACA

-continued

AGGCCACAGTGAAGGAGAAGAAGGAGAATAAGAAGAGCGTGGTGTCCCAG

AGGTTCCCACAGAACAGCATCGGAGCAGTGGGATCCGCCATGTTCCTGAG

GTTCATCAATCCCGCCATCGTGAGCCCTTATGAGGCCGGCATCCTGGACA

AGAAGCCACCCCCTAGGATCGAGAGAGGCCTGAAGCTGATGAGCAAGATC

CTGCAGTCCATCGCCAACCACGTGCTGTTCACCAAGGAGGAGCACATGCG

CCCCTTCAACGACTTTGTGAAGTCTAATTTTGATGCCGCCCGGCGCTTCT

TTCTGGACATCGCCTCTGATTGTCCTACAAGCGACGCCGTGAACCACTCT

CTGAGCTTCATCAGCGATGGCAATGTGCTGGCCCTGCACCGGCTGCTGTG

GAACAATCAGGAGAAGATCGGCCAGTACCTGAGCTCCAACAGGGACCACA

AGGCAGTGGGCAGGAGACCTTTTGATAAGATGGCCACCCTGCTGGCATAT

CTGGGACCACCAGAGCACAAGCCAGTGGCAGACACCCACTGGTCTAGCCT

GAATCTGACATCCTCTAAGTTCGAGGAGTTTATGACCCGGCACCAGGTGC

ACGAGAAGGAGGAGTTTAAGGCCCTGAAGACCCTG

An exemplary nucleotide sequence encoding a mini-NF1 having an NF1 GRD with a HA tag is set forth in SEQ ID NO: 21:

ATGGAAGCCAAGAGCCAGCTGTTTCTGAAATACTTTACCCTGTTTATGAA

TCTGCTGAACGACTGTAGTGAGGTGGAGGACGAGAGTGCCCAGACCGGCG

GCAGGAAGAGAGGCATGTCTAGGAGACTGGCCAGCCTGAGGCACTGCACA

GTGCTGGCCATGTCCAACCTGCTGAACGCCAATGTGGACTCCGGCCTGAT

GCACTCTATCGGCCTGGGCTACCACAAGGATCTGCAGACCCGCGCCACAT

TCATGGAGGTGCTGACCAAGATCCTGCAGCAGGGCACCGAGTTTGACACA

CTGGCCGAGACCGTGCTGGCAGATAGGTTCGAGCGCCTGGTGGAGCTGGT

-continued

```
GACAATGATGGGCGACCAGGGAGAGCTGCCTATCGCAATGGCACTGGCCA
ACGTGGTGCCATGCAGCCAGTGGGACGAGCTGGCCAGGGTGCTGGTGACC
CTGTTTGATTCCAGACACCTGCTGTACCAGCTGCTGTGGAACATGTTCTC
TAAGGAGGTGGAGCTGGCCGACAGCATGCAGACACTGTTTAGGGGCAATT
CCCTGGCCTCTAAGATCATGACCTTCTGTTTTAAGGTGTACGGCGCCACA
TATCTGCAGAAGCTGCTGGATCCACTGCTGAGAATCGTGATCACCAGCTC
CGACTGGCAGCACGTGTCCTTCGAGGTGGATCCTACACGGCTGGAGCCAA
GCGAGTCCCTGGAGGAGAACCAGCGCAATCTGCTGCAGATGACCGAGAAG
TTCTTTCACGCCATCATCTCTAGCTCCTCTGAGTTTCCCCCTCAGCTGCG
GTCCGTGTGCCACTGTCTGTACCAGGCCACCTGCCACTCTCTGCTGAACA
AGGCCACAGTGAAGGAGAAGAAGGAGAATAAGAAGAGCGTGGTGTCCCAG
AGGTTCCCACAGAACAGCATCGGAGCAGTGGGATCCGCCATGTTCCTGAG
GTTCATCAATCCCGCCATCGTGAGCCCTTATGAGGCCGGCATCCTGGACA
AGAAGCCACCCCCTAGGATCGAGAGAGGCCTGAAGCTGATGAGCAAGATC
CTGCAGTCCATCGCCAACCACGTGCTGTTCACCAAGGAGGAGCACATGCG
CCCCTTCAACGACTTTGTGAAGTCTAATTTTGATGCCGCCCGGCGCTTCT
TTCTGGACATCGCCTCTGATTGTCCTACAAGCGACGCCGTGAACCACTCT
CTGAGCTTCATCAGCGATGGCAATGTGCTGGCCCTGCACCGGCTGCTGTG
GAACAATCAGGAGAAGATCGGCCAGTACCTGAGCTCCAACAGGGACCACA
AGGCAGTGGGCAGGAGACCTTTTGATAAGATGGCCACCCTGCTGGCATAT
CTGGGACCACCAGAGCACAAGCCAGTGGCAGACACCCACTGGTCTAGCCT
GAATCTGACATCCTCTAAGTTCGAGGAGTTTATGACCCGGCACCAGGTGC
ACGAGAAGGAGGAGTTTAAGGCCCTGAAGACCCTGTATCCGTATGATGTG
CCGGATTATGCG
```

In some embodiments, an NF1 minigene comprises a GTPase-activating protein (GAP)-related domain (GRD) and a CRAL-TRIO domain of the wildtype NF1 protein. The CRAL-TRIO domain of NF1 protein can serve as a regulatory scaffold that binds to GRD, GTPase, and Ras to facilitate Ras suppression. In some embodiments, the mini-NF1 comprising the GRD domain and the CRAL-TRIO domain of NF1 protein is capable of acting as a GTPase activating protein (GAP) on Ras. In some embodiments, the mini-NF1 comprises (or consists of) an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 3 and 22.

An exemplary amino acid sequence of a mini-NF1 protein comprising a GRD and a CRAL-TRIO domain is set forth in SEQ ID NO: 3:

```
MEAKSQLFLKYFTLFMNLLNDCSEVEDESAQTGGRKRGMSRRLASLRHCT
VLAMSNLLNANVDSGLMHSIGLGYHKDLQTRATFMEVLTKILQQGTEFDT
LAETVLADRFERLVELVTMMGDQGELPIAMALANVVPCSQWDELARVLVT
LFDSRHLLYQLLWNMFSKEVELADSMQTLFRGNSLASKIMTFCFKVYGAT
```

-continued

```
YLQKLLDPLLRIVITSSDWQHVSFEVDPTRLEPSESLEENQRNLLQMTEK
FFHAIISSSSEFPPQLRSVCHCLYQATCHSLLNKATVKEKKENKKSVVSQ
RFPQNSIGAVGSAMFLRFINPAIVSPYEAGILDKKPPPRIERGLKLMSKI
LQSIANHVLFTKEEHMRPFNDFVKSNFDAARRFFLDIASDCPTSDAVNHS
LSFISDGNVLALHRLLWNNQEKIGQYLSSNRDHKAVGRRPFDKMATLLAY
LGPPEHKPVADTHWSSLNLTSSKFEEFMTRHQVHEKEEFKALKTLSIFYQ
AGTSKAGNPIFYYVARRFKTGQINGDLLIYHVLLTLKPYYAKPYEIVVDL
THTGPSNRFKTDFLSKWFVVFPGFAYDNVSAVYIYNCNSWVREYTKYHER
LLTGLKGSKRLVFIDCPGKLAEHIEHEQQKLPAATLALEEDLK
```

An exemplary amino acid sequence of a mini-NF1 protein comprising a GRD and a CRAL-TRIO domain with a HA tag (bold) is set forth in SEQ ID NO: 22:

```
MEAKSQLFLKYFTLFMNLLNDCSEVEDESAQTGGRKRGMSRRLASLRHCT
VLAMSNLLNANVDSGLMHSIGLGYHKDLQTRATFMEVLTKILQQGTEFDT
LAETVLADRFERLVELVTMMGDQGELPIAMALANVVPCSQWDELARVLVT
LFDSRHLLYQLLWNMFSKEVELADSMQTLFRGNSLASKIMTFCFKVYGAT
YLQKLLDPLLRIVITSSDWQHVSFEVDPTRLEPSESLEENQRNLLQMTEK
FFHAIISSSSEFPPQLRSVCHCLYQATCHSLLNKATVKEKKENKKSVVSQ
RFPQNSIGAVGSAMFLRFINPAIVSPYEAGILDKKPPPRIERGLKLMSKI
LQSIANHVLFTKEEHMRPFNDFVKSNFDAARRFFLDIASDCPTSDAVNHS
LSFISDGNVLALHRLLWNNQEKIGQYLSSNRDHKAVGRRPFDKMATLLAY
LGPPEHKPVADTHWSSLNLTSSKFEEFMTRHQVHEKEEFKALKTLSIFYQ
AGTSKAGNPIFYYVARRFKTGQINGDLLIYHVLLTLKPYYAKPYEIVVDL
THTGPSNRFKTDFLSKWFVVFPGFAYDNVSAVYIYNCNSWVREYTKYHER
LLTGLKGSKRLVFIDCPGKLAEHIEHEQQKLPAATLALEEDLKYPYDVPD
YA
```

In some embodiments, the nucleotide sequence encoding the mini-NF1 protein (e.g., mini-NF1 protein having the GRD and the CRAL-TRIO domain of the wild-type NF1 protein) comprises a nucleotide sequence at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 4 and 23.

An exemplary nucleotide sequence encoding a mini-NF1 having an NF1 GRD and the CRAL-TRIO is set forth in SEQ ID NO: 4:

```
ATGGAAGCCAAGAGCCAGCTGTTTCTGAAATACTTTACCCTGTTTATGAA
TCTGCTGAACGACTGTAGTGAGGTGGAGGACGAGAGTGCCCAGACCGGCG
GCAGGAAGAGAGGCATGTCTAGGAGACTGGCCAGCCTGAGGCACTGCACA
GTGCTGGCCATGTCCAACCTGCTGAACGCCAATGTGGACTCCGGCCTGAT
GCACTCTATCGGCCTGGGCTACCACAAGGATCTGCAGACCCGCGCCACAT
TCATGGAGGTGCTGACCAAGATCCTGCAGCAGGGCACCGAGTTTGACACA
```

-continued

CTGGCCGAGACCGTGCTGGCAGATAGGTTCGAGCGCCTGGTGGAGCTGGT
GACAATGATGGGCGACCAGGGAGAGCTGCCTATCGCAATGGCACTGGCCA
ACGTGGTGCCATGCAGCCAGTGGGACGAGCTGGCCAGGGTGCTGGTGACC
CTGTTTGATTCCAGACACCTGCTGTACCAGCTGCTGTGGAACATGTTCTC
TAAGGAGGTGGAGCTGGCCGACAGCATGCAGACACTGTTTAGGGGCAATT
CCCTGGCCTCTAAGATCATGACCTTCTGTTTTAAGGTGTACGGCGCCACA
TATCTGCAGAAGCTGCTGGATCCACTGCTGAGAATCGTGATCACCAGCTC
CGACTGGCAGCACGTGTCCTTCGAGGTGGATCCTACACGGCTGGAGCCAA
GCGAGTCCCTGGAGGAGAACCAGCGCAATCTGCTGCAGATGACCGAGAAG
TTCTTTCACGCCATCATCTCTAGCTCCTCTGAGTTTCCCCCTCAGCTGCG
GTCCGTGTGCCACTGTCTGTACCAGGCCACCTGCCACTCTCTGCTGAACA
AGGCCACAGTGAAGGAGAAGAAGGAGAATAAGAAGAGCGTGGTGTCCCAG
AGGTTCCCACAGAACAGCATCGGAGCAGTGGGATCCGCCATGTTCCTGAG
GTTCATCAATCCCGCCATCGTGAGCCCTTATGAGGCCGGCATCCTGGACA
AGAAGCCACCCCCTAGGATCGAGAGAGGCCTGAAGCTGATGAGCAAGATC
CTGCAGTCCATCGCCAACCACGTGCTGTTCACCAAGGAGGAGCACATGCG
CCCCTTCAACGACTTTGTGAAGTCTAATTTTGATGCCGCCCGGCGCTTCT

-continued

TTCTGGACATCGCCTCTGATTGTCCTACAAGCGACGCCGTGAACCACTCT
CTGAGCTTCATCAGCGATGGCAATGTGCTGGCCCTGCACCGGCTGCTGTG
GAACAATCAGGAGAAGATCGGCCAGTACCTGAGCTCCAACAGGGACCACA
AGGCAGTGGGCAGGAGACCATTTGATAAGATGGCCACACTGCTGGCCTAT
CTGGGACCACCAGAGCACAAGCCAGTGGCAGACACACACTGGTCTAGCCT
GAATCTGACCTCCTCTAAGTTCGAGGAGTTTATGACCCGGCACCAGGTGC
ACGAGAAGGAGGAGTTTAAGGCCCTGAAGACACTGTCTATCTTCTACCAG
GCAGGCACCAGCAAGGCAGGAAACCCAATCTTTTACTATGTGGCCCGGCG
CTTCAAGACAGGCCAGATCAATGGCGATCTGCTGATCTACCACGTGCTGC
TGACCCTGAAGCCATACTATGCCAAGCCCTATGAGATCGTGGTGGACCTG
ACCCACACAGGCCCCTCCAACAGGTTTAAGACCGATTTCCTGTCTAAGTG
GTTCGTGGTGTTTCCTGGCTTCGCCTATGACAATGTGAGCGCCGTGTACA
TCTATAACTGCAATTCCTGGGTGCGGGAGTACACAAAGTATCACGAGCGC
CTGCTGACCGGCCTGAAGGGATCCAAGAGACTGGTGTTCATCGATTGTCC
CGGCAAGCTGGCCGAGCACATTGAACACGAACAGCAGAAACTGCCCGCCG
CAACCCTGGCCCTGGAAGAGGACCTGAAG

An exemplary nucleotide sequence encoding a mini-NF1 having an NF1 GRD and the CRAL-TRIO with a HA tag is set forth in SEQ ID NO: 23:

ATGGAAGCCAAGAGCCAGCTGTTTCTGAAATACTTTACCCTGTTTATGAATCTGCTGAACGACT
GTAGTGAGGTGGAGGACGAGAGTGCCCAGACCGGCGGCAGGAAGAGAGGCATGTCTAGGAGACT
GGCCAGCCTGAGGCACTGCACAGTGCTGGCCATGTCCAACCTGCTGAACGCCAATGTGGACTCC
GGCCTGATGCACTCTATCGGCCTGGGCTACCACAAGGATCTGCAGACCCGCGCCACATTCATGG
AGGTGCTGACCAAGATCCTGCAGCAGGGCACCGAGTTTGACACACTGGCCGAGACCGTGCTGGC
AGATAGGTTCGAGCGCCTGGTGGAGCTGGTGACAATGATGGGCGACCAGGGAGAGCTGCCTATC
GCAATGGCACTGGCCAACGTGGTGCCATGCAGCCAGTGGGACGAGCTGGCCAGGGTGCTGGTGA
CCCTGTTTGATTCCAGACACCTGCTGTACCAGCTGCTGTGGAACATGTTCTCTAAGGAGGTGGA
GCTGGCCGACAGCATGCAGACACTGTTTAGGGGCAATTCCCTGGCCTCTAAGATCATGACCTTC
TGTTTTAAGGTGTACGGCGCCACATATCTGCAGAAGCTGCTGGATCCACTGCTGAGAATCGTGA
TCACCAGCTCCGACTGGCAGCACGTGTCCTTCGAGGTGGATCCTACACGGCTGGAGCCAAGCGA
GTCCCTGGAGGAGAACCAGCGCAATCTGCTGCAGATGACCGAGAAGTTCTTTCACGCCATCATC
TCTAGCTCCTCTGAGTTTCCCCCTCAGCTGCGGTCCGTGTGCCACTGTCTGTACCAGGCCACCT
GCCACTCTCTGCTGAACAAGGCCACAGTGAAGGAGAAGAAGGAGAATAAGAAGAGCGTGGTGTC
CCAGAGGTTCCCACAGAACAGCATCGGAGCAGTGGGATCCGCCATGTTCCTGAGGTTCATCAAT
CCCGCCATCGTGAGCCCTTATGAGGCCGGCATCCTGGACAAGAAGCCACCCCCTAGGATCGAGA
GAGGCCTGAAGCTGATGAGCAAGATCCTGCAGTCCATCGCCAACCACGTGCTGTTCACCAAGGA
GGAGCACATGCGCCCCTTCAACGACTTTGTGAAGTCTAATTTTGATGCCGCCCGGCGCTTCTTT
CTGGACATCGCCTCTGATTGTCCTACAAGCGACGCCGTGAACCACTCTCTGAGCTTCATCAGCG
ATGGCAATGTGCTGGCCCTGCACCGGCTGCTGTGGAACAATCAGGAGAAGATCGGCCAGTACCT
GAGCTCCAACAGGGACCACAAGGCAGTGGGCAGGAGACCATTTGATAAGATGGCCACACTGCTG

-continued

```
GCCTATCTGGGACCACCAGAGCACAAGCCAGTGGCAGACACACACTGGTCTAGCCTGAATCTGA

CCTCCTCTAAGTTCGAGGAGTTTATGACCCGGCACCAGGTGCACGAGAAGGAGGAGTTTAAGGC

CCTGAAGACACTGTCTATCTTCTACCAGGCAGGCACCAGCAAGGCAGGAAACCCAATCTTTTAC

TATGTGGCCCGGCGCTTCAAGACAGGCCAGATCAATGGCGATCTGCTGATCTACCACGTGCTGC

TGACCCTGAAGCCATACTATGCCAAGCCCTATGAGATCGTGGTGGACCTGACCCACACAGGCCC

CTCCAACAGGTTTAAGACCGATTTCCTGTCTAAGTGGTTCGTGGTGTTTCCTGGCTTCGCCTAT

GACAATGTGAGCGCCGTGTACATCTATAACTGCAATTCCTGGGTGCGGGAGTACACAAAGTATC

ACGAGCGCCTGCTGACCGGCCTGAAGGGATCCAAGAGACTGGTGTTCATCGATTGTCCCGGCAA

GCTGGCCGAGCACATTGAACACGAACAGCAGAAACTGCCCGCCGCAACCCTGGCCCTGGAAGAG

GACCTGAAGTATCCGTATGATGTGCCGGATTATGCG
```

In some embodiments, an NF1 minigene comprises a GTPase-activating protein (GAP)-related domain (GRD), a CRAL-TRIO domain and a bipartite phospholipid binding domain of the wildtype NF1 protein. The bipartite phospholipid binding domain includes a Sec14p homologous segment and a pleckstrin homology (PH)-like domain. The lipid binding/interacting domains (CRAL-TRIO and bipartite Sec-PH) were included in this mini-NF1 gene to enhance interaction with Ras occurs at the cell membrane and lipid binding may be important for that interaction (see, e.g., Bai et al., Feasibility of using NF1-GRD and AAV for gene replacement therapy, Gene Therapy volume 26, pages 277-286(2019)). In some embodiments, the mini-NF1 comprises (or consists of) an amino acid sequence at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 5 and 24.

An exemplary amino acid sequence of a mini-NF1 protein comprising a GRD, a CRAL-TRIO domain and a bipartite phospholipid binding domain is set forth in SEQ ID NO: 5:

```
MEAKSQLFLKYFTLFMNLLNDCSEVEDESAQTGGRKRGMSRRLASLRHCTVLAMSNLLNANVDS

GLMHSIGLGYHKDLQTRATFMEVLTKILQQGTEFDTLAETVLADRFERLVELVTMMGDQGELPI

AMALANVVPCSQWDELARVLVTLFDSRHLLYQLLWNMFSKEVELADSMQTLFRGNSLASKIMTF

CFKVYGATYLQKLLDPLLRIVITSSDWQHVSFEVDPTRLEPSESLEENQRNLLQMTEKFFHAII

SSSSEFPPQLRSVCHCLYQATCHSLLNKATVKEKKENKKSVVSQRFPQNSIGAVGSAMFLRFIN

PAIVSPYEAGILDKKPPPRIERGLKLMSKILQSIANHVLFTKEEHMRPFNDFVKSNFDAARRFF

LDIASDCPTSDAVNHSLSFISDGNVLALHRLLWNNQEKIGQYLSSNRDHKAVGRRPFDKMATLL

AYLGPPEHKPVADTHWSSLNLTSSKFEEFMTRHQVHEKEEFKALKTLSIFYQAGTSKAGNPIFY

YVARRFKTGQINGDLLIYHVLLTLKPYYAKPYEIVVDLTHTGPSNRFKTDFLSKWFVVFPGFAY

DNVSAVYIYNCNSWVREYTKYHERLLTGLKGSKRLVFIDCPGKLAEHIEHEQQKLPAATLALEE

DLKVFHNALKLAHKDTKVSIKVGSTAVQVTSAERTKVLGQSVFLNDIYYASEIEEICLVDENQF

TLTIANQGTPLTFMHQECEAIVQSIIHIRTRWELSQPD
```

An exemplary amino acid sequence of a mini-NF1 protein comprising a GRD, a CRAL-TRIO domain and a bipartite phospholipid binding domain with an HA tag (bold) is set forth in SEQ ID NO: 24:

```
MEAKSQLFLKYFTLFMNLLNDCSEVEDESAQTGGRKRGMSRRLASLRHCTVLAMSNLLNANVDS

GLMHSIGLGYHKDLQTRATFMEVLTKILQQGTEFDTLAETVLADRFERLVELVTMMGDQGELPI

AMALANVVPCSQWDELARVLVTLFDSRHLLYQLLWNMFSKEVELADSMQTLFRGNSLASKIMTF

CFKVYGATYLQKLLDPLLRIVITSSDWQHVSFEVDPTRLEPSESLEENQRNLLQMTEKFFHAII

SSSSEFPPQLRSVCHCLYQATCHSLLNKATVKEKKENKKSVVSQRFPQNSIGAVGSAMFLRFIN

PAIVSPYEAGILDKKPPPRIERGLKLMSKILQSIANHVLFTKEEHMRPFNDFVKSNFDAARRFF

LDIASDCPTSDAVNHSLSFISDGNVLALHRLLWNNQEKIGQYLSSNRDHKAVGRRPFDKMATLL
```

-continued

AYLGPPEHKPVADTHWSSLNLTSSKFEEFMTRHQVHEKEEFKALKTLSIFYQAGTSKAGNPIFY

YVARRFKTGQINGDLLIYHVLLTLKPYYAKPYEIVVDLTHTGPSNRFKTDFLSKWFVVFPGFAY

DNVSAVYIYNCNSWVREYTKYHERLLTGLKGSKRLVFIDCPGKLAEHIEHEQQKLPAATLALEE

DLKVFHNALKLAHKDTKVSIKVGSTAVQVTSAERTKVLGQSVFLNDIYYASEIEEICLVDENQF

TLTIANQGTPLTFMHQECEAIVQSIIHIRTRWELSQPDYPYDVPDY

In some embodiments, the nucleotide sequence encoding the mini-NF1 protein (e.g., mini-NF1 protein having the GRD, the CRAL-TRIO domain and the bipartite phospholipid binding domain of the wild-type NF1 protein) comprises a nucleotide sequence at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 6 and 25.

An exemplary nucleotide sequence encoding a mini-NF1 having an NF1 GRD, the CRAL-TRIO domain and the bipartite phospholipid binding domain is set forth in SEQ ID NO: 6:

ATGGAAGCCAAGAGCCAGCTGTTTCTGAAATACTTTACCCTGTTTATGAATCTGCTGAACGACT

GTAGTGAGGTGGAGGACGAGAGTGCCCAGACCGGCGGCAGGAAGAGAGGCATGTCTAGGAGACT

GGCCAGCCTGAGGCACTGCACAGTGCTGGCCATGTCCAACCTGCTGAACGCCAATGTGGACTCC

GGCCTGATGCACTCTATCGGCCTGGGCTACCACAAGGATCTGCAGACCCGCGCCACATTCATGG

AGGTGCTGACCAAGATCCTGCAGCAGGGCACCGAGTTTGACACACTGGCCGAGACCGTGCTGGC

AGATAGGTTCGAGCGCCTGGTGGAGCTGGTGACAATGATGGGCGACCAGGGAGAGCTGCCTATC

GCAATGGCACTGGCCAACGTGGTGCCATGCAGCCAGTGGGACGAGCTGGCCAGGGTGCTGGTGA

CCCTGTTTGATTCCAGACACCTGCTGTACCAGCTGCTGTGGAACATGTTCTCTAAGGAGGTGGA

GCTGGCCGACAGCATGCAGACACTGTTTAGGGGCAATTCCCTGGCCTCTAAGATCATGACCTTC

TGTTTTAAGGTGTACGGCGCCACATATCTGCAGAAGCTGCTGGATCCACTGCTGAGAATCGTGA

TCACCAGCTCCGACTGGCAGCACGTGTCCTTCGAGGTGGATCCTACACGGCTGGAGCCAAGCGA

GTCCCTGGAGGAGAACCAGCGCAATCTGCTGCAGATGACCGAGAAGTTCTTTCACGCCATCATC

TCTAGCTCCTCTGAGTTTCCCCCTCAGCTGCGGTCCGTGTGCCACTGTCTGTACCAGGCCACCT

GCCACTCTCTGCTGAACAAGGCCACAGTGAAGGAGAAGAAGGAGAATAAGAAGAGCGTGGTGTC

CCAGAGGTTCCCACAGAACAGCATCGGAGCAGTGGGATCCGCCATGTTCCTGAGGTTCATCAAT

CCCGCCATCGTGAGCCCTTATGAGGCCGGCATCCTGGACAAGAAGCCACCCCCTAGGATCGAGA

GAGGCCTGAAGCTGATGAGCAAGATCCTGCAGTCCATCGCCAACCACGTGCTGTTCACCAAGGA

GGAGCACATGCGCCCCTTCAACGACTTTGTGAAGTCTAATTTTGATGCCGCCCGGCGCTTCTTT

CTGGACATCGCCTCTGATTGTCCTACAAGCGACGCCGTGAACCACTCTCTGAGCTTCATCAGCG

ATGGCAATGTGCTGGCCCTGCACCGGCTGCTGTGGAACAATCAGGAGAAGATCGGCCAGTACCT

GAGCTCCAACAGGGACCACAAGGCAGTGGGCAGGAGACCTTTTGATAAGATGGCCACCCTGCTG

GCATATCTGGGACCACCAGAGCACAAGCCAGTGGCAGACACCCACTGGTCTAGCCTGAATCTGA

CATCCTCTAAGTTCGAGGAGTTTATGACCCGGCACCAGGTGCACGAGAAGGAGGAGTTTAAGGC

CCTGAAGACCCTGTCCATCTTCTACCAGGCCGGCACATCTAAGGCCGGCAACCCTATCTTTTAC

TATGTGGCCCGGCGCTTCAAGACCGGCCAGATCAATGGCGATCTGCTGATCTACCACGTGCTGC

TGACACTGAAGCCATACTATGCCAAGCCCTATGAGATCGTGGTGGACCTGACCCACACAGGCCC

AAGCAACAGGTTTAAGACCGATTTCCTGTCCAAGTGGTTCGTGGTGTTTCCCGGCTTCGCCTAT

GACAACGTGAGCGCCGTGTACATCTATAACTGCAATAGCTGGGTGCGGGAGTACACCAAGTATC

ACGAGCGCCTGCTGACAGGCCTGAAGGGCAGCAAGAGACTGGTGTTCATCGATTGTCCCGGCAA

-continued

GCTGGCCGAGCACATCGAGCACGAGCAGCAGAAGCTGCCTGCAGCCACCCTGGCCCTGGAGGAG

GACCTGAAGGTGTTTCACAACGCCCTGAAGCTGGCCCACAAGGATACAAAGGTGTCCATCAAGG

TCGGCTCTACAGCCGTGCAGGTGACCTCCGCCGAGAGAACAAAGGTGCTGGGCCAGAGCGTGTT

CCTGAATGACATCTACTATGCCAGCGAGATCGAGGAGATCTGCCTGGTGGATGAGAACCAGTTT

ACCCTGACAATCGCCAATCAGGGCACCCCCCTGACATTCATGCACCAGGAGTGTGAAGCAATCG

TCCAGAGCATTATTCACATTCGCACTCGGTGGGAACTGAGCCAGCCTGAC

An exemplary nucleotide sequence encoding a mini-NF1 having an NF1 GRD, the CRAL-TRIO domain and the bipartite phospholipid binding domain with a HA tag is set forth in SEQ ID NO: 25:

ATGGAAGCCAAGAGCCAGCTGTTTCTGAAATACTTTACCCTGTTTATGAATCTGCTGAACGACT

GTAGTGAGGTGGAGGACGAGAGTGCCCAGACCGGCGGCAGGAAGAGAGGCATGTCTAGGAGACT

GGCCAGCCTGAGGCACTGCACAGTGCTGGCCATGTCCAACCTGCTGAACGCCAATGTGGACTCC

GGCCTGATGCACTCTATCGGCCTGGGCTACCACAAGGATCTGCAGACCCGCGCCACATTCATGG

AGGTGCTGACCAAGATCCTGCAGCAGGGCACCGAGTTTGACACACTGGCCGAGACCGTGCTGGC

AGATAGGTTCGAGCGCCTGGTGGAGCTGGTGACAATGATGGGCGACCAGGGAGAGCTGCCTATC

GCAATGGCACTGGCCAACGTGGTGCCATGCAGCCAGTGGGACGAGCTGGCCAGGGTGCTGGTGA

CCCTGTTTGATTCCAGACACCTGCTGTACCAGCTGCTGTGGAACATGTTCTCTAAGGAGGTGGA

GCTGGCCGACAGCATGCAGACACTGTTTAGGGGCAATTCCCTGGCCTCTAAGATCATGACCTTC

TGTTTTAAGGTGTACGGCGCCACATATCTGCAGAAGCTGCTGGATCCACTGCTGAGAATCGTGA

TCACCAGCTCCGACTGGCAGCACGTGTCCTTCGAGGTGGATCCTACACGGCTGGAGCCAAGCGA

GTCCCTGGAGGAGAACCAGCGCAATCTGCTGCAGATGACCGAGAAGTTCTTTCACGCCATCATC

TCTAGCTCCTCTGAGTTTCCCCCTCAGCTGCGGTCCGTGTGCCACTGTCTGTACCAGGCCACCT

GCCACTCTCTGCTGAACAAGGCCACAGTGAAGGAGAAGAAGGAGAATAAGAAGAGCGTGGTGTC

CCAGAGGTTCCCACAGAACAGCATCGGAGCAGTGGGATCCGCCATGTTCCTGAGGTTCATCAAT

CCCGCCATCGTGAGCCCTTATGAGGCCGGCATCCTGGACAAGAAGCCACCCCCTAGGATCGAGA

GAGGCCTGAAGCTGATGAGCAAGATCCTGCAGTCCATCGCCAACCACGTGCTGTTCACCAAGGA

GGAGCACATGCGCCCCTTCAACGACTTTGTGAAGTCTAATTTTGATGCCGCCCGGCGCTTCTTT

CTGGACATCGCCTCTGATTGTCCTACAAGCGACGCCGTGAACCACTCTCTGAGCTTCATCAGCG

ATGGCAATGTGCTGGCCCTGCACCGGCTGCTGTGGAACAATCAGGAGAAGATCGGCCAGTACCT

GAGCTCCAACAGGGACCACAAGGCAGTGGGCAGGAGACCTTTTGATAAGATGGCCACCCTGCTG

GCATATCTGGGACCACCAGAGCACAAGCCAGTGGCAGACACCCACTGGTCTAGCCTGAATCTGA

CATCCTCTAAGTTCGAGGAGTTTATGACCCGGCACCAGGTGCACGAGAAGGAGGAGTTTAAGGC

CCTGAAGACCCTGTCCATCTTCTACCAGGCCGGCACATCTAAGGCCGGCAACCCTATCTTTTAC

TATGTGGCCCGGCGCTTCAAGACCGGCCAGATCAATGGCGATCTGCTGATCTACCACGTGCTGC

TGACACTGAAGCCATACTATGCCAAGCCCTATGAGATCGTGGTGGACCTGACCCACACAGGCCC

AAGCAACAGGTTTAAGACCGATTTCCTGTCCAAGTGGTTCGTGGTGTTTCCCGGCTTCGCCTAT

GACAACGTGAGCGCCGTGTACATCTATAACTGCAATAGCTGGGTGCGGGAGTACACCAAGTATC

ACGAGCGCCTGCTGACAGGCCTGAAGGGCAGCAAGAGACTGGTGTTCATCGATTGTCCCGGCAA

GCTGGCCGAGCACATCGAGCACGAGCAGCAGAAGCTGCCTGCAGCCACCCTGGCCCTGGAGGAG

GACCTGAAGGTGTTTCACAACGCCCTGAAGCTGGCCCACAAGGATACAAAGGTGTCCATCAAGG

-continued

```
TCGGCTCTACAGCCGTGCAGGTGACCTCCGCCGAGAGAACAAAGGTGCTGGGCCAGAGCGTGTT

CCTGAATGACATCTACTATGCCAGCGAGATCGAGGAGATCTGCCTGGTGGATGAGAACCAGTTT

ACCCTGACAATCGCCAATCAGGGCACCCCCCTGACATTCATGCACCAGGAGTGTGAAGCAATCG

TCCAGAGCATTATTCACATTCGCACTCGGTGGGAACTGAGCCAGCCTGACTATCCGTATGATGT

GCCGGATTATGC
```

In some embodiments, an NF1 minigene comprises (or consists of) the nucleic acid sequence set forth in any one of SEQ ID NOs: 2, 4, or 6. In some embodiments, an NF1 minigene encodes a protein (referred to as a mini-NF1 protein) that comprises (or consists of) an amino acid sequence set forth in any one of SEQ ID NOs: 1, 3, or 5.

In some embodiments, the transgene encoding the mini-NF1 proteins further comprises a nucleotide sequence encoding a polypeptide tag. A polypeptide tag, as used herein, refers to polypeptide sequences that are attached to proteins to facilitate easy detection and purification of expressed proteins. In addition, they can also be used to identify potential binding partners for the protein of interest. Non-limiting examples of a polypeptide tag includes a human influenza hemagglutinin (HA) tag, a FLAG tag, a Myc tag, a Maltose-binding protein (MBP) tag, a Calmodulin Binding Protein (CBP) tag, Poly-Histidine tag (His) tag, or a Glutathione-S transferase (GST) tag. In some embodiments, the polypeptide tag is an HA tag. In some embodiments, the HA tag is position at the N-terminal of the protein it is attached to (e.g., an mini-NF1 protein). In some embodiments, the polypeptide tag is an HA tag. In some embodiments, the HA tag is position at the C-terminal of the protein it is attached to (e.g., an mini-NF1 protein). In some embodiments, the transgene encoding the mini-NF protein does not comprise a nucleotide sequence encoding a polypeptide tag.

(ii) Dual-AAV Vector System Encoding Full-Length NF1

In some aspects, the present disclosure provides a set of isolated nucleic acids (e.g., a 5' isolated nucleic acid and/or a 3' isolated nucleic acid) each encoding a different portion of a protein (e.g., a portion of NF1 protein). The delivery of both isolated nucleic acids (e.g., by recombinant adeno-associated virus (rAAV) to the same cell results in delivery of a full-length protein (e.g., full-length NF1 protein to the cell).

In some embodiments, a 5' isolated nucleic acid, as used herein, refers to an isolated nucleic acid comprising nucleotide sequence encoding a first portion (e.g., N-terminal portion) of a protein (e.g., full-length NF1 protein. In some embodiments, the 5' isolated nucleic acid, which is flanked by adeno-associated virus (AAV) inverted terminal repeats (ITRs), comprises, from 5' to 3', a promoter operably linked to a nucleotide sequence encoding a first portion of NF1 protein, a nucleotide sequence encoding a splice donor, and a first portion of an intron.

In some embodiments, a 3' isolated nucleic acid, as used herein, refers to an isolated nucleic acid comprising nucleotide sequence encoding a second portion (e.g., C-terminal portion) of a protein (e.g., full-length NF1 protein. In some embodiments, the 3' isolated nucleic acid, which is flanked by adeno-associated virus (AAV) inverted terminal repeats (ITRs), comprises, from 5' to 3', a second portion of an intron, a nucleotide sequence encoding a splice acceptor, a nucleotide sequence encoding a second portion of NF1 protein. In some embodiments, the 3' and a polyadenylation signal positioned between the nucleotide sequence encoding a second portion of NF1 protein and the 3' ITR of the 3' isolated nucleic acid.

In some embodiments, the 5' isolated nucleic acid comprises a nucleotide sequence of exon 1 of the NF1 coding sequence, and one or more exons from exons 2-61 of the wild-type NF1 coding sequence (e.g., exons 1-25, exons 1-26, exons 1-27, exons 1-28, exons 1-29, exons 1-30, exons 1-31, exons 1-32, exons 1-33, exons 1-34, exons 1-35, exons 1-36, exons 1-37, exons 1-38, exons 1-39, exons 1-40, exons 1-41, exons 1-42, exons 1-43, exons 1-44, exons 1-45, exons 1-46, exons 1-47, exons 1-48, exons 1-49, exons 1-50, exons 1-51, exons 1-52, exons 1-53, exons 1-54, exons 1-55, exons 1-56, exons 1-57, exons 1-58, exons 1-59, or exons 1-60). In some embodiments, the 3' isolated nucleic acid comprises a nucleotide sequence of exon 61 of the NF1 coding sequence, and one or more exons from exons 1-60 of the wild-type NF1 coding sequence (e.g., exons 2-61, exons 3-61, exons 4-61, exons 5-61, exons 6-61, exons 7-61, exons 8-61, exons 9-61, exons 10-61, exons 11-61, exons 12-61, exons 13-61, exons 14-61, exons 15-61, exons 16-61, exons 17-61, exons 18-61, exons 19-61, exons 20-61, exons 21-61, exons 22-61, exons 23-61, exons 24-61, exons 25-61, exons 26-61, exons 27-61, exons 28-61, exons 29-61, exons 30-61, exons 31-61, exons 32-61, exons 33-61, exons 34-61, exons 35-61, or exons 36-61). In some embodiments, the 5' isolated nucleic acid comprises a nucleotide sequence of exon 1-31 of the NF1 coding sequence, and the 3' isolated nucleic acid comprises a nucleotide sequence of exon 32-61 of the NF1 coding sequence. In some embodiments, the 5' isolated nucleic acid comprises a nucleotide sequence of exon 1 of the NF1 coding sequence, and the 3' isolated nucleic acid comprises a nucleotide sequence of exons 2-61 of the NF1 coding sequence. In some embodiments, the 5' isolated nucleic acid comprises a nucleotide sequence of exons 1-2 of the NF1 coding sequence, and the 3' isolated nucleic acid comprises a nucleotide sequence of exons 3-61 of the NF1 coding sequence. In some embodiments, the 5' isolated nucleic acid comprises a nucleotide sequence of exons 1-3 of the NF1 coding sequence, and the 3' isolated nucleic acid comprises a nucleotide sequence of exons 4-61 of the NF1 coding sequence. In some embodiments, the 5' isolated nucleic acid comprises a nucleotide sequence of exons 1~4 of the NF1 coding sequence, and the 3' isolated nucleic acid comprises a nucleotide sequence of exons 5-61 of the NF1 coding sequence. In some embodiments, the 5' isolated nucleic acid comprises a nucleotide sequence of exons 1-5 of the NF1 coding sequence, and the 3' isolated nucleic acid comprises a nucleotide sequence of exons 6-61 of the NF1 coding sequence. In some embodiments, the 5' isolated nucleic acid comprises a nucleotide sequence of exons 1-6 of the NF1 coding sequence, and the 3' isolated nucleic acid comprises a nucleotide sequence of exons 7-61 of the NF1 coding sequence. In some embodiments, the 5' isolated nucleic acid comprises a nucleotide sequence of exons 1-7 of the NF1 coding sequence, and the 3' isolated nucleic acid comprises a nucleotide sequence of exons 8-61 of the NF1 coding sequence. In some embodiments, the 5' isolated nucleic acid comprises a nucleotide sequence of exons 1-8 of the NF1 coding sequence, and the 3' isolated nucleic acid comprises a nucleotide sequence of exons 9-61 of the NF1 coding sequence. In some embodiments, the 5' isolated nucleic acid comprises a nucleotide sequence of exons 1-9 of the NF1 coding sequence, and the 3' isolated nucleic acid comprises a nucleotide sequence of exons 10-61 of the NF1 coding sequence. In some embodiments, the 5' isolated nucleic acid comprises a nucleotide sequence of exons 1-10 of the NF1 coding sequence, and the 3' isolated nucleic acid comprises a nucleotide sequence of exons 11-61 of the NF1 coding sequence. In some embodiments, the 5' isolated nucleic acid comprises a nucleotide sequence of exons 1-11 of the NF1 coding sequence, and the 3' isolated nucleic acid comprises a nucleotide sequence of exons 12-61 of the NF1 coding sequence. In some embodiments, the 5' isolated nucleic acid comprises a nucleotide sequence of exons 1-12 of the NF1 coding sequence, and the 3' isolated nucleic acid comprises a nucleotide sequence of exons 13-61 of the NF1 coding sequence. In some embodiments, the 5' isolated nucleic acid comprises a nucleotide sequence of exons 1-13 of the NF1 coding sequence, and the 3' isolated nucleic acid comprises a nucleotide sequence of exons 14-61 of the NF1 coding sequence. In some embodiments, the 5' isolated nucleic acid comprises a nucleotide sequence of exons 1-14 of the NF1 coding sequence, and the 3' isolated nucleic acid comprises a nucleotide sequence of exons 15-61 of the NF1 coding sequence. In some embodiments, the 5' isolated nucleic acid comprises a nucleotide sequence of exons 1-15 of the NF1 coding sequence, and the 3' isolated nucleic acid comprises a nucleotide sequence of exons 16-61 of the NF1 coding sequence. In some embodiments, the 5' isolated nucleic acid comprises a nucleotide sequence of exons 1-16 of the NF1 coding sequence, and the 3' isolated nucleic acid comprises a nucleotide sequence of exons 17-61 of the NF1 coding sequence. In some embodiments, the 5' isolated nucleic acid comprises a nucleotide sequence of exons 1-17 of the NF1 coding sequence, and the 3' isolated nucleic acid comprises a nucleotide sequence of exons 18-61 of the NF1 coding sequence. In some embodiments, the 5' isolated nucleic acid comprises a nucleotide sequence of exons 1-18 of the NF1 coding sequence, and the 3' isolated nucleic acid comprises a nucleotide sequence of exons 19-61 of the NF1 coding sequence. In some embodiments, the 5' isolated nucleic acid comprises a nucleotide sequence of exons 1-19 of the NF1 coding sequence, and the 3' isolated nucleic acid comprises a nucleotide sequence of exons 20-61 of the NF1 coding sequence. In some embodiments, the 5' isolated nucleic acid comprises a nucleotide sequence of exons 1-20 of the NF1 coding sequence, and the 3' isolated nucleic acid comprises a nucleotide sequence of exons 21-61 of the NF1 coding sequence. In some embodiments, the 5' isolated nucleic acid comprises a nucleotide sequence of exons 1-21 of the NF1 coding sequence, and the 3' isolated nucleic acid comprises a nucleotide sequence of exons 22-61 of the NF1 coding sequence. In some embodiments, the 5' isolated nucleic acid comprises a nucleotide sequence of exons 1-22 of the NF1 coding sequence, and the 3' isolated nucleic acid comprises a nucleotide sequence of exons 23-61 of the NF1 coding sequence. In some embodiments, the 5' isolated nucleic acid comprises a nucleotide sequence of exons 1-23 of the NF1 coding sequence, and the 3' isolated nucleic acid comprises a nucleotide sequence of exons 24-61 of the NF1 coding sequence. In some embodiments, the 5' isolated nucleic acid comprises a nucleotide sequence of exons 1-24 of the NF1 coding sequence, and the 3' isolated nucleic acid comprises a nucleotide sequence of exons 25-61 of the NF1 coding sequence. In some embodiments, the 5' isolated nucleic acid comprises a nucleotide sequence of exons 1-25 of the NF1 coding sequence, and the 3' isolated nucleic acid comprises a nucleotide sequence of exons 25-61 of the NF1 coding sequence. In some embodiments, the 5' isolated nucleic acid comprises a nucleotide sequence of exons 1-26 of the NF1 coding sequence, and the 3' isolated nucleic acid comprises a nucleotide sequence of exons 27-61 of the NF1 coding sequence. In some embodiments, the 5' isolated nucleic acid comprises a nucleotide sequence of exons 1-28 of the NF1 coding sequence, and the 3' isolated nucleic acid comprises a nucleotide sequence of exons 29-61 of the NF1 coding sequence. In some embodiments, the 5' isolated nucleic acid comprises a nucleotide sequence of exons 1-30 of the NF1 coding sequence, and the 3' isolated nucleic acid comprises a nucleotide sequence of exons 31-61 of the NF1 coding sequence. In some embodiments, the 5' isolated nucleic acid comprises a nucleotide sequence of exons 1-32 of the NF1 coding sequence, and the 3' isolated nucleic acid comprises a nucleotide sequence of exons 33-61 of the NF1 coding sequence. In some embodiments, the 5' isolated nucleic acid comprises a nucleotide sequence of exons 1-33 of the NF1 coding sequence, and the 3' isolated nucleic acid comprises a nucleotide sequence of exons 34-61 of the NF1 coding sequence. In some embodiments, the 5' isolated nucleic acid comprises a nucleotide sequence of exons 1-34 of the NF1 coding sequence, and the 3' isolated nucleic acid comprises a nucleotide sequence of exons 35-61 of the NF1 coding sequence. In some embodiments, the 5' isolated nucleic acid comprises a nucleotide sequence of exons 1-35 of the NF1 coding sequence, and the 3' isolated nucleic acid comprises a nucleotide sequence of exons 36-61 of the NF1 coding sequence. In some embodiments, the 5' isolated nucleic acid comprises a nucleotide sequence of exons 1-36 of the NF1 coding sequence, and the 3' isolated nucleic acid comprises a nucleotide sequence of exons 37-61 of the NF1 coding sequence. In some embodiments, the 5' isolated nucleic acid comprises a nucleotide sequence of exons 1-37 of the NF1 coding sequence, and the 3' isolated nucleic acid comprises a nucleotide sequence of exons 38-61 of the NF1 coding sequence. In some embodiments, the 5' isolated nucleic acid comprises a nucleotide sequence of exons 1-38 of the NF1 coding sequence, and the 3' isolated nucleic acid comprises a nucleotide sequence of exons 39-61 of the NF1 coding sequence. In some embodiments, the 5' isolated nucleic acid comprises a nucleotide sequence of exons 1-39 of the NF1 coding sequence, and the 3' isolated nucleic acid comprises a nucleotide sequence of exons 40-61 of the NF1 coding sequence. In some embodiments, the 5' isolated nucleic acid comprises a nucleotide sequence of exons 1-40 of the NF1 coding sequence, and the 3' isolated nucleic acid comprises a nucleotide sequence of exons 41-61 of the NF1 coding sequence. In some embodiments, the 5' isolated nucleic acid comprises a nucleotide sequence of exons 1-41 of the NF1 coding sequence, and the 3' isolated nucleic acid comprises a nucleotide sequence of exons 42-61 of the NF1 coding sequence. In some embodiments, the 5' isolated nucleic acid comprises a nucleotide sequence of exons 1-42 of the NF1 coding sequence, and the 3' isolated nucleic acid comprises a nucleotide sequence of exons 43-61 of the NF1 coding sequence. In some embodiments, the 5' isolated nucleic acid comprises a nucleotide sequence of exons 1-43 of the NF1 coding sequence, and the 3' isolated nucleic acid comprises a nucleotide sequence of exons 44-61 of the NF1 coding sequence. In some embodiments, the 5' isolated nucleic acid comprises a nucleotide sequence of exons 1-44 of the NF1 coding sequence, and the 3' isolated nucleic acid comprises a nucleotide sequence of exons 45-61 of the NF1 coding sequence. In some embodiments, the 5' isolated nucleic acid comprises a nucleotide sequence of exons 1-46 of the NF1 coding sequence, and the 3' isolated nucleic acid comprises a nucleotide sequence of exons 47-61 of the NF1 coding sequence. In some embodiments, the 5' isolated nucleic acid comprises a nucleotide sequence of exons 1-47 of the NF1 coding sequence, and the 3' isolated nucleic acid comprises a nucleotide sequence of exons 48-61 of the NF1 coding sequence. In some embodiments, the 5' isolated nucleic acid comprises a nucleotide sequence of exons 1-48 of the NF1 coding sequence, and the 3' isolated nucleic acid comprises a nucleotide sequence of exons 49-61 of the NF1 coding sequence. In some embodiments, the 5' isolated nucleic acid comprises a nucleotide sequence of exons 1-49 of the NF1 coding sequence, and the 3' isolated nucleic acid comprises a nucleotide sequence of exons 50-61 of the NF1 coding sequence. In some embodiments, the 5' isolated nucleic acid comprises a nucleotide sequence of exons 1-50 of the NF1 coding sequence, and the 3' isolated nucleic acid comprises a nucleotide sequence of exons 51-61 of the NF1 coding sequence. In some embodiments, the 5' isolated nucleic acid comprises a nucleotide sequence of exons 1-51 of the NF1 coding sequence, and the 3' isolated nucleic acid comprises a nucleotide sequence of exons 52-61 of the NF1 coding sequence. In some embodiments, the 5' isolated nucleic acid comprises a nucleotide sequence of exons 1-52 of the NF1 coding sequence, and the 3' isolated nucleic acid comprises a nucleotide sequence of exons 53-61 of the NF1 coding sequence. In some embodiments, the 5' isolated nucleic acid comprises a nucleotide sequence of exons 1-53 of the NF1 coding sequence, and the 3' isolated nucleic acid comprises a nucleotide sequence of exons 54-61 of the NF1 coding sequence. In some embodiments, the 5' isolated nucleic acid comprises a nucleotide sequence of exons 1-54 of the NF1 coding sequence, and the 3' isolated nucleic acid comprises a nucleotide sequence of exons 55-61 of the NF1 coding sequence. In some embodiments, the 5' isolated nucleic acid comprises a nucleotide sequence of exons 1-55 of the NF1 coding sequence, and the 3' isolated nucleic acid comprises a nucleotide sequence of exons 56-61 of the NF1 coding sequence. In some embodiments, the 5' isolated nucleic acid comprises a nucleotide sequence of exons 1-56 of the NF1 coding sequence, and the 3' isolated nucleic acid comprises a nucleotide sequence of exons 57-61 of the NF1 coding sequence. In some embodiments, the 5' isolated nucleic acid comprises a nucleotide sequence of exons 1-57 of the NF1 coding sequence, and the 3' isolated nucleic acid comprises a nucleotide sequence of exons 58-61 of the NF1 coding sequence. In some embodiments, the 5' isolated nucleic acid comprises a nucleotide sequence of exons 1-59 of the NF1 coding sequence, and the 3' isolated nucleic acid comprises a nucleotide sequence of exons 60-61 of the NF1 coding sequence. In some embodiments, the 5' isolated nucleic acid comprises a nucleotide sequence of exons 1-60 of the NF1 coding sequence, and the 3' isolated nucleic acid comprises a nucleotide sequence of exon 61 of the NF1 coding sequence.

In some embodiments, the nucleotide sequence encoding a first portion of the NF1 protein comprises exons 1-31 of the wild-type NF1 coding sequence. In some embodiments, the first portion of the NF1 protein comprises an amino acid sequence at least 80%, at least 85%, at least 90%, at least 91%, at least 92%, at least 93%, at least 94%, at least 95%, at least 96%, at least 97%, at least 98%, at least 99%, or 100% identical to SEQ ID NO: 10. An exemplary amino acid sequence of the first portion of the NF1 protein is set forth in SEQ ID NO: 10:

```
MAAHRPVEWVQAVVSRFDEQLPIKTGQQNTHTKVSTEHNKECLINISKYKFSLVISGLTTILKN

VNNMRIFGEAAEKNLYLSQLIILDTLEKCLAGQPKDTMRLDETMLVKQLLPEICHFLHTCREGN

QHAAELRNSASGVLFSLSCNNFNAVFSRISTRLQELTVCSEDNVDVHDIELLQYINVDCAKLKR

LLKETAFKFKALKKVAQLAVINSLEKAFWNWVENYPDEFTKLYQIPQTDMAECAEKLFDLVDGF

AESTKRKAAVWPLQIILLILCPEIIQDISKDVVDENNMNKKLFLDSLRKALAGHGGSRQLTESA

AIACVKLCKASTYINWEDNSVIFLLVQSMVVDLKNLLFNPSKPFSRGSQPADVDLMIDCLVSCF

RISPHNNQHFKICLAQNSPSTFHYVLVNSLHRIITNSALDWWPKIDAVYCHSVELRNMFGETLH

KAVQGCGAHPAIRMAPSLTFKEKVTSLKFKEKPTDLETRSYKYLLLSMVKLIHADPKLLLCNPR

KQGPETQGSTAELITGLVQLVPQSHMPEIAQEAMEALLVLHQLDSIDLWNPDAPVETFWEISSQ

MLFYICKKLTSHQMLSSTEILKWLREILICRNKFLLKNKQADRSSCHFLLFYGVGCDIPSSGNT

SQMSMDHEELLRTPGASLRKGKGNSSMDSAAGCSGTPPICRQAQTKLEVALYMFLWNPDTEAVL

VAMSCFRHLCEEADIRCGVDEVSVHNLLPNYNTFMEFASVSNMMSTGRAALQKRVMALLRRIEH

PTAGNTEAWEDTHAKWEQATKLILNYPKAKMEDGQAAESLHKTIVKRRMSHVSGGGSIDLSDTD

SLQEWINMTGFLCALGGVCLQQRSNSGLATYSPPMGPVSERKGSMISVMSSEGNADTPVSKFMD

RLLSLMVCNHEKVGLQIRTNVKDLVGLELSPALYPMLFNKLKNTISKFFDSQGQVLLTDTNTQF

VEQTIAIMKNLLDNHTEGSSEHLGQASIETMMLNLVRYVRVLGNMVHAIQIKTKLCQLVEVMMA

RRDDLSFCQEMKFRNKMVEYLTDWVMGTSNQAADDDVKCLTRDLDQASMEAVVSLLAGLPLQPE

EGDGVELMEAKSQLFLKYFTLFMNLLNDCSEVEDESAQTGGRKRGMSRRLASLRHCTVLAMSNL
```

-continued

LNANVDSGLMHSIGLGYHKDLQTRATFMEVLTKILQQGTEFDTLAETVLADRFERLVELVTMMG

DQGELPIAMALANVVPCSQWDELARVLVTLFDSRHLLYQLLWNMFSKEVELADSMQTLFRGNSL

ASKIMTFCFKVYGATYLQKLLDPLLRIVITSSDWQHVSFEVDPTRLEPSESLEENQRNLLQMTE

KFFHAIISSSSEFPPQLRSVCHCLYQATCHSLLNKATVKEKKENKKS

In some embodiments, the nucleotide sequence encoding the first portion of the NF1 protein (e.g., exons 1-31) is at least at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 11. A nucleotide sequence encoding the first portion of the NF1 protein is set forth in SEQ ID NO: 11.

ATGGCCGCGCACAGGCCGGTGGAATGGGTCCAGGCCGTGGTCAGCCGCTTCGACGAGCAGCTTC

CAATAAAAACAGGACAGCAGAACACACATACCAAAGTCAGTACTGAGCACAACAAGGAATGTCT

AATCAATATTTCCAAATACAAGTTTTCTTTGGTTATAAGCGGCCTCACTACTATTTTAAAGAAT

GTTAACAATATGAGAATATTTGGAGAAGCTGCTGAAAAAAATTTATATCTCTCTCAGTTGATTA

TATTGGATACACTGGAAAAATGTCTTGCTGGGCAACCAAAGGACACAATGAGATTAGATGAAAC

GATGCTGGTCAAACAGTTGCTGCCAGAAATCTGCCATTTTCTTCACACCTGTCGTGAAGGAAAC

CAGCATGCAGCTGAACTTCGGAATTCTGCCTCTGGGGTTTTATTTTCTCTCAGCTGCAACAACT

TCAATGCAGTCTTTAGTCGCATTTCTACCAGGTTACAGGAATTAACTGTTTGTTCAGAAGACAA

TGTTGATGTTCATGATATAGAATTGTTACAGTATATCAATGTGGATTGTGCAAAATTAAAACGA

CTCCTGAAGGAAACAGCATTTAAATTTAAAGCCCTAAAGAAGGTTGCGCAGTTAGCAGTTATAA

ATAGCCTGGAAAAGGCATTTTGGAACTGGGTAGAAAATTATCCAGATGAATTTACAAAACTGTA

CCAGATCCCACAGACTGATATGGCTGAATGTGCAGAAAAGCTATTTGACTTGGTGGATGGTTTT

GCTGAAAGCACCAAACGTAAAGCAGCAGTTTGGCCACTACAAATCATTCTCCTTATCTTGTGCC

CAGAAATAATCCAGGATATATCCAAAGACGTGGTTGATGAAAACAACATGAATAAGAAGTTATT

TCTGGACAGTCTACGAAAAGCTCTTGCTGGCCATGGAGGAAGTAGGCAGCTGACAGAAAGTGCT

GCAATTGCCTGTGTCAAACTGTGTAAAGCAAGTACTTACATCAATTGGGAAGATAACTCTGTCA

TTTTCCTACTTGTTCAGTCCATGGTGGTTGATCTTAAGAACCTGCTTTTTAATCCAAGTAAGCC

ATTCTCAAGAGGCAGTCAGCCTGCAGATGTGGATCTAATGATTGACTGCCTTGTTTCTTGCTTT

CGTATAAGCCCTCACAACAACCAACACTTTAAGATCTGCCTGGCTCAGAATTCACCTTCTACAT

TTCACTATGTGCTGGTAAATTCACTCCATCGAATCATCACCAATTCCGCATTGGATTGGTGGCC

TAAGATTGATGCTGTGTATTGTCACTCGGTTGAACTTCGAAATATGTTTGGTGAAACACTTCAT

AAAGCAGTGCAAGGTTGTGGAGCACACCCAGCAATACGAATGGCACCGAGTCTTACATTTAAAG

AAAAAGTAACAAGCCTTAAATTTAAAGAAAAACCTACAGACCTGGAGACAAGAAGCTATAAGTA

TCTTCTCTTGTCCATGGTGAAACTAATTCATGCAGATCCAAAGCTCTTGCTTTGTAATCCAAGA

AAACAGGGGCCCGAAACCCAAGGCAGTACAGCAGAATTAATTACAGGGCTCGTCCAACTGGTCC

CTCAGTCACACATGCCAGAGATTGCTCAGGAAGCAATGGAGGCTCTGCTGGTTCTTCATCAGTT

AGATAGCATTGATTTGTGGAATCCTGATGCTCCTGTAGAAACATTTTGGGAGATTAGCTCACAA

ATGCTTTTTTACATCTGCAAGAAATTAACTAGTCATCAAATGCTTAGTAGCACAGAAATTCTCA

AGTGGTTGCGGGAAATATTGATCTGCAGGAATAAATTTCTTCTTAAAAATAAGCAGGCAGATAG

AAGTTCCTGTCACTTTCTCCTTTTTTACGGGGTAGGATGTGATATTCCTTCTAGTGGAAATACC

AGTCAAATGTCCATGGATCATGAAGAATTACTACGTACTCCTGGAGCCTCTCTCCGGAAGGGAA

AAGGGAACTCCTCTATGGATAGTGCAGCAGGATGCAGCGGAACCCCCCCAATTTGCCGACAAGC

CCAGACCAAACTAGAAGTGGCCCTGTACATGTTTCTGTGGAACCCTGACACTGAAGCTGTTCTG

-continued

GTTGCCATGTCCTGTTTCCGCCACCTCTGTGAGGAAGCAGATATCCGGTGTGGGGTGGATGAAG

TGTCAGTGCATAACCTCTTGCCCAACTATAACACATTCATGGAGTTTGCCTCTGTCAGCAATAT

GATGTCAACAGGAAGAGCAGCACTTCAGAAAAGAGTGATGGCACTGCTGAGGCGCATTGAGCAT

CCCACTGCAGGAAACACTGAGGCTTGGGAAGATACACATGCAAAATGGGAACAAGCAACAAAGC

TAATCCTTAACTATCCAAAAGCCAAAATGGAAGATGGCCAGGCTGCTGAAAGCCTTCACAAGAC

CATTGTTAAGAGGCGAATGTCCCATGTGAGTGGAGGAGGATCCATAGATTTGTCTGACACAGAC

TCCCTACAGGAATGGATCAACATGACTGGCTTCCTTTGTGCCCTTGGGGGAGTGTGCCTCCAGC

AGAGAAGCAATTCTGGCCTGGCAACCTATAGCCCACCCATGGGTCCAGTCAGTGAACGTAAGGG

TTCTATGATTTCAGTGATGTCTTCAGAGGGAAACGCAGATACACCTGTCAGCAAATTTATGGAT

CGGCTGTTGTCCTTAATGGTGTGTAACCATGAGAAAGTGGGACTTCAAATACGGACCAATGTTA

AGGATCTGGTGGGTCTAGAATTGAGTCCTGCTCTGTATCCAATGCTATTTAACAAATTGAAGAA

TACCATCAGCAAGTTTTTTGACTCCCAAGGACAGGTTTTATTGACTGATACCAATACTCAATTT

GTAGAACAAACCATAGCTATAATGAAGAACTTGCTAGATAATCATACTGAAGGCAGCTCTGAAC

ATCTAGGGCAAGCTAGCATTGAAACAATGATGTTAAATCTGGTCAGGTATGTTCGTGTGCTTGG

GAATATGGTCCATGCAATTCAAATAAAAACGAAACTGTGTCAATTAGTTGAAGTAATGATGGCA

AGGAGAGATGACCTCTCATTTTGCCAAGAGATGAAATTTAGGAATAAGATGGTAGAATACCTGA

CAGACTGGGTTATGGGAACATCAAACCAAGCAGCAGATGATGATGTAAAATGTCTTACAAGAGA

TTTGGACCAGGCAAGCATGGAAGCAGTAGTTTCACTTCTAGCTGGTCTCCCTCTGCAGCCTGAA

GAAGGAGATGGTGTGGAATTGATGGAAGCCAAATCACAGTTATTTCTTAAATACTTCACATTAT

TTATGAACCTTTTGAATGACTGCAGTGAAGTTGAAGATGAAAGTGCGCAAACAGGTGGCAGGAA

ACGTGGCATGTCTCGGAGGCTGGCATCACTGAGGCACTGTACGGTCCTTGCAATGTCAAACTTA

CTCAATGCCAACGTAGACAGTGGTCTCATGCACTCCATAGGCTTAGGTTACCACAAGGATCTCC

AGACAAGAGCTACATTTATGGAAGTTCTGACAAAAATCCTTCAACAAGGCACAGAATTTGACAC

ACTTGCAGAAACAGTATTGGCTGATCGGTTTGAGAGATTGGTGGAACTGGTCACAATGATGGGT

GATCAAGGAGAACTCCCTATAGCGATGGCTCTGGCCAATGTGGTTCCTTGTTCTCAGTGGGATG

AACTAGCTCGAGTTCTGGTTACTCTGTTTGATTCTCGGCATTTACTCTACCAACTGCTCTGGAA

CATGTTTTCTAAAGAAGTAGAATTGGCAGACTCCATGCAGACTCTCTTCCGAGGCAACAGCTTG

GCCAGTAAAATAATGACATTCTGTTTCAAGGTATATGGTGCTACCTATCTACAAAAACTCCTGG

ATCCTTTATTACGAATTGTGATCACATCCTCTGATTGGCAACATGTTAGCTTTGAAGTGGATCC

TACCAGGTTAGAACCATCAGAGAGCCTTGAGGAAAACCAGCGGAACCTCCTTCAGATGACTGAA

AAGTTCTTCCATGCCATCATCAGTTCCTCCTCAGAATTCCCCCCTCAACTTCGAAGTGTGTGCC

ACTGTTTATACCAGGCAACTTGCCACTCCCTACTGAATAAAGCTACAGTAAAAGAAAAAAAGGA

AAACAAAAAATCA

In some embodiments, the nucleotide sequence encoding a second portion of the NF1 protein comprises exons 32-61 of the wild-type NF1 coding sequence. In some embodiments, the second portion of the NF1 protein comprises an amino acid sequence at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 13 or 26.

An exemplary amino acid sequence of the second portion of the NF1 protein is set forth in SEQ ID NO: 13:

MVSQRFPQNSIGAVGSAMFLRFINPAIVSPYEAGILDKKPPPRIERGLKLMSKILQSIANHVLE

TKEEHMRPFNDFVKSNFDAARRFFLDIASDCPTSDAVNHSLSFISDGNVLALHRLLWNNQEKIG

QYLSSNRDHKAVGRRPFDKMATLLAYLGPPEHKPVADTHWSSLNLTSSKFEEFMTRHQVHEKEE

-continued

FKALKTLSIFYQAGTSKAGNPIFYYVARRFKTGQINGDLLIYHVLLTLKPYYAKPYEIVVDLTH

TGPSNRFKTDFLSKWFVVFPGFAYDNVSMVYIYNCNSWVREYTKYHERLLTGLKGSKRLVFIDC

PGKLAEHIEHEQQKLPAATLALEEDLKVFHNALKLAHKDTKVSIKVGSTAVQVTSAERTKVLGQ

SVFLNDIYYASEIEEICLVDENQFTLTIANQGTPLTFMHQECEAIVQSIIHIRTRWELSQPDSI

PQHTKIRPKDVPGTLLNIALLNLGSSDPSLRSAAYNLLCALTCTFNLKIEGQLLETSGLCIPAN

NTLFIVSISKTLAANEPHLTLEFLEECISGFSKSSIELKHLCLEYMTPWLSNLVRFCKHNDDAK

RQRVTAILDKLITMTINEKQMYPSIQAKIWGSLGQITDLLDVVLDSFIKTSATGGLGSIKAEVM

ADTAVALASGNVKLVSSKVIGRMCKIIDKTCLSPTPTLEQHLMWDDIAILARYMLMLSFNNSLD

VAAHLPYLFHVVTFLVATGPLSLRASTHGLVINIIHSLCTCSQLHFSEETKQVLRLSLTEFSLP

KFYLLFGISKVKSAAVIAFRSSYRDRSFSPGSYERETFALTSLETVTEALLEIMEACMRDIPTC

KWLDQWTELAQRFAFQYNPSLQPRALVVFGCISKRVSHGQIKQIIRILSKALESCLKGPDTYNS

QVLIEATVIALTKLQPLLNKDSPLHKALFWVAVAVLQLDEVNLYSAGTALLEQNLHTLDSLRIF

NDKSPEEVFMAIRNPLEWHCKQMDHFVGLNFNSNFNFALVGHLLKGYRHPSPAIVARTVRILHT

LLTLVNKHRNCDKFEVNTQSVAYLAALLTVSEEVRSRCSLKHRKSLLLTDISMENVPMDTYPIH

HGDPSYRTLKETQPWSSPKGSEGYLAATYPTVGQTSPRARKSMSLDMGQPSQANTKKLLGTRKS

FDHLISDTKAPKRQEMESGITTPPKMRRVAETDYEMETQRISSSQQHPHLRKVSVSESNVLLDE

EVLTDPKIQALLLTVLATLVKYTTDEFDQRILYEYLAEASVVFPKVFPVVHNLLDSKINTLLSL

CQDPNLLNPIHGIVQSVVYHEESPPQYQTSYLQSFGFNGLWRFAGPFSKQTQIPDYAELIVKFL

DALIDTYLPGIDEETSEESLLTPTSPYPPALQSQLSITANLNLSNSMTSLATSQHSPGIDKENV

ELSPTTGHCNSGRTRHGSASQVQKQRSAGSFKRNSIKKIV

An exemplary amino acid sequence of the second portion of the NF1 protein with a HA tag (bold) is set forth in SEQ ID NO: 26:

MVSQRFPQNSIGAVGSAMFLRFINPAIVSPYEAGILDKKPPPRIERGLKLMSKILQSIANHVLE

TKEEHMRPFNDFVKSNFDAARRFFLDIASDCPTSDAVNHSLSFISDGNVLALHRLLWNNQEKIG

QYLSSNRDHKAVGRRPFDKMATLLAYLGPPEHKPVADTHWSSLNLTSSKFEEFMTRHQVHEKEE

FKALKTLSIFYQAGTSKAGNPIFYYVARRFKTGQINGDLLIYHVLLTLKPYYAKPYEIVVDLTH

TGPSNRFKTDFLSKWFVVFPGFAYDNVSMVYIYNCNSWVREYTKYHERLLTGLKGSKRLVFIDC

PGKLAEHIEHEQQKLPAATLALEEDLKVFHNALKLAHKDTKVSIKVGSTAVQVTSAERTKVLGQ

SVFLNDIYYASEIEEICLVDENQFTLTIANQGTPLTFMHQECEAIVQSIIHIRTRWELSQPDSI

PQHTKIRPKDVPGTLLNIALLNLGSSDPSLRSAAYNLLCALTCTFNLKIEGQLLETSGLCIPAN

NTLFIVSISKTLAANEPHLTLEFLEECISGFSKSSIELKHLCLEYMTPWLSNLVRFCKHNDDAK

RORVTAILDKLITMTINEKOMYPSIQAKIWGSLGQITDLLDVVLDSFIKTSATGGLGSIKAEVM

ADTAVALASGNVKLVSSKVIGRMCKIIDKTCLSPTPTLEQHLMWDDIAILARYMLMLSFNNSLD

VAAHLPYLFHVVTFLVATGPLSLRASTHGLVINIIHSLCTCSQLHFSEETKQVLRLSLTEFSLP

KFYLLFGISKVKSAAVIAFRSSYRDRSFSPGSYERETFALTSLETVTEALLEIMEACMRDIPTC

KWLDQWTELAQRFAFQYNPSLQPRALVVFGCISKRVSHGQIKQIIRILSKALESCLKGPDTYNS

QVLIEATVIALTKLQPLLNKDSPLHKALFWVAVAVLQLDEVNLYSAGTALLEQNLHTLDSLRIF

NDKSPEEVFMAIRNPLEWHCKQMDHFVGLNFNSNFNFALVGHLLKGYRHPSPAIVARTVRILHT

LLTLVNKHRNCDKFEVNTQSVAYLAALLTVSEEVRSRCSLKHRKSLLLTDISMENVPMDTYPIH

-continued

HGDPSYRTLKETQPWSSPKGSEGYLAATYPTVGQTSPRARKSMSLDMGQPSQANTKKLLGTRKS

FDHLISDTKAPKRQEMESGITTPPKMRRVAETDYEMETQRISSSQQHPHLRKVSVSESNVLLDE

EVLTDPKIQALLLTVLATLVKYTTDEFDQRILYEYLAEASVVFPKVFPVVHNLLDSKINTLLSL

CQDPNLLNPIHGIVQSVVYHEESPPQYQTSYLQSFGFNGLWRFAGPFSKQTQIPDYAELIVKFL

DALIDTYLPGIDEETSEESLLTPTSPYPPALQSQLSITANLNLSNSMTSLATSQHSPGIDKENV

ELSPTTGHCNSGRTRHGSASQVQKQRSAGSFKRNSIKKIVYPYDVPDYA

In some embodiments, the nucleotide sequence encoding the second portion of the NF1 protein (e.g., exons 32-61) is at least at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NOs: 14 or 27.

A nucleotide sequence encoding the second portion of the NF1 protein is set forth in SEQ ID NO: 14:

GTGGTTAGCCAGCGTTTCCCTCAGAACAGCATCGGTGCAGTAGGAAGTGCCATGTTCCTCAGAT

TTATCAATCCTGCCATTGTCTCACCGTATGAAGCAGGGATTTTAGATAAAAAGCCACCACCTAG

AATCGAAAGGGGCTTGAAGTTAATGTCAAAGATACTTCAGAGTATTGCCAATCATGTTCTCTTC

ACAAAAGAAGAACATATGCGGCCTTTCAATGATTTTGTGAAAAGCAACTTTGATGCAGCACGCA

GGTTTTTCCTTGATATAGCATCTGATTGTCCTACAAGTGATGCAGTAAATCATAGTCTTTCCTT

CATAAGTGACGGCAATGTGCTTGCTTTACATCGTCTACTCTGGAACAATCAGGAGAAAATTGGG

CAGTATCTTTCCAGCAACAGGGATCATAAAGCTGTTGGAAGACGACCTTTTGATAAGATGGCAA

CACTTCTTGCATACCTGGGTCCTCCAGAGCACAAACCTGTGGCAGATACACACTGGTCCAGCCT

TAACCTTACCAGTTCAAAGTTTGAGGAATTTATGACTAGGCATCAGGTACATGAAAAAGAAGAA

TTCAAGGCTTTGAAAACGTTAAGTATTTTCTACCAAGCTGGGACTTCCAAAGCTGGGAATCCTA

TTTTTTATTATGTTGCACGGAGGTTCAAAACTGGTCAAATCAATGGTGATTTGCTGATATACCA

TGTCTTACTGACTTTAAAGCCATATTATGCAAAGCCATATGAAATTGTAGTGGACCTTACCCAT

ACCGGGCCTAGCAATCGCTTTAAAACAGACTTTCTCTCTAAGTGGTTTGTTGTTTTTCCTGGCT

TTGCTTACGACAACGTCTCCGCAGTCTATATCTATAACTGTAACTCCTGGGTCAGGGAGTACAC

CAAGTATCATGAGCGGCTGCTGACTGGCCTCAAAGGTAGCAAAAGGCTTGTTTTCATAGACTGT

CCTGGGAAACTGGCTGAGCACATAGAGCATGAACAACAGAAACTACCTGCTGCCACCTTGGCTT

TAGAAGAGGACCTGAAGGTATTCCACAATGCTCTCAAGCTAGCTCACAAAGACACCAAAGTTTC

TATTAAAGTTGGTTCTACTGCTGTCCAAGTAACTTCAGCAGAGCGAACAAAAGTCCTAGGGCAA

TCAGTCTTTCTAAATGACATTTATTATGCTTCGGAAATTGAAGAAATCTGCCTAGTAGATGAGA

ACCAGTTCACCTTAACCATTGCAAACCAGGGCACGCCGCTCACCTTCATGCACCAGGAGTGTGA

AGCCATTGTCCAGTCTATCATTCATATCCGGACCCGCTGGGAACTGTCACAGCCCGACTCTATC

CCCCAACACACCAAGATTCGGCCAAAAGATGTCCCTGGGACACTGCTCAATATCGCATTACTTA

ATTTAGGCAGTTCTGACCCGAGTTTACGGTCAGCTGCCTATAATCTTCTGTGTGCCTTAACTTG

TACCTTTAATTTAAAAATCGAGGGCCAGTTACTAGAGACATCAGGTTTATGTATCCCTGCCAAC

AACACCCTCTTTATTGTCTCTATTAGTAAGACACTGGCAGCCAATGAGCCACACCTCACGTTAG

AATTTTTGGAAGAGTGTATTTCTGGATTTAGCAAATCTAGTATTGAATTGAAACACCTTTGTTT

GGAATACATGACTCCATGGCTGTCAAATCTAGTTCGTTTTTGCAAGCATAATGATGATGCCAAA

CGACAAAGAGTTACTGCTATTCTTGACAAGCTGATAACAATGACCATCAATGAAAAACAGATGT

-continued

ACCCATCTATTCAAGCAAAAATATGGGGAAGCCTTGGGCAGATTACAGATCTGCTTGATGTTGT

ACTAGACAGTTTCATCAAAACCAGTGCAACAGGTGGCTTGGGATCAATAAAAGCTGAGGTGATG

GCAGATACTGCTGTAGCTTTGGCTTCTGGAAATGTGAAATTGGTTTCAAGCAAGGTTATTGGAA

GGATGTGCAAAATAATTGACAAGACATGCTTATCTCCAACTCCTACTTTAGAACAACATCTTAT

GTGGGATGATATTGCTATTTTAGCACGCTACATGCTGATGCTGTCCTTCAACAATTCCCTTGAT

GTGGCAGCTCATCTTCCCTACCTCTTCCACGTTGTTACTTTCTTAGTAGCCACAGGTCCGCTCT

CCCTTAGAGCTTCCACACATGGACTGGTCATTAATATCATTCACTCTCTGTGTACTTGTTCACA

GCTTCATTTTAGTGAAGAGACCAAGCAAGTTTTGAGACTCAGTCTGACAGAGTTCTCATTACCC

AAATTTTACTTGCTGTTTGGCATTAGCAAAGTCAAGTCAGCTGCTGTCATTGCCTTCCGTTCCA

GTTACCGGGACAGGTCATTCTCTCCTGGCTCCTATGAGAGAGAGACTTTTGCTTTGACATCCTT

GGAAACAGTCACAGAAGCTTTGTTGGAGATCATGGAGGCATGCATGAGAGATATTCCAACGTGC

AAGTGGCTGGACCAGTGGACAGAACTAGCTCAAAGATTTGCATTCCAATATAATCCATCCCTGC

AACCAAGAGCTCTTGTTGTCTTTGGGTGTATTAGCAAACGAGTGTCTCATGGGCAGATAAAGCA

GATAATCCGTATTCTTAGCAAGGCACTTGAGAGTTGCTTAAAAGGACCTGACACTTACAACAGT

CAAGTTCTGATAGAAGCTACAGTAATAGCACTAACCAAATTACAGCCACTTCTTAATAAGGACT

CGCCTCTGCACAAAGCCCTCTTTTGGGTAGCTGTGGCTGTGCTGCAGCTTGATGAGGTCAACTT

GTATTCAGCAGGTACCGCACTTCTTGAACAAAACCTGCATACTTTAGATAGTCTCCGTATATTC

AATGACAAGAGTCCAGAGGAAGTATTTATGGCAATCCGGAATCCTCTGGAGTGGCACTGCAAGC

AAATGGATCATTTTGTTGGACTCAATTTCAACTCTAACTTTAACTTTGCATTGGTTGGACACCT

TTTAAAAGGGTACAGGCATCCTTCACCTGCTATTGTTGCAAGAACAGTCAGAATTTTACATACA

CTACTAACTCTGGTTAACAAACACAGAAATTGTGACAAATTTGAAGTGAATACACAGAGCGTGG

CCTACTTAGCAGCTTTACTTACAGTGTCTGAAGAAGTTCGAAGTCGCTGCAGCCTAAAACATAG

AAAGTCACTTCTTCTTACTGATATTTCAATGGAAAATGTTCCTATGGATACATATCCCATTCAT

CATGGTGACCCTTCCTATAGGACACTAAAGGAGACTCAGCCATGGTCCTCTCCCAAAGGTTCTG

AAGGATACCTTGCAGCCACCTATCCAACTGTCGGCCAGACCAGTCCCCGAGCCAGGAAATCCAT

GAGCCTGGACATGGGGCAACCTTCTCAGGCCAACACTAAGAAGTTGCTTGGAACAAGGAAAAGT

TTTGATCACTTGATATCAGACACAAAGGCTCCTAAAAGGCAAGAAATGGAATCAGGGATCACAA

CACCCCCCAAAATGAGGAGAGTAGCAGAAACTGATTATGAAATGGAAACTCAGAGGATTTCCTC

ATCACAACAGCACCCACATTTACGTAAAGTTTCAGTGTCTGAATCAAATGTTCTCTTGGATGAA

GAAGTACTTACTGATCCGAAGATCCAGGCGCTGCTTCTTACTGTTCTAGCTACACTGGTAAAAT

ATACCACAGATGAGTTTGATCAACGAATTCTTTATGAATACTTAGCAGAGGCCAGTGTTGTGTT

TCCCAAAGTCTTTCCTGTTGTGCATAATTTGTTGGACTCTAAGATCAACACCCTGTTATCATTG

TGCCAAGATCCAAATTTGTTAAATCCAATCCATGGAATTGTGCAGAGTGTGGTGTACCATGAAG

AATCCCCACCACAATACCAAACATCTTACCTGCAAAGTTTTGGTTTTAATGGCTTGTGGCGGTT

TGCAGGACCGTTTTCAAAGCAAACACAAATTCCAGACTATGCTGAGCTTATTGTTAAGTTTCTT

GATGCCTTGATTGACACGTACCTGCCTGGAATTGATGAAGAAACCAGTGAAGAATCCCTCCTGA

CTCCCACATCTCCTTACCCTCCTGCACTGCAGAGCCAGCTTAGTATCACTGCCAACCTTAACCT

TTCTAATTCCATGACCTCACTTGCAACTTCCCAGCATTCCCCAGGAATCGACAAGGAGAACGTT

GAACTCTCCCCTACCACTGGCCACTGTAACAGTGGACGAACTCGCCACGGATCCGCAAGCCAAG

TGCAGAAGCAAAGAAGCGCTGGCAGTTTCAAACGTAATAGCATTAAGAAGATCGTG

A nucleotide sequence encoding the second portion of the NF1 protein with a HA tag is set forth in SEQ ID NO: 27:

GTGGTTAGCCAGCGTTTCCCTCAGAACAGCATCGGTGCAGTAGGAAGTGCCATGTTCCTCAGAT

TTATCAATCCTGCCATTGTCTCACCGTATGAAGCAGGGATTTTAGATAAAAAGCCACCACCTAG

AATCGAAAGGGGCTTGAAGTTAATGTCAAAGATACTTCAGAGTATTGCCAATCATGTTCTCTTC

ACAAAAGAAGAACATATGCGGCCTTTCAATGATTTTGTGAAAAGCAACTTTGATGCAGCACGCA

GGTTTTTCCTTGATATAGCATCTGATTGTCCTACAAGTGATGCAGTAAATCATAGTCTTTCCTT

CATAAGTGACGGCAATGTGCTTGCTTTACATCGTCTACTCTGGAACAATCAGGAGAAAATTGGG

CAGTATCTTTCCAGCAACAGGGATCATAAAGCTGTTGGAAGACGACCTTTTGATAAGATGGCAA

CACTTCTTGCATACCTGGGTCCTCCAGAGCACAAACCTGTGGCAGATACACACTGGTCCAGCCT

TAACCTTACCAGTTCAAAGTTTGAGGAATTTATGACTAGGCATCAGGTACATGAAAAAGAAGAA

TTCAAGGCTTTGAAAACGTTAAGTATTTTCTACCAAGCTGGGACTTCCAAAGCTGGGAATCCTA

TTTTTTATTATGTTGCACGGAGGTTCAAAACTGGTCAAATCAATGGTGATTTGCTGATATACCA

TGTCTTACTGACTTTAAAGCCATATTATGCAAAGCCATATGAAATTGTAGTGGACCTTACCCAT

ACCGGGCCTAGCAATCGCTTTAAAACAGACTTTCTCTCTAAGTGGTTTGTTGTTTTTCCTGGCT

TTGCTTACGACAACGTCTCCGCAGTCTATATCTATAACTGTAACTCCTGGGTCAGGGAGTACAC

CAAGTATCATGAGCGGCTGCTGACTGGCCTCAAAGGTAGCAAAAGGCTTGTTTTCATAGACTGT

CCTGGGAAACTGGCTGAGCACATAGAGCATGAACAACAGAAACTACCTGCTGCCACCTTGGCTT

TAGAAGAGGACCTGAAGGTATTCCACAATGCTCTCAAGCTAGCTCACAAAGACACCAAAGTTTC

TATTAAAGTTGGTTCTACTGCTGTCCAAGTAACTTCAGCAGAGCGAACAAAAGTCCTAGGGCAA

TCAGTCTTTCTAAATGACATTTATTATGCTTCGGAAATTGAAGAAATCTGCCTAGTAGATGAGA

ACCAGTTCACCTTAACCATTGCAAACCAGGGCACGCCGCTCACCTTCATGCACCAGGAGTGTGA

AGCCATTGTCCAGTCTATCATTCATATCCGGACCCGCTGGGAACTGTCACAGCCCGACTCTATC

CCCCAACACACCAAGATTCGGCCAAAAGATGTCCCTGGGACACTGCTCAATATCGCATTACTTA

ATTTAGGCAGTTCTGACCCGAGTTTACGGTCAGCTGCCTATAATCTTCTGTGTGCCTTAACTTG

TACCTTTAATTTAAAAATCGAGGGCCAGTTACTAGAGACATCAGGTTTATGTATCCCTGCCAAC

AACACCCTCTTTATTGTCTCTATTAGTAAGACACTGGCAGCCAATGAGCCACACCTCACGTTAG

AATTTTTGGAAGAGTGTATTTCTGGATTTAGCAAATCTAGTATTGAATTGAAACACCTTTGTTT

GGAATACATGACTCCATGGCTGTCAAATCTAGTTCGTTTTTGCAAGCATAATGATGATGCCAAA

CGACAAAGAGTTACTGCTATTCTTGACAAGCTGATAACAATGACCATCAATGAAAAACAGATGT

ACCCATCTATTCAAGCAAAAATATGGGGAAGCCTTGGGCAGATTACAGATCTGCTTGATGTTGT

ACTAGACAGTTTCATCAAAACCAGTGCAACAGGTGGCTTGGGATCAATAAAAGCTGAGGTGATG

GCAGATACTGCTGTAGCTTTGGCTTCTGGAAATGTGAAATTGGTTTCAAGCAAGGTTATTGGAA

GGATGTGCAAAATAATTGACAAGACATGCTTATCTCCAACTCCTACTTTAGAACAACATCTTAT

GTGGGATGATATTGCTATTTTAGCACGCTACATGCTGATGCTGTCCTTCAACAATTCCCTTGAT

GTGGCAGCTCATCTTCCCTACCTCTTCCACGTTGTTACTTTCTTAGTAGCCACAGGTCCGCTCT

CCCTTAGAGCTTCCACACATGGACTGGTCATTAATATCATTCACTCTCTGTGTACTTGTTCACA

GCTTCATTTTAGTGAAGAGACCAAGCAAGTTTTGAGACTCAGTCTGACAGAGTTCTCATTACCC

AAATTTTACTTGCTGTTTGGCATTAGCAAAGTCAAGTCAGCTGCTGTCATTGCCTTCCGTTCCA

GTTACCGGGACAGGTCATTCTCTCCTGGCTCCTATGAGAGAGAGACTTTTGCTTTGACATCCTT

GGAAACAGTCACAGAAGCTTTGTTGGAGATCATGGAGGCATGCATGAGAGATATTCCAACGTGC

-continued

```
AAGTGGCTGGACCAGTGGACAGAACTAGCTCAAAGATTTGCATTCCAATATAATCCATCCCTGC

AACCAAGAGCTCTTGTTGTCTTTGGGTGTATTAGCAAACGAGTGTCTCATGGGCAGATAAAGCA

GATAATCCGTATTCTTAGCAAGGCACTTGAGAGTTGCTTAAAAGGACCTGACACTTACAACAGT

CAAGTTCTGATAGAAGCTACAGTAATAGCACTAACCAAATTACAGCCACTTCTTAATAAGGACT

CGCCTCTGCACAAAGCCCTCTTTTGGGTAGCTGTGGCTGTGCTGCAGCTTGATGAGGTCAACTT

GTATTCAGCAGGTACCGCACTTCTTGAACAAAACCTGCATACTTTAGATAGTCTCCGTATATTC

AATGACAAGAGTCCAGAGGAAGTATTTATGGCAATCCGGAATCCTCTGGAGTGGCACTGCAAGC

AAATGGATCATTTTGTTGGACTCAATTTCAACTCTAACTTTAACTTTGCATTGGTTGGACACCT

TTTAAAAGGGTACAGGCATCCTTCACCTGCTATTGTTGCAAGAACAGTCAGAATTTTACATACA

CTACTAACTCTGGTTAACAAACACAGAAATTGTGACAAATTTGAAGTGAATACACAGAGCGTGG

CCTACTTAGCAGCTTTACTTACAGTGTCTGAAGAAGTTCGAAGTCGCTGCAGCCTAAAACATAG

AAAGTCACTTCTTCTTACTGATATTTCAATGGAAAATGTTCCTATGGATACATATCCCATTCAT

CATGGTGACCCTTCCTATAGGACACTAAAGGAGACTCAGCCATGGTCCTCTCCCAAAGGTTCTG

AAGGATACCTTGCAGCCACCTATCCAACTGTCGGCCAGACCAGTCCCCGAGCCAGGAAATCCAT

GAGCCTGGACATGGGGCAACCTTCTCAGGCCAACACTAAGAAGTTGCTTGGAACAAGGAAAAGT

TTTGATCACTTGATATCAGACACAAAGGCTCCTAAAAGGCAAGAAATGGAATCAGGGATCACAA

CACCCCCCAAAATGAGGAGAGTAGCAGAAACTGATTATGAAATGGAAACTCAGAGGATTTCCTC

ATCACAACAGCACCCACATTTACGTAAAGTTTCAGTGTCTGAATCAAATGTTCTCTTGGATGAA

GAAGTACTTACTGATCCGAAGATCCAGGCGCTGCTTCTTACTGTTCTAGCTACACTGGTAAAAT

ATACCACAGATGAGTTTGATCAACGAATTCTTTATGAATACTTAGCAGAGGCCAGTGTTGTGTT

TCCCAAAGTCTTTCCTGTTGTGCATAATTTGTTGGACTCTAAGATCAACACCCTGTTATCATTG

TGCCAAGATCCAAATTTGTTAAATCCAATCCATGGAATTGTGCAGAGTGTGGTGTACCATGAAG

AATCCCCACCACAATACCAAACATCTTACCTGCAAAGTTTTGGTTTTAATGGCTTGTGGCGGTT

TGCAGGACCGTTTTCAAAGCAAACACAAATTCCAGACTATGCTGAGCTTATTGTTAAGTTTCTT

GATGCCTTGATTGACACGTACCTGCCTGGAATTGATGAAGAAACCAGTGAAGAATCCCTCCTGA

CTCCCACATCTCCTTACCCTCCTGCACTGCAGAGCCAGCTTAGTATCACTGCCAACCTTAACCT

TTCTAATTCCATGACCTCACTTGCAACTTCCCAGCATTCCCCAGGAATCGACAAGGAGAACGTT

GAACTCTCCCCTACCACTGGCCACTGTAACAGTGGACGAACTCGCCACGGATCCGCAAGCCAAG

TGCAGAAGCAAAGAAGCGCTGGCAGTTTCAAACGTAATAGCATTAAGAAGATCGTGTATCCGTA

TGATGTGCCGGATTATGCGT
```

In some embodiments, the 3' isolated nucleic acid further comprises a polyadenylation signal positioned between the nucleotide sequence encoding a second portion of NF1 protein and the 3' ITR. Any of the polyadenylation signal described herein can be used in the 3' isolated nucleic. In some embodiments, the polyadenylation signal is an SV40 polyadenylation signal.

In some embodiments, the 3' isolated nucleic acid further comprises a nucleotide sequence encoding a polypeptide tag. Non-limiting examples of a polypeptide tag includes a human influenza hemagglutinin (HA) tag, a FLAG tag, a Myc tag, a Maltose-binding protein (MBP) tag, a Calmodulin Binding Protein (CBP) tag, Poly-Histidine tag (His) tag, or a Glutathione-S transferase (GST) tag. In some embodiments, the polypeptide tag is a HA tag. In some embodiments, the HA tag is position at the C-terminal of the protein it is attached to (e.g., the second portion of the full-length NF1 protein). In some embodiments, the 3' isolated nucleic acid does not comprise a nucleotide sequence encoding a polypeptide tag.

In some embodiments, the 5' isolated nucleic acid further comprises nucleotide sequence encoding a splice donor located of an intron between the nucleotide sequence encoding the first portion of a protein (e.g., NF1 protein) and the 3' ITR. In addition, the 3' isolated nucleic acid comprises a nucleotide sequence encoding a splice acceptor of an intron between the 5' ITR and the nucleotide sequence encoding the second portion of a protein (e.g., NF1 protein). In some embodiments, the splice donor in the 5' isolated nucleic acid and the splice acceptor in the 3' isolated nucleic acid are derived from the same intron. Any intronic splice donor/splice acceptor sequence can be used in the 5' and 5' isolated nucleic acid described herein. In some embodiments, the intron is a human dysferlin intron.

In some embodiments, the nucleotide sequence encoding the splicing donor comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 18. An exemplary nucleotide sequence of a splicing donor is set forth in SEQ ID NO: 18.

```
GTGGGCAGCATGTGGAACCTGGCGAGCCCCATCCCCGGCAAGCTCTCAAGCCATGCTGGTGGGG
ACGACTGAATGCCAGGGCCCTTCACTGGGCTATTTCACCCAGGGACGCTTCTTGAAGGCACCCC
CCACTCCAAGCTCAATTGAA
```

In some embodiments, the nucleotide sequence encoding the splicing acceptor comprises a nucleotide sequence at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identical to SEQ ID NO: 19. An exemplary nucleotide sequence of a splicing donor is set forth in SEQ ID NO: 19.

```
GCAAATTAGGACCGAGAGTCAGTGGCCGCTCAAGAGTCTGTGACCATGCCCCAAATTCAGAGAT
GGTCCCAGGAGAGATGGGGGGAACTGCCAAGCAATGAGTGACCGGTTCCCCCTCCCCCAG
```

As disclosed herein, "identity" of sequences refers to the measurement or calculation of the percent of identical matches between two or more sequences with gap alignments addressed by a mathematical model, algorithm, or computer program that is known to one of ordinary skill in the art. The percent identity of two sequences (e.g., nucleic acid or amino acid sequences) may, for example, be determined using Basic Local Alignment Search Tool (BLAST®) such as NBLAST® and XBLAST® programs (version 2.0). Alignment technique such as Clustal Omega may be used for multiple sequence alignments. Other algorithms or alignment methods may include but are not limited to the Smith-Waterman algorithm, the Needleman-Wunsch algorithm, or Fast Optimal Global Sequence Alignment Algorithm (FOGSAA).

In some embodiments, the present disclosure provides a 5' isolated nucleic acid encoding a first portion of a protein (e.g., NF1 protein) and a 3' isolated nucleic acid encoding a second portion of a protein (e.g., NF1 protein) in a way (e.g., delivered to the same target cell by a 5' rAAV comprising the 5' isolated nucleic acid and an 3' rAAV comprising the 3' isolated nucleic acid) that the two isolated nucleic acids form a full length (e.g., NF1 protein) mRNA in a target cell after transcription and trans-splicing. Once the 5' isolated nucleic acid and the 3' isolated nucleic acid are delivered to a target cell (e.g., by rAAVs), the two isolated nucleic acid would go through head to tail concatemerization from 3' ITR of the 5' isolated nucleic acid and 5' ITR of the 3' isolated nucleic acid such that the two isolated nucleic acids are combined in one single AAV genome. After transcription, the mRNA comprises the NF1 first portion mRNA, splicing sites including the splicing donor, concactemerized ITR, and splicing acceptor, and NF1 second portion mRNA. Trans-splicing, as used herein, refers to a special form of RNA processing where exons from two different primary RNA transcripts are joined end to end and ligated. It is usually found in eukaryotes and mediated by the spliceosome. In eukaryotic cells, mRNA splicing occurs at intronic sites. A splice donor (e.g., 5' end of the intron) and a splice acceptor (e.g., 3' end of the intron) are required for splicing. Accordingly, as part of the RNA splicing mechanism, the spliceosome in the cell will then splice out the splicing sites, thereby stitching the NF1 first portion mRNA and NF1 second portion mRNA to form a complete mRNA encoding a full-length NF1.

An isolated nucleic acid sequence described herein (e.g., the isolated nucleic acid comprising a transgene which encodes a mini-NF1 protein or the 5' isolated nucleic acid in the dual AAV vector system) may further comprise a promoter operably linked to the coding sequences (e.g., NF1 minigenes, or the nucleotide sequence encoding the first portion of the NF1 protein). A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. A promoter may be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter comprises a chicken beta-actin (CBA) promoter. In some embodiments, a promoter is an enhanced chicken β-actin promoter. In some embodiments, a promoter is a U6 promoter. In some embodiments, a promoter is a chicken beta-actin (CBA) promoter. In some embodiments, the promoter is a minimal promoter. In some embodiments, the promoter is a mini-CMV promoter. In some embodiments, the promoter is a jet promoter. In some embodiments, the promoter is a short Mecp2 promoter. In some embodiments, the transgene encoding the mini-NF1 proteins comprises a CBA promoter. In some embodiments, the 5' isolated nucleic acid described herein comprises a short Mecp2 promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. In some embodiments, the tissue-specific promoter is a neuron-specific promoter.

In some embodiments, a promoter is a RNA polymerase III (pol III) promoter. Non-limiting examples of pol III promoters include U6 and H1 promoter sequences. In some embodiments, a promoter is a RNA polymerase II (pol II) promoter. Non-limiting examples of pol II promoters include T7, T3, SP6, RSV, and cytomegalovirus promoter sequences.

Aspects of the disclosure relate to gene therapy vectors comprising an isolated nucleic acid as described herein. A gene therapy vector may be a viral vector (e.g., a lentiviral vector, an adeno-associated virus vector, an adenoviral (Ad) vector, etc.), a plasmid, a closed-ended DNA (e.g., ceDNA), a lipid/DNA nanoparticle, etc. In some embodiments, a gene therapy vector is a viral vector. In some embodiments, a transgene (e.g., a minigene) encoding a mini protein (e.g., mini-NF1 protein) is flanked by one or more viral replication sequences, for example lentiviral long terminal repeats (LTRs) or adeno-associated virus (AAV) inverted terminal repeats (ITRs). In some embodiments, a viral vector is a Baculovirus vector. In some embodiments, the 5' isolated nucleic acid and the 3' isolated nucleic acid for expressing full-length NF1 protein are flanked by one or more viral replication sequences, for example lentiviral long terminal repeats (LTRs) or adeno-associated virus (AAV) inverted terminal repeats (ITRs). In some embodiments, a viral vector is a Baculovirus vector.

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The isolated nucleic acids may comprise, as disclosed elsewhere herein, one or more regions that encode one or more proteins (e.g., mini-NF1 protein, or a portion of NF1 protein). The isolated nucleic acids may also comprise a region encoding, for example, a miRNA binding site, and/or an expression control sequence (e.g., a poly-A tail).

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second AAV ITR is an AAV2 ITR. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR, or ΔITR). Without wishing to be bound by any particular theory, a rAAV vector comprising an ITR lacking a functional TRS produces a self-complementary rAAV vector, for example as described by McCarthy (2008) Molecular Therapy 16(10):1648-1656.

An isolated nucleic acid described herein may also contain an intron, desirably located between the promoter/enhancer sequence and the transgene. In some embodiments, an intron is a synthetic or artificial (e.g., heterologous) intron. Examples of synthetic introns include an intron sequence derived from SV-40 (referred to as the SV-40 T intron sequence) and intron sequences derived from chicken beta-actin gene. In some embodiments, a transgene described by the disclosure comprises one or more (1, 2, 3, 4, 5, or more) artificial introns. In some embodiments, the one or more artificial introns are positioned between a promoter and a nucleotide sequence encoding a transgene.

In some embodiments, the rAAV vector described herein comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70

(Hsp70 5'UTR). In some embodiments, the rAAV vector comprises a woodchuck hepatitis virus posttranscriptional regulatory element (WPRE).

In some embodiments, the vector further comprises conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

A polyadenylation sequence generally is inserted following the coding sequences and optionally before a 3' AAV ITR sequence. A rAAV construct useful in the disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional, and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989].

In some embodiments, the rAAV vector encoding the mini-NF1 proteins comprises a nucleic acid as set forth in SEQ ID NOs: 7-9 or 28-30.

An exemplary AAV vector sequence encoding a mini-NF1 having an NF1 GRD is set forth in SEQ ID NO: 7:

```
CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTTCAATATTGGCCATTAGCCATATTATTCATTGGTTATAT

AGCATAAATCAATATTGGCTATTGGCCATTGCATACGTTGTATCTATATCATAATATGTACATT

TATATTGGCTCATGTCCAATATGACCGCCATGTTGGCATTGATTATTGACTAGTTATTAATAGT

AATCAATTACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGGTAAACTG

CCCACTTGGCAGTACATCAAGTGTATCATATGCCAAGTCCGCCCCCTATTGACGTCAATGACGG

TAAATGGCCCGCCTGGCATTATGCCCAGTACATGACCTTACGGGACTTTCCTACTTGGCAGTAC

ATCTACGTATTAGTCATCGCTATTACCATGGTCGAGGTGAGCCCCACGTTCTGCTTCACTCTCC

CCATCTCCCCCCCCTCCCCACCCCCAATTTTGTATTTATTTATTTTTTAATTATTTTGTGCAGC

GATGGGGGCGGGGGGGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGGAGTCGCTGC

GCGCTGCCTTCGCCCCGTGCCCCGCTCCGCCGCCGCCTCGCGCCGCCCGCCCCGGCTCTGACTG

ACCGCGTTACTCCCACAGGTGAGCGGGCGGGACGGCCCTTCTCCTCCGGGCTGTAATTAGCGCT

TGGTTTAATGACGGCTTGTTTCTTTTCTGTGGCTGCGTGAAAGCCTTGAGGGGCTCCGGGAGGG

CCCTTTGTGCGGGGGGAGCGGCTCGGGGGGTGCGTGCGTGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGGCTGCGAGGG

GAACAAAGGCTGCGTGCGGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA
```

-continued

```
GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

ACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA

AGAGCCAGCTGTTTCTGAAATACTTTACCCTGTTTATGAATCTGCTGAACGACTGTAGTGAGGT

GGAGGACGAGAGTGCCCAGACCGGCGGCAGGAAGAGAGGCATGTCTAGGAGACTGGCCAGCCTG

AGGCACTGCACAGTGCTGGCCATGTCCAACCTGCTGAACGCCAATGTGGACTCCGGCCTGATGC

ACTCTATCGGCCTGGGCTACCACAAGGATCTGCAGACCCGCGCCACATTCATGGAGGTGCTGAC

CAAGATCCTGCAGCAGGGCACCGAGTTTGACACACTGGCCGAGACCGTGCTGGCAGATAGGTTC

GAGCGCCTGGTGGAGCTGGTGACAATGATGGGCGACCAGGGAGAGCTGCCTATCGCAATGGCAC

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

GCTGGCCCTGCACCGGCTGCTGTGGAACAATCAGGAGAAGATCGGCCAGTACCTGAGCTCCAAC

AGGGACCACAAGGCAGTGGGCAGGAGACCTTTTGATAAGATGGCCACCCTGCTGGCATATCTGG

GACCACCAGAGCACAAGCCAGTGGCAGACACCCACTGGTCTAGCCTGAATCTGACATCCTCTAA

GTTCGAGGAGTTTATGACCCGGCACCAGGTGCACGAGAAGGAGGAGTTTAAGGCCCTGAAGACC

CTGGATGACTCGAGTTTTTTTTTGCGGCCGCTTCGAGCAGACATGATAAGATACATTGATGAGT

TTGGACAAACCACAACTAGAATGCAGTGAAAAAAATGCTTTATTTGTGAAATTTGTGATGCTAT

TGCTTTATTTGTAACCATTATAAGCTGCAATAAACAAGTTAACAACAACAATTGCATTCATTTT

ATGTTTCAGGTTCAGGGGGAGATGTGGGAGGTTTTTTAAAGCAAGTAAAACCTCTACAAATGTG

GTAAAATCGATAGGCCGCAGGAACCCCTAGTGATGGAGTTGGCCACTCCCTCTCTGCGCGCTCG

CTCGCTCACTGAGGCCGGGCGACCAAAGGTCGCCCGACGCCCGGGCGGCCTCAGTGAGCGAGCG

AGCGCGCAGCTGCCTGCAGGACATGTGAGCAAAAGGCCAGCAAAAGGCCAGGAACCGTAAAAAG

GCCGCGTTGCTGGCGTTTTTCCATAGGCTCCGCCCCCCTGACGAGCATCACAAAAATCGACGCT

CAAGTCAGAGGTGGCGAAACCCGACAGGACTATAAAGATACCAGGCGTTTCCCCCTGGAAGCTC

CCTCGTGCGCTCTCCTGTTCCGACCCTGCCGCTTACCGGATACCTGTCCGCCTTTCTCCCTTCG

GGAAGCGTGGCGCTTTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCCTTATCCGGTAACTA
```

-continued

```
TCGTCTTGAGTCCAACCCGGTAAGACACGACTTATCGCCACTGGCAGCAGCCACTGGTAACAGG

ATTAGCAGAGCGAGGTATGTAGGCGGTGCTACAGAGTTCTTGAAGTGGTGGCCTAACTACGGCT

ACACTAGAAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTGCAAGCAG

CAGATTACGCGCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAAAGGATCTTCAC

CTAGATCCTTTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTATTTCGTTCAT

CCATAGTTGCCTGACTCCCCGTCGTGTAGATAACTACGATACGGGAGGGCTTACCATCTGGCCC

CAGTGCTGCAATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTGTTGCCAT

TGCTACAGGCATCGTGGTGTCACGCTCGTCGTTTGGTATGGCTTCATTCAGCTCCGGTTCCCAA

CGATCAAGGCGAGTTACATGATCCCCCATGTTGTGCAAAAAAGCGGTTAGCTCCTTCGGTCCTC

CGATCGTTGTCAGAAGTAAGTTGGCCGCAGTGTTATCACTCATGGTTATGGCAGCACTGCATAA

TTCTCTTACTGTCATGCCATCCGTAAGATGCTTTTCTGTGACTGGTGAGTACTCAACCAAGTCA

TTCTGAGAATAGTGTATGCGGCGACCGAGTTGCTCTTGCCCGGCGTCAATACGGGATAATACCG

CGCCACATAGCAGAACTTTAAAAGTGCTCATCATTGGAAAACGTTCTTCGGGGCGAAAACTCTC

AAGGATCTTACCGCTGTTGAGATCCAGTTCGATGTAACCCACTCGTGCACCCAACTGATCTTCA

GCATCTTTTACTTTCACCAGCGTTTCTGGGTGAGCAAAAACAGGAAGGCAAAATGCCGCAAAAA

AGGGAATAAGGGCGACACGGAAATGTTGAATACTCATACTCTTCCTTTTTCAATATTATTGAAG

CATTTATCAGGGTTATTGTCTCATGAGCGGATACATATTTGAATGTATTTAGAAAAATAAACAA

ATAGGGGTTCCGCGCACATTTCCCCGAAAAGTGCCACCTGACGTCTAAGAAACCATTATTATCA

TGACATTAACCTATAAAAATAGGCGTATCACGAGGCCCTTTCGTCTCGCGCGTTTCGGTGATGA

CGGTGAAAACCTCTGACACATGCAGCTCCCGGAGACGGTCACAGCTTGTCTGTAAGCGGATGCC

GGGAGCAGACAAGCCCGTCAGGGCGCGTCAGCGGGTGTTGGCGGGTGTCGGGGCTGGCTTAACT

ATGCGGCATCAGAGCAGATTGTACTGAGAGTGCACCATAAAATTGTAAACGTTAATATTTTGTT

AAAATTCGCGTTAAATTTTTGTTAAATCAGCTCATTTTTTAACCAATAGGCCGAAATCGGCAAA

ATCCCTTATAAATCAAAAGAATAGCCCGAGATAGGGTTGAGTGTTGTTCCAGTTTGGAACAAGA

GTCCACTATTAAAGAACGTGGACTCCAACGTCAAAGGGCGAAAAACCGTCTATCAGGGCGATGG

CCCACTACGTGAACCATCACCCAAATCAAGTTTTTTGGGGTCGAGGTGCCGTAAAGCACTAAAT

CGGAACCCTAAAGGGAGCCCCCGATTTAGAGCTTGACGGGGAAAGCCGGCGAACGTGGCGAGAA

AGGAAGGGAAGAAAGCGAAAGGAGCGGGCGCTAAGGCGCTGGCAAGTGTAGCGGTCACGCTGCG

CGTAACCACCACACCCGCCGCGCTTAATGCGCCGCTACAGGGCGCGTACTATGGTTGCTTTGAC

GTATGCGGTGTGAAATACCGCACAGATGCGTAAGGAGAAAATACCGCATCAGGCGCC
```

An exemplary AAV vector sequence encoding a mini-NF1 having an NF1 GRD, and the CRAL-TRIO domain is set forth in SEQ ID NO: 8:

```
CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC
```

-continued

ACTAGGGGTTCCTGCGGCCAGATCTTCAATATTGGCCATTAGCCATATTATTCATTGGTTATAT

AGCATAAATCAATATTGGCTATTGGCCATTGCATACGTTGTATCTATATCATAATATGTACATT

TATATTGGCTCATGTCCAATATGACCGCCATGTTGGCATTGATTATTGACTAGTTATTAATAGT

AATCAATTACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGGTAAACTG

CCCACTTGGCAGTACATCAAGTGTATCATATGCCAAGTCCGCCCCCTATTGACGTCAATGACGG

TAAATGGCCCGCCTGGCATTATGCCCAGTACATGACCTTACGGGACTTTCCTACTTGGCAGTAC

ATCTACGTATTAGTCATCGCTATTACCATGGTCGAGGTGAGCCCCACGTTCTGCTTCACTCTCC

CCATCTCCCCCCCCTCCCCACCCCCAATTTTGTATTTATTTATTTTTTAATTATTTTGTGCAGC

GATGGGGGCGGGGGGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGGAGTCGCTGC

GCGCTGCCTTCGCCCCGTGCCCCGCTCCGCCGCCGCCTCGCGCCGCCCGCCCCGGCTCTGACTG

ACCGCGTTACTCCCACAGGTGAGCGGGCGGGACGGCCCTTCTCCTCCGGGCTGTAATTAGCGCT

TGGTTTAATGACGGCTTGTTTCTTTTCTGTGGCTGCGTGAAAGCCTTGAGGGGCTCCGGGAGGG

CCCTTTGTGCGGGGGGAGCGGCTCGGGGGGTGCGTGCGTGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGGCTGCGAGGG

GAACAAAGGCTGCGTGCGGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

ACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA

AGAGCCAGCTGTTTCTGAAATACTTTACCCTGTTTATGAATCTGCTGAACGACTGTAGTGAGGT

GGAGGACGAGAGTGCCCAGACCGGCGGCAGGAAGAGAGGCATGTCTAGGAGACTGGCCAGCCTG

AGGCACTGCACAGTGCTGGCCATGTCCAACCTGCTGAACGCCAATGTGGACTCCGGCCTGATGC

ACTCTATCGGCCTGGGCTACCACAAGGATCTGCAGACCCGCGCCACATTCATGGAGGTGCTGAC

CAAGATCCTGCAGCAGGGCACCGAGTTTGACACACTGGCCGAGACCGTGCTGGCAGATAGGTTC

GAGCGCCTGGTGGAGCTGGTGACAATGATGGGCGACCAGGGAGAGCTGCCTATCGCAATGGCAC

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

-continued

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

GCTGGCCCTGCACCGGCTGCTGTGGAACAATCAGGAGAAGATCGGCCAGTACCTGAGCTCCAAC

AGGGACCACAAGGCAGTGGGCAGGAGACCATTTGATAAGATGGCCACACTGCTGGCCTATCTGG

GACCACCAGAGCACAAGCCAGTGGCAGACACACACTGGTCTAGCCTGAATCTGACCTCCTCTAA

GTTCGAGGAGTTTATGACCCGGCACCAGGTGCACGAGAAGGAGGAGTTTAAGGCCCTGAAGACA

CTGTCTATCTTCTACCAGGCAGGCACCAGCAAGGCAGGAAACCCAATCTTTTACTATGTGGCCC

GGCGCTTCAAGACAGGCCAGATCAATGGCGATCTGCTGATCTACCACGTGCTGCTGACCCTGAA

GCCATACTATGCCAAGCCCTATGAGATCGTGGTGGACCTGACCCACACAGGCCCCTCCAACAGG

TTTAAGACCGATTTCCTGTCTAAGTGGTTCGTGGTGTTTCCTGGCTTCGCCTATGACAATGTGA

GCGCCGTGTACATCTATAACTGCAATTCCTGGGTGCGGGAGTACACAAAGTATCACGAGCGCCT

GCTGACCGGCCTGAAGGGATCCAAGAGACTGGTGTTCATCGATTGTCCCGGCAAGCTGGCCGAG

CACATTGAACACGAACAGCAGAAACTGCCCGCCGCAACCCTGGCCCTGGAAGAGGACCTGAAGG

ATGACTCGAGTTTTTTTTTGCGGCCGCTTCGAGCAGACATGATAAGATACATTGATGAGTTTGG

ACAAACCACAACTAGAATGCAGTGAAAAAAATGCTTTATTTGTGAAATTTGTGATGCTATTGCT

TTATTTGTAACCATTATAAGCTGCAATAAACAAGTTAACAACAACAATTGCATTCATTTTATGT

TTCAGGTTCAGGGGGAGATGTGGGAGGTTTTTTAAAGCAAGTAAAACCTCTACAAATGTGGTAA

AATCGATAGGCCGCAGGAACCCCTAGTGATGGAGTTGGCCACTCCCTCTCTGCGCGCTCGCTCG

CTCACTGAGGCCGGGCGACCAAAGGTCGCCCGACGCCCGGGCGGCCTCAGTGAGCGAGCGAGCG

CGCAGCTGCCTGCAGGACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTGGAAGCTCCCTC

GTGCGCTCTCCTGTTCCGACCCTGCCGCTTACCGGATACCTGTCCGCCTTTCTCCCTTCGGGAA

GCGTGGCGCTTTCTCATAGCTCACGCTGTAGGTATCTCAGTTCGGTGTAGGTCGTTCGCTCCAA

GCTGGGCTGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTACGGCTACAC

TAGAAGAACAGTATTTGGTATCTGCGCTCTGCTGAAGCCAGTTACCTTCGGAAAAAGAGTTGGT

AGCTCTTGATCCGGCAAACAAACCACCGCTGGTAGCGGTGGTTTTTTTGTTTGCAAGCAGCAGA

TTACGCGCAGAAAAAAAGGATCTCAAGAAGATCCTTTGATCTTTTCTACGGGGTCTGACGCTCA

GTGGAACGAAAACTCACGTTAAGGGATTTTGGTCATGAGATTATCAAAAAGGATCTTCACCTAG

ATCCTTTTAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCCCAGT

-continued

```
GCTGCAATGATACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCCAACGAT

CAAGGCGAGTTACATGATCCCCCATGTTGTGCAAAAAAGCGGTTAGCTCCTTCGGTCCTCCGAT

CGTTGTCAGAAGTAAGTTGGCCGCAGTGTTATCACTCATGGTTATGGCAGCACTGCATAATTCT

CTTACTGTCATGCCATCCGTAAGATGCTTTTCTGTGACTGGTGAGTACTCAACCAAGTCATTCT

GAGAATAGTGTATGCGGCGACCGAGTTGCTCTTGCCCGGCGTCAATACGGGATAATACCGCGCC

ACATAGCAGAACTTTAAAAGTGCTCATCATTGGAAAACGTTCTTCGGGGCGAAAACTCTCAAGG

ATCTTACCGCTGTTGAGATCCAGTTCGATGTAACCCACTCGTGCACCCAACTGATCTTCAGCAT

CTTTTACTTTCACCAGCGTTTCTGGGTGAGCAAAAACAGGAAGGCAAAATGCCGCAAAAAAGGG

AATAAGGGCGACACGGAAATGTTGAATACTCATACTCTTCCTTTTTCAATATTATTGAAGCATT

TATCAGGGTTATTGTCTCATGAGCGGATACATATTTGAATGTATTTAGAAAAATAAACAAATAG

GGGTTCCGCGCACATTTCCCCGAAAAGTGCCACCTGACGTCTAAGAAACCATTATTATCATGAC

ATTAACCTATAAAAATAGGCGTATCACGAGGCCCTTTCGTCTCGCGCGTTTCGGTGATGACGGT

GAAAACCTCTGACACATGCAGCTCCCGGAGACGGTCACAGCTTGTCTGTAAGCGGATGCCGGGA

GCAGACAAGCCCGTCAGGGCGCGTCAGCGGGTGTTGGCGGGTGTCGGGGCTGGCTTAACTATGC

GGCATCAGAGCAGATTGTACTGAGAGTGCACCATAAAATTGTAAACGTTAATATTTTGTTAAAA

TTCGCGTTAAATTTTTGTTAAATCAGCTCATTTTTTAACCAATAGGCCGAAATCGGCAAAATCC

CTTATAAATCAAAAGAATAGCCCGAGATAGGGTTGAGTGTTGTTCCAGTTTGGAACAAGAGTCC

ACTATTAAAGAACGTGGACTCCAACGTCAAAGGGCGAAAAACCGTCTATCAGGGCGATGGCCCA

CTACGTGAACCATCACCCAAATCAAGTTTTTTGGGGTCGAGGTGCCGTAAAGCACTAAATCGGA

ACCCTAAAGGGAGCCCCCGATTTAGAGCTTGACGGGGAAAGCCGGCGAACGTGGCGAGAAAGGA

AGGGAAGAAAGCGAAAGGAGCGGGCGCTAAGGCGCTGGCAAGTGTAGCGGTCACGCTGCGCGTA

ACCACCACACCCGCCGCGCTTAATGCGCCGCTACAGGGCGCGTACTATGGTTGCTTTGACGTAT

GCGGTGTGAAATACCGCACAGATGCGTAAGGAGAAAATACCGCATCAGGCGCC
```

An exemplary AAV vector sequence encoding a mini-NF1 having an NF1 GRD, the CRAL-TRIO domain and the bipartite phospholipid binding domain is set forth in SEQ ID NO: 9:

```
CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTTCAATATTGGCCATTAGCCATATTATTCATTGGTTATAT

AGCATAAATCAATATTGGCTATTGGCCATTGCATACGTTGTATCTATATCATAATATGTACATT

TATATTGGCTCATGTCCAATATGACCGCCATGTTGGCATTGATTATTGACTAGTTATTAATAGT

AATCAATTACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGGTAAACTG

CCCACTTGGCAGTACATCAAGTGTATCATATGCCAAGTCCGCCCCCTATTGACGTCAATGACGG

TAAATGGCCCGCCTGGCATTATGCCCAGTACATGACCTTACGGGACTTTCCTACTTGGCAGTAC
```

-continued

ATCTACGTATTAGTCATCGCTATTACCATGGTCGAGGTGAGCCCCACGTTCTGCTTCACTCTCC

CCATCTCCCCCCCCTCCCCACCCCCAATTTTGTATTTATTTATTTTTTAATTATTTTGTGCAGC

GATGGGGGCGGGGGGGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGGAGTCGCTGC

GCGCTGCCTTCGCCCCGTGCCCCGCTCCGCCGCCGCCTCGCGCCGCCCGCCCCGGCTCTGACTG

ACCGCGTTACTCCCACAGGTGAGCGGGCGGGACGGCCCTTCTCCTCCGGGCTGTAATTAGCGCT

TGGTTTAATGACGGCTTGTTTCTTTTCTGTGGCTGCGTGAAAGCCTTGAGGGGCTCCGGGAGGG

CCCTTTGTGCGGGGGGAGCGGCTCGGGGGGTGCGTGCGTGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGGCTGCGAGGG

GAACAAAGGCTGCGTGCGGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

ACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA

AGAGCCAGCTGTTTCTGAAATACTTTACCCTGTTTATGAATCTGCTGAACGACTGTAGTGAGGT

GGAGGACGAGAGTGCCCAGACCGGCGGCAGGAAGAGAGGCATGTCTAGGAGACTGGCCAGCCTG

AGGCACTGCACAGTGCTGGCCATGTCCAACCTGCTGAACGCCAATGTGGACTCCGGCCTGATGC

ACTCTATCGGCCTGGGCTACCACAAGGATCTGCAGACCCGCGCCACATTCATGGAGGTGCTGAC

CAAGATCCTGCAGCAGGGCACCGAGTTTGACACACTGGCCGAGACCGTGCTGGCAGATAGGTTC

GAGCGCCTGGTGGAGCTGGTGACAATGATGGGCGACCAGGGAGAGCTGCCTATCGCAATGGCAC

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

-continued

GCTGGCCCTGCACCGGCTGCTGTGGAACAATCAGGAGAAGATCGGCCAGTACCTGAGCTCCAAC
AGGGACCACAAGGCAGTGGGCAGGAGACCTTTTGATAAGATGGCCACCCTGCTGGCATATCTGG
GACCACCAGAGCACAAGCCAGTGGCAGACACCCACTGGTCTAGCCTGAATCTGACATCCTCTAA
GTTCGAGGAGTTTATGACCCGGCACCAGGTGCACGAGAAGGAGGAGTTTAAGGCCCTGAAGACC
CTGTCCATCTTCTACCAGGCCGGCACATCTAAGGCCGGCAACCCTATCTTTTACTATGTGGCCC
GGCGCTTCAAGACCGGCCAGATCAATGGCGATCTGCTGATCTACCACGTGCTGCTGACACTGAA
GCCATACTATGCCAAGCCCTATGAGATCGTGGTGGACCTGACCCACACAGGCCCAAGCAACAGG
TTTAAGACCGATTTCCTGTCCAAGTGGTTCGTGGTGTTTCCCGGCTTCGCCTATGACAACGTGA
GCGCCGTGTACATCTATAACTGCAATAGCTGGGTGCGGGAGTACACCAAGTATCACGAGCGCCT
GCTGACAGGCCTGAAGGGCAGCAAGAGACTGGTGTTCATCGATTGTCCCGGCAAGCTGGCCGAG
CACATCGAGCACGAGCAGCAGAAGCTGCCTGCAGCCACCCTGGCCCTGGAGGAGGACCTGAAGG
TGTTTCACAACGCCCTGAAGCTGGCCCACAAGGATACAAAGGTGTCCATCAAGGTCGGCTCTAC
AGCCGTGCAGGTGACCTCCGCCGAGAGAACAAAGGTGCTGGGCCAGAGCGTGTTCCTGAATGAC
ATCTACTATGCCAGCGAGATCGAGGAGATCTGCCTGGTGGATGAGAACCAGTTTACCCTGACAA
TCGCCAATCAGGGCACCCCCCTGACATTCATGCACCAGGAGTGTGAAGCAATCGTCCAGAGCAT
TATTCACATTCGCACTCGGTGGGAACTGAGCCAGCCTGACGATGACTCGAGTTTTTTTTTGCGG
CCGCTTCGAGCAGACATGATAAGATACATTGATGAGTTTGGACAAACCACAACTAGAATGCAGT
GAAAAAAATGCTTTATTTGTGAAATTTGTGATGCTATTGCTTTATTTGTAACCATTATAAGCTG
CAATAAACAAGTTAACAACAACAATTGCATTCATTTTATGTTTCAGGTTCAGGGGGAGATGTGG
GAGGTTTTTTAAAGCAAGTAAAACCTCTACAAATGTGGTAAAATCGATAGGCCGCAGGAACCCC
TAGTGATGGAGTTGGCCACTCCCTCTCTGCGCGCTCGCTCGCTCACTGAGGCCGGGCGACCAAA
GGTCGCCCGACGCCCGGGCGGCCTCAGTGAGCGAGCGAGCGCGCAGCTGCCTGCAGGACATGTG
AGCAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGACAG
GACTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAAAAAAAGGATCT
CAAGAAGATCCTTTGATCTTTTCTACGGGGTCTGACGCTCAGTGGAACGAAAACTCACGTTAAG
GGATTTTGGTCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGCTTAATCAGT
GAGGCACCTATCTCAGCGATCTGTCTATTTCGTTCATCCATAGTTGCCTGACTCCCCGTCGTGT
AGATAACTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCGTGGTGTCACGCTC

-continued

GTCGTTTGGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAGTTGGCCG

CAGTGTTATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCGGCGACCG

AGTTGCTCTTGCCCGGCGTCAATACGGGATAATACCGCGCCACATAGCAGAACTTTAAAAGTGC

TCATCATTGGAAAACGTTCTTCGGGGCGAAAACTCTCAAGGATCTTACCGCTGTTGAGATCCAG

TTCGATGTAACCCACTCGTGCACCCAACTGATCTTCAGCATCTTTTACTTTCACCAGCGTTTCT

GGGTGAGCAAAAACAGGAAGGCAAAATGCCGCAAAAAAGGGAATAAGGGCGACACGGAAATGTT

GAATACTCATACTCTTCCTTTTTCAATATTATTGAAGCATTTATCAGGGTTATTGTCTCATGAG

CGGATACATATTTGAATGTATTTAGAAAAATAAACAAATAGGGGTTCCGCGCACATTTCCCCGA

AAAGTGCCACCTGACGTCTAAGAAACCATTATTATCATGACATTAACCTATAAAAATAGGCGTA

TCACGAGGCCCTTTCGTCTCGCGCGTTTCGGTGATGACGGTGAAAACCTCTGACACATGCAGCT

CCCGGAGACGGTCACAGCTTGTCTGTAAGCGGATGCCGGGAGCAGACAAGCCCGTCAGGGCGCG

TCAGCGGGTGTTGGCGGGTGTCGGGGCTGGCTTAACTATGCGGCATCAGAGCAGATTGTACTGA

GAGTGCACCATAAAATTGTAAACGTTAATATTTTGTTAAAATTCGCGTTAAATTTTTGTTAAAT

CAGCTCATTTTTTAACCAATAGGCCGAAATCGGCAAAATCCCTTATAAATCAAAAGAATAGCCC

GAGATAGGGTTGAGTGTTGTTCCAGTTTGGAACAAGAGTCCACTATTAAAGAACGTGGACTCCA

ACGTCAAAGGGCGAAAAACCGTCTATCAGGGCGATGGCCCACTACGTGAACCATCACCCAAATC

AAGTTTTTTGGGGTCGAGGTGCCGTAAAGCACTAAATCGGAACCCTAAAGGGAGCCCCCGATTT

AGAGCTTGACGGGGAAAGCCGGCGAACGTGGCGAGAAAGGAAGGGAAGAAAGCGAAAGGAGCGG

GCGCTAAGGCGCTGGCAAGTGTAGCGGTCACGCTGCGCGTAACCACCACACCCGCCGCGCTTAA

TGCGCCGCTACAGGGCGCGTACTATGGTTGCTTTGACGTATGCGGTGTGAAATACCGCACAGAT

GCGTAAGGAGAAAATACCGCATCAGGCGCC

An exemplary AAV vector sequence encoding a mini-NF1 having an NF1 GRD with a HA tag is set forth in SEQ ID NO: 28:

CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTTCAATATTGGCCATTAGCCATATTATTCATTGGTTATAT

AGCATAAATCAATATTGGCTATTGGCCATTGCATACGTTGTATCTATATCATAATATGTACATT

TATATTGGCTCATGTCCAATATGACCGCCATGTTGGCATTGATTATTGACTAGTTATTAATAGT

AATCAATTACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGGTAAACTG

CCCACTTGGCAGTACATCAAGTGTATCATATGCCAAGTCCGCCCCCTATTGACGTCAATGACGG

TAAATGGCCCGCCTGGCATTATGCCCAGTACATGACCTTACGGGACTTTCCTACTTGGCAGTAC

ATCTACGTATTAGTCATCGCTATTACCATGGTCGAGGTGAGCCCCACGTTCTGCTTCACTCTCC

CCATCTCCCCCCCCTCCCCACCCCCAATTTTGTATTTATTTATTTTTTAATTATTTTGTGCAGC

GATGGGGGCGGGGGGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCGAAAGTTTCCTTTTA

-continued

TGGCGAGGCGGCGGCGGCGGCGGCCCTATAAAAAGCGAAGCGCGCGGCGGGCGGGAGTCGCTGC

GCGCTGCCTTCGCCCCGTGCCCCGCTCCGCCGCCGCCTCGCGCCGCCCGCCCCGGCTCTGACTG

ACCGCGTTACTCCCACAGGTGAGCGGGCGGGACGGCCCTTCTCCTCCGGGCTGTAATTAGCGCT

TGGTTTAATGACGGCTTGTTTCTTTTCTGTGGCTGCGTGAAAGCCTTGAGGGGCTCCGGGAGGG

CCCTTTGTGCGGGGGGAGCGGCTCGGGGGGTGCGTGCGTGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGGCTGCGAGGG

GAACAAAGGCTGCGTGCGGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

ACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA

AGAGCCAGCTGTTTCTGAAATACTTTACCCTGTTTATGAATCTGCTGAACGACTGTAGTGAGGT

GGAGGACGAGAGTGCCCAGACCGGCGGCAGGAAGAGAGGCATGTCTAGGAGACTGGCCAGCCTG

AGGCACTGCACAGTGCTGGCCATGTCCAACCTGCTGAACGCCAATGTGGACTCCGGCCTGATGC

ACTCTATCGGCCTGGGCTACCACAAGGATCTGCAGACCCGCGCCACATTCATGGAGGTGCTGAC

CAAGATCCTGCAGCAGGGCACCGAGTTTGACACACTGGCCGAGACCGTGCTGGCAGATAGGTTC

GAGCGCCTGGTGGAGCTGGTGACAATGATGGGCGACCAGGGAGAGCTGCCTATCGCAATGGCAC

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

GCTGGCCCTGCACCGGCTGCTGTGGAACAATCAGGAGAAGATCGGCCAGTACCTGAGCTCCAAC

AGGGACCACAAGGCAGTGGGCAGGAGACCTTTTGATAAGATGGCCACCCTGCTGGCATATCTGG

GACCACCAGAGCACAAGCCAGTGGCAGACACCCACTGGTCTAGCCTGAATCTGACATCCTCTAA

GTTCGAGGAGTTTATGACCCGGCACCAGGTGCACGAGAAGGAGGAGTTTAAGGCCCTGAAGACC

-continued

CTGTATCCGTATGATGTGCCGGATTATGCGTGATGACTCGAGTTTTTTTTTGCGGCCGCTTCGA

GCAGACATGATAAGATACATTGATGAGTTTGGACAAACCACAACTAGAATGCAGTGAAAAAAAT

GCTTTATTTGTGAAATTTGTGATGCTATTGCTTTATTTGTAACCATTATAAGCTGCAATAAACA

AGTTAACAACAACAATTGCATTCATTTTATGTTTCAGGTTCAGGGGGAGATGTGGGAGGTTTTT

TAAAGCAAGTAAAACCTCTACAAATGTGGTAAAATCGATAGGCCGCAGGAACCCCTAGTGATGG

AGTTGGCCACTCCCTCTCTGCGCGCTCGCTCGCTCACTGAGGCCGGGCGACCAAAGGTCGCCCG

ACGCCCGGGCGGCCTCAGTGAGCGAGCGAGCGCGCAGCTGCCTGCAGGACATGTGAGCAAAAGG

CCAGCAAAAGGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACAGGACTATAAA

GATACCAGGCGTTTCCCCCTGGAAGCTCCCTCGTGCGCTCTCCTGTTCCGACCCTGCCGCTTAC

CGGATACCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCCGTTCAGC

CCGACCGCTGCGCCTTATCCGGTAACTATCGTCTTGAGTCCAACCCGGTAAGACACGACTTATC

GCCACTGGCAGCAGCCACTGGTAACAGGATTAGCAGAGCGAGGTATGTAGGCGGTGCTACAGAG

TTCTTGAAGTGGTGGCCTAACTACGGCTACACTAGAAGAACAGTATTTGGTATCTGCGCTCTGC

TGAAGCCAGTTACCTTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACGTTAAGGGATTTTGG

TCATGAGATTATCAAAAAGGATCTTCACCTAGATCCTTTTAAATTAAAAATGAAGTTTTAAATC

AATCTAAAGTATATATGAGTAAACTTGGTCTGACAGTTACCAATGCTTAATCAGTGAGGCACCT

ATCTCAGCGATCTGTCTATTTCGTTCATCCATAGTTGCCTGACTCCCCGTCGTGTAGATAACTA

CGATACGGGAGGGCTTACCATCTGGCCCCAGTGCTGCAATGATACCGCGAGACCCACGCTCACC

GGCTCCAGATTTATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGTAGTTCGCCAG

TTAATAGTTTGCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCCCATGTTGTGC

AAAAAAGCGGTTAGCTCCTTCGGTCCTCCGATCGTTGTCAGAAGTAAGTTGGCCGCAGTGTTAT

CACTCATGGTTATGGCAGCACTGCATAATTCTCTTACTGTCATGCCATCCGTAAGATGCTTTTC

TGTGACTGGTGAGTACTCAACCAAGTCATTCTGAGAATAGTGTATGCGGCGACCGAGTTGCTCT

TGCCCGGCGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTTCGATGTA

ACCCACTCGTGCACCCAACTGATCTTCAGCATCTTTTACTTTCACCAGCGTTTCTGGGTGAGCA

AAAACAGGAAGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGGATACAT

ATTTGAATGTATTTAGAAAAATAAACAAATAGGGGTTCCGCGCACATTTCCCCGAAAAGTGCCA

CCTGACGTCTAAGAAACCATTATTATCATGACATTAACCTATAAAAATAGGCGTATCACGAGGC

CCTTTCGTCTCGCGCGTTTCGGTGATGACGGTGAAAACCTCTGACACATGCAGCTCCCGGAGAC

GGTCACAGCTTGTCTGTAAGCGGATGCCGGGAGCAGACAAGCCCGTCAGGGCGCGTCAGCGGGT

GTTGGCGGGTGTCGGGGCTGGCTTAACTATGCGGCATCAGAGCAGATTGTACTGAGAGTGCACC

ATAAAATTGTAAACGTTAATATTTTGTTAAAATTCGCGTTAAATTTTTGTTAAATCAGCTCATT

-continued

TTTTAACCAATAGGCCGAAATCGGCAAAATCCCTTATAAATCAAAAGAATAGCCCGAGATAGGG

TTGAGTGTTGTTCCAGTTTGGAACAAGAGTCCACTATTAAAGAACGTGGACTCCAACGTCAAAG

GGCGAAAAACCGTCTATCAGGGCGATGGCCCACTACGTGAACCATCACCCAAATCAAGTTTTTT

GGGGTCGAGGTGCCGTAAAGCACTAAATCGGAACCCTAAAGGGAGCCCCCGATTTAGAGCTTGA

CGGGGAAAGCCGGCGAACGTGGCGAGAAAGGAAGGGAAGAAAGCGAAAGGAGCGGGCGCTAAGG

CGCTGGCAAGTGTAGCGGTCACGCTGCGCGTAACCACCACACCCGCCGCGCTTAATGCGCCGCT

ACAGGGCGCGTACTATGGTTGCTTTGACGTATGCGGTGTGAAATACCGCACAGATGCGTAAGGA

GAAAATACCGCATCAGGCGCC

An exemplary AAV vector sequence encoding a mini-NF1 having an NF1 GRD, and the CRAL-TRIO domain with a HA tag is set forth in SEQ ID NO: 29:

CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTTCAATATTGGCCATTAGCCATATTATTCATTGGTTATAT

AGCATAAATCAATATTGGCTATTGGCCATTGCATACGTTGTATCTATATCATAATATGTACATT

TATATTGGCTCATGTCCAATATGACCGCCATGTTGGCATTGATTATTGACTAGTTATTAATAGT

AATCAATTACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGACGTATGTT

CCCATAGTAACGCCAATAGGGACTTTCCATTGACGTCAATGGGTGGAGTATTTACGGTAAACTG

CCCACTTGGCAGTACATCAAGTGTATCATATGCCAAGTCCGCCCCCTATTGACGTCAATGACGG

TAAATGGCCCGCCTGGCATTATGCCCAGTACATGACCTTACGGGACTTTCCTACTTGGCAGTAC

ATCTACGTATTAGTCATCGCTATTACCATGGTCGAGGTGAGCCCCACGTTCTGCTTCACTCTCC

CCATCTCCCCCCCCTCCCCACCCCCAATTTTGTATTTATTTATTTTTTAATTATTTTGTGCAGC

GATGGGGGCGGGGGGGGGGGGGGGGCGCGCGCCAGGCGGGGCGGGGCGGGGCGAGGGGCGGGGC

GGGGCGAGGCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGGAGTCGCTGC

GCGCTGCCTTCGCCCCGTGCCCCGCTCCGCCGCCGCCTCGCGCCGCCCGCCCCGGCTCTGACTG

ACCGCGTTACTCCCACAGGTGAGCGGGCGGGACGGCCCTTCTCCTCCGGGCTGTAATTAGCGCT

TGGTTTAATGACGGCTTGTTTCTTTTCTGTGGCTGCGTGAAAGCCTTGAGGGGCTCCGGGAGGG

CCCTTTGTGCGGGGGGAGCGGCTCGGGGGGTGCGTGCGTGTGTGTGTGCGTGGGGAGCGCCGCG

TGCGGCTCCGCGCTGCCCGGCGGCTGTGAGCGCTGCGGGCGCGGCGCGGGGCTTTGTGCGCTCC

GCAGTGTGCGCGAGGGGAGCGCGGCCGGGGGCGGTGCCCCGCGGTGCGGGGGGGGCTGCGAGGG

GAACAAAGGCTGCGTGCGGGGTGTGTGCGTGGGGGGGTGAGCAGGGGGTGTGGGCGCGTCGGTC

GGGCTGCAACCCCCCCTGCACCCCCCTCCCCGAGTTGCTGAGCACGGCCCGGCTTCGGGTGCGG

GGCTCCGTACGGGGCGTGGCGCGGGGCTCGCCGTGCCGGGCGGGGGGTGGCGGCAGGTGGGGGT

GCCGGGCGGGGCGGGGCCGCCTCGGGCCGGGGAGGGCTCGGGGGAGGGGCGCGGCGGCCCCCGG

AGCGCCGGCGGCTGTCGAGGCGCGGCGAGCCGCAGCCATTGCCTTTTATGGTAATCGTGCGAGA

GGGCGCAGGGACTTCCTTTGTCCCAAATCTGTGCGGAGCCGAAATCTGGGAGGCGCCGCCGCAC

CCCCTCTAGCGGGCGCGGGGCGAAGCGGTGCGGCGCCGGCAGGAAGGAAATGGGCGGGGAGGGC

CTTCGTGCGTCGCCGCGCCGCCGTCCCCTTCTCCCTCTCCAGCCTCGGGGCTGTCCGCGGGGGG

-continued

ACGGCTGCCTTCGGGGGGGACGGGGCAGGGCGGGGTTCGGCTTCTGGCGTGTGACCGGCGGCTC

TAGAGCCTCTGCTAACCATGTTCATGCCTTCTTCTTTTTCCTACAGCTCCTGGGCAACGTGCTG

GTTATTGTGCTGTCTCATCATTTTGGCAAAGAATTCGATATCAAGCTTGCCACCATGGAAGCCA

AGAGCCAGCTGTTTCTGAAATACTTTACCCTGTTTATGAATCTGCTGAACGACTGTAGTGAGGT

GGAGGACGAGAGTGCCCAGACCGGCGGCAGGAAGAGAGGCATGTCTAGGAGACTGGCCAGCCTG

AGGCACTGCACAGTGCTGGCCATGTCCAACCTGCTGAACGCCAATGTGGACTCCGGCCTGATGC

ACTCTATCGGCCTGGGCTACCACAAGGATCTGCAGACCCGCGCCACATTCATGGAGGTGCTGAC

CAAGATCCTGCAGCAGGGCACCGAGTTTGACACACTGGCCGAGACCGTGCTGGCAGATAGGTTC

GAGCGCCTGGTGGAGCTGGTGACAATGATGGGCGACCAGGGAGAGCTGCCTATCGCAATGGCAC

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

GCTGGCCCTGCACCGGCTGCTGTGGAACAATCAGGAGAAGATCGGCCAGTACCTGAGCTCCAAC

AGGGACCACAAGGCAGTGGGCAGGAGACCATTTGATAAGATGGCCACACTGCTGGCCTATCTGG

GACCACCAGAGCACAAGCCAGTGGCAGACACACACTGGTCTAGCCTGAATCTGACCTCCTCTAA

GTTCGAGGAGTTTATGACCCGGCACCAGGTGCACGAGAAGGAGGAGTTTAAGGCCCTGAAGACA

CTGTCTATCTTCTACCAGGCAGGCACCAGCAAGGCAGGAAACCCAATCTTTTACTATGTGGCCC

GGCGCTTCAAGACAGGCCAGATCAATGGCGATCTGCTGATCTACCACGTGCTGCTGACCCTGAA

GCCATACTATGCCAAGCCCTATGAGATCGTGGTGGACCTGACCCACACAGGCCCCTCCAACAGG

TTTAAGACCGATTTCCTGTCTAAGTGGTTCGTGGTGTTTCCTGGCTTCGCCTATGACAATGTGA

GCGCCGTGTACATCTATAACTGCAATTCCTGGGTGCGGGAGTACACAAAGTATCACGAGCGCCT

GCTGACCGGCCTGAAGGGATCCAAGAGACTGGTGTTCATCGATTGTCCCGGCAAGCTGGCCGAG

CACATTGAACACGAACAGCAGAAACTGCCCGCCGCAACCCTGGCCCTGGAAGAGGACCTGAAGT

ATCCGTATGATGTGCCGGATTATGCGTGATGACTCGAGTTTTTTTTGCGGCCGCTTCGAGCAG

ACATGATAAGATACATTGATGAGTTTGGACAAACCACAACTAGAATGCAGTGAAAAAAATGCTT

TATTTGTGAAATTTGTGATGCTATTGCTTTATTTGTAACCATTATAAGCTGCAATAAACAAGTT

AACAACAACAATTGCATTCATTTTATGTTTCAGGTTCAGGGGGAGATGTGGGAGGTTTTTTAAA

GCAAGTAAAACCTCTACAAATGTGGTAAAATCGATAGGCCGCAGGAACCCCTAGTGATGGAGTT

GGCCACTCCCTCTCTGCGCGCTCGCTCGCTCACTGAGGCCGGGCGACCAAAGGTCGCCCGACGC

CCGGGCGGCCTCAGTGAGCGAGCGAGCGCGCAGCTGCCTGCAGGACATGTGAGCAAAAGGCCAG

CAAAAGGCCAGGAACCGTAAAAAGGCCGCGTTGCTGGCGTTTTTCCATAGGCTCCGCCCCCCTG

-continued

ACGAGCATCACAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACAGAGTTCT
TGAAGTGGTGGCCTAACTACGGCTACACTAGAAGAACAGTATTTGGTATCTGCGCTCTGCTGAA
GCCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGATCCTT
TGATCTTTTCTACGGGGTCTGACGCTCAGTGGAACGAAAACTCACGTTAAGGGATTTTGGTCAT
GAGATTATCAAAAAGGATCTTCACCTAGATCCTTTTAAATTAAAAATGAAGTTTTAAATCAATC
TAAAGTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGGCT
CCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTCTGTG
ACTGGTGAGTACTCAACCAAGTCATTCTGAGAATAGTGTATGCGGCGACCGAGTTGCTCTTGCC
CGGCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCTT
TCGTCTCGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCGGGTGTTG
GCGGGTGTCGGGGCTGGCTTAACTATGCGGCATCAGAGCAGATTGTACTGAGAGTGCACCATAA
AATTGTAAACGTTAATATTTTGTTAAAATTCGCGTTAAATTTTTGTTAAATCAGCTCATTTTTT
AACCAATAGGCCGAAATCGGCAAAATCCCTTATAAATCAAAAGAATAGCCCGAGATAGGGTTGA
GTGTTGTTCCAGTTTGGAACAAGAGTCCACTATTAAAGAACGTGGACTCCAACGTCAAAGGGCG
AAAAACCGTCTATCAGGGCGATGGCCCACTACGTGAACCATCACCCAAATCAAGTTTTTTGGGG
TCGAGGTGCCGTAAAGCACTAAATCGGAACCCTAAAGGGAGCCCCCGATTTAGAGCTTGACGGG
GAAAGCCGGCGAACGTGGCGAGAAAGGAAGGGAAGAAAGCGAAAGGAGCGGGCGCTAAGGCGCT
GGCAAGTGTAGCGGTCACGCTGCGCGTAACCACCACACCCGCCGCGCTTAATGCGCCGCTACAG
GGCGCGTACTATGGTTGCTTTGACGTATGCGGTGTGAAATACCGCACAGATGCGTAAGGAGAAA
ATACCGCATCAGGCGCC

An exemplary AAV vector sequence encoding a mini-NF1 having an NF1 GRD, the CRAL-TRIO domain and the bipartite phospholipid binding domain with a HA tag is set forth in SEQ ID NO: 30:

CCTGCAGGCAGCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCCATC
ACTAGGGGTTCCTGCGGCCAGATCTTCAATATTGGCCATTAGCCATATTATTCATTGGTTATAT
AGCATAAATCAATATTGGCTATTGGCCATTGCATACGTTGTATCTATATCATAATATGTACATT
TATATTGGCTCATGTCCAATATGACCGCCATGTTGGCATTGATTATTGACTAGTTATTAATAGT
AATCAATTACGGGGTCATTAGTTCATAGCCCATATATGGAGTTCCGCGTTACATAACTTACGGT
AAATGGCCCGCCTGGCTGACCGCCCAACGACCCCCGCCCATTGACGTCAATAATGACGTATGTT
CCCATAGTAACGCCAATAGGGACTTTCCATTGACGTCAATGGGTGGAGTATTTACGGTAAACTG
CCCACTTGGCAGTACATCAAGTGTATCATATGCCAAGTCCGCCCCCTATTGACGTCAATGACGG
TAAATGGCCCGCCTGGCATTATGCCCAGTACATGACCTTACGGGACTTTCCTACTTGGCAGTAC
ATCTACGTATTAGTCATCGCTATTACCATGGTCGAGGTGAGCCCCACGTTCTGCTTCACTCTCC
CCATCTCCCCCCCCTCCCCACCCCCAATTTTGTATTTATTTATTTTTTAATTATTTTGTGCAGC
GATGGGGGCGGGGGGGGGGGGGGGGCGCGCGCCAGGCGGGGCGGGGCGGGGCGAGGGGCGGGGC
GGGGCGAGGCGGAGAGGTGCGGCGGCAGCCAATCAGAGCGGCGCGCTCCGAAAGTTTCCTTTTA
TGGCGAGGCGGCGGCGGCGGCGGCCCTATAAAAAGCGAAGCGCGCGGCGGGCGGGAGTCGCTGC
GCGCTGCCTTCGCCCCGTGCCCCGCTCCGCCGCCGCCTCGCGCCGCCCGCCCCGGCTCTGACTG
ACCGCGTTACTCCCACAGGTGAGCGGGCGGGACGGCCCTTCTCCTCCGGGCTGTAATTAGCGCT
TGGTTTAATGACGGCTTGTTTCTTTTCTGTGGCTGCGTGAAAGCCTTGAGGGGCTCCGGGAGGG
CCCTTTGTGCGGGGGGAGCGGCTCGGGGGGTGCGTGCGTGTGTGTGTGCGTGGGGAGCGCCGCG
TGCGGCTCCGCGCTGCCCGGCGGCTGTGAGCGCTGCGGGCGCGGCGCGGGGCTTTGTGCGCTCC
GCAGTGTGCGCGAGGGGAGCGCGGCCGGGGGCGGTGCCCCGCGGTGCGGGGGGGGCTGCGAGGG
GAACAAAGGCTGCGTGCGGGGTGTGTGCGTGGGGGGGTGAGCAGGGGGTGTGGGCGCGTCGGTC
GGGCTGCAACCCCCCCTGCACCCCCCTCCCCGAGTTGCTGAGCACGGCCCGGCTTCGGGTGCGG
GGCTCCGTACGGGGCGTGGCGCGGGGCTCGCCGTGCCGGGCGGGGGGTGGCGGCAGGTGGGGGT
GCCGGGCGGGGCGGGGCCGCCTCGGGCCGGGGAGGGCTCGGGGGAGGGGCGCGGCGGCCCCCGG
AGCGCCGGCGGCTGTCGAGGCGCGGCGAGCCGCAGCCATTGCCTTTTATGGTAATCGTGCGAGA
GGGCGCAGGGACTTCCTTTGTCCCAAATCTGTGCGGAGCCGAAATCTGGGAGGCGCCGCCGCAC
CCCCTCTAGCGGGCGCGGGGCGAAGCGGTGCGGCGCCGGCAGGAAGGAAATGGGCGGGGAGGGC
CTTCGTGCGTCGCCGCGCCGCCGTCCCCTTCTCCCTCTCCAGCCTCGGGGCTGTCCGCGGGGGG
ACGGCTGCCTTCGGGGGGGACGGGGCAGGGCGGGGTTCGGCTTCTGGCGTGTGACCGGCGGCTC
TAGAGCCTCTGCTAACCATGTTCATGCCTTCTTCTTTTTCCTACAGCTCCTGGGCAACGTGCTG
GTTATTGTGCTGTCTCATCATTTTGGCAAAGAATTCGATATCAAGCTTGCCACCATGGAAGCCA
AGAGCCAGCTGTTTCTGAAATACTTTACCCTGTTTATGAATCTGCTGAACGACTGTAGTGAGGT
GGAGGACGAGAGTGCCCAGACCGGCGGCAGGAAGAGAGGCATGTCTAGGAGACTGGCCAGCCTG
AGGCACTGCACAGTGCTGGCCATGTCCAACCTGCTGAACGCCAATGTGGACTCCGGCCTGATGC
ACTCTATCGGCCTGGGCTACCACAAGGATCTGCAGACCCGCGCCACATTCATGGAGGTGCTGAC
CAAGATCCTGCAGCAGGGCACCGAGTTTGACACACTGGCCGAGACCGTGCTGGCAGATAGGTTC
GAGCGCCTGGTGGAGCTGGTGACAATGATGGGCGACCAGGGAGAGCTGCCTATCGCAATGGCAC

-continued

TGGCCAACGTGGTGCCATGCAGCCAGTGGGACGAGCTGGCCAGGGTGCTGGTGACCCTGTTTGA

TTCCAGACACCTGCTGTACCAGCTGCTGTGGAACATGTTCTCTAAGGAGGTGGAGCTGGCCGAC

AGCATGCAGACACTGTTTAGGGGCAATTCCCTGGCCTCTAAGATCATGACCTTCTGTTTTAAGG

TGTACGGCGCCACATATCTGCAGAAGCTGCTGGATCCACTGCTGAGAATCGTGATCACCAGCTC

CGACTGGCAGCACGTGTCCTTCGAGGTGGATCCTACACGGCTGGAGCCAAGCGAGTCCCTGGAG

GAGAACCAGCGCAATCTGCTGCAGATGACCGAGAAGTTCTTTCACGCCATCATCTCTAGCTCCT

CTGAGTTTCCCCCTCAGCTGCGGTCCGTGTGCCACTGTCTGTACCAGGCCACCTGCCACTCTCT

GCTGAACAAGGCCACAGTGAAGGAGAAGAAGGAGAATAAGAAGAGCGTGGTGTCCCAGAGGTTC

CCACAGAACAGCATCGGAGCAGTGGGATCCGCCATGTTCCTGAGGTTCATCAATCCCGCCATCG

TGAGCCCTTATGAGGCCGGCATCCTGGACAAGAAGCCACCCCCTAGGATCGAGAGAGGCCTGAA

GCTGATGAGCAAGATCCTGCAGTCCATCGCCAACCACGTGCTGTTCACCAAGGAGGAGCACATG

CGCCCCTTCAACGACTTTGTGAAGTCTAATTTTGATGCCGCCCGGCGCTTCTTTCTGGACATCG

CCTCTGATTGTCCTACAAGCGACGCCGTGAACCACTCTCTGAGCTTCATCAGCGATGGCAATGT

GCTGGCCCTGCACCGGCTGCTGTGGAACAATCAGGAGAAGATCGGCCAGTACCTGAGCTCCAAC

AGGGACCACAAGGCAGTGGGCAGGAGACCTTTTGATAAGATGGCCACCCTGCTGGCATATCTGG

GACCACCAGAGCACAAGCCAGTGGCAGACACCCACTGGTCTAGCCTGAATCTGACATCCTCTAA

GTTCGAGGAGTTTATGACCCGGCACCAGGTGCACGAGAAGGAGGAGTTTAAGGCCCTGAAGACC

CTGTCCATCTTCTACCAGGCCGGCACATCTAAGGCCGGCAACCCTATCTTTTACTATGTGGCCC

GGCGCTTCAAGACCGGCCAGATCAATGGCGATCTGCTGATCTACCACGTGCTGCTGACACTGAA

GCCATACTATGCCAAGCCCTATGAGATCGTGGTGGACCTGACCCACACAGGCCCAAGCAACAGG

TTTAAGACCGATTTCCTGTCCAAGTGGTTCGTGGTGTTTCCCGGCTTCGCCTATGACAACGTGA

GCGCCGTGTACATCTATAACTGCAATAGCTGGGTGCGGGAGTACACCAAGTATCACGAGCGCCT

GCTGACAGGCCTGAAGGGCAGCAAGAGACTGGTGTTCATCGATTGTCCCGGCAAGCTGGCCGAG

CACATCGAGCACGAGCAGCAGAAGCTGCCTGCAGCCACCCTGGCCCTGGAGGAGGACCTGAAGG

TGTTTCACAACGCCCTGAAGCTGGCCCACAAGGATACAAAGGTGTCCATCAAGGTCGGCTCTAC

AGCCGTGCAGGTGACCTCCGCCGAGAGAACAAAGGTGCTGGGCCAGAGCGTGTTCCTGAATGAC

ATCTACTATGCCAGCGAGATCGAGGAGATCTGCCTGGTGGATGAGAACCAGTTTACCCTGACAA

TCGCCAATCAGGGCACCCCCCTGACATTCATGCACCAGGAGTGTGAAGCAATCGTCCAGAGCAT

TATTCACATTCGCACTCGGTGGGAACTGAGCCAGCCTGACTATCCGTATGATGTGCCGGATTAT

GCGTGATGACTCGAGTTTTTTTTTGCGGCCGCTTCGAGCAGACATGATAAGATACATTGATGAG

TTTGGACAAACCACAACTAGAATGCAGTGAAAAAAATGCTTTATTTGTGAAATTTGTGATGCTA

TTGCTTTATTTGTAACCATTATAAGCTGCAATAAACAAGTTAACAACAACAATTGCATTCATTT

TATGTTTCAGGTTCAGGGGGAGATGTGGGAGGTTTTTTAAAGCAAGTAAAACCTCTACAAATGT

GGTAAAATCGATAGGCCGCAGGAACCCCTAGTGATGGAGTTGGCCACTCCCTCTCTGCGCGCTC

GCTCGCTCACTGAGGCCGGGCGACCAAAGGTCGCCCGACGCCCGGGCGGCCTCAGTGAGCGAGC

GAGCGCGCAGCTGCCTGCAGGACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAATCGACGC

TCAAGTCAGAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAGGTCGTTCGC

-continued

TCCAAGCTGGGCTGTGTGCACGAACCCCCCGTTCAGCCCGACCGCTGCGCCTTATCCGGTAACT

ATCGTCTTGAGTCCAACCCGGTAAGACACGACTTATCGCCACTGGCAGCAGCCACTGGTAACAG

GATTAGCAGAGCGAGGTATGTAGGCGGTGCTACAGAGTTCTTGAAGTGGTGGCCTAACTACGGC

TACACTAGAAGAACAGTATTTGGTATCTGCGCTCTGCTGAAGCCAGTTACCTTCGGAAAAAGAG

TTGGTAGCTCTTGATCCGGCAAACAAACCACCGCTGGTAGCGGTGGTTTTTTTGTTTGCAAGCA

GCAGATTACGCGCAGAAAAAAAGGATCTCAAGAAGATCCTTTGATCTTTTCTACGGGGTCTGAC

GCTCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACTTG

GTCTGACAGTTACCAATGCTTAATCAGTGAGGCACCTATCTCAGCGATCTGTCTATTTCGTTCA

TCCATAGTTGCCTGACTCCCCGTCGTGTAGATAACTACGATACGGGAGGGCTTACCATCTGGCC

CCAGTGCTGCAATGATACCGCGAGACCCACGCTCACCGGCTCCAGATTTATCAGCAATAAACCA

GCCAGCCGGAAGGGCCGAGCGCAGAAGTGGTCCTGCAACTTTATCCGCCTCCATCCAGTCTATT

AATTGTTGCCGGGAAGCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATTCAGCTCCGGTTCCCA

ACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATA

ATTCTCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAATACGGGATAATACC

GCGCCACATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTATTGAA

GCATTTATCAGGGTTATTGTCTCATGAGCGGATACATATTTGAATGTATTTAGAAAAATAAACA

AATAGGGGTTCCGCGCACATTTCCCCGAAAAGTGCCACCTGACGTCTAAGAAACCATTATTATC

ATGACATTAACCTATAAAAATAGGCGTATCACGAGGCCCTTTCGTCTCGCGCGTTTCGGTGATG

ACGGTGAAAACCTCTGACACATGCAGCTCCCGGAGACGGTCACAGCTTGTCTGTAAGCGGATGC

CGGGAGCAGACAAGCCCGTCAGGGCGCGTCAGCGGGTGTTGGCGGGTGTCGGGGCTGGCTTAAC

TATGCGGCATCAGAGCAGATTGTACTGAGAGTGCACCATAAAATTGTAAACGTTAATATTTTGT

TAAAATTCGCGTTAAATTTTTGTTAAATCAGCTCATTTTTTAACCAATAGGCCGAAATCGGCAA

AATCCCTTATAAATCAAAAGAATAGCCCGAGATAGGGTTGAGTGTTGTTCCAGTTTGGAACAAG

AGTCCACTATTAAAGAACGTGGACTCCAACGTCAAAGGGCGAAAAACCGTCTATCAGGGCGATG

GCCCACTACGTGAACCATCACCCAAATCAAGTTTTTTGGGGTCGAGGTGCCGTAAAGCACTAAA

TCGGAACCCTAAAGGGAGCCCCCGATTTAGAGCTTGACGGGGAAAGCCGGCGAACGTGGCGAGA

AAGGAAGGGAAGAAAGCGAAAGGAGCGGGCGCTAAGGCGCTGGCAAGTGTAGCGGTCACGCTGC

GCGTAACCACCACACCCGCCGCGCTTAATGCGCCGCTACAGGGCGCGTACTATGGTTGCTTTGA

CGTATGCGGTGTGAAATACCGCACAGATGCGTAAGGAGAAAATACCGCATCAGGCGCC

In some embodiments, the 5' AAV vector and the 3' AAV vector encoding the full-length NF1 proteins comprises a nucleic acid as set forth in SEQ ID NOs: 12 and 15 or 31.

An exemplary 5' AAV vector sequence comprising the 5' isolated nucleic acid of the dual AAV vector system encoding full-length NF1 protein is set forth in SEQ ID NO: 12:

CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTGTCGACAATTGAGGGCGTCACCGCTAAGGCTCCGCCCCA

GCCTGGGCTCCACAACCAATGAAGGGTAATCTCGACAAAGAGCAAGGGGTGGGGCGCGGGCGCG

CAGGTGCAGCAGCACACAGGCTGGTCGGGAGGGCGGGGCGCGACGTCTGCCGTGCGGGGTCCCG

GCATCGGTTGCGCGCGCGCTCCCTCCTCTCGGAGAGAGGGCTGTGGTAAAACCCGTCCGGAAAA

CTAGTGCCACCATGGCCGCGCACAGGCCGGTGGAATGGGTCCAGGCCGTGGTCAGCCGCTTCGA

CGAGCAGCTTCCAATAAAAACAGGACAGCAGAACACACATACCAAAGTCAGTACTGAGCACAAC

AAGGAATGTCTAATCAATATTTCCAAATACAAGTTTTCTTTGGTTATAAGCGGCCTCACTACTA

TTTTAAAGAATGTTAACAATATGAGAATATTTGGAGAAGCTGCTGAAAAAAATTTATATCTCTC

TCAGTTGATTATATTGGATACACTGGAAAAATGTCTTGCTGGGCAACCAAAGGACACAATGAGA

TTAGATGAAACGATGCTGGTCAAACAGTTGCTGCCAGAAATCTGCCATTTTCTTCACACCTGTC

GTGAAGGAAACCAGCATGCAGCTGAACTTCGGAATTCTGCCTCTGGGGTTTTATTTTCTCTCAG

CTGCAACAACTTCAATGCAGTCTTTAGTCGCATTTCTACCAGGTTACAGGAATTAACTGTTTGT

TCAGAAGACAATGTTGATGTTCATGATATAGAATTGTTACAGTATATCAATGTGGATTGTGCAA

AATTAAAACGACTCCTGAAGGAAACAGCATTTAAATTTAAAGCCCTAAAGAAGGTTGCGCAGTT

AGCAGTTATAAATAGCCTGGAAAAGGCATTTTGGAACTGGGTAGAAAATTATCCAGATGAATTT

ACAAAACTGTACCAGATCCCACAGACTGATATGGCTGAATGTGCAGAAAAGCTATTTGACTTGG

TGGATGGTTTTGCTGAAAGCACCAAACGTAAAGCAGCAGTTTGGCCACTACAAATCATTCTCCT

TATCTTGTGCCCAGAAATAATCCAGGATATATCCAAAGACGTGGTTGATGAAAACAACATGAAT

AAGAAGTTATTTCTGGACAGTCTACGAAAAGCTCTTGCTGGCCATGGAGGAAGTAGGCAGCTGA

CAGAAAGTGCTGCAATTGCCTGTGTCAAACTGTGTAAAGCAAGTACTTACATCAATTGGGAAGA

TAACTCTGTCATTTTCCTACTTGTTCAGTCCATGGTGGTTGATCTTAAGAACCTGCTTTTTAAT

CCAAGTAAGCCATTCTCAAGAGGCAGTCAGCCTGCAGATGTGGATCTAATGATTGACTGCCTTG

TTTCTTGCTTTCGTATAAGCCCTCACAACAACCAACACTTTAAGATCTGCCTGGCTCAGAATTC

ACCTTCTACATTTCACTATGTGCTGGTAAATTCACTCCATCGAATCATCACCAATTCCGCATTG

GATTGGTGGCCTAAGATTGATGCTGTGTATTGTCACTCGGTTGAACTTCGAAATATGTTTGGTG

AAACACTTCATAAAGCAGTGCAAGGTTGTGGAGCACACCCAGCAATACGAATGGCACCGAGTCT

TACATTTAAAGAAAAAGTAACAAGCCTTAAATTTAAAGAAAAACCTACAGACCTGGAGACAAGA

AGCTATAAGTATCTTCTCTTGTCCATGGTGAAACTAATTCATGCAGATCCAAAGCTCTTGCTTT

GTAATCCAAGAAAACAGGGGCCCGAAACCCAAGGCAGTACAGCAGAATTAATTACAGGGCTCGT

CCAACTGGTCCCTCAGTCACACATGCCAGAGATTGCTCAGGAAGCAATGGAGGCTCTGCTGGTT

CTTCATCAGTTAGATAGCATTGATTTGTGGAATCCTGATGCTCCTGTAGAAACATTTTGGGAGA

TTAGCTCACAAATGCTTTTTTACATCTGCAAGAAATTAACTAGTCATCAAATGCTTAGTAGCAC

AGAAATTCTCAAGTGGTTGCGGGAAATATTGATCTGCAGGAATAAATTTCTTCTTAAAAATAAG

CAGGCAGATAGAAGTTCCTGTCACTTTCTCCTTTTTTACGGGGTAGGATGTGATATTCCTTCTA

GTGGAAATACCAGTCAAATGTCCATGGATCATGAAGAATTACTACGTACTCCTGGAGCCTCTCT

CCGGAAGGGAAAAGGGAACTCCTCTATGGATAGTGCAGCAGGATGCAGCGGAACCCCCCCAATT

-continued

TGCCGACAAGCCCAGACCAAACTAGAAGTGGCCCTGTACATGTTTCTGTGGAACCCTGACACTG

AAGCTGTTCTGGTTGCCATGTCCTGTTTCCGCCACCTCTGTGAGGAAGCAGATATCCGGTGTGG

GGTGGATGAAGTGTCAGTGCATAACCTCTTGCCCAACTATAACACATTCATGGAGTTTGCCTCT

GTCAGCAATATGATGTCAACAGGAAGAGCAGCACTTCAGAAAAGAGTGATGGCACTGCTGAGGC

GCATTGAGCATCCCACTGCAGGAAACACTGAGGCTTGGGAAGATACACATGCAAAATGGGAACA

AGCAACAAAGCTAATCCTTAACTATCCAAAAGCCAAAATGGAAGATGGCCAGGCTGCTGAAAGC

CTTCACAAGACCATTGTTAAGAGGCGAATGTCCCATGTGAGTGGAGGAGGATCCATAGATTTGT

CTGACACAGACTCCCTACAGGAATGGATCAACATGACTGGCTTCCTTTGTGCCCTTGGGGGAGT

GTGCCTCCAGCAGAGAAGCAATTCTGGCCTGGCAACCTATAGCCCACCCATGGGTCCAGTCAGT

GAACGTAAGGGTTCTATGATTTCAGTGATGTCTTCAGAGGGAAACGCAGATACACCTGTCAGCA

AATTTATGGATCGGCTGTTGTCCTTAATGGTGTGTAACCATGAGAAAGTGGGACTTCAAATACG

GACCAATGTTAAGGATCTGGTGGGTCTAGAATTGAGTCCTGCTCTGTATCCAATGCTATTTAAC

AAATTGAAGAATACCATCAGCAAGTTTTTTGACTCCCAAGGACAGGTTTTATTGACTGATACCA

ATACTCAATTTGTAGAACAAACCATAGCTATAATGAAGAACTTGCTAGATAATCATACTGAAGG

CAGCTCTGAACATCTAGGGCAAGCTAGCATTGAAACAATGATGTTAAATCTGGTCAGGTATGTT

CGTGTGCTTGGGAATATGGTCCATGCAATTCAAATAAAAACGAAACTGTGTCAATTAGTTGAAG

TAATGATGGCAAGGAGAGATGACCTCTCATTTTGCCAAGAGATGAAATTTAGGAATAAGATGGT

AGAATACCTGACAGACTGGGTTATGGGAACATCAAACCAAGCAGCAGATGATGATGTAAAATGT

CTTACAAGAGATTTGGACCAGGCAAGCATGGAAGCAGTAGTTTCACTTCTAGCTGGTCTCCCTC

TGCAGCCTGAAGAAGGAGATGGTGTGGAATTGATGGAAGCCAAATCACAGTTATTTCTTAAATA

CTTCACATTATTTATGAACCTTTTGAATGACTGCAGTGAAGTTGAAGATGAAAGTGCGCAAACA

GGTGGCAGGAAACGTGGCATGTCTCGGAGGCTGGCATCACTGAGGCACTGTACGGTCCTTGCAA

TGTCAAACTTACTCAATGCCAACGTAGACAGTGGTCTCATGCACTCCATAGGCTTAGGTTACCA

CAAGGATCTCCAGACAAGAGCTACATTTATGGAAGTTCTGACAAAAATCCTTCAACAAGGCACA

GAATTTGACACACTTGCAGAAACAGTATTGGCTGATCGGTTTGAGAGATTGGTGGAACTGGTCA

CAATGATGGGTGATCAAGGAGAACTCCCTATAGCGATGGCTCTGGCCAATGTGGTTCCTTGTTC

TCAGTGGGATGAACTAGCTCGAGTTCTGGTTACTCTGTTTGATTCTCGGCATTTACTCTACCAA

CTGCTCTGGAACATGTTTTCTAAAGAAGTAGAATTGGCAGACTCCATGCAGACTCTCTTCCGAG

GCAACAGCTTGGCCAGTAAAATAATGACATTCTGTTTCAAGGTATATGGTGCTACCTATCTACA

AAAACTCCTGGATCCTTTATTACGAATTGTGATCACATCCTCTGATTGGCAACATGTTAGCTTT

GAAGTGGATCCTACCAGGTTAGAACCATCAGAGAGCCTTGAGGAAAACCAGCGGAACCTCCTTC

AGATGACTGAAAAGTTCTTCCATGCCATCATCAGTTCCTCCTCAGAATTCCCCCCTCAACTTCG

AAGTGTGTGCCACTGTTTATACCAGGCAACTTGCCACTCCCTACTGAATAAAGCTACAGTAAAA

GAAAAAAAGGAAAACAAAAAATCAGTGGGCAGCATGTGGAACCTGGCGAGCCCCATCCCCGGCA

AGCTCTCAAGCCATGCTGGTGGGGACGACTGAATGCCAGGGCCCTTCACTGGGCTATTTCACCC

AGGGACGCTTCTTGAAGGCACCCCCCACTCCAAGCTCAATTGAACTCGAGAATCGATAGGCCGC

AGGAACCCCTAGTGATGGAGTTGGCCACTCCCTCTCTGCGCGCTCGCTCGCTCACTGAGGCCGG

GCGACCAAAGGTCGCCCGACGCCCGGGCGGCCTCAGTGAGCGAGCGAGCGCGCAGCTGCCTGCA

GGACATGTGAGCAAAAGGCCAGCAAAAGGCCAGGAACCGTAAAAAGGCCGCGTTGCTGGCGTTT

TTCCATAGGCTCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGCGCTCTCCTGT

-continued

TCCGACCCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCAACCC

GGTAAGACACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAGAACAGTAT

TTGGTATCTGCGCTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACCAATGC

TTAATCAGTGAGGCACCTATCTCAGCGATCTGTCTATTTCGTTCATCCATAGTTGCCTGACTCC

CCGTCGTGTAGATAACTACGATACGGGAGGGCTTACCATCTGGCCCCAGTGCTGCAATGATACC

GCGAGACCCACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGGCATCGTGGT

GTCACGCTCGTCGTTTGGTATGGCTTCATTCAGCTCCGGTTCCCAACGATCAAGGCGAGTTACA

TGATCCCCCATGTTGTGCAAAAAAGCGGTTAGCTCCTTCGGTCCTCCGATCGTTGTCAGAAGTA

AGTTGGCCGCAGTGTTATCACTCATGGTTATGGCAGCACTGCATAATTCTCTTACTGTCATGCC

ATCCGTAAGATGCTTTTCTGTGACTGGTGAGTACTCAACCAAGTCATTCTGAGAATAGTGTATG

CGGCGACCGAGTTGCTCTTGCCCGGCGTCAATACGGGATAATACCGCGCCACATAGCAGAACTT

TAAAAGTGCTCATCATTGGAAAACGTTCTTCGGGGCGAAAACTCTCAAGGATCTTACCGCTGTT

GAGATCCAGTTCGATGTAACCCACTCGTGCACCCAACTGATCTTCAGCATCTTTTACTTTCACC

AGCGTTTCTGGGTGAGCAAAAACAGGAAGGCAAAATGCCGCAAAAAAGGGAATAAGGGCGACAC

GGAAATGTTGAATACTCATACTCTTCCTTTTTCAATATTATTGAAGCATTTATCAGGGTTATTG

TCTCATGAGCGGATACATATTTGAATGTATTTAGAAAAATAAACAAATAGGGGTTCCGCGCACA

TTTCCCCGAAAAGTGCCACCTGACGTCTAAGAAACCATTATTATCATGACATTAACCTATAAAA

ATAGGCGTATCACGAGGCCCTTTCGTCTCGCGCGTTTCGGTGATGACGGTGAAAACCTCTGACA

CATGCAGCTCCCGGAGACGGTCACAGCTTGTCTGTAAGCGGATGCCGGGAGCAGACAAGCCCGT

CAGGGCGCGTCAGCGGGTGTTGGCGGGTGTCGGGGCTGGCTTAACTATGCGGCATCAGAGCAGA

TTGTACTGAGAGTGCACCATAAAATTGTAAACGTTAATATTTTGTTAAAATTCGCGTTAAATTT

TTGTTAAATCAGCTCATTTTTTAACCAATAGGCCGAAATCGGCAAAATCCCTTATAAATCAAAA

GAATAGCCCGAGATAGGGTTGAGTGTTGTTCCAGTTTGGAACAAGAGTCCACTATTAAAGAACG

TGGACTCCAACGTCAAAGGGCGAAAAACCGTCTATCAGGGCGATGGCCCACTACGTGAACCATC

ACCCAAATCAAGTTTTTTGGGGTCGAGGTGCCGTAAAGCACTAAATCGGAACCCTAAAGGGAGC

CCCCGATTTAGAGCTTGACGGGGAAAGCCGGCGAACGTGGCGAGAAAGGAAGGGAAGAAAGCGA

AAGGAGCGGGCGCTAAGGCGCTGGCAAGTGTAGCGGTCACGCTGCGCGTAACCACCACACCCGC

CGCGCTTAATGCGCCGCTACAGGGCGCGTACTATGGTTGCTTTGACGTATGCGGTGTGAAATAC

CGCACAGATGCGTAAGGAGAAAATACCGCATCAGGCGCC

An exemplary 3' AAV vector sequence comprising the 3' isolated nucleic acid of the dual AAV vector system encoding full-length NF1 protein is set forth in SEQ ID NO: 15:

CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTGCAAATTAGGACCGAGAGTCAGTGGCCGCTCAAGAGTCT

GTGACCATGCCCCAAATTCAGAGATGGTCCCAGGAGAGATGGGGGGAACTGCCAAGCAATGAGT

GACCGGTTCCCCCTCCCCCAGGTGGTTAGCCAGCGTTTCCCTCAGAACAGCATCGGTGCAGTAG

GAAGTGCCATGTTCCTCAGATTTATCAATCCTGCCATTGTCTCACCGTATGAAGCAGGGATTTT

AGATAAAAAGCCACCACCTAGAATCGAAAGGGGCTTGAAGTTAATGTCAAAGATACTTCAGAGT

ATTGCCAATCATGTTCTCTTCACAAAAGAAGAACATATGCGGCCTTTCAATGATTTTGTGAAAA

GCAACTTTGATGCAGCACGCAGGTTTTTCCTTGATATAGCATCTGATTGTCCTACAAGTGATGC

AGTAAATCATAGTCTTTCCTTCATAAGTGACGGCAATGTGCTTGCTTTACATCGTCTACTCTGG

AACAATCAGGAGAAAATTGGGCAGTATCTTTCCAGCAACAGGGATCATAAAGCTGTTGGAAGAC

GACCTTTTGATAAGATGGCAACACTTCTTGCATACCTGGGTCCTCCAGAGCACAAACCTGTGGC

AGATACACACTGGTCCAGCCTTAACCTTACCAGTTCAAAGTTTGAGGAATTTATGACTAGGCAT

CAGGTACATGAAAAAGAAGAATTCAAGGCTTTGAAAACGTTAAGTATTTTCTACCAAGCTGGGA

CTTCCAAAGCTGGGAATCCTATTTTTTATTATGTTGCACGGAGGTTCAAAACTGGTCAAATCAA

TGGTGATTTGCTGATATACCATGTCTTACTGACTTTAAAGCCATATTATGCAAAGCCATATGAA

ATTGTAGTGGACCTTACCCATACCGGGCCTAGCAATCGCTTTAAAACAGACTTTCTCTCTAAGT

GGTTTGTTGTTTTTCCTGGCTTTGCTTACGACAACGTCTCCGCAGTCTATATCTATAACTGTAA

CTCCTGGGTCAGGGAGTACACCAAGTATCATGAGCGGCTGCTGACTGGCCTCAAAGGTAGCAAA

AGGCTTGTTTTCATAGACTGTCCTGGGAAACTGGCTGAGCACATAGAGCATGAACAACAGAAAC

TACCTGCTGCCACCTTGGCTTTAGAAGAGGACCTGAAGGTATTCCACAATGCTCTCAAGCTAGC

TCACAAAGACACCAAAGTTTCTATTAAAGTTGGTTCTACTGCTGTCCAAGTAACTTCAGCAGAG

CGAACAAAAGTCCTAGGGCAATCAGTCTTTCTAAATGACATTTATTATGCTTCGGAAATTGAAG

AAATCTGCCTAGTAGATGAGAACCAGTTCACCTTAACCATTGCAAACCAGGGCACGCCGCTCAC

CTTCATGCACCAGGAGTGTGAAGCCATTGTCCAGTCTATCATTCATATCCGGACCCGCTGGGAA

CTGTCACAGCCCGACTCTATCCCCCAACACACCAAGATTCGGCCAAAAGATGTCCCTGGGACAC

TGCTCAATATCGCATTACTTAATTTAGGCAGTTCTGACCCGAGTTTACGGTCAGCTGCCTATAA

TCTTCTGTGTGCCTTAACTTGTACCTTTAATTTAAAAATCGAGGGCCAGTTACTAGAGACATCA

GGTTTATGTATCCCTGCCAACAACACCCTCTTTATTGTCTCTATTAGTAAGACACTGGCAGCCA

ATGAGCCACACCTCACGTTAGAATTTTTGGAAGAGTGTATTTCTGGATTTAGCAAATCTAGTAT

TGAATTGAAACACCTTTGTTTGGAATACATGACTCCATGGCTGTCAAATCTAGTTCGTTTTTGC

AAGCATAATGATGATGCCAAACGACAAAGAGTTACTGCTATTCTTGACAAGCTGATAACAATGA

CCATCAATGAAAAACAGATGTACCCATCTATTCAAGCAAAAATATGGGGAAGCCTTGGGCAGAT

TACAGATCTGCTTGATGTTGTACTAGACAGTTTCATCAAAACCAGTGCAACAGGTGGCTTGGGA

TCAATAAAAGCTGAGGTGATGGCAGATACTGCTGTAGCTTTGGCTTCTGGAAATGTGAAATTGG

TTTCAAGCAAGGTTATTGGAAGGATGTGCAAAATAATTGACAAGACATGCTTATCTCCAACTCC

TACTTTAGAACAACATCTTATGTGGGATGATATTGCTATTTTAGCACGCTACATGCTGATGCTG

TCCTTCAACAATTCCCTTGATGTGGCAGCTCATCTTCCCTACCTCTTCCACGTTGTTACTTTCT

-continued

TAGTAGCCACAGGTCCGCTCTCCCTTAGAGCTTCCACACATGGACTGGTCATTAATATCATTCA

CTCTCTGTGTACTTGTTCACAGCTTCATTTTAGTGAAGAGACCAAGCAAGTTTTGAGACTCAGT

CTGACAGAGTTCTCATTACCCAAATTTTACTTGCTGTTTGGCATTAGCAAAGTCAAGTCAGCTG

CTGTCATTGCCTTCCGTTCCAGTTACCGGGACAGGTCATTCTCTCCTGGCTCCTATGAGAGAGA

GACTTTTGCTTTGACATCCTTGGAAACAGTCACAGAAGCTTTGTTGGAGATCATGGAGGCATGC

ATGAGAGATATTCCAACGTGCAAGTGGCTGGACCAGTGGACAGAACTAGCTCAAAGATTTGCAT

TCCAATATAATCCATCCCTGCAACCAAGAGCTCTTGTTGTCTTTGGGTGTATTAGCAAACGAGT

GTCTCATGGGCAGATAAAGCAGATAATCCGTATTCTTAGCAAGGCACTTGAGAGTTGCTTAAAA

GGACCTGACACTTACAACAGTCAAGTTCTGATAGAAGCTACAGTAATAGCACTAACCAAATTAC

AGCCACTTCTTAATAAGGACTCGCCTCTGCACAAAGCCCTCTTTTGGGTAGCTGTGGCTGTGCT

GCAGCTTGATGAGGTCAACTTGTATTCAGCAGGTACCGCACTTCTTGAACAAAACCTGCATACT

TTAGATAGTCTCCGTATATTCAATGACAAGAGTCCAGAGGAAGTATTTATGGCAATCCGGAATC

CTCTGGAGTGGCACTGCAAGCAAATGGATCATTTTGTTGGACTCAATTTCAACTCTAACTTTAA

CTTTGCATTGGTTGGACACCTTTTAAAAGGGTACAGGCATCCTTCACCTGCTATTGTTGCAAGA

ACAGTCAGAATTTTACATACACTACTAACTCTGGTTAACAAACACAGAAATTGTGACAAATTTG

AAGTGAATACACAGAGCGTGGCCTACTTAGCAGCTTTACTTACAGTGTCTGAAGAAGTTCGAAG

TCGCTGCAGCCTAAAACATAGAAAGTCACTTCTTCTTACTGATATTTCAATGGAAAATGTTCCT

ATGGATACATATCCCATTCATCATGGTGACCCTTCCTATAGGACACTAAAGGAGACTCAGCCAT

GGTCCTCTCCCAAAGGTTCTGAAGGATACCTTGCAGCCACCTATCCAACTGTCGGCCAGACCAG

TCCCCGAGCCAGGAAATCCATGAGCCTGGACATGGGGCAACCTTCTCAGGCCAACACTAAGAAG

TTGCTTGGAACAAGGAAAAGTTTTGATCACTTGATATCAGACACAAAGGCTCCTAAAAGGCAAG

AAATGGAATCAGGGATCACAACACCCCCCAAAATGAGGAGAGTAGCAGAAACTGATTATGAAAT

GGAAACTCAGAGGATTTCCTCATCACAACAGCACCCACATTTACGTAAAGTTTCAGTGTCTGAA

TCAAATGTTCTCTTGGATGAAGAAGTACTTACTGATCCGAAGATCCAGGCGCTGCTTCTTACTG

TTCTAGCTACACTGGTAAAATATACCACAGATGAGTTTGATCAACGAATTCTTTATGAATACTT

AGCAGAGGCCAGTGTTGTGTTTCCCAAAGTCTTTCCTGTTGTGCATAATTTGTTGGACTCTAAG

ATCAACACCCTGTTATCATTGTGCCAAGATCCAAATTTGTTAAATCCAATCCATGGAATTGTGC

AGAGTGTGGTGTACCATGAAGAATCCCCACCACAATACCAAACATCTTACCTGCAAAGTTTTGG

TTTTAATGGCTTGTGGCGGTTTGCAGGACCGTTTTCAAAGCAAACACAAATTCCAGACTATGCT

GAGCTTATTGTTAAGTTTCTTGATGCCTTGATTGACACGTACCTGCCTGGAATTGATGAAGAAA

CCAGTGAAGAATCCCTCCTGACTCCCACATCTCCTTACCCTCCTGCACTGCAGAGCCAGCTTAG

TATCACTGCCAACCTTAACCTTTCTAATTCCATGACCTCACTTGCAACTTCCCAGCATTCCCCA

GGAATCGACAAGGAGAACGTTGAACTCTCCCCTACCACTGGCCACTGTAACAGTGGACGAACTC

GCCACGGATCCGCAAGCCAAGTGCAGAAGCAAAGAAGCGCTGGCAGTTTCAAACGTAATAGCAT

TAAGAAGATCGTGGAGCGGCCGCTTCGAGCAGACATGATAAGATACATTGATGAGTTTGGACAA

ACCACAACTAGAATGCAGTGAAAAAAATGCTTTATTTGTGAAATTTGTGATGCTATTGCTTTAT

TTGTAACCATTATAAGCTGCAATAAACAAGTTAACAACAACAATTGCATTCATTTTATGTTTCA

GGTTCAGGGGGAGATGTGGGAGGTTTTTTAAAGCAAGTAAAACCTCTACAAATGTGGTAAAATC

GATAGGCCGCAGGAACCCCTAGTGATGGAGTTGGCCACTCCCTCTCTGCGCGCTCGCTCGCTCA

CTGAGGCCGGGCGACCAAAGGTCGCCCGACGCCCGGGCGGCCTCAGTGAGCGAGCGAGCGCGCA

GCTGCCTGCAGGACATGTGAGCAAAAGGCCAGCAAAAGGCCAGGAACCGTAAAAAGGCCGCGTT

-continued

GCTGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGGCTACACTAGA
AGAACAGTATTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGCTCAGTGG
AACGAAAACTCACGTTAAGGGATTTTGGTCATGAGATTATCAAAAAGGATCTTCACCTAGATCC
TTTTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGG
AAGGGCCGAGCGCAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCCCAACGATCAAG
GCGAGTTACATGATCCCCCATGTTGTGCAAAAAAGCGGTTAGCTCCTTCGGTCCTCCGATCGTT
GTCAGAAGTAAGTTGGCCGCAGTGTTATCACTCATGGTTATGGCAGCACTGCATAATTCTCTTA
CTGTCATGCCATCCGTAAGATGCTTTTCTGTGACTGGTGAGTACTCAACCAAGTCATTCTGAGA
ATAGTGTATGCGGCGACCGAGTTGCTCTTGCCCGGCGTCAATACGGGATAATACCGCGCCACAT
AGCAGAACTTTAAAAGTGCTCATCATTGGAAAACGTTCTTCGGGGCGAAAACTCTCAAGGATCT
TACCGCTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGCATTTATC
AGGGTTATTGTCTCATGAGCGGATACATATTTGAATGTATTTAGAAAAATAAACAAATAGGGGT
TCCGCGCACATTTCCCCGAAAAGTGCCACCTGACGTCTAAGAAACCATTATTATCATGACATTA
ACCTATAAAAATAGGCGTATCACGAGGCCCTTTCGTCTCGCGCGTTTCGGTGATGACGGTGAAA
ACCTCTGACACATGCAGCTCCCGGAGACGGTCACAGCTTGTCTGTAAGCGGATGCCGGGAGCAG
ACAAGCCCGTCAGGGCGCGTCAGCGGGTGTTGGCGGGTGTCGGGGCTGGCTTAACTATGCGGCA
TCAGAGCAGATTGTACTGAGAGTGCACCATAAAATTGTAAACGTTAATATTTTGTTAAAATTCG
CGTTAAATTTTTGTTAAATCAGCTCATTTTTTAACCAATAGGCCGAAATCGGCAAAATCCCTTA
TAAATCAAAAGAATAGCCCGAGATAGGGTTGAGTGTTGTTCCAGTTTGGAACAAGAGTCCACTA
TTAAAGAACGTGGACTCCAACGTCAAAGGGCGAAAAACCGTCTATCAGGGCGATGGCCCACTAC
GTGAACCATCACCCAAATCAAGTTTTTTGGGGTCGAGGTGCCGTAAAGCACTAAATCGGAACCC
TAAAGGGAGCCCCCGATTTAGAGCTTGACGGGGAAAGCCGGCGAACGTGGCGAGAAAGGAAGGG
AAGAAAGCGAAAGGAGCGGGCGCTAAGGCGCTGGCAAGTGTAGCGGTCACGCTGCGCGTAACCA
CCACACCCGCCGCGCTTAATGCGCCGCTACAGGGCGCGTACTATGGTTGCTTTGACGTATGCGG
TGTGAAATACCGCACAGATGCGTAAGGAGAAAATACCGCATCAGGCGCC

An exemplary 3' AAV vector sequence comprising the 3' isolated nucleic acid of the dual AAV vector system encoding full-length NF1 protein with a HA tag is set forth in SEQ ID NO: 31:

```
CCTGCAGGCAGCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCCATC

ACTAGGGGTTCCTGCGGCCAGATCTGCAAATTAGGACCGAGAGTCAGTGGCCGCTCAAGAGTCT

GTGACCATGCCCCAAATTCAGAGATGGTCCCAGGAGAGATGGGGGGAACTGCCAAGCAATGAGT

GACCGGTTCCCCCTCCCCCAGGTGGTTAGCCAGCGTTTCCCTCAGAACAGCATCGGTGCAGTAG

GAAGTGCCATGTTCCTCAGATTTATCAATCCTGCCATTGTCTCACCGTATGAAGCAGGGATTTT

AGATAAAAAGCCACCACCTAGAATCGAAAGGGGCTTGAAGTTAATGTCAAAGATACTTCAGAGT

ATTGCCAATCATGTTCTCTTCACAAAAGAAGAACATATGCGGCCTTTCAATGATTTTGTGAAAA

GCAACTTTGATGCAGCACGCAGGTTTTTCCTTGATATAGCATCTGATTGTCCTACAAGTGATGC

AGTAAATCATAGTCTTTCCTTCATAAGTGACGGCAATGTGCTTGCTTTACATCGTCTACTCTGG

AACAATCAGGAGAAAATTGGGCAGTATCTTTCCAGCAACAGGGATCATAAAGCTGTTGGAAGAC

GACCTTTTGATAAGATGGCAACACTTCTTGCATACCTGGGTCCTCCAGAGCACAAACCTGTGGC

AGATACACACTGGTCCAGCCTTAACCTTACCAGTTCAAAGTTTGAGGAATTTATGACTAGGCAT

CAGGTACATGAAAAAGAAGAATTCAAGGCTTTGAAAACGTTAAGTATTTTCTACCAAGCTGGGA

CTTCCAAAGCTGGGAATCCTATTTTTTATTATGTTGCACGGAGGTTCAAAACTGGTCAAATCAA

TGGTGATTTGCTGATATACCATGTCTTACTGACTTTAAAGCCATATTATGCAAAGCCATATGAA

ATTGTAGTGGACCTTACCCATACCGGGCCTAGCAATCGCTTTAAAACAGACTTTCTCTCTAAGT

GGTTTGTTGTTTTTCCTGGCTTTGCTTACGACAACGTCTCCGCAGTCTATATCTATAACTGTAA

CTCCTGGGTCAGGGAGTACACCAAGTATCATGAGCGGCTGCTGACTGGCCTCAAAGGTAGCAAA

AGGCTTGTTTTCATAGACTGTCCTGGGAAACTGGCTGAGCACATAGAGCATGAACAACAGAAAC

TACCTGCTGCCACCTTGGCTTTAGAAGAGGACCTGAAGGTATTCCACAATGCTCTCAAGCTAGC

TCACAAAGACACCAAAGTTTCTATTAAAGTTGGTTCTACTGCTGTCCAAGTAACTTCAGCAGAG

CGAACAAAAGTCCTAGGGCAATCAGTCTTTCTAAATGACATTTATTATGCTTCGGAAATTGAAG

AAATCTGCCTAGTAGATGAGAACCAGTTCACCTTAACCATTGCAAACCAGGGCACGCCGCTCAC

CTTCATGCACCAGGAGTGTGAAGCCATTGTCCAGTCTATCATTCATATCCGGACCCGCTGGGAA

CTGTCACAGCCCGACTCTATCCCCCAACACACCAAGATTCGGCCAAAAGATGTCCCTGGGACAC

TGCTCAATATCGCATTACTTAATTTAGGCAGTTCTGACCCGAGTTTACGGTCAGCTGCCTATAA

TCTTCTGTGTGCCTTAACTTGTACCTTTAATTTAAAAATCGAGGGCCAGTTACTAGAGACATCA

GGTTTATGTATCCCTGCCAACAACACCCTCTTTATTGTCTCTATTAGTAAGACACTGGCAGCCA

ATGAGCCACACCTCACGTTAGAATTTTTGGAAGAGTGTATTTCTGGATTTAGCAAATCTAGTAT

TGAATTGAAACACCTTTGTTTGGAATACATGACTCCATGGCTGTCAAATCTAGTTCGTTTTTGC

AAGCATAATGATGATGCCAAACGACAAAGAGTTACTGCTATTCTTGACAAGCTGATAACAATGA

CCATCAATGAAAAACAGATGTACCCATCTATTCAAGCAAAAATATGGGGAAGCCTTGGGCAGAT

TACAGATCTGCTTGATGTTGTACTAGACAGTTTCATCAAAACCAGTGCAACAGGTGGCTTGGGA

TCAATAAAAGCTGAGGTGATGGCAGATACTGCTGTAGCTTTGGCTTCTGGAAATGTGAAATTGG

TTTCAAGCAAGGTTATTGGAAGGATGTGCAAAATAATTGACAAGACATGCTTATCTCCAACTCC

TACTTTAGAACAACATCTTATGTGGGATGATATTGCTATTTTAGCACGCTACATGCTGATGCTG

TCCTTCAACAATTCCCTTGATGTGGCAGCTCATCTTCCCTACCTCTTCCACGTTGTTACTTTCT
```

-continued

TAGTAGCCACAGGTCCGCTCTCCCTTAGAGCTTCCACACATGGACTGGTCATTAATATCATTCA

CTCTCTGTGTACTTGTTCACAGCTTCATTTTAGTGAAGAGACCAAGCAAGTTTTGAGACTCAGT

CTGACAGAGTTCTCATTACCCAAATTTTACTTGCTGTTTGGCATTAGCAAAGTCAAGTCAGCTG

CTGTCATTGCCTTCCGTTCCAGTTACCGGGACAGGTCATTCTCTCCTGGCTCCTATGAGAGAGA

GACTTTTGCTTTGACATCCTTGGAAACAGTCACAGAAGCTTTGTTGGAGATCATGGAGGCATGC

ATGAGAGATATTCCAACGTGCAAGTGGCTGGACCAGTGGACAGAACTAGCTCAAAGATTTGCAT

TCCAATATAATCCATCCCTGCAACCAAGAGCTCTTGTTGTCTTTGGGTGTATTAGCAAACGAGT

GTCTCATGGGCAGATAAAGCAGATAATCCGTATTCTTAGCAAGGCACTTGAGAGTTGCTTAAAA

GGACCTGACACTTACAACAGTCAAGTTCTGATAGAAGCTACAGTAATAGCACTAACCAAATTAC

AGCCACTTCTTAATAAGGACTCGCCTCTGCACAAAGCCCTCTTTTGGGTAGCTGTGGCTGTGCT

GCAGCTTGATGAGGTCAACTTGTATTCAGCAGGTACCGCACTTCTTGAACAAAACCTGCATACT

TTAGATAGTCTCCGTATATTCAATGACAAGAGTCCAGAGGAAGTATTTATGGCAATCCGGAATC

CTCTGGAGTGGCACTGCAAGCAAATGGATCATTTTGTTGGACTCAATTTCAACTCTAACTTTAA

CTTTGCATTGGTTGGACACCTTTTAAAAGGGTACAGGCATCCTTCACCTGCTATTGTTGCAAGA

ACAGTCAGAATTTTACATACACTACTAACTCTGGTTAACAAACACAGAAATTGTGACAAATTTG

AAGTGAATACACAGAGCGTGGCCTACTTAGCAGCTTTACTTACAGTGTCTGAAGAAGTTCGAAG

TCGCTGCAGCCTAAAACATAGAAAGTCACTTCTTCTTACTGATATTTCAATGGAAAATGTTCCT

ATGGATACATATCCCATTCATCATGGTGACCCTTCCTATAGGACACTAAAGGAGACTCAGCCAT

GGTCCTCTCCCAAAGGTTCTGAAGGATACCTTGCAGCCACCTATCCAACTGTCGGCCAGACCAG

TCCCCGAGCCAGGAAATCCATGAGCCTGGACATGGGGCAACCTTCTCAGGCCAACACTAAGAAG

TTGCTTGGAACAAGGAAAAGTTTTGATCACTTGATATCAGACACAAAGGCTCCTAAAAGGCAAG

AAATGGAATCAGGGATCACAACACCCCCCAAAATGAGGAGAGTAGCAGAAACTGATTATGAAAT

GGAAACTCAGAGGATTTCCTCATCACAACAGCACCCACATTTACGTAAAGTTTCAGTGTCTGAA

TCAAATGTTCTCTTGGATGAAGAAGTACTTACTGATCCGAAGATCCAGGCGCTGCTTCTTACTG

TTCTAGCTACACTGGTAAAATATACCACAGATGAGTTTGATCAACGAATTCTTTATGAATACTT

AGCAGAGGCCAGTGTTGTGTTTCCCAAAGTCTTTCCTGTTGTGCATAATTTGTTGGACTCTAAG

ATCAACACCCTGTTATCATTGTGCCAAGATCCAAATTTGTTAAATCCAATCCATGGAATTGTGC

AGAGTGTGGTGTACCATGAAGAATCCCCACCACAATACCAAACATCTTACCTGCAAAGTTTTGG

TTTTAATGGCTTGTGGCGGTTTGCAGGACCGTTTTCAAAGCAAACACAAATTCCAGACTATGCT

GAGCTTATTGTTAAGTTTCTTGATGCCTTGATTGACACGTACCTGCCTGGAATTGATGAAGAAA

CCAGTGAAGAATCCCTCCTGACTCCCACATCTCCTTACCCTCCTGCACTGCAGAGCCAGCTTAG

TATCACTGCCAACCTTAACCTTTCTAATTCCATGACCTCACTTGCAACTTCCCAGCATTCCCCA

GGAATCGACAAGGAGAACGTTGAACTCTCCCCTACCACTGGCCACTGTAACAGTGGACGAACTC

GCCACGGATCCGCAAGCCAAGTGCAGAAGCAAAGAAGCGCTGGCAGTTTCAAACGTAATAGCAT

TAAGAAGATCGTGTATCCGTATGATGTGCCGGATTATGCGTGAGCGGCCGCTTCGAGCAGACAT

GATAAGATACATTGATGAGTTTGGACAAACCACAACTAGAATGCAGTGAAAAAAATGCTTTATT

TGTGAAATTTGTGATGCTATTGCTTTATTTGTAACCATTATAAGCTGCAATAAACAAGTTAACA

ACAACAATTGCATTCATTTTATGTTTCAGGTTCAGGGGGAGATGTGGGAGGTTTTTTAAAGCAA

GTAAAACCTCTACAAATGTGGTAAAATCGATAGGCCGCAGGAACCCCTAGTGATGGAGTTGGCC

ACTCCCTCTCTGCGCGCTCGCTCGCTCACTGAGGCCGGGCGACCAAAGGTCGCCCGACGCCCGG

-continued

GCGGCCTCAGTGAGCGAGCGAGCGCGCAGCTGCCTGCAGGACATGTGAGCAAAAGGCCAGCAAA

AGGCCAGGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAGATACCAG

GCGTTTCCCCCTGGAAGCTCCCTCGTGCGCTCTCCTGTTCCGACCCTGCCGCTTACCGGATACC

TGTCCGCCTTTCTCCCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCGTTCAGCCCGACCGC

TGCGCCTTATCCGGTAACTATCGTCTTGAGTCCAACCCGGTAAGACACGACTTATCGCCACTGG

CAGCAGCCACTGGTAACAGGATTAGCAGAGCGAGGTATGTAGGCGGTGCTACAGAGTTCTTGAA

GTGGTGGCCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGTAGCGGTG

GTTTTTTTGTTTGCAAGCAGCAGATTACGCGCAGAAAAAAAGGATCTCAAGAAGATCCTTTGAT

CTTTTCTACGGGGTCTGACGCTCAGTGGAACGAAAACTCACGTTAAGGGATTTTGGTCATGAGA

TTATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCAGC

GATCTGTCTATTTCGTTCATCCATAGTTGCCTGACTCCCCGTCGTGTAGATAACTACGATACGG

GAGGGCTTACCATCTGGCCCCAGTGCTGCAATGATACCGCGAGACCCACGCTCACCGGCTCCAG

ATTTATCAGCAATAAACCAGCCAGCCGGAAGGGCCGAGCGCAGAAGTGGTCCTGCAACTTTATC

CGCCTCCATCCAGTCTATTAATTGTTGCCGGGAAGCTAGAGTAAGTAGTTCGCCAGTTAATAGT

TTGCGCAACGTTGTTGCCATTGCTACAGGCATCGTGGTGTCACGCTCGTCGTTTGGTATGGCTT

CATTCAGCTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATCACTCATG

GTTATGGCAGCACTGCATAATTCTCTTACTGTCATGCCATCCGTAAGATGCTTTTCTGTGACTG

GTGAGTACTCAACCAAGTCATTCTGAGAATAGTGTATGCGGCGACCGAGTTGCTCTTGCCCGGC

GTCAATACGGGATAATACCGCGCCACATAGCAGAACTTTAAAAGTGCTCATCATTGGAAAACGT

TCTTCGGGGCGAAAACTCTCAAGGATCTTACCGCTGTTGAGATCCAGTTCGATGTAACCCACTC

GTGCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCTTC

GTTTTTGAATATTATTGAAGGATTTATGAGGGTTATTGTGTGATGAGGGGATAGATATTTGAAT

GTATTTAGAAAAATAAACAAATAGGGGTTCCGCGCACATTTCCCCGAAAAGTGCCACCTGACGT

CTAAGAAACCATTATTATCATGACATTAACCTATAAAAATAGGCGTATCACGAGGCCCTTTCGT

CTCGCGCGTTTCGGTGATGACGGTGAAAACCTCTGACACATGCAGCTCCCGGAGACGGTCACAG

CTTGTCTGTAAGCGGATGCCGGGAGCAGACAAGCCCGTCAGGGCGCGTCAGCGGGTGTTGGCGG

GTGTCGGGGCTGGCTTAACTATGCGGCATCAGAGCAGATTGTACTGAGAGTGCACCATAAAATT

GTAAACGTTAATATTTTGTTAAAATTCGCGTTAAATTTTTGTTAAATCAGCTCATTTTTTAACC

AATAGGCCGAAATCGGCAAAATCCCTTATAAATCAAAAGAATAGCCCGAGATAGGGTTGAGTGT

TGTTCCAGTTTGGAACAAGAGTCCACTATTAAAGAACGTGGACTCCAACGTCAAAGGGCGAAAA

ACCGTCTATCAGGGCGATGGCCCACTACGTGAACCATCACCCAAATCAAGTTTTTTGGGGTCGA

GGTGCCGTAAAGCACTAAATCGGAACCCTAAAGGGAGCCCCCGATTTAGAGCTTGACGGGGAAA

GCCGGCGAACGTGGCGAGAAAGGAAGGGAAGAAAGCGAAAGGAGCGGGCGCTAAGGCGCTGGCA

-continued

```
AGTGTAGCGGTCACGCTGCGCGTAACCACCACACCCGCCGCGCTTAATGCGCCGCTACAGGGCG

CGTACTATGGTTGCTTTGACGTATGCGGTGTGAAATACCGCACAGATGCGTAAGGAGAAAATAC

CGCATCAGGCGCC
```

Recombinant Adeno-Associated Viruses (rAAVs)

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, and AAV10. In some embodiments, an AAV capsid protein is of a serotype derived from a non-human primate, for example AAVrh8 serotype. In some embodiments, the AAV capsid protein is of a serotype that has tropism for the CNS tissue of a subject, for example an AAV (e.g., AAV5, AAV6, AAV6.2, AAV7, AAV8, AAV9, AAVrh.8, AAVrh.10, AAV-Anc80, AAVrh.39 and AAVrh.43) that transduces neuron cells of a subject more efficiently than other AAV capsid proteins. In some embodiments, an AAV capsid protein is of an AAV9 serotype. In some embodiments, the AAV capsid is of AAV9.PHP.eB. In some embodiments, the AAV capsid is of AAV9.PHP.B. In some embodiments, an AAV capsid protein is a chimeric capsid protein. In some embodiments, the AAV capsid protein is AAV-DJ. In some embodiments, the AAV capsid protein is AAV-Anc80.

In some embodiments, the AAV capsid is of a serotype that has tropism to cells of the nervous system. In some embodiments, the AAV capsid is of a serotype that has tropism to cells of the central nervous system (CNS). In some embodiments, the AAV capsid is of a serotype that has tropism to cells of the peripheral nervous system. In some embodiments, the AAV capsid is of a serotype that has tropism for glial cells (e.g., satellite cells, Schwann cells). In some embodiments, the AAV capsid is of a serotype that has tropism for Schwann cells. In some embodiments, the AAV capsid is of a serotype that has tropism for neurons. In some embodiments, the AAV capsid is of a serotype that has tropism for benign neuron fibroma cells. In some embodiments, the AAV capsid is of a serotype that has tropism for optic glioma cells. In some embodiments, the AAV capsid is of a serotype that has tropism for malignant peripheral nerve sheath tumors cells.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component (s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a coding sequence encoding a protein (e.g., a mini-NF1 protein). In some embodiments, the host cell is a mammalian cell (e.g., HEK293 cell, or MPNST cells) or an insect cell (e.g., SF9 cell). In some embodiments, the disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV plasmid (e.g., AAV vectors encoding mini-NF1 protein, or dual-AAV vectors encoding the full-length NF1 protein), an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

In some embodiments, the present disclosure provides a rAAV comprises the isolated nucleic acid encoding any of the mini-NF1 proteins; and an AAV capsid protein described herein. In some embodiments, the capsid protein is AAV-DJ capsid or AAV. PHP.eB In some embodiments, the present disclosure provides an A 5' recombinant adeno-associated virus (rAAV) comprising the 5' isolated nucleic acid encoding the first portion of an NF1 protein; and an AAV capsid protein. In some embodiments, the present disclosure provides an 3' recombinant adeno-associated virus (rAAV) comprising the 3' isolated nucleic acid encoding the second portion of an NF1 protein; and an AAV capsid protein. In some embodiments, the capsid protein is AAV-DJ capsid or AAV. PHP.eB.

Also provided herein, is a neurofibromin (NF1) expression system comprising: the 5' rAAV and the 3' rAAV as described herein. Upon co-infection of a target cell by both the 5' rAAV and the 3' rAAV, the two rAAV genomes would go through head to tail concatemerization from 3' ITR of the 5' isolated nucleic acid and 5' ITR of the 3' isolated nucleic acid such that the two isolated nucleic acids form one single AAV genome. After transcription, the mRNA comprises the NF1 first portion mRNA, splicing sites including the splicing donor, concactemerized ITR, and splicing acceptor, and NF1 second portion mRNA. The splicing sites can be removed by spliceosome via trans-splicing, thereby stitching the NF1 first portion mRNA and NF1 second portion mRNA to form a complete mRNA encoding a full-length NF1.

Methods

Methods for inhibiting Ras activity in a cell (e.g., MPNST cells) or in a subject in need thereof are provided herein. The methods typically involve administering to a subject in need thereof an effective amount of a rAAV comprising a nucleic acid for expressing a transgene (e.g., a mini-NF1 protein) in the subject. Alternatively, the methods involve administering to a subject in need thereof an effective amount of dual rAAVs comprising nucleic acids for expressing a full-length protein (e.g., full-length NF1 protein).

Methods for treating NF1 associated diseases in a subject are provided herein. The methods typically involve administering to a subject an amount (e.g., an effective amount) of a rAAV comprising a nucleic acid for expressing a transgene (e.g., a mini-NF1 protein) in the subject. Alternatively, the methods involve administering to a subject an amount (e.g., an effective amount) of dual rAAVs comprising nucleic acids for expressing a full-length protein (e.g., full-length NF1 protein). Non-limiting NF1 associated diseases include Neurofibromatosis Type I, Neurofibromatosis-Noonan Syndrome, juvenile myelomonocytic leukemia, or Watson syndrome. In some embodiments, the NF1-associated disease is Neurofibromatosis type I.

Methods for treating Neurofibromatosis type I in a subject are provided herein. The methods typically involve administering to a subject an amount (e.g., an effective amount) of a rAAV comprising a nucleic acid for expressing a transgene (e.g., a mini-NF1 protein) in the subject. Alternatively, the methods involve administering to a subject an amount (e.g., an effective amount) of dual rAAVs comprising nucleic acids for expressing a full-length protein (e.g., full-length NF1 protein). In some embodiments, the Neurofibromatosis type I includes skin lesions, bone deformities, benign neurofibroma, tumor on the optic nerve (e.g., optic glioma), malignant peripheral nerve sheath tumors (MPNST), and/or cognitive impairment.

Methods for preventing or treating cognitive impairment associated with NF1 are provided herein. Neurofibromatosis type 1 (NF1) is associated with cognitive dysfunctions in several domains such as executive functioning, language, visual perception, motor skills, social skills, memory and/or attention (see, e.g., Baudon et al., Can the Cognitive Phenotype in Neurofibromatosis Type 1 (NF1) Be Explained by Neuroimaging? A Review, *Front. Neurol.* 10:1373, which is incorporated herein by reference). The methods typical involve administering to a subject an amount (e.g., an effective amount) of a rAAV comprising a nucleic acid for expressing a transgene (e.g., a mini-NF1 protein) in the subject. Alternatively, the method involves administering to a subject an amount (e.g., an effective amount) of dual rAAVs comprising nucleic acids for expressing a full-length protein (e.g., full-length NF1 protein). In some embodiments, the administration results in the delivery of NF1 protein in the central nervous system (CNS). In some embodiments, the administration involves direct injection into the CNS (e.g., via intracranial injection, nerve injection, cerebral spinal fluid (CSF) injection via cerebral lateral ventricles, cisterna *magna* (CM) injection, intrathecal (IT) injection, or intracerebroventricular injection).

In some embodiments, the administration comprises direct injection into the CNS via intrathecal (IT) injection. In some embodiments, the administration comprises direct injection into the CNS via intracerebroventricular injection. In some embodiments, the administration comprises any methods that may be suitable for the method or the isolated nucleic acid disclosed herein.

An "effective amount" or "amount effective" of a rAAV is an amount sufficient to infect a sufficient number of cells of a target tissue in a subject. In some embodiments, a target tissue is nervous system (e.g., neuron cells having loss of function of NF1, etc.) tissue. In some embodiments, a transgene is delivered to neurons (e.g., peripheral neurons such as optic nerve).

An effective amount of a rAAV may be an amount sufficient to have a therapeutic benefit in a subject, e.g., to improve in the subject one or more symptoms of disease, e.g., a symptom of Neurofibromatosis type I (e.g., a disease associated with a mutation of NF1 gene). Examples of mutations in NF1 gene include those described by The Human Gene Mutation Database (HGMD, Institute of Medical Genetics, Cardiff, http://www.hgmd.org), by the Leiden Open Variation Database (LOVD), which are incorporated herein by reference. In some embodiments, the mutations in the NF1 gene include those described in Wu-Chou et al, Genetic diagnosis of neurofibromatosis type 1: targeted next-generation sequencing with Multiple Ligation-Dependent Probe Amplification analysis, Journal of Biomedical Science (2018) 25:72; Yang et al., The investigation for potential modifier genes in patients with neurofibromatosis type 1 based on next-generation sequencing, OncoTargets and Therapy 2018:11 919-932, which are incorporated herein by reference). The effective amount will depend on a variety of factors such as, for example, the species, age, weight, health of the subject, and the tissue to be targeted, and may thus vary among subject and tissue. An effective amount may also depend on the rAAV used.

In some embodiments, the administration results in reduction of tumor burden in a subject in need thereof by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a control subject. In some embodiments, the control subject is a subject in need thereof who is not administered with the rAAV, the dual-AAV vector system, and/or the NF system. In some embodiments, the control subject is a healthy subject.

In some embodiments, the administration results in changes of molecular markers of NF1 signaling pathway. In some embodiments, the changes of the molecular markers of NF1 signaling pathway may reverse the pre-existing neurological deficits associated with NF1. In some embodiments, the changes of the molecular markers of NF1 signaling pathway may prevent neurological deficits associated with NF1. In some embodiments, the molecular markers of NF1 signaling pathway comprise at least pCREB, pSynapsinI, pERK1/2, pDARP32 and tyrosine hydroxylase (TH). In some embodiments, the administration results in an increase of pCREB. In some embodiments, the administration results in a decrease of pERK1/2. In some embodiments, the molecular markers of NF1 signaling pathway can comprise any biological markers that are known or unknown in the art.

In some embodiments, the administration results in changes of molecular markers of NF1 signaling pathway in a subject in need thereof by at least 5%, 10%, 20%, 30%, 40%, 50%, 60%, 70%, 80%, 90%, 100%, or by at least 2-fold, at least 5-fold, at least 10-fold, at least 20-fold, at least 50-fold, at least 100-fold, or at least 1000-fold compared to a subject in need thereof who is not administered.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

Aspects of the disclosure relate to methods for treating Neurofibromatosis type I in a subject in need thereof. In some embodiments, a subject is a mammal, for example a human, mouse, rat, dog, cat, non-human primate, etc. In some embodiments, a subject is a human.

As used herein, the term "treating" refers to the application or administration of a composition (e.g., an isolated nucleic acid or rAAV as described herein) to a subject who exhibits one or more signs or symptoms of Neurofibromatosis type I (e.g., skin lesions, bone deformities, benign neurofibroma, tumor on the optic nerve (e.g., optic glioma), malignant peripheral nerve sheath tumors (MPNST), cognitive impairment, one or more mutations in an NF1 gene, etc.), with the purpose to cure, heal, alleviate, relieve, alter, remedy, ameliorate, improve, or affect the disorder, the symptom of the disease, or the predisposition toward Neurofibromatosis type I.

Alleviating Neurofibromatosis type I includes delaying the development or progression of the disease, or reducing disease severity. Alleviating the disease does not necessarily require curative results. As used therein, "delaying" the development of Neurofibromatosis type I means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

An effective amount may also depend on the mode of administration. For example, targeting a nervous tissue (e.g., peripheral neuron, etc.) tissue by intrastromal administration or subcutaneous injection may require different (e.g., higher or lower) doses, in some cases, than targeting a nervous tissue (e.g., peripheral neuron, etc.) by another method (e.g., systemic administration, topical administration). In some embodiments, intrastromal injection (IS) of rAAV having certain serotypes (e.g., AAV-DJ, AAV9, AAV1, AAVrh10, or AAV9.PHP.eB) mediates efficient transduction of a nervous tissue (e.g., peripheral neuron, etc.). Thus, in some embodiments, the injection is intrastromal injection (IS). In some embodiments, the administration is via injection, optionally via intratumoral injection, etc. In some embodiments, the injection is topical administration (e.g., topical administration to the skin lesion). In some cases, multiple doses of a rAAV are administered.

The rAAVs and/or the NF1 expression system may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs or the NF1 expression to a mammalian subject may be by, for example, local injection to the affected tissues (e.g., CNS, brain, skin, optical nerve, peripheral nerve tumor or optic glioma tissue). Combinations of administration methods (e.g., topical administration to the skin and injection to the optical nerve) can also be used.

The compositions of the disclosure may comprise administering a rAAV (e.g., a mini-NF1) alone, or in combination with one or more other viruses (e.g., a second rAAV encoding having one or more different transgenes, such as a transgene encoding a different mini-NF1 protein). In some embodiments, the method may comprise administering a NF1 expression system alone, or in combination with one or more other viruses (e.g., an additional rAAV encoding having one or more different transgenes, such as a transgene encoding a mini-NF1 protein). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline).

Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect the cells of a desired tissue (e.g., nervous tissue, such as optical nerve, etc., tissue) and to provide sufficient levels of gene transfer and expression without undue adverse effects. Examples of pharmaceutically acceptable routes of administration include, but are not limited to, direct delivery to the selected organ (e.g., delivery to the optical nerve, skin or peripheral nerve tumors), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

An effective amount of a rAAV is an amount sufficient to target infect an animal, target a desired tissue. The effective amount will depend primarily on factors such as the species, age, weight, health of the subject, and the tissue to be targeted, and may thus vary among animal and tissue. For example, an effective amount of the rAAV is generally in the range of from about 1 mL to about 100 mL of solution containing from about $10^9$ to $10^{16}$ genome copies. In some cases, a dosage between about $10^{11}$ to $10^{13}$ rAAV genome copies is appropriate. In certain embodiments, $10^9$rAAV genome copies is effective to target diseased tissue (e.g., skin tissue). In some embodiments, a dose more concentrated than $10^9$ rAAV genome copies is toxic when administered to a subject. In some embodiments, an effective amount is produced by multiple doses of a rAAV.

In some embodiments, delivery of the NF1 expression system involves co-delivery of the 5' and the 3' rAAV such that the target cell can express a full-length NFL In some embodiments, the effective amount of the NF1 expression system sufficient to infect a target cell may be higher than delivering a single rAAV. For example, an effective amount of the NF1 expression system maybe in the range of from about 1 ml to about 100 ml of solution containing from about $10^{13}$ to $10^{16}$ genome copies for each of the 5' rAAV and the 3' rAAV. In some cases, a dosage between about $10^{11}$ to $10^{13}$ rAAV genome copies is appropriate. In some embodiments, an effective amount is produced by multiple doses of the 5' rAAV and the 3' rAAV.

In some embodiments, a dose of rAAV or the NF1 expression system is administered to a subject no more than once per calendar day (e.g., a 24-hour period). In some embodiments, a dose of rAAV or the NF1 expression system is administered to a subject no more than once per 2, 3, 4, 5, 6, or 7 calendar days. In some embodiments, a dose of rAAV or the NF1 expression system is administered to a subject no more than once per calendar week (e.g., 7 calendar days). In some embodiments, a dose of rAAV or the NF1 expression system is administered to a subject no more than bi-weekly (e.g., once in a two-calendar week period). In some embodiments, a dose of rAAV or the NF1 expression system is administered to a subject no more than once per calendar month (e.g., once in 30 calendar days). In some embodiments, a dose of rAAV or the NF1 expression system is administered to a subject no more than once per six calendar months. In some embodiments, a dose of rAAV or the NF1 expression system is administered to a subject no more than once per calendar year (e.g., 365 days or 366 days in a leap year).

In some embodiments, rAAV or the NF1 expression system compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright FR, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

EXAMPLES

Example 1: Design and Testing of Gene Expression Constructs

Neurofibromatosis type I (NF1) is caused by sporadic or inherited germline mutations in the NF1 gene. Sporadic loss of the remaining wild-type allele is associated with skin lesions and benign neurofibromas, which develop along peripheral nerves. Malignant complications include optic pathway gliomas and malignant peripheral nerve sheath tumors (MPNST). In addition, NF1 haploinsufficiency can cause cognitive deficits and NF1 deficiency plays an important supporting role in tumor formation. Treatment options are limited. However, genetic interventions using recombinant adeno-associated virus (AAV) vectors and antisense oligonucleotide (ASO) drugs have begun to yield transformative outcomes in patients afflicted with other devastating inherited neurological diseases such as Spinal Muscular Atrophy. The NF1 protein is a GTPase-activating protein (GAP) that inactivates Ras through activation of GTP to GDP hydrolysis. Loss of NF1 GAP function leaves Ras in the activated state (Ras-GTP), which leads to over-activation of RAS signaling pathway (RAF-MEK-ERK). Ras activation stimulates cell growth and most often formation of benign tumors that often times progress to malignancies such as MPNSTs and optic gliomas. NF1 patients also show cognitive deficits, suggesting that NF1 plays an important role in normal neuronal function. The NF1 coding sequence is 8,540 bp, far exceeding the packaging capacity of recombinant AAV vectors. Two approaches were explored in order to restore normal NF1 function using AAV-mediated gene therapy. One is to develop a dual AAV vector system to restore full length NF1 expression through trans-splicing of genomes in transduced cells, and the other is to develop minimal NF1 proteins (mini-NF1) capable of regulating the Ras pathway, and at the same time, small enough to be packaged into a single AAV vector. The NF1 GAP-related domain (GRD) has been shown to be sufficient to restore normal growth of various $NF1^{-/-}$ cell types, including MPNSTs. It is possible that a mini-NF1 containing only the GRD domain and additional modifications is sufficient to restore regulation of Ras in MPNST cell lines (e.g., Bai et al., Feasibility of using NF1-GRD and AAV for gene replacement therapy, Gene Therapy volume 26, pages 277-286(2019)). In Bai et al, it was discovered that the most effective mini-NF1 was one where the GRD was fused to ten amino acids (GCMSCKCVLS (SEQ ID NO: 32)) from the H-Ras C-terminal. The present disclosure has taken a different approach to engineer a minimal NF1 gene by adding additional NF1 domains to the minimal GRD.

Figure 1B:
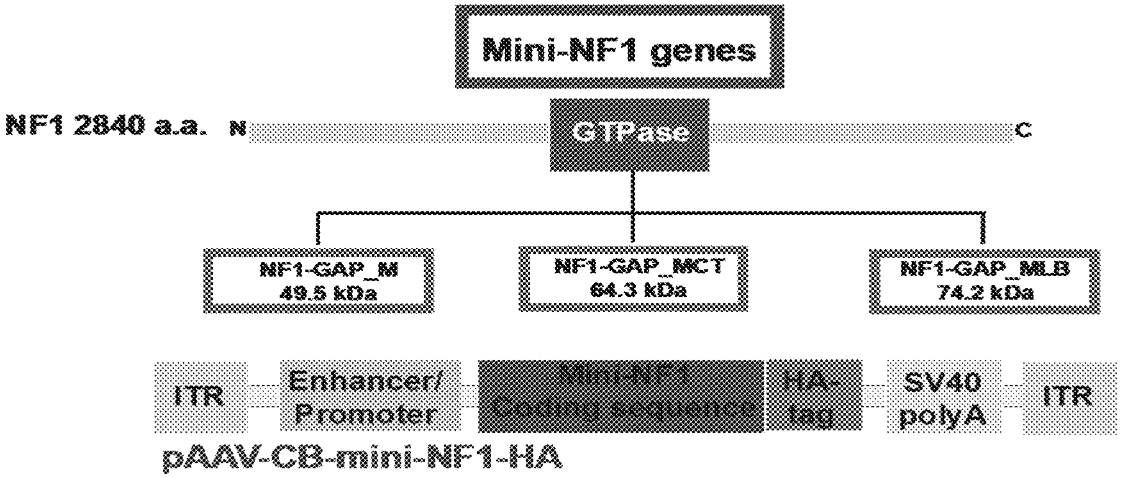
Figure 1C:
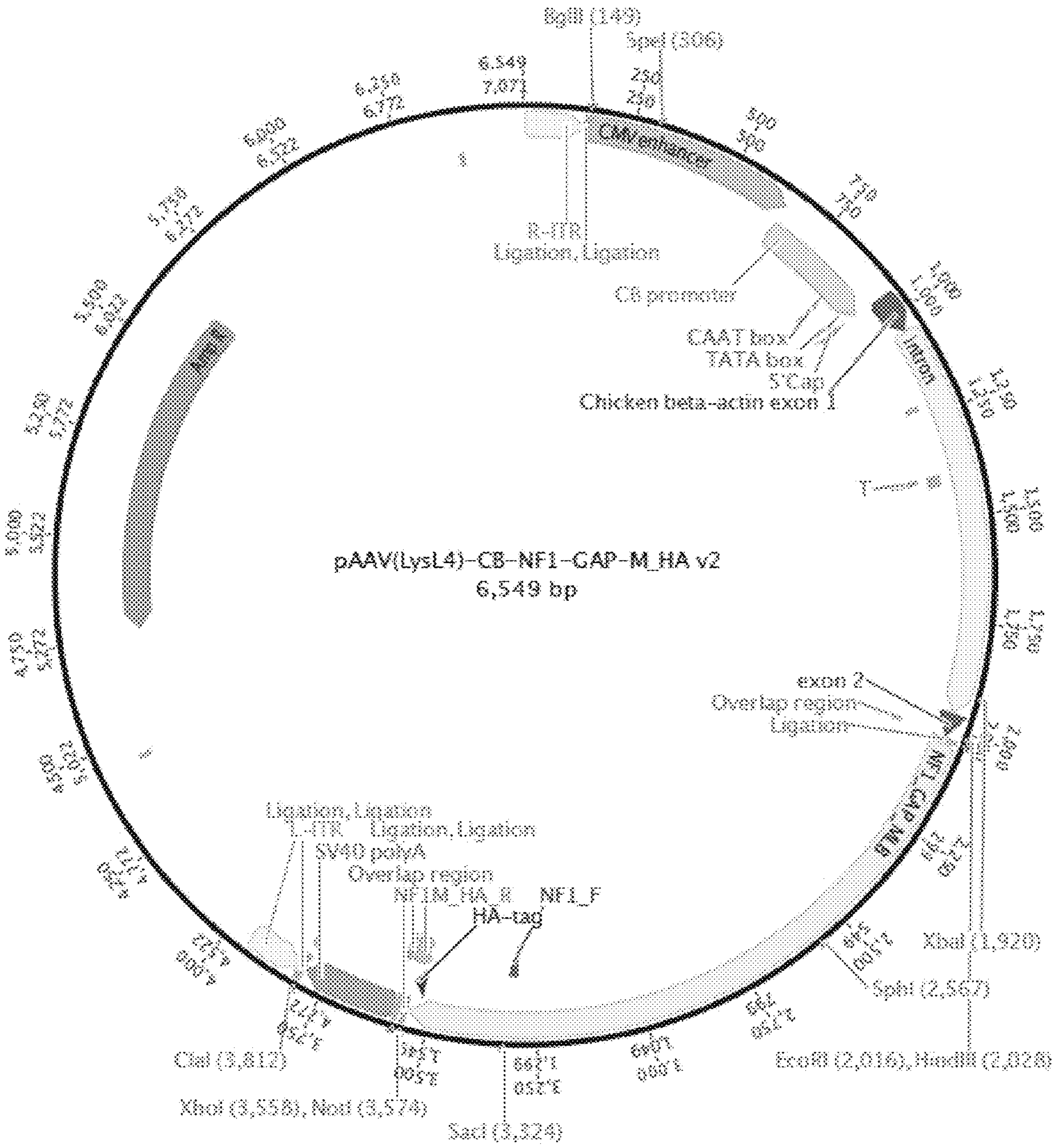
Figure 1D:
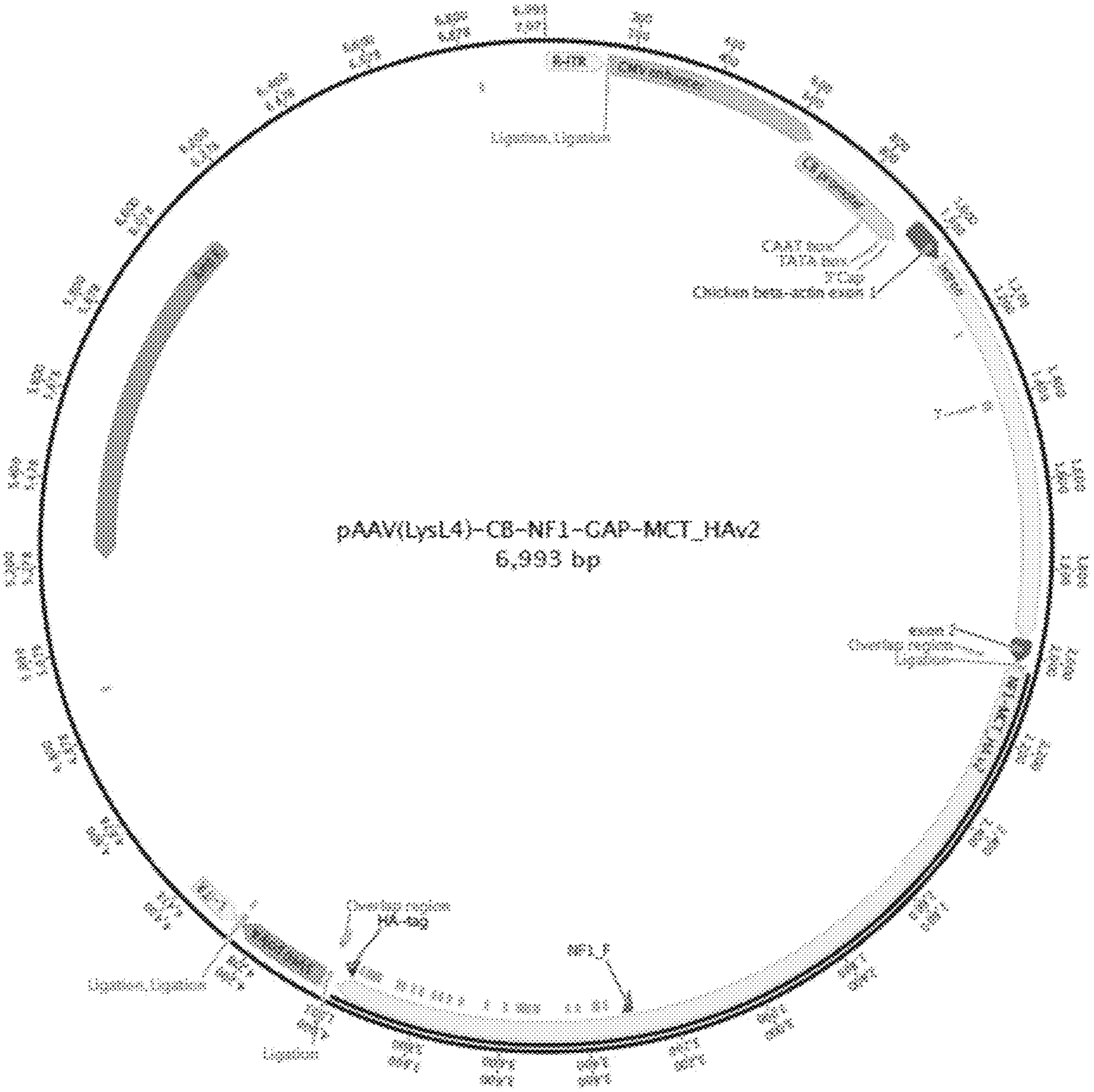
Figure 1E:
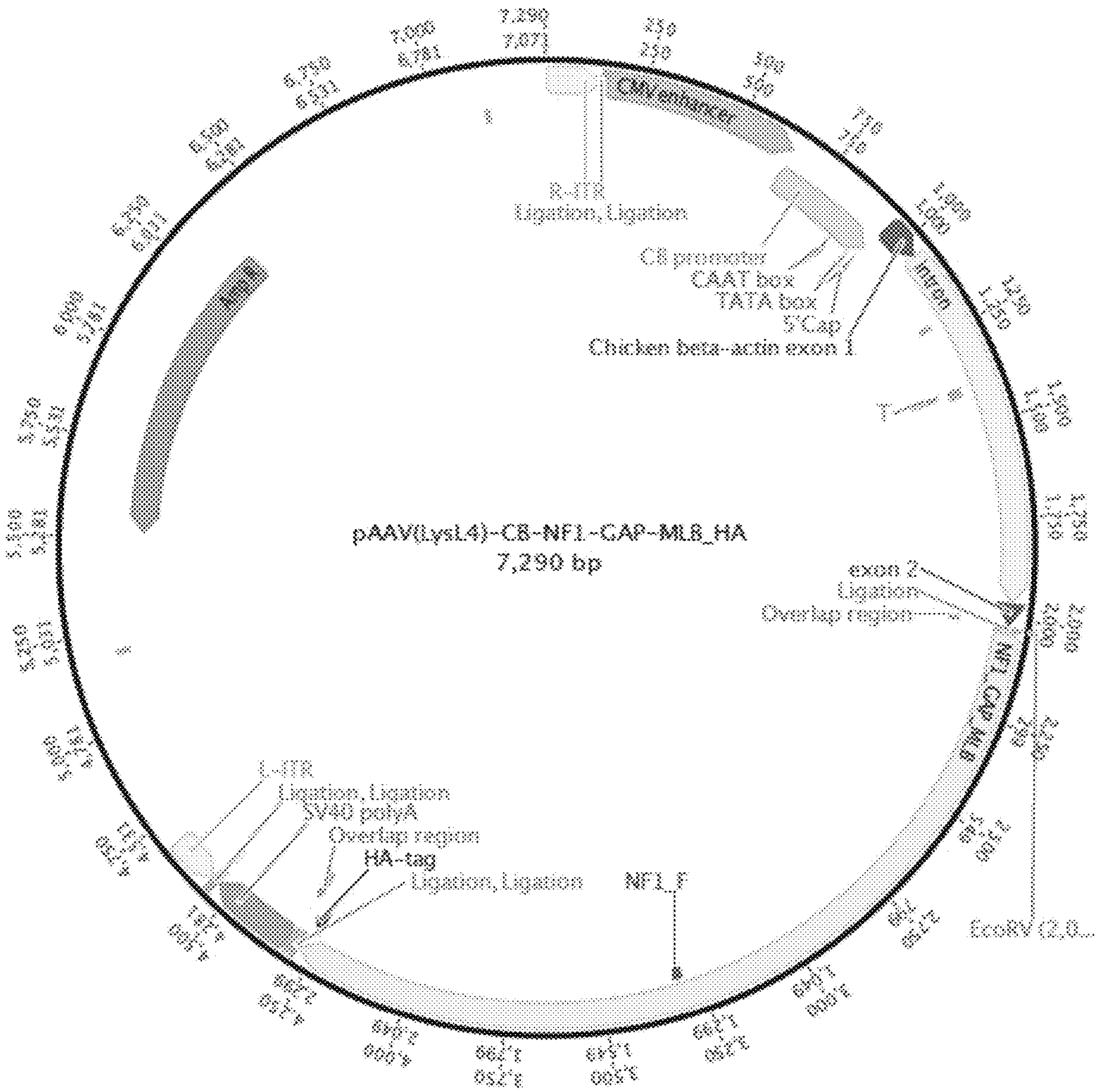
Figure 1F:
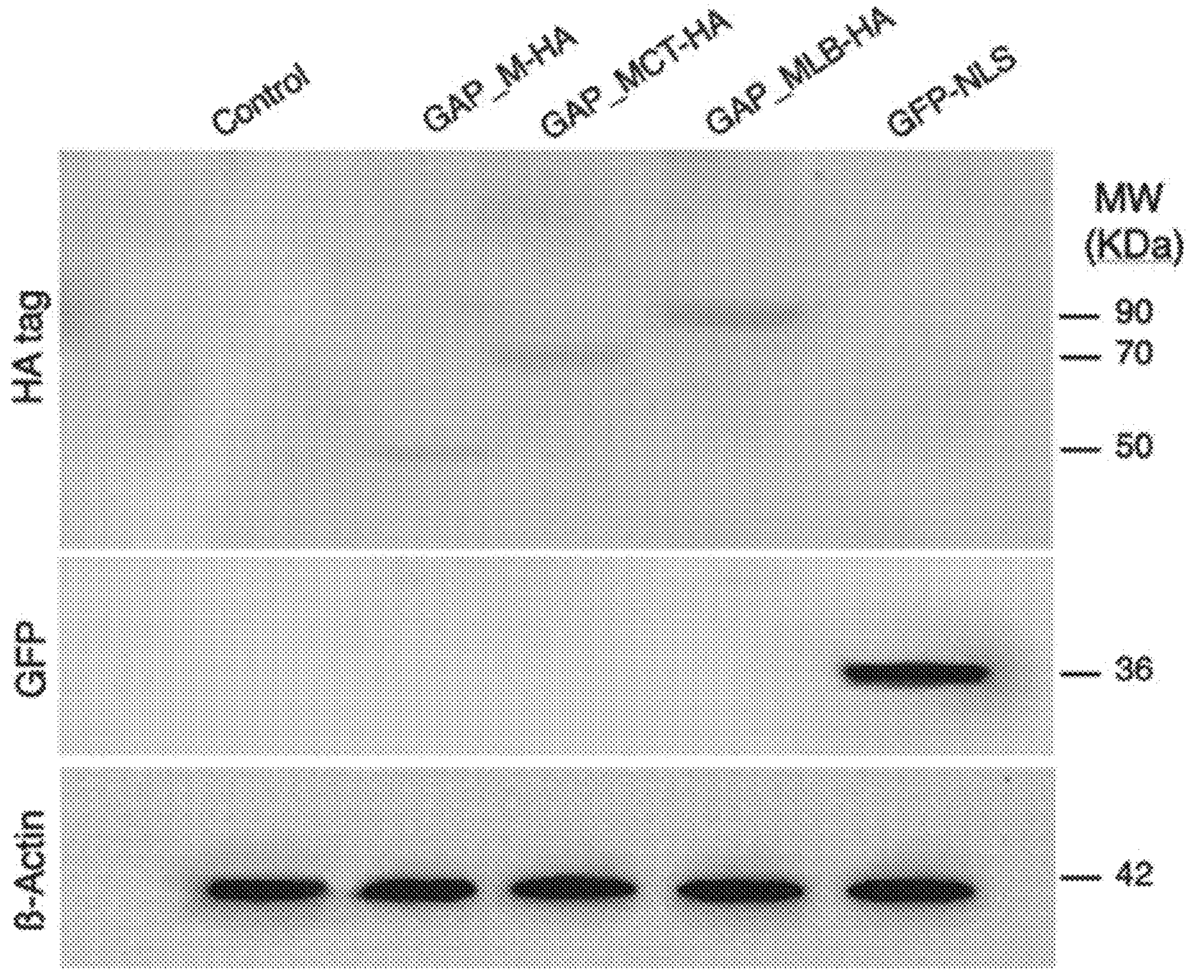

AAV vectors encoding three different mini-NF1 genes (FIG. 1A) were constructed: (i) a small version containing NF1-GRD only (NF1-GAP_M); (ii) a second version which extends the mini-NF1 coding sequence to the CRAL-TRIO domain (NF1-GAP_MCT); and (iii) a third version which extends the NF1 coding sequence to the end of the bipartite phospholipid binding domain (NF1-GAP_MLB), which is composed of a Sec14p homologous segment and a pleckstrin homology (PH)-like domain. All three mini-NF1 genes carry an HA-tag epitope fused to the C-terminus to allow detection by western blot and histologically. All three genes were codon optimized for expression in human cells, synthesized and cloned into a single stranded AAV vector genome driving gene expression from a CBA promoter, and an HA tag at the C-terminus (FIG. 1B). The lipid binding/interacting domains (CRAL-TRIO and bipartite Sec-PH) were included in the third mini-NF1 genes as interaction with Ras occurs at the cell membrane and lipid binding may be important for that interaction. AAV-DJ viron stocks were prepared and tested in HEK293T cells for protein expression. The rAAV vector maps encoding each of the mini-NF1 are show in FIGS. 1C-1E. As expected, 72 hours after infection, HEK293T cells transduced with AAV-DJ virons encoding HA-tagged NF1-GAP transgenes expressed HA-positive proteins of the expected sizes of~50, 70 and 90 KDa. (FIG. 1F).

Figure 2A:
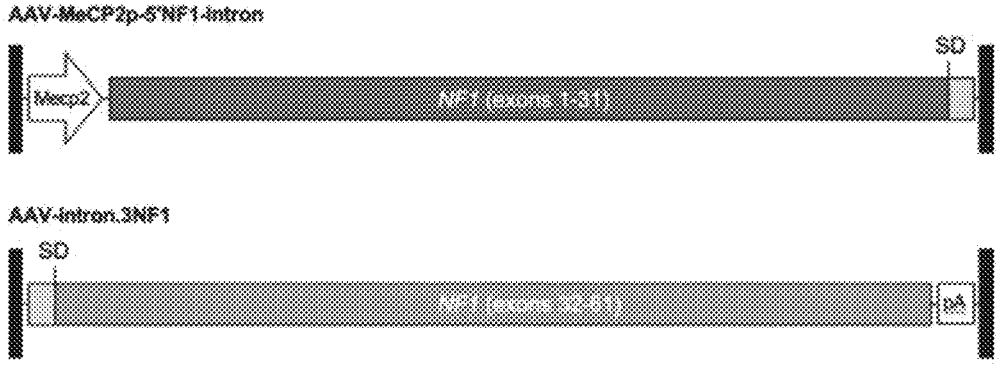
FIGS. 2A-2F show dual-AAV vector system for full-length NF1 expression.
Figure 2B:
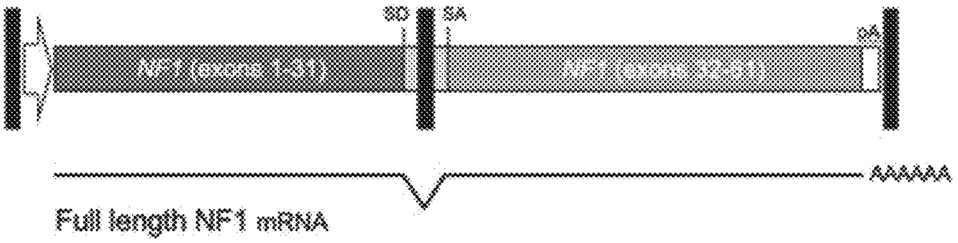
Figure 2C:
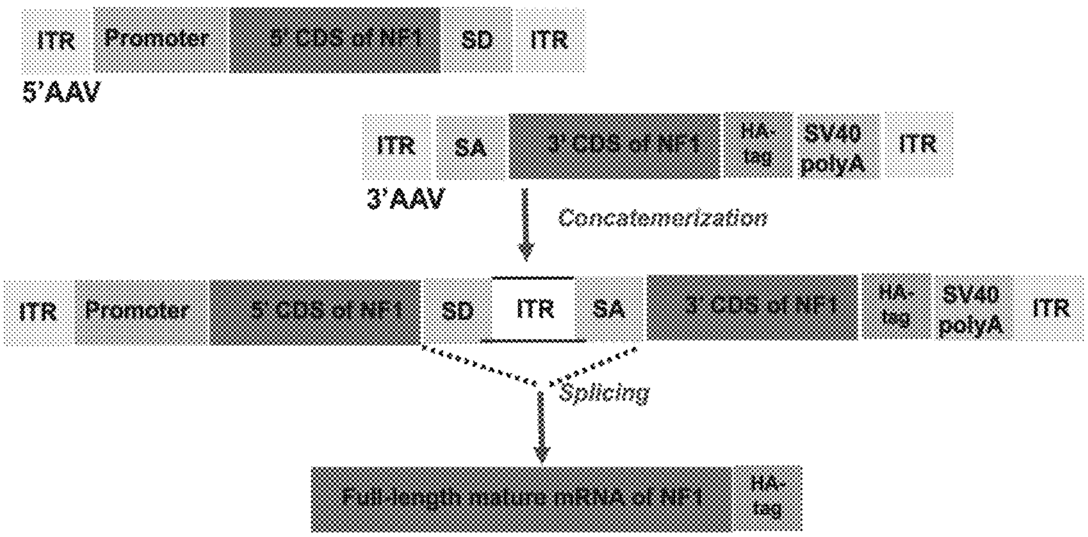
Figure 2D:
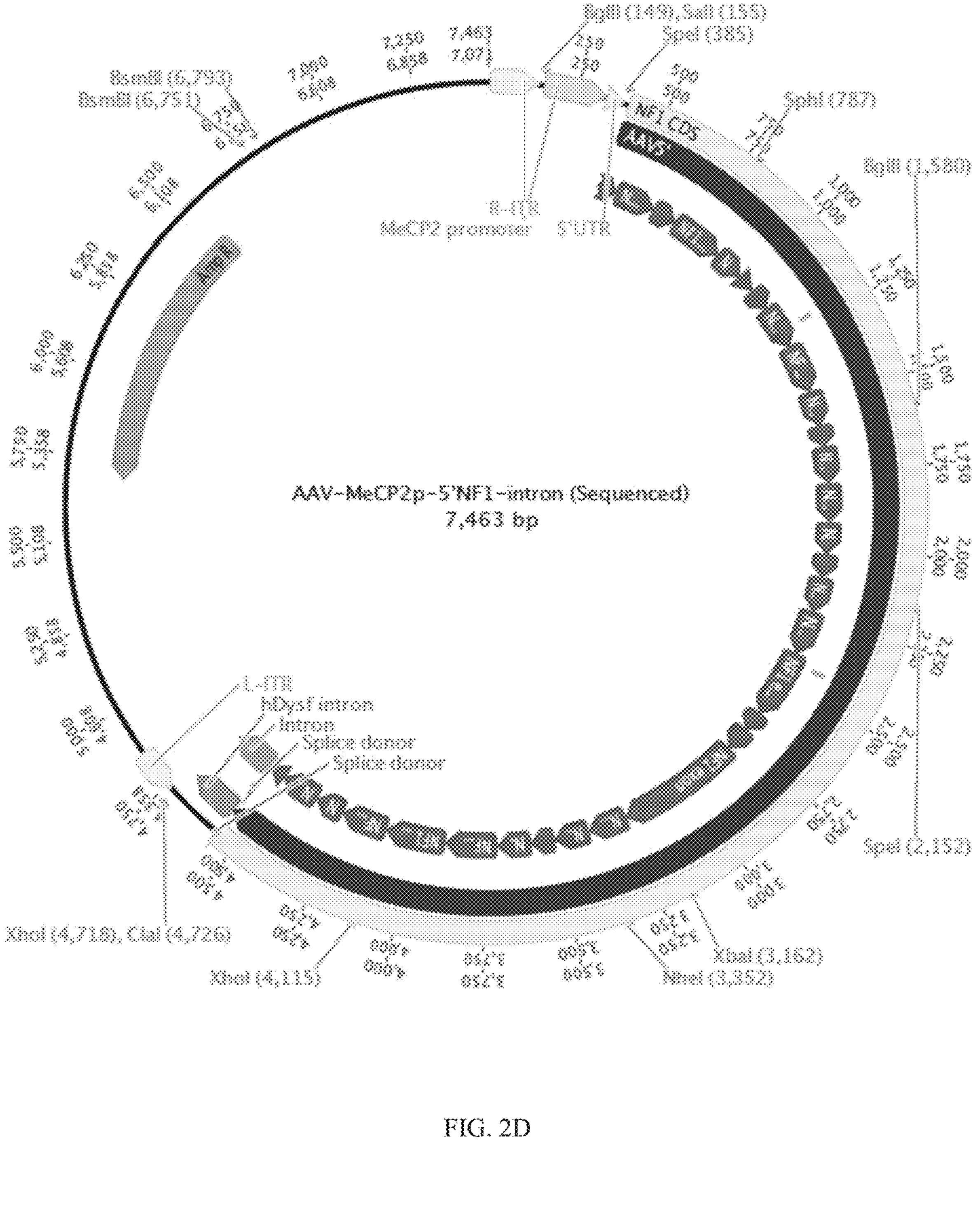
Figure 2E:
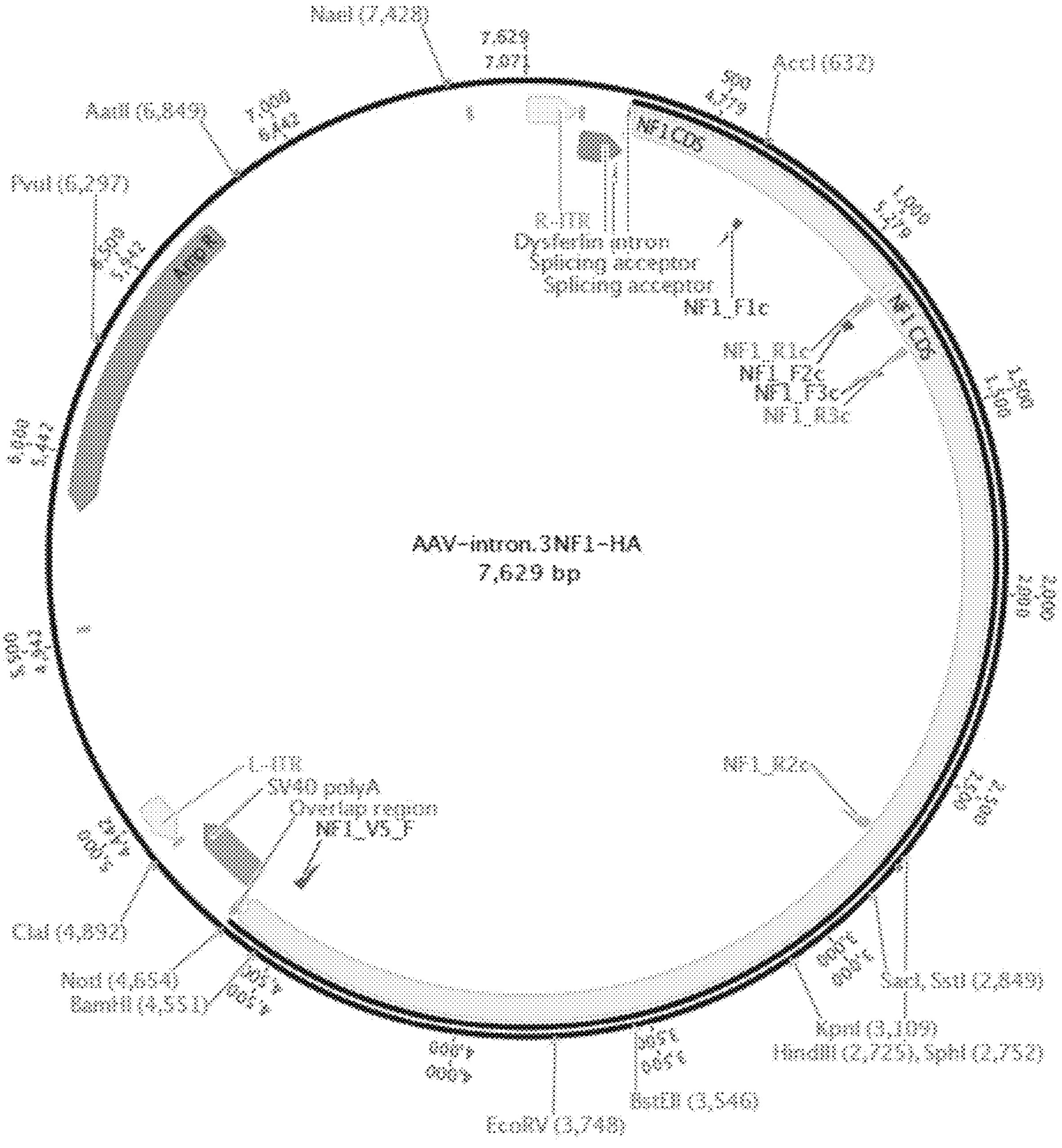
Figure 2F:
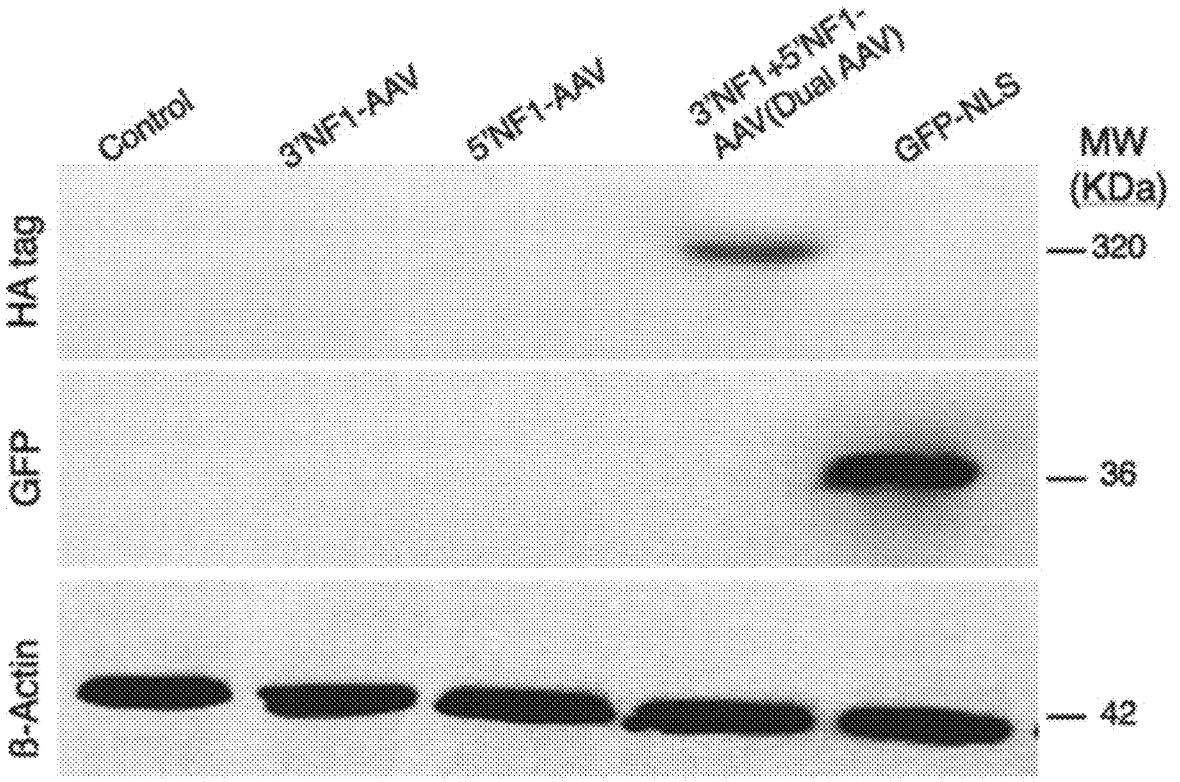

Alternatively, a dual AAV vector system comprised of AAV-MeCP2p-5'NF1-intron and AAV-intron.3'NF1 was designed, for expression of full length human NF1 after concatemerization in the nucleus of doubly infected target cells. As shown in FIG. 2A, in 5' AAV vector consists of a small ubiquitous promoter (e.g., short mouse Mecp2 promoter), 5' sequence of NF1 cDNA (e.g., exons 1-31 of NF1 gene) and a splice donor (SD) signal from NF1 intronic sequences (AAV-MeCP2p-5'NF1-intron vector). The 3' AAV vector consists of splice acceptor (SA) also from NF1 intronic sequences, 3' sequence of NF1 cDNA (e.g., exon 32-81 of NF1 gene) and HA-tag before the ployA signal from SV40 (AAV-intron.3NF1). After both rAAVs that encode each of the two parts of the transgenes are delivered to the same cell, concatemerization of the right side ITR of the 5' vector and left side ITR of the 3' vector reconstitutes the full-length NF1 gene. After transcription, trans-splicing leads to the removal of the ITR structure formed at the middle, which in-turn restores the mature RNA of the transgene (FIGS. 2B-2C). The rAAV vector maps encoding the first and the second portion of NF-1 protein are shown in FIGS. 2D-2E. AAV-DJ virons stocks were produced for each of the two vectors and were tested in HEK293T cells infected with each vector alone, or both vectors simultaneously. As anticipated, expression of a large ~320 KDa HA-positive protein was documented only in cells transduced with both AAV-DJ vectors (FIG. 2F).

Figure 3A:
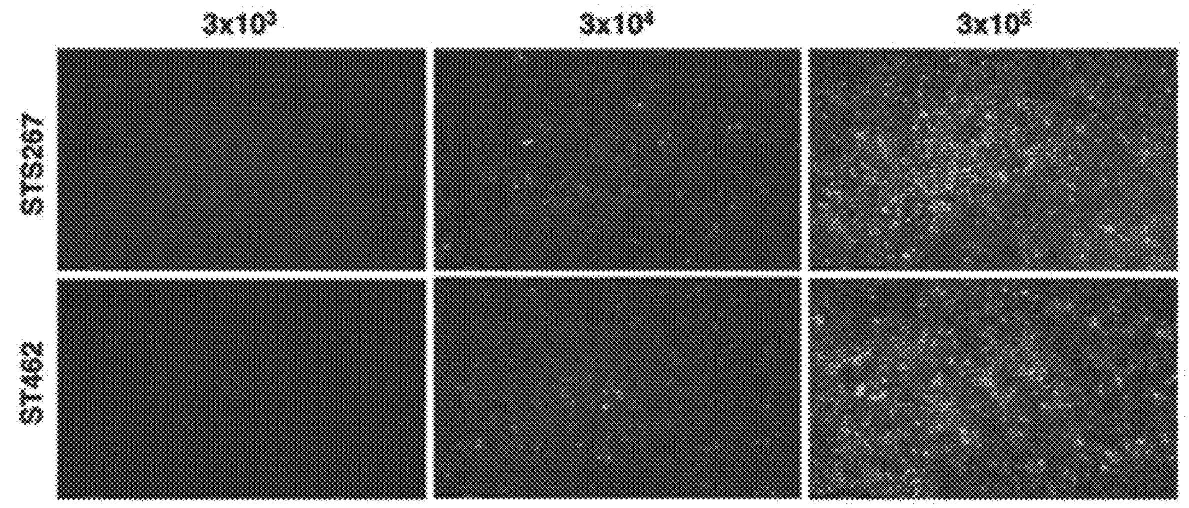
FIGS. 3A-3C are graphs showing that transduction of human MPNST cell lines (ST267 and ST642) with AAV-NF1 vectors reduced Ras pathway activity.
Figure 3B:
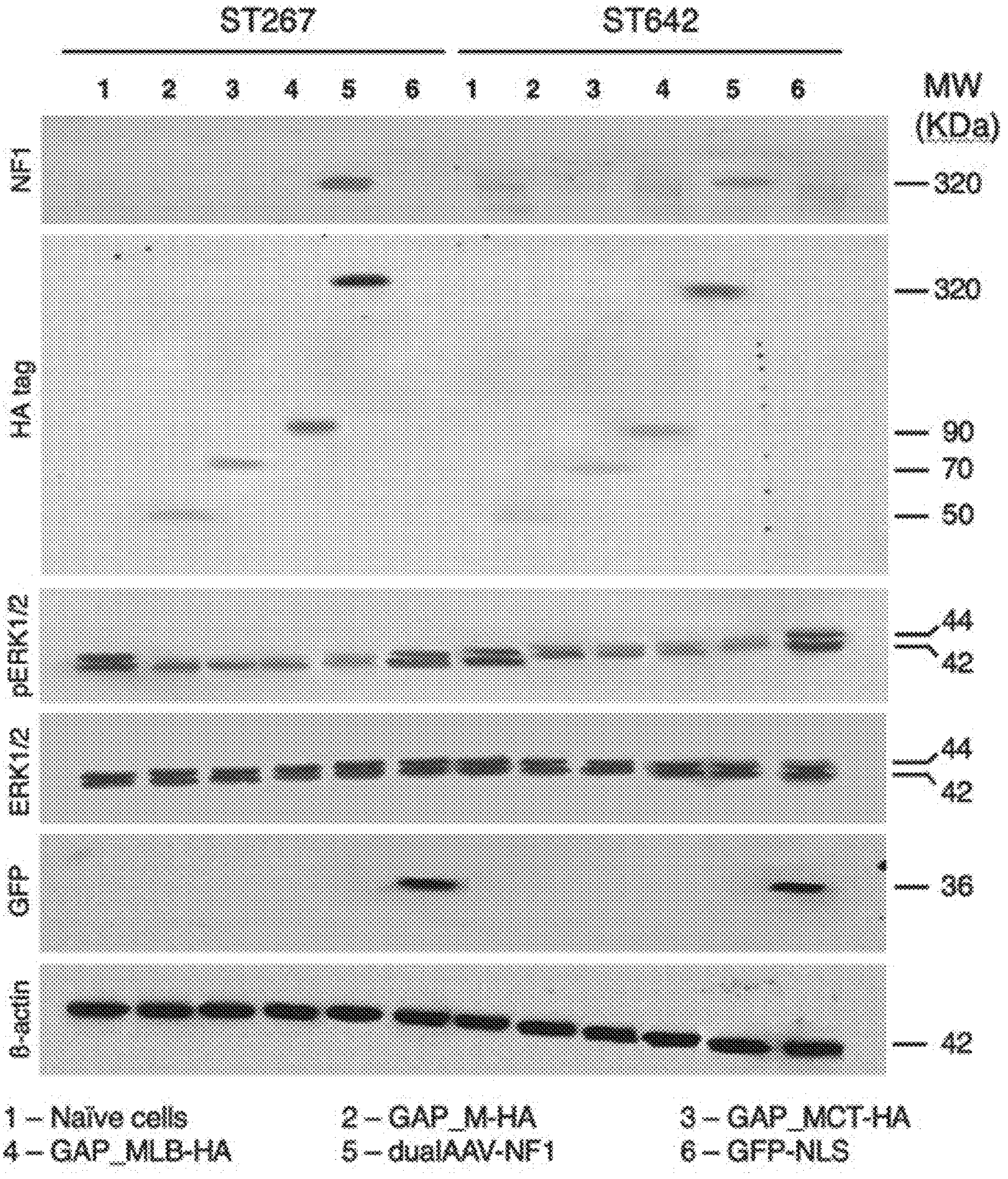
Figure 3C:
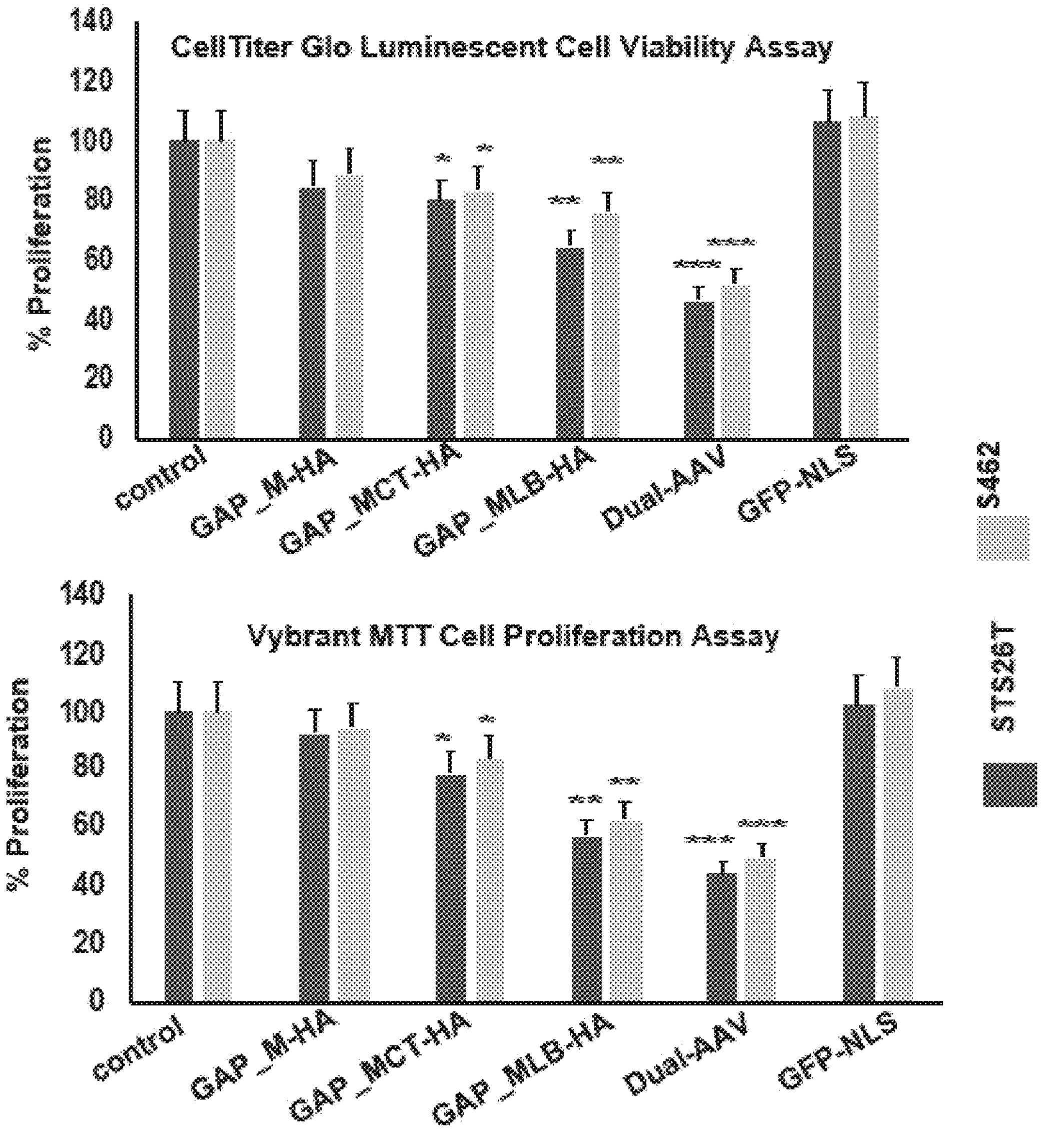

The functionality of the new mini-NF1 genes and the dual AAV-NF1 vector system was tested in human malignant peripheral nerve sheath tumor (MPNST) cell lines for their ability to decrease the activity of the Ras pathway. In the absence of NF1, the Ras pathway is overactive and several downstream signaling mediators are continually activated, through phosphorylation, as evidenced by phospho-ERK1/2 (pERK1/2). Two human MPNST cell lines, ST267 and ST642, were used to assess the ability of mini-NF1 proteins and the dual AAV-NF1 vector system to regulate the Ras pathway by indirectly measuring changes in pERK1/2 levels by western blot. A dose escalation study with a GFP-NLS encoding vector showed the transduction efficiency of AAV-DJ to be comparable for both ST267 and ST642 cell lines (FIG. 3A). Western blot analysis of ST267 and ST642 cells transduced with AAV-DJ vectors encoding mini-NF1s, or dualAAV-NF1 vector system showed expression of appropriately sized HA-tagged proteins, and also full length NF1 protein (FIG. 3B). Detection with an anti-NF1 antibody was only possible for the full length NF1 protein because the antibody was raised against an epitope in the N-terminus of full length NF1, which is absent in the mini-NF1 proteins (FIG. 1A). Expression of mini-NF1 proteins and full length NF1 decreased the levels of p-ERK1/2 compared to controls (naïve cells and cells infected with AAV-DJ vector encoding GFP-NLS), while the total levels of ERK1/2 protein remained unchanged across experimental groups (FIG. 3B). In addition, over-activation of Ras signaling pathway also leads to cell proliferation. Expression of mini-NF1 proteins and full length NF1 decreased ST267 and ST642 cell proliferation rate compared to controls (naïve cells and cells infected with AAV-DJ vector encoding GFP-NLS) (FIG. 3C). These data indicate that AAV expressed mini-NF1 and full length NF1 are biologically active in regulating the Ras pathway. Further, in vivo studies are conducted in $Nf1^{+/-}$ mice to assess expression levels, spatial distribution and functionality of the mini-NF1 proteins, and dual AAV NF1 expression system after systemic delivery of AAV-PHP.eB-NF1 virons.

Example 2: Effects of AAV-NF1 Gene Therapy in $Nf1^{Arg681*}$; DhhCre Mice

To determine the effects of the AAV-NF1 gene therapy in vivo, Four $Nf1^{Arg681*}$; DhhCre mice (3 females numbered 001, 002, 003, and one male numbered 613) were used for conducting an assessment of the impact of AAV-NF1 gene therapy on tumor burden in these mice. Tumor burden in each $Nf1^{Arg681*}$; DhhCre mouse was assessed in the 3T MRI focusing on the spinal cord, particularly in the cervical and thoracic regions. T2-weighted images were collected which displayed the tumors as hyperintensities compared to the spinal cord.

One week after MRI, mice were injected intrathecally with AAV vectors. Two mice (mouse Nos. 003 and 613) were treated with $1\times10^{12}$ vg AAV-PHP.eB-GAP_MLB-HA (mini-NF1). The other two mice (mouse Nos. 001 and 002) were treated with $1\times10^{12}$ vg dual-AAVs (5'NF1 AAV+3'NF1-HA AAV). Tumor burden in these AAV treated $Nf1^{Arg681*}$; DhhCre mice was assessed again at one month after treatment. For volumetric analysis of pre-treated and post-treated tumors, the images were normalized relative to the normal part of the spine with no tumors. The thresholding was applied to isolate the tumors from the image. This thresholding was based on the normalized intensity which captures the proton relaxation or proton density. Anything greater than 1 mm was recognized as a tumor.

Figure 4A:
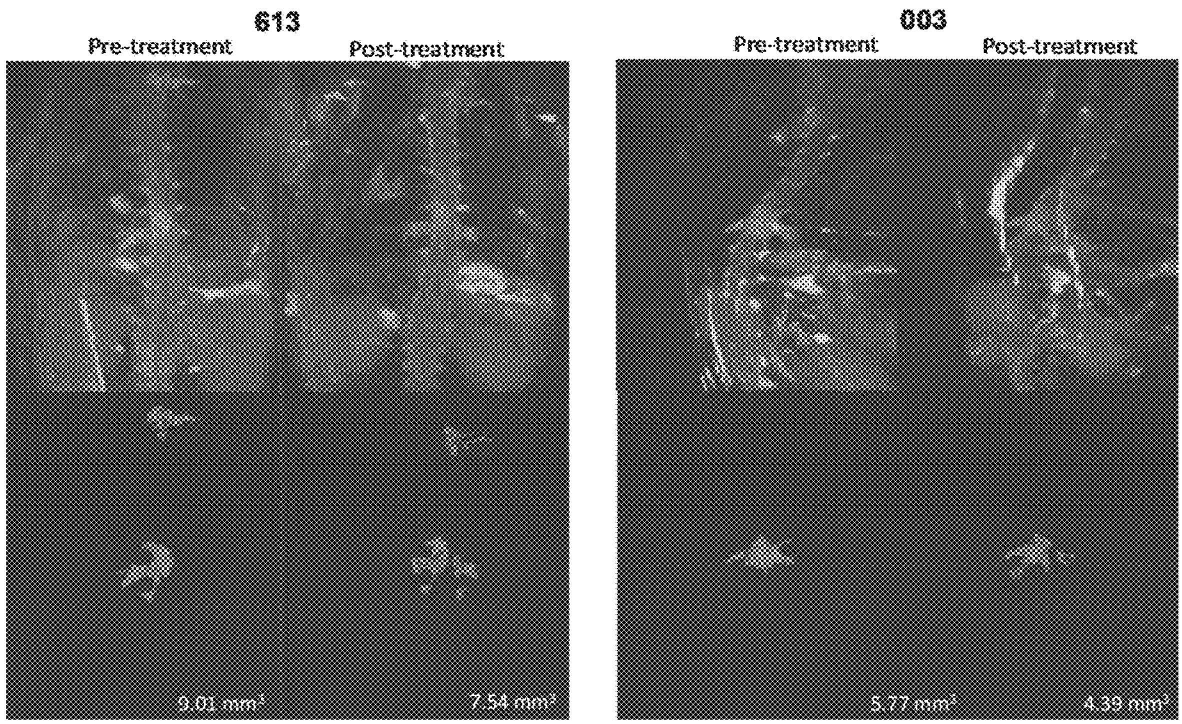
FIGS. 4A-4B show MRI detection of tumors in the spinal cord of $Nf1^{Arg681*}$; DhhCre mice.
Figure 4B:
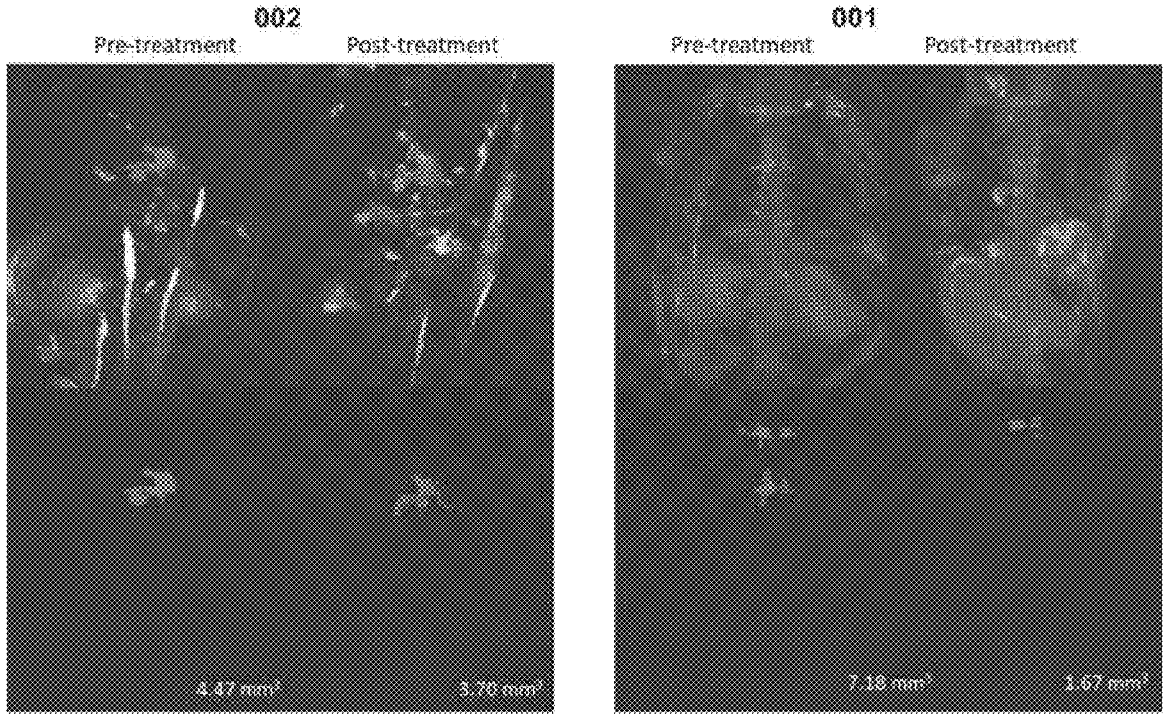

The scanned MRI image revealed a decrease of 16.3% and 23.9% in tumor burden in mice treated with mini-NF1 vector (mouse Nos. 613 and 003) (FIG. 4A). Interestingly, the scanned MRI image revealed a decrease of 17.22% and 76.7% in tumor burden in mice (mouse Nos. 002 and 001) treated with dual-AAV vectors (FIG. 4B). These mice remained alive even after untreated $Nf1^{Arg681*}$; DhhCre reached the humane endpoint (due to hindlimb paralysis) about 5 months of age.

Example 3: Determination of Molecular Markers of Neurobehavior Disease in Neurofibromatosis Type I (NF1)

To evaluate the expression of the potential molecular markers in vivo, $Nf1^{+/-}$ mice were treated with AAV-NF1 vectors at 6-8 weeks of age by systemic delivery (Table 2) and neonatal intracerebroventricular injection (Table 3). Behavioral tests will be conducted on $Nf1^{+/-}$ and wild type mice in the Morris water maze using a developed protocol.

TABLE 2

$Nf1^{+/-}$ male mice treated at 6-8 weeks of age by systemic delivery of AAV-NF1 vectors

| | WT | Group A | Group B | Group C |
|---|---|---|---|---|
| No. of animals | 12 | 12 | 12 | 12 |

TABLE 3

$Nf1^{+/-}$ mice treated at post-natal day 1 by intracerebroventricular injection of AAV-NF1 vectors

| | AAV Mini-NF1 (encoding NF1-GAP_MLB) | Dual-AAV-NF1 |
|---|---|---|
| No. of animals | 28 | 14 |

Upon completion of behavioral testing on the mice, various parameters in the CNS including western blot analysis of several proteins previously shown to be altered in the $Nf1^{+/-}$ mouse brain will be assessed. The western blot conditions for those proteins, which can be considered molecular markers of neurobehavior disease in NF1, were optimized.

Figure 5:
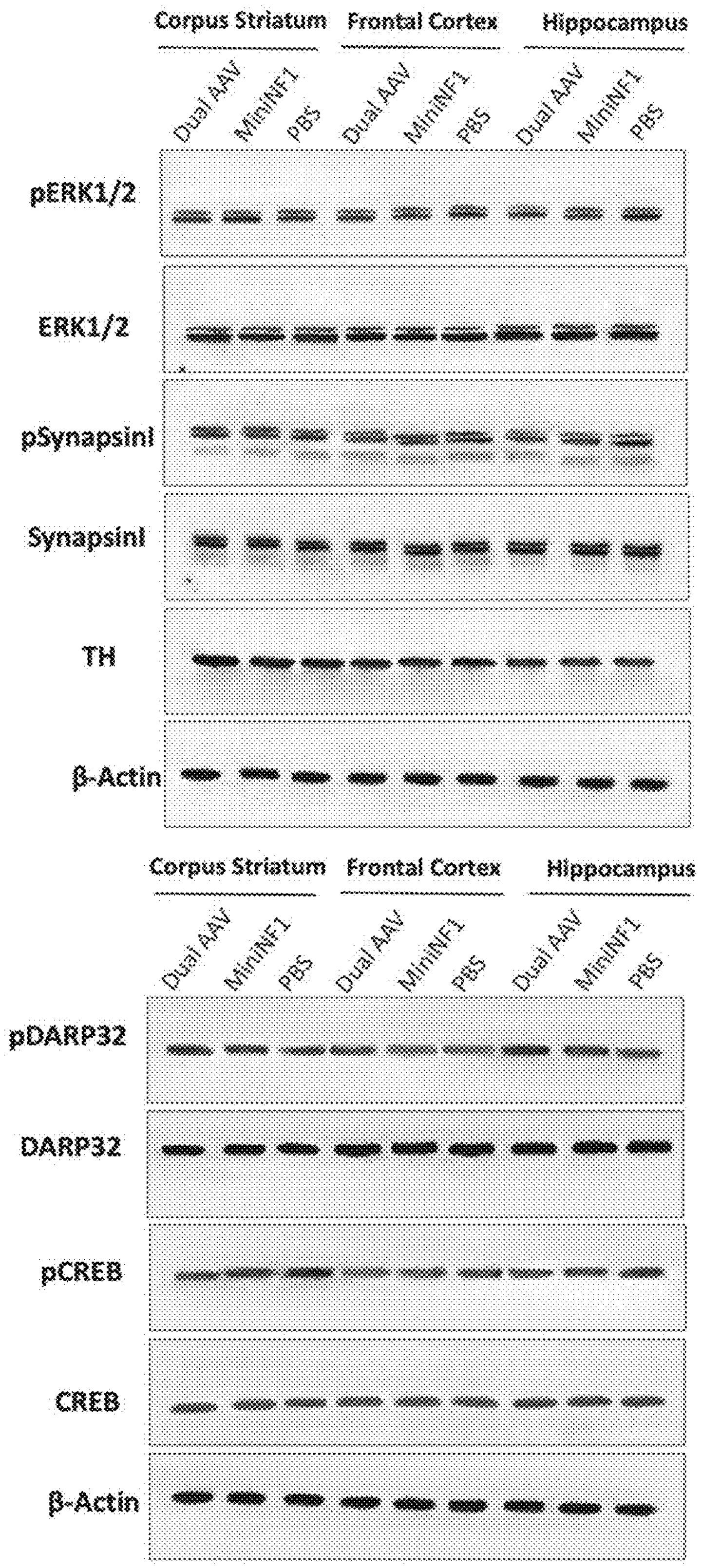
FIG. 5 shows western blot analysis of selected molecular markers of NF1 signaling in mice that were injected with PBS, $1\times10^{12}$ vg AAV-PHP.eB-GAP_MLB-HA, or $1\times10^{12}$ vg dual AAV(5'NF1+3'NF1-HA).

The lead candidates AAV-mini-NF1, encoding NF1-GAP_MLB, and the trans splicing dual-AAV-NF1 vector system, were previously tested in normal C57BL/6 for their ability to express NF1 in the CNS and peripheral tissues after systemic delivery as AAV-PHP.eB vectors. Mice received tail vein injections of vehicle (PBS; group 1), $1\times10^{12}$ vg AAV-PHP.eB-GAP_MLB-HA (group 2; Mini-NF1) or $1\times10^{12}$ vg dual-AAV(dual AAV; 5'NF1+3'NF1-HA) (group 3) vectors. Mice were euthanized at 4 weeks post-infusion and the following brain parts were collected: hippocampus, frontal cortex and corpus striatum, regions which are involved with cognition deficits and behavioral problems related to NF1 disease and tissue lysates were prepared for Western blot analysis. As these mice represented normal mice expressing normal levels of neurofibromin, expression of various neurobehavioral markers such as pERK1/2, pSynapsinI, pCREB, pDARP32 and tyrosine hydroxylase (TH) assessed (FIG. 5). The expression of phosphorylated proteins was normalized against the total protein using anti-ERK1/2, anti-SynapsinI, anti-CREB and anti-DARP32 antibodies. The anti-β-actin antibody was used as loading control throughout the validation process. Expression of all protein markers in the analyzed brain structures in animals from all three groups was observed. Changes in phosphorylated forms of various marker proteins expected after increased expression of NF1 (AAV treated groups) was observed, such as decrease in pERK1/2 and increase in pCREB in various structures with no changes in total protein. These encouraging results indicate that sufficient CNS transduction was obtained to change the levels of downstream NF1 signaling targets, especially ones that correlate with neurobehavior disease in NFL As part of the follow-up studies, $Nf1^{+/-}$ mice treated systemically with AAV-PHP.eB-$NF1^{dual}$ system for determining the efficacy of prevention, or reversal, of neurological deficits caused by NF1 gene mutations. Specifically, systemic delivery of high dose AAV-PHP.eB-$NF1^{dual}$ in $Nf1^{+/-}$, $Nf1^{+/-}/p53^{+/-}$ (cis); $Nf1^{+/-}/p53^{+/-}/Suz12^{+/-}$ (cis) mice at 4 weeks of age will be conducted. NF1 expression and cell signaling in CNS and peripheral nerve at 4, 8 and 12 months of age (or humane endpoint) will be assessed, and correlative neuropathologic evaluation will be conducted. Longitudinal assessment of neurological function and survival to 1 year of age will be conducted.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. The terms "about" and "substantially" preceding a numerical value represent ±10% of the recited numerical value.

---

What is claimed is:

1. An isolated nucleic acid comprising a transgene, wherein the transgene comprises a nucleotide sequence encoding a mini-neurofibromin (mini-NF1) protein comprising a GTPase-activating protein (GAP)-related domain (GRD) comprising the amino acid sequence set forth in SEQ ID NO:1, and wherein the transgene is flanked by adeno-associated virus (AAV) inverted terminal repeats (ITRs).

2. The isolated nucleic acid of claim 1, wherein the transgene further comprises a promoter operably linked to the nucleotide sequence encoding the mini-NF1 protein.

3. The isolated nucleic acid of claim 2, wherein the promoter is a constitutive promoter, an inducible promoter, or a minimal promoter.

4. The isolated nucleic acid of claim 2, wherein the promoter is a chicken B-actin (CBA) promoter, a CAG promoter, a short Mecp2 promoter, a mini-CMV promoter, or a jet promoter.

5. The isolated nucleic acid of claim 1, wherein the mini-NF1 protein further comprises:

a CRAL-TRIO domain, or a bipartite phospholipid binding domain.

6. The isolated nucleic acid of claim 5, wherein the mini-NF comprises the amino acid sequence of SEQ ID NO: 3 or 5.

7. The isolated nucleic acid of claim 1, wherein the nucleotide sequence encoding the mini-NF comprises a nucleotide sequence at least 80% identical to any one of SEQ ID NOs: 2, 4, or 6.

8. The isolated nucleic acid of claim 1, wherein the ITRs are adeno-associated virus ITRs of a serotype selected from the group consisting of AAV1 ITR, AAV2 ITR, AAV3 ITR, AAV4 ITR, AAV5 ITR, and AAV6 ITR.

9. The isolated nucleic acid sequence of claim 8, wherein the ITRs are AAV2 ITR.

10. The isolated nucleic acid of claim 1, wherein the isolated nucleic acid further comprises a polyadenylation signal.

11. A vector comprising the isolated nucleic acid of claim 1.

12. A host cell comprising the isolated nucleic acid of claim 1.

13. A pharmaceutical composition comprising the isolated nucleic acid of claim 1.

* * * * *

SEQUENCE LISTING

```
<160> NUMBER OF SEQ ID NOS: 32

<210> SEQ ID NO 1
<211> LENGTH: 495
<212> TYPE: PRT
<213> ORGANISM: Artificial Sequence
<220> FEATURE:
<223> OTHER INFORMATION: Synthetic

<400> SEQUENCE: 1

Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
    50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
    210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
    290                 295                 300

Asn Ser Ile Gly Ala Val Gly Ser Ala Met Phe Leu Arg Phe Ile Asn
```

```
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
    370                 375                 380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu
        435                 440                 445

Ala Tyr Leu Gly Pro Pro Glu His Lys Pro Val Ala Asp Thr His Trp
    450                 455                 460

Ser Ser Leu Asn Leu Thr Ser Ser Lys Phe Glu Glu Phe Met Thr Arg
465                 470                 475                 480

His Gln Val His Glu Lys Glu Glu Phe Lys Ala Leu Lys Thr Leu
                485                 490                 495


<210> SEQ ID NO 2
<211> LENGTH: 1485
<212> TYPE: DNA
<213> ORGANISM: Artificial Sequence
<220> FEATURE:
<223> OTHER INFORMATION: Synthetic

<400> SEQUENCE: 2

atggaagcca agagccagct gtttctgaaa tactttaccc tgtttatgaa tctgctgaac     60

gactgtagtg aggtggagga cgagagtgcc cagaccggcg gcaggaagag aggcatgtct    120

aggagactgg ccagcctgag gcactgcaca gtgctggcca tgtccaacct gctgaacgcc    180

aatgtggact ccggcctgat gcactctatc ggcctgggct accacaagga tctgcagacc    240

cgcgccacat tcatggaggt gctgaccaag atcctgcagc agggcaccga gtttgacaca    300

ctggccgaga ccgtgctggc agataggttc gagcgcctgg tggagctggt gacaatgatg    360

ggcgaccagg gagagctgcc tatcgcaatg gcactggcca acgtggtgcc atgcagccag    420

tgggacgagc tggccagggt gctggtgacc ctgtttgatt ccagacacct gctgtaccag    480

ctgctgtgga acatgttctc taaggaggtg gagctggccg acagcatgca gacactgttt    540

aggggcaatt ccctggcctc taagatcatg accttctgtt ttaaggtgta cggcgccaca    600

tatctgcaga agctgctgga tccactgctg agaatcgtga tcaccagctc cgactggcag    660

cacgtgtcct tcgaggtgga tcctacacgg ctggagccaa gcgagtccct ggaggagaac    720

cagcgcaatc tgctgcagat gaccgagaag ttctttcacg ccatcatctc tagctcctct    780

gagtttcccc ctcagctgcg gtccgtgtgc cactgtctgt accaggccac ctgccactct    840

ctgctgaaca aggccacagt gaaggagaag aaggagaata agaagagcgt ggtgtcccag    900

aggttcccac agaacagcat cggagcagtg ggatccgcca tgttcctgag gttcatcaat    960

cccgccatcg tgagccctta tgaggccggc atcctggaca agaagccacc ccctaggatc   1020
```

gagagaggcc tgaagctgat gagcaagatc ctgcagtcca tcgccaacca cgtgctgttc 1080
accaaggagg agcacatgcg ccccttcaac gactttgtga agtctaattt tgatgccgcc 1140
cggcgcttct ttctggacat cgcctctgat tgtcctacaa gcgacgccgt gaaccactct 1200
ctgagcttca tcagcgatgg caatgtgctg gccctgcacc ggctgctgtg gaacaatcag 1260
gagaagatcg gccagtacct gagctccaac agggaccaca aggcagtggg caggagacct 1320
tttgataaga tggccaccct gctggcatat ctgggaccac cagagcacaa gccagtggca 1380
gacacccact ggtctagcct gaatctgaca tcctctaagt tcgaggagtt tatgacccgg 1440
caccaggtgc acgagaagga ggagtttaag gccctgaaga ccctg 1485

<210> SEQ ID NO 3
<211> LENGTH: 643
<212> TYPE: PRT
<213> ORGANISM: Artificial Sequence
<220> FEATURE:
<223> OTHER INFORMATION: Synthetic

<400> SEQUENCE: 3

Met Glu Ala Lys Ser Gln Leu Phe Leu Lys Tyr Phe Thr Leu Phe Met
1 5 10 15

Asn Leu Leu Asn Asp Cys Ser Glu Val Glu Asp Glu Ser Ala Gln Thr
20 25 30

Gly Gly Arg Lys Arg Gly Met Ser Arg Arg Leu Ala Ser Leu Arg His
35 40 45

Cys Thr Val Leu Ala Met Ser Asn Leu Leu Asn Ala Asn Val Asp Ser
50 55 60

Gly Leu Met His Ser Ile Gly Leu Gly Tyr His Lys Asp Leu Gln Thr
65 70 75 80

Arg Ala Thr Phe Met Glu Val Leu Thr Lys Ile Leu Gln Gln Gly Thr
85 90 95

Glu Phe Asp Thr Leu Ala Glu Thr Val Leu Ala Asp Arg Phe Glu Arg
100 105 110

Leu Val Glu Leu Val Thr Met Met Gly Asp Gln Gly Glu Leu Pro Ile
115 120 125

Ala Met Ala Leu Ala Asn Val Val Pro Cys Ser Gln Trp Asp Glu Leu
130 135 140

Ala Arg Val Leu Val Thr Leu Phe Asp Ser Arg His Leu Leu Tyr Gln
145 150 155 160

Leu Leu Trp Asn Met Phe Ser Lys Glu Val Glu Leu Ala Asp Ser Met
165 170 175

Gln Thr Leu Phe Arg Gly Asn Ser Leu Ala Ser Lys Ile Met Thr Phe
180 185 190

Cys Phe Lys Val Tyr Gly Ala Thr Tyr Leu Gln Lys Leu Leu Asp Pro
195 200 205

Leu Leu Arg Ile Val Ile Thr Ser Ser Asp Trp Gln His Val Ser Phe
210 215 220

Glu Val Asp Pro Thr Arg Leu Glu Pro Ser Glu Ser Leu Glu Glu Asn
225 230 235 240

Gln Arg Asn Leu Leu Gln Met Thr Glu Lys Phe Phe His Ala Ile Ile
245 250 255

Ser Ser Ser Ser Glu Phe Pro Pro Gln Leu Arg Ser Val Cys His Cys
260 265 270

Leu Tyr Gln Ala Thr Cys His Ser Leu Leu Asn Lys Ala Thr Val Lys
275 280 285

Glu Lys Lys Glu Asn Lys Lys Ser Val Val Ser Gln Arg Phe Pro Gln
290 295 300

Asn Ser Ile Gly Ala Val Gly Ser Ala Met Phe Leu Arg Phe Ile Asn
305 310 315 320

Pro Ala Ile Val Ser Pro Tyr Glu Ala Gly Ile Leu Asp Lys Lys Pro
325 330 335

Pro Pro Arg Ile Glu Arg Gly Leu Lys Leu Met Ser Lys Ile Leu Gln
340 345 350

Ser Ile Ala Asn His Val Leu Phe Thr Lys Glu Glu His Met Arg Pro
355 360 365

Phe Asn Asp Phe Val Lys Ser Asn Phe Asp Ala Ala Arg Arg Phe Phe
370 375 380

Leu Asp Ile Ala Ser Asp Cys Pro Thr Ser Asp Ala Val Asn His Ser
385 390 395 400

Leu Ser Phe Ile Ser Asp Gly Asn Val Leu Ala Leu His Arg Leu Leu
405 410 415

Trp Asn Asn Gln Glu Lys Ile Gly Gln Tyr Leu Ser Ser Asn Arg Asp
420 425 430

His Lys Ala Val Gly Arg Arg Pro Phe Asp Lys Met Ala Thr Leu Leu
435 440 445

Ala Tyr Leu Gly Pro Pro Glu His Lys Pro Val Ala Asp Thr His Trp
450 455 460

Ser Ser Leu Asn Leu Thr Ser Ser Lys Phe Glu Glu Phe Met Thr Arg
465 470 475 480

His Gln Val His Glu Lys Glu Glu Phe Lys Ala Leu Lys Thr Leu Ser
485 490 495

Ile Phe Tyr Gln Ala Gly Thr Ser Lys Ala Gly Asn Pro Ile Phe Tyr
500 505 510

Tyr Val Ala Arg Arg Phe Lys Thr Gly Gln Ile Asn Gly Asp Leu Leu
515 520 525

Ile Tyr His Val Leu Leu Thr Leu Lys Pro Tyr Tyr Ala Lys Pro Tyr
530 535 540

Glu Ile Val Val Asp Leu Thr His Thr Gly Pro Ser Asn Arg Phe Lys
545 550 555 560

Thr Asp Phe Leu Ser Lys Trp Phe Val Val Phe Pro Gly Phe Ala Tyr
565 570 575

Asp Asn Val Ser Ala Val Tyr Ile Tyr Asn Cys Asn Ser Trp Val Arg
580 585 590

Glu Tyr Thr Lys Tyr His Glu Arg Leu Leu Thr Gly Leu Lys Gly Ser
595 600 605

Lys Arg Leu Val Phe Ile Asp Cys Pro Gly Lys Leu Ala Glu His Ile
610 615 620

Glu His Glu Gln Gln Lys Leu Pro Ala Ala Thr Leu Ala Leu Glu Glu
625 630 635 640

Asp Leu Lys

<210> SEQ ID NO 4
<211> LENGTH: 1929
<212> TYPE: DNA
<213> ORGANISM: Artificial Sequence
<220> FEATURE:
<223> OTHER INFORMATION: Synthetic

<400> SEQUENCE: 4

```
atggaagcca agagccagct gtttctgaaa tactttaccc tgtttatgaa tctgctgaac      60

gactgtagtg aggtggagga cgagagtgcc cagaccggcg gcaggaagag aggcatgtct     120

aggagactgg ccagcctgag gcactgcaca gtgctggcca tgtccaacct gctgaacgcc     180

aatgtggact ccggcctgat gcactctatc ggcctgggct accacaagga tctgcagacc     240

cgcgccacat tcatggaggt gctgaccaag atcctgcagc agggcaccga gtttgacaca     300

ctggccgaga ccgtgctggc agataggttc gagcgcctgg tggagctggt gacaatgatg     360

ggcgaccagg gagagctgcc tatcgcaatg gcactggcca acgtggtgcc atgcagccag     420

tgggacgagc tggccagggt gctggtgacc ctgtttgatt ccagacacct gctgtaccag     480

ctgctgtgga acatgttctc taaggaggtg gagctggccg acagcatgca gacactgttt     540

aggggcaatt ccctggcctc taagatcatg accttctgtt ttaaggtgta cggcgccaca     600

tatctgcaga agctgctgga tccactgctg agaatcgtga tcaccagctc cgactggcag     660

cacgtgtcct tcgaggtgga tcctacacgg ctggagccaa gcgagtccct ggaggagaac     720

cagcgcaatc tgctgcagat gaccgagaag ttctttcacg ccatcatctc tagctcctct     780

gagtttcccc ctcagctgcg gtccgtgtgc cactgtctgt accaggccac ctgccactct     840

ctgctgaaca aggccacagt gaaggagaag aaggagaata agaagagcgt ggtgtcccag     900

aggttcccac agaacagcat cggagcagtg ggatccgcca tgttcctgag gttcatcaat     960

cccgccatcg tgagccctta tgaggccggc atcctggaca agaagccacc ccctaggatc    1020

gagagaggcc tgaagctgat gagcaagatc ctgcagtcca tcgccaacca cgtgctgttc    1080

accaaggagg agcacatgcg ccccttcaac gactttgtga agtctaattt tgatgccgcc    1140

cggcgcttct ttctggacat cgcctctgat tgtcctacaa gcgacgccgt gaaccactct    1200

ctgagcttca tcagcgatgg caatgtgctg gccctgcacc ggctgctgtg gaacaatcag    1260

gagaagatcg gccagtacct gagctccaac agggaccaca aggcagtggg caggagacca    1320

tttgataaga tggccacact gctggcctat ctgggaccac cagagcacaa gccagtggca    1380

gacacacact ggtctagcct gaatctgacc tcctctaagt tcgaggagtt tatgacccgg    1440

caccaggtgc acgagaagga ggagtttaag gccctgaaga cactgtctat cttctaccag    1500

gcaggcacca gcaaggcagg aaacccaatc ttttactatg tggcccggcg cttcaagaca    1560

ggccagatca atggcgatct gctgatctac cacgtgctgc tgaccctgaa gccatactat    1620

gccaagccct atgagatcgt ggtggacctg acccacacag gcccctccaa caggtttaag    1680

accgatttcc tgtctaagtg gttcgtggtg tttcctggct tcgcctatga caatgtgagc    1740

gccgtgtaca tctataactg caattcctgg gtgcgggagt acacaaagta tcacgagcgc    1800

ctgctgaccg gcctgaaggg atccaagaga ctggtgttca tcgattgtcc cggcaagctg    1860

gccgagcaca ttgaacacga acagcagaaa ctgcccgccg caaccctggc cctggaagag    1920

gacctgaag                                                            1929
```

<210> SEQ ID NO 5
<211> LENGTH: 742
<212> TYPE: PRT
<213> ORGANISM: Artificial Sequence
<220> FEATURE:
<223> OTHER INFORMATION: Synthetic

<400> SEQUENCE: 5

```
Met Glu Ala Lys Ser Gln Leu Phe Leu Lys Tyr Phe Thr Leu Phe Met
1               5                   10                  15
```

-continued

```
Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
    50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
    210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
    290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
    370                 375                 380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu
```

```
        435                 440                 445

Ala Tyr Leu Gly Pro Pro Glu His Lys Pro Val Ala Asp Thr His Trp
    450                 455                 460

Ser Ser Leu Asn Leu Thr Ser Ser Lys Phe Glu Glu Phe Met Thr Arg
465                 470                 475                 480

His Gln Val His Glu Lys Glu Glu Phe Lys Ala Leu Lys Thr Leu Ser
                485                 490                 495

Ile Phe Tyr Gln Ala Gly Thr Ser Lys Ala Gly Asn Pro Ile Phe Tyr
            500                 505                 510

Tyr Val Ala Arg Arg Phe Lys Thr Gly Gln Ile Asn Gly Asp Leu Leu
        515                 520                 525

Ile Tyr His Val Leu Leu Thr Leu Lys Pro Tyr Tyr Ala Lys Pro Tyr
    530                 535                 540

Glu Ile Val Val Asp Leu Thr His Thr Gly Pro Ser Asn Arg Phe Lys
545                 550                 555                 560

Thr Asp Phe Leu Ser Lys Trp Phe Val Val Phe Pro Gly Phe Ala Tyr
                565                 570                 575

Asp Asn Val Ser Ala Val Tyr Ile Tyr Asn Cys Asn Ser Trp Val Arg
            580                 585                 590

Glu Tyr Thr Lys Tyr His Glu Arg Leu Leu Thr Gly Leu Lys Gly Ser
        595                 600                 605

Lys Arg Leu Val Phe Ile Asp Cys Pro Gly Lys Leu Ala Glu His Ile
    610                 615                 620

Glu His Glu Gln Gln Lys Leu Pro Ala Ala Thr Leu Ala Leu Glu Glu
625                 630                 635                 640

Asp Leu Lys Val Phe His Asn Ala Leu Lys Leu Ala His Lys Asp Thr
                645                 650                 655

Lys Val Ser Ile Lys Val Gly Ser Thr Ala Val Gln Val Thr Ser Ala
            660                 665                 670

Glu Arg Thr Lys Val Leu Gly Gln Ser Val Phe Leu Asn Asp Ile Tyr
        675                 680                 685

Tyr Ala Ser Glu Ile Glu Glu Ile Cys Leu Val Asp Glu Asn Gln Phe
    690                 695                 700

Thr Leu Thr Ile Ala Asn Gln Gly Thr Pro Leu Thr Phe Met His Gln
705                 710                 715                 720

Glu Cys Glu Ala Ile Val Gln Ser Ile Ile His Ile Arg Thr Arg Trp
                725                 730                 735

Glu Leu Ser Gln Pro Asp
            740
```

<210> SEQ ID NO 6
<211> LENGTH: 2226
<212> TYPE: DNA
<213> ORGANISM: Artificial Sequence
<220> FEATURE:
<223> OTHER INFORMATION: Synthetic

<400> SEQUENCE: 6

```
atggaagcca agagccagct gtttctgaaa tactttaccc tgtttatgaa tctgctgaac      60

gactgtagtg aggtggagga cgagagtgcc cagaccggcg gcaggaagag aggcatgtct     120

aggagactgg ccagcctgag gcactgcaca gtgctggcca tgtccaacct gctgaacgcc     180

aatgtggact ccggcctgat gcactctatc ggcctgggct accacaagga tctgcagacc     240

cgcgccacat tcatggaggt gctgaccaag atcctgcagc agggcaccga gtttgacaca     300
```

```
ctggccgaga ccgtgctggc agataggttc gagcgcctgg tggagctggt gacaatgatg    360

ggcgaccagg gagagctgcc tatcgcaatg gcactggcca acgtggtgcc atgcagccag    420

tgggacgagc tggccagggt gctggtgacc ctgtttgatt ccagacacct gctgtaccag    480

ctgctgtgga acatgttctc taaggaggtg gagctggccg acagcatgca gacactgttt    540

aggggcaatt ccctggcctc taagatcatg accttctgtt ttaaggtgta cggcgccaca    600

tatctgcaga agctgctgga tccactgctg agaatcgtga tcaccagctc cgactggcag    660

cacgtgtcct tcgaggtgga tcctacacgg ctggagccaa gcgagtccct ggaggagaac    720

cagcgcaatc tgctgcagat gaccgagaag ttctttcacg ccatcatctc tagctcctct    780

gagtttcccc ctcagctgcg gtccgtgtgc cactgtctgt accaggccac ctgccactct    840

ctgctgaaca aggccacagt gaaggagaag aaggagaata agaagagcgt ggtgtcccag    900

aggttcccac agaacagcat cggagcagtg ggatccgcca tgttcctgag gttcatcaat    960

cccgccatcg tgagccctta tgaggccggc atcctggaca agaagccacc ccctaggatc   1020

gagagaggcc tgaagctgat gagcaagatc ctgcagtcca tcgccaacca cgtgctgttc   1080

accaaggagg agcacatgcg ccccttcaac gactttgtga agtctaattt tgatgccgcc   1140

cggcgcttct ttctggacat cgcctctgat tgtcctacaa gcgacgccgt gaaccactct   1200

ctgagcttca tcagcgatgg caatgtgctg gccctgcacc ggctgctgtg gaacaatcag   1260

gagaagatcg gccagtacct gagctccaac agggaccaca aggcagtggg caggagacct   1320

tttgataaga tggccaccct gctggcatat ctgggaccac cagagcacaa gccagtggca   1380

gacacccact ggtctagcct gaatctgaca tcctctaagt tcgaggagtt tatgacccgg   1440

caccaggtgc acgagaagga ggagtttaag gccctgaaga ccctgtccat cttctaccag   1500

gccggcacat ctaaggccgg caaccctatc ttttactatg tggcccggcg cttcaagacc   1560

ggccagatca atggcgatct gctgatctac cacgtgctgc tgacactgaa gccatactat   1620

gccaagccct atgagatcgt ggtggacctg acccacacag gcccaagcaa caggtttaag   1680

accgatttcc tgtccaagtg gttcgtggtg tttcccggct tcgcctatga caacgtgagc   1740

gccgtgtaca tctataactg caatagctgg gtgcgggagt acaccaagta tcacgagcgc   1800

ctgctgacag gcctgaaggg cagcaagaga ctggtgttca tcgattgtcc cggcaagctg   1860

gccgagcaca tcgagcacga gcagcagaag ctgcctgcag ccaccctggc cctggaggag   1920

gacctgaagg tgtttcacaa cgccctgaag ctggcccaca aggatacaaa ggtgtccatc   1980

aaggtcggct ctacagccgt gcaggtgacc tccgccgaga gaacaaaggt gctgggccag   2040

agcgtgttcc tgaatgacat ctactatgcc agcgagatcg aggagatctg cctggtggat   2100

gagaaccagt ttaccctgac aatcgccaat cagggcaccc ccctgacatt catgcaccag   2160

gagtgtgaag caatcgtcca gagcattatt cacattcgca ctcggtggga actgagccag   2220

cctgac                                                              2226
```

<210> SEQ ID NO 7
<211> LENGTH: 6521
<212> TYPE: DNA
<213> ORGANISM: Artificial Sequence
<220> FEATURE:
<223> OTHER INFORMATION: Synthetic

<400> SEQUENCE: 7

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120
```

```
actccatcac taggggttcc tgcggccaga tcttcaatat tggccattag ccatattatt    180
cattggttat atagcataaa tcaatattgg ctattggcca ttgcatacgt tgtatctata    240
tcataatatg tacatttata ttggctcatg tccaatatga ccgccatgtt ggcattgatt    300
attgactagt tattaatagt aatcaattac ggggtcatta gttcatagcc catatatgga    360
gttccgcgtt acataactta cggtaaatgg cccgcctggc tgaccgccca acgacccccg    420
cccattgacg tcaataatga cgtatgttcc catagtaacg ccaataggga ctttccattg    480
acgtcaatgg gtggagtatt tacggtaaac tgcccacttg gcagtacatc aagtgtatca    540
tatgccaagt ccgcccccta ttgacgtcaa tgacggtaaa tggcccgcct ggcattatgc    600
ccagtacatg accttacggg actttcctac ttggcagtac atctacgtat tagtcatcgc    660
tattaccatg gtcgaggtga gccccacgtt ctgcttcact ctccccatct cccccccctc    720
cccaccccca attttgtatt tatttatttt ttaattattt tgtgcagcga tgggggcggg    780
gggggggggg gggcgcgcgc caggcggggc ggggcggggc gaggggcggg gcggggcgag    840
gcggagaggt gcggcggcag ccaatcagag cggcgcgctc cgaaagtttc cttttatggc    900
gaggcggcgg cggcggcggc cctataaaaa gcgaagcgcg cggcgggcgg gagtcgctgc    960
gcgctgcctt cgccccgtgc cccgctccgc cgccgcctcg cgccgcccgc cccggctctg   1020
actgaccgcg ttactcccac aggtgagcgg gcgggacggc ccttctcctc cgggctgtaa   1080
ttagcgcttg gtttaatgac ggcttgtttc ttttctgtgg ctgcgtgaaa gccttgaggg   1140
gctccgggag ggccctttgt gcggggggag cggctcgggg ggtgcgtgcg tgtgtgtgtg   1200
cgtggggagc gccgcgtgcg gctccgcgct gcccggcggc tgtgagcgct gcgggcgcgg   1260
cgcggggctt tgtgcgctcc gcagtgtgcg cgaggggagc gcggccgggg gcggtgcccc   1320
gcggtgcggg gggggctgcg aggggaacaa aggctgcgtg cggggtgtgt gcgtgggggg   1380
gtgagcaggg ggtgtgggcg cgtcggtcgg gctgcaaccc cccctgcacc cccctccccg   1440
agttgctgag cacggcccgg cttcgggtgc ggggctccgt acggggcgtg gcgcggggct   1500
cgccgtgccg ggcggggggt ggcggcaggt gggggtgccg ggcggggcgg ggccgcctcg   1560
ggccggggag ggctcggggg aggggcgcgg cggcccccgg agcgccggcg gctgtcgagg   1620
cgcggcgagc cgcagccatt gccttttatg gtaatcgtgc gagagggcgc agggacttcc   1680
tttgtcccaa atctgtgcgg agccgaaatc tgggaggcgc cgccgcaccc cctctagcgg   1740
gcgcggggcg aagcggtgcg gcgccggcag gaaggaaatg ggcggggagg gccttcgtgc   1800
gtcgccgcgc cgccgtcccc ttctccctct ccagcctcgg ggctgtccgc ggggggacgg   1860
ctgccttcgg gggggacggg gcagggcggg gttcggcttc tggcgtgtga ccggcggctc   1920
tagagcctct gctaaccatg ttcatgcctt cttctttttc ctacagctcc tgggcaacgt   1980
gctggttatt gtgctgtctc atcattttgg caaagaattc gatatcaagc ttgccaccat   2040
ggaagccaag agccagctgt ttctgaaata ctttaccctg tttatgaatc tgctgaacga   2100
ctgtagtgag gtggaggacg agagtgccca gaccggcggc aggaagagag gcatgtctag   2160
gagactggcc agcctgaggc actgcacagt gctggccatg tccaacctgc tgaacgccaa   2220
tgtggactcc ggcctgatgc actctatcgg cctgggctac cacaaggatc tgcagacccg   2280
cgccacattc atggaggtgc tgaccaagat cctgcagcag ggcaccgagt ttgacacact   2340
ggccgagacc gtgctggcag ataggttcga gcgcctggtg gagctggtga caatgatggg   2400
cgaccaggga gagctgccta tcgcaatggc actggccaac gtggtgccat gcagccagtg   2460
```

-continued

```
ggacgagctg gccagggtgc tggtgaccct gtttgattcc agacacctgc tgtaccagct   2520
gctgtggaac atgttctcta aggaggtgga gctggccgac agcatgcaga cactgtttag   2580
gggcaattcc ctggcctcta agatcatgac cttctgtttt aaggtgtacg gcgccacata   2640
tctgcagaag ctgctggatc cactgctgag aatcgtgatc accagctccg actggcagca   2700
cgtgtccttc gaggtggatc ctacacggct ggagccaagc gagtccctgg aggagaacca   2760
gcgcaatctg ctgcagatga ccgagaagtt ctttcacgcc atcatctcta gctcctctga   2820
gtttcccccct cagctgcggt ccgtgtgcca ctgtctgtac caggccacct gccactctct   2880
gctgaacaag gccacagtga aggagaagaa ggagaataag aagagcgtgg tgtcccagag   2940
gttcccacag aacagcatcg gagcagtggg atccgccatg ttcctgaggt tcatcaatcc   3000
cgccatcgtg agcccttatg aggccggcat cctggacaag aagccacccc ctaggatcga   3060
gagaggcctg aagctgatga gcaagatcct gcagtccatc gccaaccacg tgctgttcac   3120
caaggaggag cacatgcgcc ccttcaacga ctttgtgaag tctaattttg atgccgcccg   3180
gcgcttcttt ctggacatcg cctctgattg tcctacaagc gacgccgtga accactctct   3240
gagcttcatc agcgatggca atgtgctggc cctgcaccgg ctgctgtgga acaatcagga   3300
gaagatcggc cagtacctga gctccaacag ggaccacaag gcagtgggca ggagaccttt   3360
tgataagatg gccaccctgc tggcatatct gggaccacca gagcacaagc cagtggcaga   3420
cacccactgg tctagcctga atctgacatc ctctaagttc gaggagttta tgacccggca   3480
ccaggtgcac gagaaggagg agtttaaggc cctgaagacc ctggatgact cgagtttttt   3540
tttgcggccg cttcgagcag acatgataag atacattgat gagtttggac aaaccacaac   3600
tagaatgcag tgaaaaaaat gctttatttg tgaaatttgt gatgctattg ctttatttgt   3660
aaccattata agctgcaata aacaagttaa caacaacaat tgcattcatt ttatgtttca   3720
ggttcagggg gagatgtggg aggtttttta aagcaagtaa aacctctaca aatgtggtaa   3780
aatcgatagg ccgcaggaac ccctagtgat ggagttggcc actccctctc tgcgcgctcg   3840
ctcgctcact gaggccgggc gaccaaaggt cgcccgacgc ccgggcggcc tcagtgagcg   3900
agcgagcgcg cagctgcctg caggacatgt gagcaaaagg ccagcaaaag gccaggaacc   3960
gtaaaaaggc cgcgttgctg gcgtttttcc ataggctccg cccccctgac gagcatcaca   4020
aaaatcgacg ctcaagtcag aggtggcgaa acccgacagg actataaaga taccaggcgt   4080
ttccccctgg aagctccctc gtgcgctctc ctgttccgac cctgccgctt accggatacc   4140
tgtccgcctt tctcccttcg ggaagcgtgg cgctttctca tagctcacgc tgtaggtatc   4200
tcagttcggt gtaggtcgtt cgctccaagc tgggctgtgt gcacgaaccc cccgttcagc   4260
ccgaccgctg cgccttatcc ggtaactatc gtcttgagtc caacccggta agacacgact   4320
tatcgccact ggcagcagcc actggtaaca ggattagcag agcgaggtat gtaggcggtg   4380
ctacagagtt cttgaagtgg tggcctaact acggctacac tagaagaaca gtatttggta   4440
tctgcgctct gctgaagcca gttaccttcg gaaaaagagt tggtagctct tgatccggca   4500
aacaaaccac cgctggtagc ggtggttttt ttgtttgcaa gcagcagatt acgcgcagaa   4560
aaaaaggatc tcaagaagat cctttgatct tttctacggg gtctgacgct cagtggaacg   4620
aaaactcacg ttaagggatt ttggtcatga gattatcaaa aaggatcttc acctagatcc   4680
ttttaaatta aaaatgaagt tttaaatcaa tctaaagtat atatgagtaa acttggtctg   4740
acagttacca atgcttaatc agtgaggcac ctatctcagc gatctgtcta tttcgttcat   4800
ccatagttgc ctgactcccc gtcgtgtaga taactacgat acgggagggc ttaccatctg   4860
```

gccccagtgc tgcaatgata ccgcgagacc cacgctcacc ggctccagat ttatcagcaa 4920
taaaccagcc agccggaagg gccgagcgca gaagtggtcc tgcaacttta tccgcctcca 4980
tccagtctat taattgttgc cgggaagcta gagtaagtag ttcgccagtt aatagtttgc 5040
gcaacgttgt tgccattgct acaggcatcg tggtgtcacg ctcgtcgttt ggtatggctt 5100
cattcagctc cggttcccaa cgatcaaggc gagttacatg atcccccatg ttgtgcaaaa 5160
aagcggttag ctccttcggt cctccgatcg ttgtcagaag taagttggcc gcagtgttat 5220
cactcatggt tatggcagca ctgcataatt ctcttactgt catgccatcc gtaagatgct 5280
tttctgtgac tggtgagtac tcaaccaagt cattctgaga atagtgtatg cggcgaccga 5340
gttgctcttg cccggcgtca atacgggata ataccgcgcc acatagcaga actttaaaag 5400
tgctcatcat tggaaaacgt tcttcggggc gaaaactctc aaggatctta ccgctgttga 5460
gatccagttc gatgtaaccc actcgtgcac ccaactgatc ttcagcatct tttactttca 5520
ccagcgtttc tgggtgagca aaaacaggaa ggcaaaatgc cgcaaaaaag ggaataaggg 5580
cgacacggaa atgttgaata ctcatactct tcctttttca atattattga agcatttatc 5640
agggttattg tctcatgagc ggatacatat ttgaatgtat ttagaaaaat aaacaaatag 5700
gggttccgcg cacatttccc cgaaaagtgc cacctgacgt ctaagaaacc attattatca 5760
tgacattaac ctataaaaat aggcgtatca cgaggccctt tcgtctcgcg cgtttcggtg 5820
atgacggtga aaacctctga cacatgcagc tcccggagac ggtcacagct tgtctgtaag 5880
cggatgccgg gagcagacaa gcccgtcagg gcgcgtcagc gggtgttggc gggtgtcggg 5940
gctggcttaa ctatgcggca tcagagcaga ttgtactgag agtgcaccat aaaattgtaa 6000
acgttaatat tttgttaaaa ttcgcgttaa atttttgtta aatcagctca ttttttaacc 6060
aataggccga aatcggcaaa atcccttata aatcaaaaga atagcccgag atagggttga 6120
gtgttgttcc agtttggaac aagagtccac tattaaagaa cgtggactcc aacgtcaaag 6180
ggcgaaaaac cgtctatcag ggcgatggcc cactacgtga accatcaccc aaatcaagtt 6240
ttttggggtc gaggtgccgt aaagcactaa atcggaaccc taaagggagc ccccgattta 6300
gagcttgacg gggaaagccg gcgaacgtgg cgagaaagga agggaagaaa gcgaaaggag 6360
cgggcgctaa ggcgctggca agtgtagcgg tcacgctgcg cgtaaccacc acacccgccg 6420
cgcttaatgc gccgctacag ggcgcgtact atggttgctt tgacgtatgc ggtgtgaaat 6480
accgcacaga tgcgtaagga gaaaataccg catcaggcgc c 6521

<210> SEQ ID NO 8
<211> LENGTH: 6965
<212> TYPE: DNA
<213> ORGANISM: Artificial Sequence
<220> FEATURE:
<223> OTHER INFORMATION: Synthetic

<400> SEQUENCE: 8
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaga tcttcaatat tggccattag ccatattatt 180
cattggttat atagcataaa tcaatattgg ctattggcca ttgcatacgt tgtatctata 240
tcataatatg tacatttata ttggctcatg tccaatatga ccgccatgtt ggcattgatt 300
attgactagt tattaatagt aatcaattac ggggtcatta gttcatagcc catatatgga 360

-continued

```
gttccgcgtt acataactta cggtaaatgg cccgcctggc tgaccgccca acgacccccg    420
cccattgacg tcaataatga cgtatgttcc catagtaacg ccaataggga ctttccattg    480
acgtcaatgg gtggagtatt tacggtaaac tgcccacttg gcagtacatc aagtgtatca    540
tatgccaagt ccgcccccta ttgacgtcaa tgacggtaaa tggcccgcct ggcattatgc    600
ccagtacatg accttacggg actttcctac ttggcagtac atctacgtat tagtcatcgc    660
tattaccatg gtcgaggtga gccccacgtt ctgcttcact ctccccatct cccccccctc    720
cccaccccca attttgtatt tatttatttt ttaattattt tgtgcagcga tgggggcggg    780
gggggggggg gggcgcgcgc caggcggggc ggggcggggc gaggggcggg gcggggcgag    840
gcggagaggt gcggcggcag ccaatcagag cggcgcgctc cgaaagtttc cttttatggc    900
gaggcggcgg cggcggcggc cctataaaaa gcgaagcgcg cggcgggcgg gagtcgctgc    960
gcgctgcctt cgccccgtgc cccgctccgc cgccgcctcg cgccgcccgc cccggctctg   1020
actgaccgcg ttactcccac aggtgagcgg gcgggacggc ccttctcctc cgggctgtaa   1080
ttagcgcttg gtttaatgac ggcttgtttc ttttctgtgg ctgcgtgaaa gccttgaggg   1140
gctccgggag ggccctttgt gcggggggag cggctcgggg ggtgcgtgcg tgtgtgtgtg   1200
cgtggggagc gccgcgtgcg gctccgcgct gcccggcggc tgtgagcgct gcgggcgcgg   1260
cgcggggctt tgtgcgctcc gcagtgtgcg cgaggggagc gcggccgggg gcggtgcccc   1320
gcggtgcggg gggggctgcg aggggaacaa aggctgcgtg cggggtgtgt gcgtgggggg   1380
gtgagcaggg ggtgtgggcg cgtcggtcgg gctgcaaccc cccctgcacc cccctccccg   1440
agttgctgag cacggcccgg cttcgggtgc ggggctccgt acggggcgtg gcgcggggct   1500
cgccgtgccg ggcggggggt ggcggcaggt gggggtgccg ggcggggcgg ggccgcctcg   1560
ggccggggag ggctcggggg aggggcgcgg cggcccccgg agcgccggcg gctgtcgagg   1620
cgcggcgagc cgcagccatt gccttttatg gtaatcgtgc gagagggcgc agggacttcc   1680
tttgtcccaa atctgtgcgg agccgaaatc tgggaggcgc cgccgcaccc cctctagcgg   1740
gcgcggggcg aagcggtgcg gcgccggcag gaaggaaatg ggcggggagg gccttcgtgc   1800
gtcgccgcgc cgccgtcccc ttctccctct ccagcctcgg ggctgtccgc ggggggacgg   1860
ctgccttcgg gggggacggg gcagggcggg gttcggcttc tggcgtgtga ccggcggctc   1920
tagagcctct gctaaccatg ttcatgcctt cttctttttc ctacagctcc tgggcaacgt   1980
gctggttatt gtgctgtctc atcattttgg caaagaattc gatatcaagc ttgccaccat   2040
ggaagccaag agccagctgt ttctgaaata ctttaccctg tttatgaatc tgctgaacga   2100
ctgtagtgag gtggaggacg agagtgccca gaccggcggc aggaagagag gcatgtctag   2160
gagactggcc agcctgaggc actgcacagt gctggccatg tccaacctgc tgaacgccaa   2220
tgtggactcc ggcctgatgc actctatcgg cctgggctac cacaaggatc tgcagacccg   2280
cgccacattc atggaggtgc tgaccaagat cctgcagcag ggcaccgagt ttgacacact   2340
ggccgagacc gtgctggcag ataggttcga gcgcctggtg gagctggtga caatgatggg   2400
cgaccaggga gagctgccta tcgcaatggc actggccaac gtggtgccat gcagccagtg   2460
ggacgagctg gccagggtgc tggtgaccct gtttgattcc agacacctgc tgtaccagct   2520
gctgtggaac atgttctcta aggaggtgga gctggccgac agcatgcaga cactgtttag   2580
gggcaattcc ctggcctcta agatcatgac cttctgtttt aaggtgtacg gcgccacata   2640
tctgcagaag ctgctggatc cactgctgag aatcgtgatc accagctccg actggcagca   2700
cgtgtccttc gaggtggatc ctacacggct ggagccaagc gagtccctgg aggagaacca   2760
```

```
gcgcaatctg ctgcagatga ccgagaagtt ctttcacgcc atcatctcta gctcctctga   2820

gtttccccct cagctgcggt ccgtgtgcca ctgtctgtac caggccacct gccactctct   2880

gctgaacaag gccacagtga aggagaagaa ggagaataag aagagcgtgg tgtcccagag   2940

gttcccacag aacagcatcg gagcagtggg atccgccatg ttcctgaggt tcatcaatcc   3000

cgccatcgtg agcccttatg aggccggcat cctggacaag aagccacccc ctaggatcga   3060

gagaggcctg aagctgatga gcaagatcct gcagtccatc gccaaccacg tgctgttcac   3120

caaggaggag cacatgcgcc ccttcaacga ctttgtgaag tctaattttg atgccgcccg   3180

gcgcttcttt ctggacatcg cctctgattg tcctacaagc gacgccgtga accactctct   3240

gagcttcatc agcgatggca atgtgctggc cctgcaccgg ctgctgtgga acaatcagga   3300

gaagatcggc cagtacctga gctccaacag ggaccacaag gcagtgggca ggagaccatt   3360

tgataagatg gccacactgc tggcctatct gggaccacca gagcacaagc cagtggcaga   3420

cacacactgg tctagcctga atctgacctc ctctaagttc gaggagttta tgacccggca   3480

ccaggtgcac gagaaggagg agtttaaggc cctgaagaca ctgtctatct tctaccaggc   3540

aggcaccagc aaggcaggaa acccaatctt ttactatgtg gcccggcgct tcaagacagg   3600

ccagatcaat ggcgatctgc tgatctacca cgtgctgctg accctgaagc catactatgc   3660

caagccctat gagatcgtgg tggacctgac ccacacaggc cctccaaca ggtttaagac   3720

cgatttcctg tctaagtggt tcgtggtgtt tcctggcttc gcctatgaca atgtgagcgc   3780

cgtgtacatc tataactgca attcctgggt gcgggagtac acaaagtatc acgagcgcct   3840

gctgaccggc ctgaagggat ccaagagact ggtgttcatc gattgtcccg gcaagctggc   3900

cgagcacatt gaacacgaac agcagaaact gcccgccgca accctggccc tggaagagga   3960

cctgaaggat gactcgagtt ttttttgcg gccgcttcga gcagacatga taagatacat   4020

tgatgagttt ggacaaacca caactagaat gcagtgaaaa aaatgcttta tttgtgaaat   4080

ttgtgatgct attgctttat ttgtaaccat tataagctgc aataaacaag ttaacaacaa   4140

caattgcatt cattttatgt ttcaggttca gggggagatg tgggaggttt tttaaagcaa   4200

gtaaaacctc tacaaatgtg gtaaaatcga taggccgcag gaacccctag tgatggagtt   4260

ggccactccc tctctgcgcg ctcgctcgct cactgaggcc gggcgaccaa aggtcgcccg   4320

acgcccgggc ggcctcagtg agcgagcgag cgcgcagctg cctgcaggac atgtgagcaa   4380

aaggccagca aaaggccagg aaccgtaaaa aggccgcgtt gctggcgttt ttccataggc   4440

tccgcccccc tgacgagcat cacaaaaatc gacgctcaag tcagaggtgg cgaaacccga   4500

caggactata aagataccag gcgtttcccc ctggaagctc cctcgtgcgc tctcctgttc   4560

cgaccctgcc gcttaccgga tacctgtccg cctttctccc ttcgggaagc gtggcgcttt   4620

ctcatagctc acgctgtagg tatctcagtt cggtgtaggt cgttcgctcc aagctgggct   4680

gtgtgcacga accccccgtt cagcccgacc gctgcgcctt atccggtaac tatcgtcttg   4740

agtccaaccc ggtaagacac gacttatcgc cactggcagc agccactggt aacaggatta   4800

gcagagcgag gtatgtaggc ggtgctacag agttcttgaa gtggtggcct aactacggct   4860

acactagaag aacagtattt ggtatctgcg ctctgctgaa gccagttacc ttcggaaaaa   4920

gagttggtag ctcttgatcc ggcaaacaaa ccaccgctgg tagcggtggt ttttttgttt   4980

gcaagcagca gattacgcgc agaaaaaaag gatctcaaga agatcctttg atcttttcta   5040

cggggtctga cgctcagtgg aacgaaaact cacgttaagg gattttggtc atgagattat   5100
```

caaaaaggat cttcacctag atccttttaa attaaaaatg aagttttaaa tcaatctaaa 5160
gtatatatga gtaaacttgg tctgacagtt accaatgctt aatcagtgag gcacctatct 5220
cagcgatctg tctatttcgt tcatccatag ttgcctgact ccccgtcgtg tagataacta 5280
cgatacggga gggcttacca tctggcccca gtgctgcaat gataccgcga gacccacgct 5340
caccggctcc agatttatca gcaataaacc agccagccgg aagggccgag cgcagaagtg 5400
gtcctgcaac tttatccgcc tccatccagt ctattaattg ttgccgggaa gctagagtaa 5460
gtagttcgcc agttaatagt ttgcgcaacg ttgttgccat tgctacaggc atcgtggtgt 5520
cacgctcgtc gtttggtatg gcttcattca gctccggttc ccaacgatca aggcgagtta 5580
catgatcccc catgttgtgc aaaaaagcgg ttagctcctt cggtcctccg atcgttgtca 5640
gaagtaagtt ggccgcagtg ttatcactca tggttatggc agcactgcat aattctctta 5700
ctgtcatgcc atccgtaaga tgcttttctg tgactggtga gtactcaacc aagtcattct 5760
gagaatagtg tatgcggcga ccgagttgct cttgcccggc gtcaatacgg gataataccg 5820
cgccacatag cagaacttta aaagtgctca tcattggaaa acgttcttcg gggcgaaaac 5880
tctcaaggat cttaccgctg ttgagatcca gttcgatgta acccactcgt gcacccaact 5940
gatcttcagc atcttttact ttcaccagcg tttctgggtg agcaaaaaca ggaaggcaaa 6000
atgccgcaaa aaagggaata agggcgacac ggaaatgttg aatactcata ctcttccttt 6060
ttcaatatta ttgaagcatt tatcagggtt attgtctcat gagcggatac atatttgaat 6120
gtatttagaa aaataaacaa ataggggttc cgcgcacatt tccccgaaaa gtgccacctg 6180
acgtctaaga aaccattatt atcatgacat taacctataa aaataggcgt atcacgaggc 6240
cctttcgtct cgcgcgtttc ggtgatgacg gtgaaaacct ctgacacatg cagctcccgg 6300
agacggtcac agcttgtctg taagcggatg ccgggagcag acaagcccgt cagggcgcgt 6360
cagcgggtgt tggcgggtgt cggggctggc ttaactatgc ggcatcagag cagattgtac 6420
tgagagtgca ccataaaatt gtaaacgtta atattttgtt aaaattcgcg ttaaattttt 6480
gttaaatcag ctcatttttt aaccaatagg ccgaaatcgg caaaatccct tataaatcaa 6540
aagaatagcc cgagataggg ttgagtgttg ttccagtttg gaacaagagt ccactattaa 6600
agaacgtgga ctccaacgtc aaagggcgaa aaaccgtcta tcagggcgat ggcccactac 6660
gtgaaccatc acccaaatca agttttttgg ggtcgaggtg ccgtaaagca ctaaatcgga 6720
accctaaagg gagcccccga tttagagctt gacggggaaa gccggcgaac gtggcgagaa 6780
aggaagggaa gaaagcgaaa ggagcgggcg ctaaggcgct ggcaagtgta gcggtcacgc 6840
tgcgcgtaac caccacaccc gccgcgctta atgcgccgct acagggcgcg tactatggtt 6900
gctttgacgt atgcggtgtg aaataccgca cagatgcgta aggagaaaat accgcatcag 6960
gcgcc 6965

<210> SEQ ID NO 9
<211> LENGTH: 7262
<212> TYPE: DNA
<213> ORGANISM: Artificial Sequence
<220> FEATURE:
<223> OTHER INFORMATION: Synthetic

<400> SEQUENCE: 9
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaga tcttcaatat tggccattag ccatattatt 180

```
cattggttat atagcataaa tcaatattgg ctattggcca ttgcatacgt tgtatctata    240
tcataatatg tacatttata ttggctcatg tccaatatga ccgccatgtt ggcattgatt    300
attgactagt tattaatagt aatcaattac ggggtcatta gttcatagcc catatatgga    360
gttccgcgtt acataactta cggtaaatgg cccgcctggc tgaccgccca acgacccccg    420
cccattgacg tcaataatga cgtatgttcc catagtaacg ccaataggga ctttccattg    480
acgtcaatgg gtggagtatt tacggtaaac tgcccacttg gcagtacatc aagtgtatca    540
tatgccaagt ccgcccccta ttgacgtcaa tgacggtaaa tggcccgcct ggcattatgc    600
ccagtacatg accttacggg actttcctac ttggcagtac atctacgtat tagtcatcgc    660
tattaccatg gtcgaggtga gccccacgtt ctgcttcact ctccccatct cccccccctc    720
cccaccccca attttgtatt tatttatttt ttaattattt tgtgcagcga tgggggcggg    780
gggggggggg gggcgcgcgc caggcggggc ggggcggggc gaggggcggg gcggggcgag    840
gcggagaggt gcggcggcag ccaatcagag cggcgcgctc cgaaagtttc cttttatggc    900
gaggcggcgg cggcggcggc cctataaaaa gcgaagcgcg cggcgggcgg gagtcgctgc    960
gcgctgcctt cgccccgtgc cccgctccgc cgccgcctcg cgccgcccgc cccggctctg   1020
actgaccgcg ttactcccac aggtgagcgg gcgggacggc ccttctcctc cgggctgtaa   1080
ttagcgcttg gtttaatgac ggcttgtttc ttttctgtgg ctgcgtgaaa gccttgaggg   1140
gctccgggag ggccctttgt gcggggggag cggctcgggg ggtgcgtgcg tgtgtgtgtg   1200
cgtggggagc gccgcgtgcg gctccgcgct gcccggcggc tgtgagcgct gcgggcgcgg   1260
cgcggggctt tgtgcgctcc gcagtgtgcg cgaggggagc gcggccgggg gcggtgcccc   1320
gcggtgcggg gggggctgcg aggggaacaa aggctgcgtg cggggtgtgt gcgtgggggg   1380
gtgagcaggg ggtgtgggcg cgtcggtcgg gctgcaaccc cccctgcacc cccctccccg   1440
agttgctgag cacggcccgg cttcgggtgc ggggctccgt acggggcgtg gcgcggggct   1500
cgccgtgccg ggcggggggt ggcggcaggt gggggtgccg ggcggggcgg ggccgcctcg   1560
ggccggggag ggctcggggg aggggcgcgg cggcccccgg agcgccggcg gctgtcgagg   1620
cgcggcgagc cgcagccatt gccttttatg gtaatcgtgc gagagggcgc agggacttcc   1680
tttgtcccaa atctgtgcgg agccgaaatc tgggaggcgc cgccgcaccc cctctagcgg   1740
gcgcggggcg aagcggtgcg gcgccggcag gaaggaaatg ggcggggagg gccttcgtgc   1800
gtcgccgcgc cgccgtcccc ttctccctct ccagcctcgg ggctgtccgc ggggggacgg   1860
ctgccttcgg gggggacggg gcagggcggg gttcggcttc tggcgtgtga ccggcggctc   1920
tagagcctct gctaaccatg ttcatgcctt cttctttttc ctacagctcc tgggcaacgt   1980
gctggttatt gtgctgtctc atcattttgg caaagaattc gatatcaagc ttgccaccat   2040
ggaagccaag agccagctgt ttctgaaata ctttaccctg tttatgaatc tgctgaacga   2100
ctgtagtgag gtggaggacg agagtgccca gaccggcggc aggaagagag gcatgtctag   2160
gagactggcc agcctgaggc actgcacagt gctggccatg tccaacctgc tgaacgccaa   2220
tgtggactcc ggcctgatgc actctatcgg cctgggctac cacaaggatc tgcagacccg   2280
cgccacattc atggaggtgc tgaccaagat cctgcagcag ggcaccgagt ttgacacact   2340
ggccgagacc gtgctggcag ataggttcga gcgcctggtg gagctggtga caatgatggg   2400
cgaccaggga gagctgccta tcgcaatggc actggccaac gtggtgccat gcagccagtg   2460
ggacgagctg gccagggtgc tggtgaccct gtttgattcc agacacctgc tgtaccagct   2520
```

-continued

```
gctgtggaac atgttctcta aggaggtgga gctggccgac agcatgcaga cactgtttag   2580
gggcaattcc ctggcctcta agatcatgac cttctgtttt aaggtgtacg gcgccacata   2640
tctgcagaag ctgctggatc cactgctgag aatcgtgatc accagctccg actggcagca   2700
cgtgtccttc gaggtggatc ctacacggct ggagccaagc gagtccctgg aggagaacca   2760
gcgcaatctg ctgcagatga ccgagaagtt ctttcacgcc atcatctcta gctcctctga   2820
gtttcccccct cagctgcggt ccgtgtgcca ctgtctgtac caggccacct gccactctct   2880
gctgaacaag gccacagtga aggagaagaa ggagaataag aagagcgtgg tgtcccagag   2940
gttcccacag aacagcatcg gagcagtggg atccgccatg ttcctgaggt tcatcaatcc   3000
cgccatcgtg agcccttatg aggccggcat cctggacaag aagccacccc ctaggatcga   3060
gagaggcctg aagctgatga gcaagatcct gcagtccatc gccaaccacg tgctgttcac   3120
caaggaggag cacatgcgcc ccttcaacga ctttgtgaag tctaattttg atgccgcccg   3180
gcgcttcttt ctggacatcg cctctgattg tcctacaagc gacgccgtga accactctct   3240
gagcttcatc agcgatggca atgtgctggc cctgcaccgg ctgctgtgga acaatcagga   3300
gaagatcggc cagtacctga gctccaacag ggaccacaag gcagtgggca ggagaccttt   3360
tgataagatg gccaccctgc tggcatatct gggaccacca gagcacaagc cagtggcaga   3420
cacccactgg tctagcctga atctgacatc ctctaagttc gaggagttta tgacccggca   3480
ccaggtgcac gagaaggagg agtttaaggc cctgaagacc ctgtccatct tctaccaggc   3540
cggcacatct aaggccggca accctatctt ttactatgtg gcccggcgct tcaagaccgg   3600
ccagatcaat ggcgatctgc tgatctacca cgtgctgctg acactgaagc catactatgc   3660
caagccctat gagatcgtgg tggacctgac ccacacaggc ccaagcaaca ggtttaagac   3720
cgatttcctg tccaagtggt tcgtggtgtt tcccggcttc gcctatgaca acgtgagcgc   3780
cgtgtacatc tataactgca atagctgggt gcgggagtac accaagtatc acgagcgcct   3840
gctgacaggc ctgaagggca gcaagagact ggtgttcatc gattgtcccg gcaagctggc   3900
cgagcacatc gagcacgagc agcagaagct gcctgcagcc accctggccc tggaggagga   3960
cctgaaggtg tttcacaacg ccctgaagct ggcccacaag gatacaaagg tgtccatcaa   4020
ggtcggctct acagccgtgc aggtgacctc cgccgagaga acaaaggtgc tgggccagag   4080
cgtgttcctg aatgacatct actatgccag cgagatcgag gagatctgcc tggtggatga   4140
gaaccagttt accctgacaa tcgccaatca gggcaccccc ctgacattca tgcaccagga   4200
gtgtgaagca atcgtccaga gcattattca cattcgcact cggtgggaac tgagccagcc   4260
tgacgatgac tcgagttttt ttttgcggcc gcttcgagca gacatgataa gatacattga   4320
tgagtttgga caaaccacaa ctagaatgca gtgaaaaaaa tgctttattt gtgaaatttg   4380
tgatgctatt gctttatttg taaccattat aagctgcaat aaacaagtta acaacaacaa   4440
ttgcattcat tttatgtttc aggttcaggg ggagatgtgg gaggtttttt aaagcaagta   4500
aaacctctac aaatgtggta aaatcgatag gccgcaggaa cccctagtga tggagttggc   4560
cactccctct ctgcgcgctc gctcgctcac tgaggccggg cgaccaaagg tcgcccgacg   4620
cccgggcggc ctcagtgagc gagcgagcgc gcagctgcct gcaggacatg tgagcaaaag   4680
gccagcaaaa ggccaggaac cgtaaaaagg ccgcgttgct ggcgtttttc cataggctcc   4740
gcccccctga cgagcatcac aaaaatcgac gctcaagtca gaggtggcga aacccgacag   4800
gactataaag ataccaggcg tttccccctg gaagctccct cgtgcgctct cctgttccga   4860
ccctgccgct taccggatac ctgtccgcct ttctcccttc gggaagcgtg gcgctttctc   4920
```

```
atagctcacg ctgtaggtat ctcagttcgg tgtaggtcgt tcgctccaag ctgggctgtg   4980
tgcacgaacc ccccgttcag cccgaccgct gcgccttatc cggtaactat cgtcttgagt   5040
ccaacccggt aagacacgac ttatcgccac tggcagcagc cactggtaac aggattagca   5100
gagcgaggta tgtaggcggt gctacagagt tcttgaagtg gtggcctaac tacggctaca   5160
ctagaagaac agtatttggt atctgcgctc tgctgaagcc agttaccttc ggaaaaagag   5220
ttggtagctc ttgatccggc aaacaaacca ccgctggtag cggtggtttt tttgtttgca   5280
agcagcagat tacgcgcaga aaaaaaggat ctcaagaaga tcctttgatc ttttctacgg   5340
ggtctgacgc tcagtggaac gaaaactcac gttaagggat tttggtcatg agattatcaa   5400
aaaggatctt cacctagatc cttttaaatt aaaaatgaag ttttaaatca atctaaagta   5460
tatatgagta aacttggtct gacagttacc aatgcttaat cagtgaggca cctatctcag   5520
cgatctgtct atttcgttca tccatagttg cctgactccc cgtcgtgtag ataactacga   5580
tacgggaggg cttaccatct ggccccagtg ctgcaatgat accgcgagac ccacgctcac   5640
cggctccaga tttatcagca ataaaccagc cagccggaag ggccgagcgc agaagtggtc   5700
ctgcaacttt atccgcctcc atccagtcta ttaattgttg ccgggaagct agagtaagta   5760
gttcgccagt taatagtttg cgcaacgttg ttgccattgc tacaggcatc gtggtgtcac   5820
gctcgtcgtt tggtatggct tcattcagct ccggttccca acgatcaagg cgagttacat   5880
gatcccccat gttgtgcaaa aaagcggtta gctccttcgg tcctccgatc gttgtcagaa   5940
gtaagttggc cgcagtgtta tcactcatgg ttatggcagc actgcataat tctcttactg   6000
tcatgccatc cgtaagatgc ttttctgtga ctggtgagta ctcaaccaag tcattctgag   6060
aatagtgtat gcggcgaccg agttgctctt gcccggcgtc aatacgggat aataccgcgc   6120
cacatagcag aactttaaaa gtgctcatca ttggaaaacg ttcttcgggg cgaaaactct   6180
caaggatctt accgctgttg agatccagtt cgatgtaacc cactcgtgca cccaactgat   6240
cttcagcatc ttttactttc accagcgttt ctgggtgagc aaaaacagga aggcaaaatg   6300
ccgcaaaaaa gggaataagg gcgacacgga aatgttgaat actcatactc ttcctttttc   6360
aatattattg aagcatttat cagggttatt gtctcatgag cggatacata tttgaatgta   6420
tttagaaaaa taaacaaata ggggttccgc gcacatttcc ccgaaaagtg ccacctgacg   6480
tctaagaaac cattattatc atgacattaa cctataaaaa taggcgtatc acgaggccct   6540
ttcgtctcgc gcgtttcggt gatgacggtg aaaacctctg acacatgcag ctcccggaga   6600
cggtcacagc ttgtctgtaa gcggatgccg ggagcagaca agcccgtcag ggcgcgtcag   6660
cgggtgttgg cgggtgtcgg ggctggctta actatgcggc atcagagcag attgtactga   6720
gagtgcacca taaaattgta aacgttaata ttttgttaaa attcgcgtta aatttttgtt   6780
aaatcagctc attttttaac caataggccg aaatcggcaa aatcccttat aaatcaaaag   6840
aatagcccga gatagggttg agtgttgttc cagtttggaa caagagtcca ctattaaaga   6900
acgtggactc caacgtcaaa gggcgaaaaa ccgtctatca gggcgatggc ccactacgtg   6960
aaccatcacc caaatcaagt tttttggggt cgaggtgccg taaagcacta aatcggaacc   7020
ctaaagggag cccccgattt agagcttgac ggggaaagcc ggcgaacgtg gcgagaaagg   7080
aagggaagaa agcgaaagga gcgggcgcta aggcgctggc aagtgtagcg gtcacgctgc   7140
gcgtaaccac cacacccgcc gcgcttaatg cgccgctaca gggcgcgtac tatggttgct   7200
ttgacgtatg cggtgtgaaa taccgcacag atgcgtaagg agaaaatacc gcatcaggcg   7260
```

cc 7262

<210> SEQ ID NO 10
<211> LENGTH: 1391
<212> TYPE: PRT
<213> ORGANISM: Artificial Sequence
<220> FEATURE:
<223> OTHER INFORMATION: Synthetic

<400> SEQUENCE: 10

Met Ala Ala His Arg Pro Val Glu Trp Val Gln Ala Val Val Ser Arg
1 5 10 15

Phe Asp Glu Gln Leu Pro Ile Lys Thr Gly Gln Gln Asn Thr His Thr
20 25 30

Lys Val Ser Thr Glu His Asn Lys Glu Cys Leu Ile Asn Ile Ser Lys
35 40 45

Tyr Lys Phe Ser Leu Val Ile Ser Gly Leu Thr Thr Ile Leu Lys Asn
50 55 60

Val Asn Asn Met Arg Ile Phe Gly Glu Ala Ala Glu Lys Asn Leu Tyr
65 70 75 80

Leu Ser Gln Leu Ile Ile Leu Asp Thr Leu Glu Lys Cys Leu Ala Gly
85 90 95

Gln Pro Lys Asp Thr Met Arg Leu Asp Glu Thr Met Leu Val Lys Gln
100 105 110

Leu Leu Pro Glu Ile Cys His Phe Leu His Thr Cys Arg Glu Gly Asn
115 120 125

Gln His Ala Ala Glu Leu Arg Asn Ser Ala Ser Gly Val Leu Phe Ser
130 135 140

Leu Ser Cys Asn Asn Phe Asn Ala Val Phe Ser Arg Ile Ser Thr Arg
145 150 155 160

Leu Gln Glu Leu Thr Val Cys Ser Glu Asp Asn Val Asp Val His Asp
165 170 175

Ile Glu Leu Leu Gln Tyr Ile Asn Val Asp Cys Ala Lys Leu Lys Arg
180 185 190

Leu Leu Lys Glu Thr Ala Phe Lys Phe Lys Ala Leu Lys Lys Val Ala
195 200 205

Gln Leu Ala Val Ile Asn Ser Leu Glu Lys Ala Phe Trp Asn Trp Val
210 215 220

Glu Asn Tyr Pro Asp Glu Phe Thr Lys Leu Tyr Gln Ile Pro Gln Thr
225 230 235 240

Asp Met Ala Glu Cys Ala Glu Lys Leu Phe Asp Leu Val Asp Gly Phe
245 250 255

Ala Glu Ser Thr Lys Arg Lys Ala Ala Val Trp Pro Leu Gln Ile Ile
260 265 270

Leu Leu Ile Leu Cys Pro Glu Ile Ile Gln Asp Ile Ser Lys Asp Val
275 280 285

Val Asp Glu Asn Asn Met Asn Lys Lys Leu Phe Leu Asp Ser Leu Arg
290 295 300

Lys Ala Leu Ala Gly His Gly Gly Ser Arg Gln Leu Thr Glu Ser Ala
305 310 315 320

Ala Ile Ala Cys Val Lys Leu Cys Lys Ala Ser Thr Tyr Ile Asn Trp
325 330 335

Glu Asp Asn Ser Val Ile Phe Leu Leu Val Gln Ser Met Val Val Asp
340 345 350

Leu Lys Asn Leu Leu Phe Asn Pro Ser Lys Pro Phe Ser Arg Gly Ser

```
        355                 360                 365

Gln Pro Ala Asp Val Asp Leu Met Ile Asp Cys Leu Val Ser Cys Phe
    370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
        435                 440                 445

Lys Ala Val Gln Gly Cys Gly Ala His Pro Ala Ile Arg Met Ala Pro
    450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Gly Ser Thr Ala Glu Leu Ile Thr Gly
        515                 520                 525

Leu Val Gln Leu Val Pro Gln Ser His Met Pro Glu Ile Ala Gln Glu
    530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Phe
    610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Gly
            660                 665                 670

Cys Ser Gly Thr Pro Pro Ile Cys Arg Gln Ala Gln Thr Lys Leu Glu
        675                 680                 685

Val Ala Leu Tyr Met Phe Leu Trp Asn Pro Asp Thr Glu Ala Val Leu
    690                 695                 700

Val Ala Met Ser Cys Phe Arg His Leu Cys Glu Glu Ala Asp Ile Arg
705                 710                 715                 720

Cys Gly Val Asp Glu Val Ser Val His Asn Leu Leu Pro Asn Tyr Asn
                725                 730                 735

Thr Phe Met Glu Phe Ala Ser Val Ser Asn Met Met Ser Thr Gly Arg
            740                 745                 750

Ala Ala Leu Gln Lys Arg Val Met Ala Leu Leu Arg Arg Ile Glu His
        755                 760                 765

Pro Thr Ala Gly Asn Thr Glu Ala Trp Glu Asp Thr His Ala Lys Trp
    770                 775                 780
```

```
Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
                805                 810                 815

Met Ser His Val Ser Gly Gly Gly Ser Ile Asp Leu Ser Asp Thr Asp
            820                 825                 830

Ser Leu Gln Glu Trp Ile Asn Met Thr Gly Phe Leu Cys Ala Leu Gly
        835                 840                 845

Gly Val Cys Leu Gln Gln Arg Ser Asn Ser Gly Leu Ala Thr Tyr Ser
    850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
                885                 890                 895

Arg Leu Leu Ser Leu Met Val Cys Asn His Glu Lys Val Gly Leu Gln
            900                 905                 910

Ile Arg Thr Asn Val Lys Asp Leu Val Gly Leu Glu Leu Ser Pro Ala
        915                 920                 925

Leu Tyr Pro Met Leu Phe Asn Lys Leu Lys Asn Thr Ile Ser Lys Phe
    930                 935                 940

Phe Asp Ser Gln Gly Gln Val Leu Leu Thr Asp Thr Asn Thr Gln Phe
945                 950                 955                 960

Val Glu Gln Thr Ile Ala Ile Met Lys Asn Leu Leu Asp Asn His Thr
                965                 970                 975

Glu Gly Ser Ser Glu His Leu Gly Gln Ala Ser Ile Glu Thr Met Met
            980                 985                 990

Leu Asn Leu Val Arg Tyr Val Arg  Val Leu Gly Asn Met  Val His Ala
        995                 1000                1005

Ile Gln  Ile Lys Thr Lys Leu  Cys Gln Leu Val Glu  Val Met Met
    1010                 1015                 1020

Ala Arg  Arg Asp Asp Leu Ser  Phe Cys Gln Glu Met  Lys Phe Arg
    1025                 1030                 1035

Asn Lys  Met Val Glu Tyr Leu  Thr Asp Trp Val Met  Gly Thr Ser
    1040                 1045                 1050

Asn Gln  Ala Ala Asp Asp Asp  Val Lys Cys Leu Thr  Arg Asp Leu
    1055                 1060                 1065

Asp Gln  Ala Ser Met Glu Ala  Val Val Ser Leu Leu  Ala Gly Leu
    1070                 1075                 1080

Pro Leu  Gln Pro Glu Glu Gly  Asp Gly Val Glu Leu  Met Glu Ala
    1085                 1090                 1095

Lys Ser  Gln Leu Phe Leu Lys  Tyr Phe Thr Leu Phe  Met Asn Leu
    1100                 1105                 1110

Leu Asn  Asp Cys Ser Glu Val  Glu Asp Glu Ser Ala  Gln Thr Gly
    1115                 1120                 1125

Gly Arg  Lys Arg Gly Met Ser  Arg Arg Leu Ala Ser  Leu Arg His
    1130                 1135                 1140

Cys Thr  Val Leu Ala Met Ser  Asn Leu Leu Asn Ala  Asn Val Asp
    1145                 1150                 1155

Ser Gly  Leu Met His Ser Ile  Gly Leu Gly Tyr His  Lys Asp Leu
    1160                 1165                 1170

Gln Thr  Arg Ala Thr Phe Met  Glu Val Leu Thr Lys  Ile Leu Gln
    1175                 1180                 1185
```

```
Gln Gly  Thr Glu Phe Asp Thr  Leu Ala Glu Thr Val  Leu Ala Asp
    1190                 1195                 1200

Arg Phe  Glu Arg Leu Val Glu  Leu Val Thr Met Met  Gly Asp Gln
    1205                 1210                 1215

Gly Glu  Leu Pro Ile Ala Met  Ala Leu Ala Asn Val  Val Pro Cys
    1220                 1225                 1230

Ser Gln  Trp Asp Glu Leu Ala  Arg Val Leu Val Thr  Leu Phe Asp
    1235                 1240                 1245

Ser Arg  His Leu Leu Tyr Gln  Leu Leu Trp Asn Met  Phe Ser Lys
    1250                 1255                 1260

Glu Val  Glu Leu Ala Asp Ser  Met Gln Thr Leu Phe  Arg Gly Asn
    1265                 1270                 1275

Ser Leu  Ala Ser Lys Ile Met  Thr Phe Cys Phe Lys  Val Tyr Gly
    1280                 1285                 1290

Ala Thr  Tyr Leu Gln Lys Leu  Leu Asp Pro Leu Leu  Arg Ile Val
    1295                 1300                 1305

Ile Thr  Ser Ser Asp Trp Gln  His Val Ser Phe Glu  Val Asp Pro
    1310                 1315                 1320

Thr Arg  Leu Glu Pro Ser Glu  Ser Leu Glu Glu Asn  Gln Arg Asn
    1325                 1330                 1335

Leu Leu  Gln Met Thr Glu Lys  Phe Phe His Ala Ile  Ile Ser Ser
    1340                 1345                 1350

Ser Ser  Glu Phe Pro Pro Gln  Leu Arg Ser Val Cys  His Cys Leu
    1355                 1360                 1365

Tyr Gln  Ala Thr Cys His Ser  Leu Leu Asn Lys Ala  Thr Val Lys
    1370                 1375                 1380

Glu Lys  Lys Glu Asn Lys Lys  Ser
    1385                 1390
```

<210> SEQ ID NO 11
<211> LENGTH: 4173
<212> TYPE: DNA
<213> ORGANISM: Artificial Sequence
<220> FEATURE:
<223> OTHER INFORMATION: Synthetic

<400> SEQUENCE: 11

```
atggccgcgc acaggccggt ggaatgggtc caggccgtgg tcagccgctt cgacgagcag     60

cttccaataa aaacaggaca gcagaacaca cataccaaag tcagtactga gcacaacaag    120

gaatgtctaa tcaatatttc caaatacaag ttttctttgg ttataagcgg cctcactact    180

attttaaaga atgttaacaa tatgagaata tttggagaag ctgctgaaaa aaatttatat    240

ctctctcagt tgattatatt ggatacactg gaaaaatgtc ttgctgggca accaaaggac    300

acaatgagat tagatgaaac gatgctggtc aaacagttgc tgccagaaat ctgccatttt    360

cttcacacct gtcgtgaagg aaaccagcat gcagctgaac ttcggaattc tgcctctggg    420

gttttatttt ctctcagctg caacaacttc aatgcagtct ttagtcgcat ttctaccagg    480

ttacaggaat taactgtttg ttcagaagac aatgttgatg ttcatgatat agaattgtta    540

cagtatatca atgtggattg tgcaaaatta aaacgactcc tgaaggaaac agcatttaaa    600

tttaaagccc taaagaaggt tgcgcagtta gcagttataa atagcctgga aaaggcattt    660

tggaactggg tagaaaatta tccagatgaa tttacaaaac tgtaccagat cccacagact    720

gatatggctg aatgtgcaga aaagctattt gacttggtgg atggttttgc tgaaagcacc    780

aaacgtaaag cagcagtttg gccactacaa atcattctcc ttatcttgtg cccagaaata    840
```

```
atccaggata tatccaaaga cgtggttgat gaaaacaaca tgaataagaa gttatttctg     900
gacagtctac gaaaagctct tgctggccat ggaggaagta ggcagctgac agaaagtgct     960
gcaattgcct gtgtcaaact gtgtaaagca agtacttaca tcaattggga agataactct    1020
gtcattttcc tacttgttca gtccatggtg gttgatctta agaacctgct ttttaatcca    1080
agtaagccat tctcaagagg cagtcagcct gcagatgtgg atctaatgat tgactgcctt    1140
gtttcttgct ttcgtataag ccctcacaac aaccaacact ttaagatctg cctggctcag    1200
aattcacctt ctacatttca ctatgtgctg gtaaattcac tccatcgaat catcaccaat    1260
tccgcattgg attggtggcc taagattgat gctgtgtatt gtcactcggt tgaacttcga    1320
aatatgtttg gtgaaacact tcataaagca gtgcaaggtt gtggagcaca cccagcaata    1380
cgaatggcac cgagtcttac atttaaagaa aaagtaacaa gccttaaatt taaagaaaaa    1440
cctacagacc tggagacaag aagctataag tatcttctct tgtccatggt gaaactaatt    1500
catgcagatc caaagctctt gctttgtaat ccaagaaaac aggggcccga aacccaaggc    1560
agtacagcag aattaattac agggctcgtc caactggtcc ctcagtcaca catgccagag    1620
attgctcagg aagcaatgga ggctctgctg gttcttcatc agttagatag cattgatttg    1680
tggaatcctg atgctcctgt agaaacattt tgggagatta gctcacaaat gctttttttac   1740
atctgcaaga aattaactag tcatcaaatg cttagtagca cagaaattct caagtggttg    1800
cgggaaatat tgatctgcag gaataaattt cttcttaaaa ataagcaggc agatagaagt    1860
tcctgtcact ttctcctttt ttacggggta ggatgtgata ttccttctag tggaaatacc    1920
agtcaaatgt ccatggatca tgaagaatta ctacgtactc ctggagcctc tctccggaag    1980
ggaaaaggga actcctctat ggatagtgca gcaggatgca gcggaacccc cccaatttgc    2040
cgacaagccc agaccaaact agaagtggcc ctgtacatgt ttctgtggaa ccctgacact    2100
gaagctgttc tggttgccat gtcctgtttc cgccacctct gtgaggaagc agatatccgg    2160
tgtggggtgg atgaagtgtc agtgcataac ctcttgccca actataacac attcatggag    2220
tttgcctctg tcagcaatat gatgtcaaca ggaagagcag cacttcagaa aagagtgatg    2280
gcactgctga ggcgcattga gcatcccact gcaggaaaca ctgaggcttg ggaagataca    2340
catgcaaaat gggaacaagc aacaaagcta atccttaact atccaaaagc caaaatggaa    2400
gatggccagg ctgctgaaag ccttcacaag accattgtta agaggcgaat gtcccatgtg    2460
agtggaggag gatccataga tttgtctgac acagactccc tacaggaatg gatcaacatg    2520
actggcttcc tttgtgccct tgggggagtg tgcctccagc agagaagcaa ttctggcctg    2580
gcaacctata gcccacccat gggtccagtc agtgaacgta agggttctat gatttcagtg    2640
atgtcttcag agggaaacgc agatacacct gtcagcaaat ttatggatcg gctgttgtcc    2700
ttaatggtgt gtaaccatga gaaagtggga cttcaaatac ggaccaatgt taaggatctg    2760
gtgggtctag aattgagtcc tgctctgtat ccaatgctat ttaacaaatt gaagaatacc    2820
atcagcaagt tttttgactc ccaaggacag gttttattga ctgataccaa tactcaattt    2880
gtagaacaaa ccatagctat aatgaagaac ttgctagata atcatactga aggcagctct    2940
gaacatctag ggcaagctag cattgaaaca atgatgttaa atctggtcag gtatgttcgt    3000
gtgcttggga atatggtcca tgcaattcaa ataaaaacga aactgtgtca attagttgaa    3060
gtaatgatgg caaggagaga tgacctctca ttttgccaag agatgaaatt taggaataag    3120
atggtagaat acctgacaga ctgggttatg ggaacatcaa accaagcagc agatgatgat    3180
```

```
gtaaaatgtc ttacaagaga tttggaccag gcaagcatgg aagcagtagt ttcacttcta   3240

gctggtctcc ctctgcagcc tgaagaagga gatggtgtgg aattgatgga agccaaatca   3300

cagttatttc ttaaatactt cacattattt atgaaccttt tgaatgactg cagtgaagtt   3360

gaagatgaaa gtgcgcaaac aggtggcagg aaacgtggca tgtctcggag gctggcatca   3420

ctgaggcact gtacggtcct tgcaatgtca aacttactca atgccaacgt agacagtggt   3480

ctcatgcact ccataggctt aggttaccac aaggatctcc agacaagagc tacatttatg   3540

gaagttctga caaaaatcct tcaacaaggc acagaatttg acacacttgc agaaacagta   3600

ttggctgatc ggtttgagag attggtggaa ctggtcacaa tgatgggtga tcaaggagaa   3660

ctccctatag cgatggctct ggccaatgtg gttccttgtt ctcagtggga tgaactagct   3720

cgagttctgg ttactctgtt tgattctcgg catttactct accaactgct ctggaacatg   3780

ttttctaaag aagtagaatt ggcagactcc atgcagactc tcttccgagg caacagcttg   3840

gccagtaaaa taatgacatt ctgtttcaag gtatatggtg ctacctatct acaaaaactc   3900

ctggatcctt tattacgaat tgtgatcaca tcctctgatt ggcaacatgt tagctttgaa   3960

gtggatccta ccaggttaga accatcagag agccttgagg aaaaccagcg gaacctcctt   4020

cagatgactg aaaagttctt ccatgccatc atcagttcct cctcagaatt cccccctcaa   4080

cttcgaagtg tgtgccactg tttataccag gcaacttgcc actccctact gaataaagct   4140

acagtaaaag aaaaaaagga aaacaaaaaa tca                                4173
```

<210> SEQ ID NO 12
<211> LENGTH: 7463
<212> TYPE: DNA
<213> ORGANISM: Artificial Sequence
<220> FEATURE:
<223> OTHER INFORMATION: Synthetic

<400> SEQUENCE: 12

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccaga tctgtcgaca attgagggcg tcaccgctaa    180

ggctccgccc cagcctgggc tccacaacca atgaagggta atctcgacaa agagcaaggg    240

gtggggcgcg ggcgcgcagg tgcagcagca cacaggctgg tcgggagggc ggggcgcgac    300

gtctgccgtg cggggtcccg gcatcggttg cgcgcgcgct ccctcctctc ggagagaggg    360

ctgtggtaaa acccgtccgg aaaactagtg ccaccatggc cgcgcacagg ccggtggaat    420

gggtccaggc cgtggtcagc cgcttcgacg agcagcttcc aataaaaaca ggacagcaga    480

acacacatac caaagtcagt actgagcaca acaaggaatg tctaatcaat atttccaaat    540

acaagttttc tttggttata agcggcctca ctactatttt aaagaatgtt aacaatatga    600

gaatatttgg agaagctgct gaaaaaaatt tatatctctc tcagttgatt atattggata    660

cactggaaaa atgtcttgct gggcaaccaa aggacacaat gagattagat gaaacgatgc    720

tggtcaaaca gttgctgcca gaaatctgcc attttcttca cacctgtcgt gaaggaaacc    780

agcatgcagc tgaacttcgg aattctgcct ctggggtttt attttctctc agctgcaaca    840

acttcaatgc agtctttagt cgcatttcta ccaggttaca ggaattaact gtttgttcag    900

aagacaatgt tgatgttcat gatatagaat tgttacagta tatcaatgtg gattgtgcaa    960

aattaaaacg actcctgaag gaaacagcat ttaaatttaa agccctaaag aaggttgcgc   1020

agttagcagt tataaatagc ctggaaaagg cattttggaa ctgggtagaa aattatccag   1080
```

```
atgaatttac aaaactgtac cagatcccac agactgatat ggctgaatgt gcagaaaagc   1140
tatttgactt ggtggatggt tttgctgaaa gcaccaaacg taaagcagca gtttggccac   1200
tacaaatcat tctccttatc ttgtgcccag aaataatcca ggatatatcc aaagacgtgg   1260
ttgatgaaaa caacatgaat aagaagttat ttctggacag tctacgaaaa gctcttgctg   1320
gccatggagg aagtaggcag ctgacagaaa gtgctgcaat tgcctgtgtc aaactgtgta   1380
aagcaagtac ttacatcaat tgggaagata actctgtcat tttcctactt gttcagtcca   1440
tggtggttga tcttaagaac ctgcttttta atccaagtaa gccattctca agaggcagtc   1500
agcctgcaga tgtggatcta atgattgact gccttgtttc ttgctttcgt ataagccctc   1560
acaacaacca acactttaag atctgcctgg ctcagaattc accttctaca tttcactatg   1620
tgctggtaaa ttcactccat cgaatcatca ccaattccgc attggattgg tggcctaaga   1680
ttgatgctgt gtattgtcac tcggttgaac ttcgaaatat gtttggtgaa acacttcata   1740
aagcagtgca aggttgtgga gcacacccag caatacgaat ggcaccgagt cttacattta   1800
aagaaaaagt aacaagcctt aaatttaaag aaaaacctac agacctggag acaagaagct   1860
ataagtatct tctcttgtcc atggtgaaac taattcatgc agatccaaag ctcttgcttt   1920
gtaatccaag aaaacagggg cccgaaaccc aaggcagtac agcagaatta attacagggc   1980
tcgtccaact ggtccctcag tcacacatgc cagagattgc tcaggaagca atggaggctc   2040
tgctggttct tcatcagtta gatagcattg atttgtggaa tcctgatgct cctgtagaaa   2100
cattttggga gattagctca caaatgcttt tttacatctg caagaaatta actagtcatc   2160
aaatgcttag tagcacagaa attctcaagt ggttgcggga aatattgatc tgcaggaata   2220
aatttcttct taaaaataag caggcagata gaagttcctg tcactttctc ctttttttacg   2280
gggtaggatg tgatattcct tctagtggaa ataccagtca aatgtccatg gatcatgaag   2340
aattactacg tactcctgga gcctctctcc ggaagggaaa agggaactcc tctatggata   2400
gtgcagcagg atgcagcgga acccccccaa tttgccgaca agcccagacc aaactagaag   2460
tggccctgta catgtttctg tggaaccctg acactgaagc tgttctggtt gccatgtcct   2520
gtttccgcca cctctgtgag gaagcagata tccggtgtgg ggtggatgaa gtgtcagtgc   2580
ataacctctt gcccaactat aacacattca tggagtttgc ctctgtcagc aatatgatgt   2640
caacaggaag agcagcactt cagaaaagag tgatggcact gctgaggcgc attgagcatc   2700
ccactgcagg aaacactgag gcttgggaag atacacatgc aaaatgggaa caagcaacaa   2760
agctaatcct taactatcca aaagccaaaa tggaagatgg ccaggctgct gaaagccttc   2820
acaagaccat tgttaagagg cgaatgtccc atgtgagtgg aggaggatcc atagatttgt   2880
ctgacacaga ctccctacag gaatggatca acatgactgg cttcctttgt gcccttgggg   2940
gagtgtgcct ccagcagaga agcaattctg gcctggcaac ctatagccca cccatgggtc   3000
cagtcagtga acgtaagggt tctatgattt cagtgatgtc ttcagaggga aacgcagata   3060
cacctgtcag caaatttatg gatcggctgt tgtccttaat ggtgtgtaac catgagaaag   3120
tgggacttca aatacggacc aatgttaagg atctggtggg tctagaattg agtcctgctc   3180
tgtatccaat gctatttaac aaattgaaga ataccatcag caagtttttt gactcccaag   3240
gacaggtttt attgactgat accaatactc aatttgtaga acaaaccata gctataatga   3300
agaacttgct agataatcat actgaaggca gctctgaaca tctagggcaa gctagcattg   3360
aaacaatgat gttaaatctg gtcaggtatg ttcgtgtgct tgggaatatg gtccatgcaa   3420
```

ttcaaataaa aacgaaactg tgtcaattag ttgaagtaat gatggcaagg agagatgacc 3480
tctcattttg ccaagagatg aaatttagga ataagatggt agaatacctg acagactggg 3540
ttatgggaac atcaaaccaa gcagcagatg atgatgtaaa atgtcttaca agagatttgg 3600
accaggcaag catggaagca gtagtttcac ttctagctgg tctccctctg cagcctgaag 3660
aaggagatgg tgtggaattg atggaagcca aatcacagtt atttcttaaa tacttcacat 3720
tatttatgaa ccttttgaat gactgcagtg aagttgaaga tgaaagtgcg caaacaggtg 3780
gcaggaaacg tggcatgtct cggaggctgg catcactgag gcactgtacg gtccttgcaa 3840
tgtcaaactt actcaatgcc aacgtagaca gtggtctcat gcactccata ggcttaggtt 3900
accacaagga tctccagaca agagctacat ttatggaagt tctgacaaaa atccttcaac 3960
aaggcacaga atttgacaca cttgcagaaa cagtattggc tgatcggttt gagagattgg 4020
tggaactggt cacaatgatg ggtgatcaag gagaactccc tatagcgatg gctctggcca 4080
atgtggttcc ttgttctcag tgggatgaac tagctcgagt tctggttact ctgtttgatt 4140
ctcggcattt actctaccaa ctgctctgga acatgttttc taaagaagta gaattggcag 4200
actccatgca gactctcttc cgaggcaaca gcttggccag taaaataatg acattctgtt 4260
tcaaggtata tggtgctacc tatctacaaa aactcctgga tcctttatta cgaattgtga 4320
tcacatcctc tgattggcaa catgttagct ttgaagtgga tcctaccagg ttagaaccat 4380
cagagagcct tgaggaaaac cagcggaacc tccttcagat gactgaaaag ttcttccatg 4440
ccatcatcag ttcctcctca gaattccccc ctcaacttcg aagtgtgtgc cactgtttat 4500
accaggcaac ttgccactcc ctactgaata aagctacagt aaaagaaaaa aaggaaaaca 4560
aaaaatcagt gggcagcatg tggaacctgg cgagccccat ccccggcaag ctctcaagcc 4620
atgctggtgg ggacgactga atgccagggc ccttcactgg gctatttcac ccagggacgc 4680
ttcttgaagg caccccccac tccaagctca attgaactcg agaatcgata ggccgcagga 4740
acccctagtg atggagttgg ccactccctc tctgcgcgct cgctcgctca ctgaggccgg 4800
gcgaccaaag gtcgcccgac gcccgggcgg cctcagtgag cgagcgagcg cgcagctgcc 4860
tgcaggacat gtgagcaaaa ggccagcaaa aggccaggaa ccgtaaaaag gccgcgttgc 4920
tggcgttttt ccataggctc cgcccccctg acgagcatca caaaaatcga cgctcaagtc 4980
agaggtggcg aaacccgaca ggactataaa gataccaggc gtttccccct ggaagctccc 5040
tcgtgcgctc tcctgttccg accctgccgc ttaccggata cctgtccgcc tttctccctt 5100
cgggaagcgt ggcgctttct catagctcac gctgtaggta tctcagttcg gtgtaggtcg 5160
ttcgctccaa gctgggctgt gtgcacgaac cccccgttca gcccgaccgc tgcgccttat 5220
ccggtaacta tcgtcttgag tccaacccgg taagacacga cttatcgcca ctggcagcag 5280
ccactggtaa caggattagc agagcgaggt atgtaggcgg tgctacagag ttcttgaagt 5340
ggtggcctaa ctacggctac actagaagaa cagtatttgg tatctgcgct ctgctgaagc 5400
cagttacctt cggaaaaaga gttggtagct cttgatccgg caaacaaacc accgctggta 5460
gcggtggttt ttttgtttgc aagcagcaga ttacgcgcag aaaaaaagga tctcaagaag 5520
atcctttgat cttttctacg gggtctgacg ctcagtggaa cgaaaactca cgttaaggga 5580
ttttggtcat gagattatca aaaaggatct tcacctagat ccttttaaat taaaaatgaa 5640
gttttaaatc aatctaaagt atatatgagt aaacttggtc tgacagttac caatgcttaa 5700
tcagtgaggc acctatctca gcgatctgtc tatttcgttc atccatagtt gcctgactcc 5760
ccgtcgtgta gataactacg atacgggagg gcttaccatc tggccccagt gctgcaatga 5820

```
taccgcgaga cccacgctca ccggctccag atttatcagc aataaaccag ccagccggaa   5880

gggccgagcg cagaagtggt cctgcaactt tatccgcctc catccagtct attaattgtt   5940

gccgggaagc tagagtaagt agttcgccag ttaatagttt gcgcaacgtt gttgccattg   6000

ctacaggcat cgtggtgtca cgctcgtcgt ttggtatggc ttcattcagc tccggttccc   6060

aacgatcaag gcgagttaca tgatccccca tgttgtgcaa aaaagcggtt agctccttcg   6120

gtcctccgat cgttgtcaga agtaagttgg ccgcagtgtt atcactcatg gttatggcag   6180

cactgcataa ttctcttact gtcatgccat ccgtaagatg cttttctgtg actggtgagt   6240

actcaaccaa gtcattctga gaatagtgta tgcggcgacc gagttgctct tgcccggcgt   6300

caatacggga taataccgcg ccacatagca gaactttaaa agtgctcatc attggaaaac   6360

gttcttcggg gcgaaaactc tcaaggatct taccgctgtt gagatccagt tcgatgtaac   6420

ccactcgtgc acccaactga tcttcagcat cttttacttt caccagcgtt tctgggtgag   6480

caaaaacagg aaggcaaaat gccgcaaaaa agggaataag ggcgacacgg aaatgttgaa   6540

tactcatact cttccttttt caatattatt gaagcattta tcagggttat tgtctcatga   6600

gcggatacat atttgaatgt atttagaaaa ataaacaaat aggggttccg cgcacatttc   6660

cccgaaaagt gccacctgac gtctaagaaa ccattattat catgacatta acctataaaa   6720

ataggcgtat cacgaggccc tttcgtctcg cgcgtttcgg tgatgacggt gaaaacctct   6780

gacacatgca gctcccggag acggtcacag cttgtctgta agcggatgcc gggagcagac   6840

aagcccgtca gggcgcgtca gcgggtgttg gcgggtgtcg gggctggctt aactatgcgg   6900

catcagagca gattgtactg agagtgcacc ataaaattgt aaacgttaat attttgttaa   6960

aattcgcgtt aaatttttgt taaatcagct cattttttaa ccaataggcc gaaatcggca   7020

aaatccctta taaatcaaaa gaatagcccg agatagggtt gagtgttgtt ccagtttgga   7080

acaagagtcc actattaaag aacgtggact ccaacgtcaa agggcgaaaa accgtctatc   7140

agggcgatgg cccactacgt gaaccatcac ccaaatcaag ttttttgggg tcgaggtgcc   7200

gtaaagcact aaatcggaac cctaaaggga gcccccgatt tagagcttga cggggaaagc   7260

cggcgaacgt ggcgagaaag gaagggaaga aagcgaaagg agcgggcgct aaggcgctgg   7320

caagtgtagc ggtcacgctg cgcgtaacca ccacacccgc cgcgcttaat gcgccgctac   7380

agggcgcgta ctatggttgc tttgacgtat gcggtgtgaa ataccgcaca gatgcgtaag   7440

gagaaaatac cgcatcaggc gcc                                           7463
```

```
<210> SEQ ID NO 13
<211> LENGTH: 1448
<212> TYPE: PRT
<213> ORGANISM: Artificial Sequence
<220> FEATURE:
<223> OTHER INFORMATION: Synthetic

<400> SEQUENCE: 13

Met Val Ser Gln Arg Phe Pro Gln Asn Ser Ile Gly Ala Val Gly Ser
1               5                   10                  15

Ala Met Phe Leu Arg Phe Ile Asn Pro Ala Ile Val Ser Pro Tyr Glu
            20                  25                  30

Ala Gly Ile Leu Asp Lys Lys Pro Pro Pro Arg Ile Glu Arg Gly Leu
        35                  40                  45

Lys Leu Met Ser Lys Ile Leu Gln Ser Ile Ala Asn His Val Leu Phe
    50                  55                  60
```

-continued

```
Thr Lys Glu Glu His Met Arg Pro Phe Asn Asp Phe Val Lys Ser Asn
65                  70                  75                  80

Phe Asp Ala Ala Arg Arg Phe Phe Leu Asp Ile Ala Ser Asp Cys Pro
                85                  90                  95

Thr Ser Asp Ala Val Asn His Ser Leu Ser Phe Ile Ser Asp Gly Asn
            100                 105                 110

Val Leu Ala Leu His Arg Leu Leu Trp Asn Asn Gln Glu Lys Ile Gly
        115                 120                 125

Gln Tyr Leu Ser Ser Asn Arg Asp His Lys Ala Val Gly Arg Arg Pro
    130                 135                 140

Phe Asp Lys Met Ala Thr Leu Leu Ala Tyr Leu Gly Pro Pro Glu His
145                 150                 155                 160

Lys Pro Val Ala Asp Thr His Trp Ser Ser Leu Asn Leu Thr Ser Ser
                165                 170                 175

Lys Phe Glu Glu Phe Met Thr Arg His Gln Val His Glu Lys Glu Glu
            180                 185                 190

Phe Lys Ala Leu Lys Thr Leu Ser Ile Phe Tyr Gln Ala Gly Thr Ser
        195                 200                 205

Lys Ala Gly Asn Pro Ile Phe Tyr Tyr Val Ala Arg Arg Phe Lys Thr
    210                 215                 220

Gly Gln Ile Asn Gly Asp Leu Leu Ile Tyr His Val Leu Leu Thr Leu
225                 230                 235                 240

Lys Pro Tyr Tyr Ala Lys Pro Tyr Glu Ile Val Val Asp Leu Thr His
                245                 250                 255

Thr Gly Pro Ser Asn Arg Phe Lys Thr Asp Phe Leu Ser Lys Trp Phe
            260                 265                 270

Val Val Phe Pro Gly Phe Ala Tyr Asp Asn Val Ser Met Val Tyr Ile
        275                 280                 285

Tyr Asn Cys Asn Ser Trp Val Arg Glu Tyr Thr Lys Tyr His Glu Arg
    290                 295                 300

Leu Leu Thr Gly Leu Lys Gly Ser Lys Arg Leu Val Phe Ile Asp Cys
305                 310                 315                 320

Pro Gly Lys Leu Ala Glu His Ile Glu His Glu Gln Gln Lys Leu Pro
                325                 330                 335

Ala Ala Thr Leu Ala Leu Glu Glu Asp Leu Lys Val Phe His Asn Ala
            340                 345                 350

Leu Lys Leu Ala His Lys Asp Thr Lys Val Ser Ile Lys Val Gly Ser
        355                 360                 365

Thr Ala Val Gln Val Thr Ser Ala Glu Arg Thr Lys Val Leu Gly Gln
    370                 375                 380

Ser Val Phe Leu Asn Asp Ile Tyr Tyr Ala Ser Glu Ile Glu Glu Ile
385                 390                 395                 400

Cys Leu Val Asp Glu Asn Gln Phe Thr Leu Thr Ile Ala Asn Gln Gly
                405                 410                 415

Thr Pro Leu Thr Phe Met His Gln Glu Cys Glu Ala Ile Val Gln Ser
            420                 425                 430

Ile Ile His Ile Arg Thr Arg Trp Glu Leu Ser Gln Pro Asp Ser Ile
        435                 440                 445

Pro Gln His Thr Lys Ile Arg Pro Lys Asp Val Pro Gly Thr Leu Leu
    450                 455                 460

Asn Ile Ala Leu Leu Asn Leu Gly Ser Ser Asp Pro Ser Leu Arg Ser
465                 470                 475                 480

Ala Ala Tyr Asn Leu Leu Cys Ala Leu Thr Cys Thr Phe Asn Leu Lys
```

```
                485                 490                 495

Ile Glu Gly Gln Leu Leu Glu Thr Ser Gly Leu Cys Ile Pro Ala Asn
            500                 505                 510

Asn Thr Leu Phe Ile Val Ser Ile Ser Lys Thr Leu Ala Ala Asn Glu
        515                 520                 525

Pro His Leu Thr Leu Glu Phe Leu Glu Glu Cys Ile Ser Gly Phe Ser
    530                 535                 540

Lys Ser Ser Ile Glu Leu Lys His Leu Cys Leu Glu Tyr Met Thr Pro
545                 550                 555                 560

Trp Leu Ser Asn Leu Val Arg Phe Cys Lys His Asn Asp Asp Ala Lys
                565                 570                 575

Arg Gln Arg Val Thr Ala Ile Leu Asp Lys Leu Ile Thr Met Thr Ile
            580                 585                 590

Asn Glu Lys Gln Met Tyr Pro Ser Ile Gln Ala Lys Ile Trp Gly Ser
        595                 600                 605

Leu Gly Gln Ile Thr Asp Leu Leu Asp Val Val Leu Asp Ser Phe Ile
    610                 615                 620

Lys Thr Ser Ala Thr Gly Gly Leu Gly Ser Ile Lys Ala Glu Val Met
625                 630                 635                 640

Ala Asp Thr Ala Val Ala Leu Ala Ser Gly Asn Val Lys Leu Val Ser
                645                 650                 655

Ser Lys Val Ile Gly Arg Met Cys Lys Ile Ile Asp Lys Thr Cys Leu
            660                 665                 670

Ser Pro Thr Pro Thr Leu Glu Gln His Leu Met Trp Asp Asp Ile Ala
        675                 680                 685

Ile Leu Ala Arg Tyr Met Leu Met Leu Ser Phe Asn Asn Ser Leu Asp
    690                 695                 700

Val Ala Ala His Leu Pro Tyr Leu Phe His Val Val Thr Phe Leu Val
705                 710                 715                 720

Ala Thr Gly Pro Leu Ser Leu Arg Ala Ser Thr His Gly Leu Val Ile
                725                 730                 735

Asn Ile Ile His Ser Leu Cys Thr Cys Ser Gln Leu His Phe Ser Glu
            740                 745                 750

Glu Thr Lys Gln Val Leu Arg Leu Ser Leu Thr Glu Phe Ser Leu Pro
        755                 760                 765

Lys Phe Tyr Leu Leu Phe Gly Ile Ser Lys Val Lys Ser Ala Ala Val
    770                 775                 780

Ile Ala Phe Arg Ser Ser Tyr Arg Asp Arg Ser Phe Ser Pro Gly Ser
785                 790                 795                 800

Tyr Glu Arg Glu Thr Phe Ala Leu Thr Ser Leu Glu Thr Val Thr Glu
                805                 810                 815

Ala Leu Leu Glu Ile Met Glu Ala Cys Met Arg Asp Ile Pro Thr Cys
            820                 825                 830

Lys Trp Leu Asp Gln Trp Thr Glu Leu Ala Gln Arg Phe Ala Phe Gln
        835                 840                 845

Tyr Asn Pro Ser Leu Gln Pro Arg Ala Leu Val Val Phe Gly Cys Ile
    850                 855                 860

Ser Lys Arg Val Ser His Gly Gln Ile Lys Gln Ile Ile Arg Ile Leu
865                 870                 875                 880

Ser Lys Ala Leu Glu Ser Cys Leu Lys Gly Pro Asp Thr Tyr Asn Ser
                885                 890                 895

Gln Val Leu Ile Glu Ala Thr Val Ile Ala Leu Thr Lys Leu Gln Pro
            900                 905                 910
```

```
Leu Leu Asn Lys Asp Ser Pro Leu His Lys Ala Leu Phe Trp Val Ala
        915                 920                 925

Val Ala Val Leu Gln Leu Asp Glu Val Asn Leu Tyr Ser Ala Gly Thr
    930                 935                 940

Ala Leu Leu Glu Gln Asn Leu His Thr Leu Asp Ser Leu Arg Ile Phe
945                 950                 955                 960

Asn Asp Lys Ser Pro Glu Glu Val Phe Met Ala Ile Arg Asn Pro Leu
                965                 970                 975

Glu Trp His Cys Lys Gln Met Asp His Phe Val Gly Leu Asn Phe Asn
            980                 985                 990

Ser Asn Phe Asn Phe Ala Leu Val  Gly His Leu Leu Lys  Gly Tyr Arg
        995                 1000                1005

His Pro  Ser Pro Ala Ile Val  Ala Arg Thr Val Arg  Ile Leu His
    1010                1015                1020

Thr Leu  Leu Thr Leu Val Asn  Lys His Arg Asn Cys  Asp Lys Phe
    1025                1030                1035

Glu Val  Asn Thr Gln Ser Val  Ala Tyr Leu Ala Ala  Leu Leu Thr
    1040                1045                1050

Val Ser  Glu Glu Val Arg Ser  Arg Cys Ser Leu Lys  His Arg Lys
    1055                1060                1065

Ser Leu  Leu Leu Thr Asp Ile  Ser Met Glu Asn Val  Pro Met Asp
    1070                1075                1080

Thr Tyr  Pro Ile His His Gly  Asp Pro Ser Tyr Arg  Thr Leu Lys
    1085                1090                1095

Glu Thr  Gln Pro Trp Ser Ser  Pro Lys Gly Ser Glu  Gly Tyr Leu
    1100                1105                1110

Ala Ala  Thr Tyr Pro Thr Val  Gly Gln Thr Ser Pro  Arg Ala Arg
    1115                1120                1125

Lys Ser  Met Ser Leu Asp Met  Gly Gln Pro Ser Gln  Ala Asn Thr
    1130                1135                1140

Lys Lys  Leu Leu Gly Thr Arg  Lys Ser Phe Asp His  Leu Ile Ser
    1145                1150                1155

Asp Thr  Lys Ala Pro Lys Arg  Gln Glu Met Glu Ser  Gly Ile Thr
    1160                1165                1170

Thr Pro  Pro Lys Met Arg Arg  Val Ala Glu Thr Asp  Tyr Glu Met
    1175                1180                1185

Glu Thr  Gln Arg Ile Ser Ser  Ser Gln Gln His Pro  His Leu Arg
    1190                1195                1200

Lys Val  Ser Val Ser Glu Ser  Asn Val Leu Leu Asp  Glu Glu Val
    1205                1210                1215

Leu Thr  Asp Pro Lys Ile Gln  Ala Leu Leu Leu Thr  Val Leu Ala
    1220                1225                1230

Thr Leu  Val Lys Tyr Thr Thr  Asp Glu Phe Asp Gln  Arg Ile Leu
    1235                1240                1245

Tyr Glu  Tyr Leu Ala Glu Ala  Ser Val Val Phe Pro  Lys Val Phe
    1250                1255                1260

Pro Val  Val His Asn Leu Leu  Asp Ser Lys Ile Asn  Thr Leu Leu
    1265                1270                1275

Ser Leu  Cys Gln Asp Pro Asn  Leu Leu Asn Pro Ile  His Gly Ile
    1280                1285                1290

Val Gln  Ser Val Val Tyr His  Glu Glu Ser Pro Pro  Gln Tyr Gln
    1295                1300                1305
```

```
Thr Ser  Tyr Leu Gln Ser Phe  Gly Phe Asn Gly Leu  Trp Arg Phe
    1310                 1315                 1320

Ala Gly  Pro Phe Ser Lys Gln  Thr Gln Ile Pro Asp  Tyr Ala Glu
    1325                 1330                 1335

Leu Ile  Val Lys Phe Leu Asp  Ala Leu Ile Asp Thr  Tyr Leu Pro
    1340                 1345                 1350

Gly Ile  Asp Glu Glu Thr Ser  Glu Glu Ser Leu Leu  Thr Pro Thr
    1355                 1360                 1365

Ser Pro  Tyr Pro Pro Ala Leu  Gln Ser Gln Leu Ser  Ile Thr Ala
    1370                 1375                 1380

Asn Leu  Asn Leu Ser Asn Ser  Met Thr Ser Leu Ala  Thr Ser Gln
    1385                 1390                 1395

His Ser  Pro Gly Ile Asp Lys  Glu Asn Val Glu Leu  Ser Pro Thr
    1400                 1405                 1410

Thr Gly  His Cys Asn Ser Gly  Arg Thr Arg His Gly  Ser Ala Ser
    1415                 1420                 1425

Gln Val  Gln Lys Gln Arg Ser  Ala Gly Ser Phe Lys  Arg Asn Ser
    1430                 1435                 1440

Ile Lys  Lys Ile Val
    1445
```

<210> SEQ ID NO 14
<211> LENGTH: 4344
<212> TYPE: DNA
<213> ORGANISM: Artificial Sequence
<220> FEATURE:
<223> OTHER INFORMATION: Synthetic

<400> SEQUENCE: 14

```
gtggttagcc agcgtttccc tcagaacagc atcggtgcag taggaagtgc catgttcctc     60

agatttatca atcctgccat tgtctcaccg tatgaagcag ggattttaga taaaaagcca    120

ccacctagaa tcgaaagggg cttgaagtta atgtcaaaga tacttcagag tattgccaat    180

catgttctct tcacaaaaga agaacatatg cggcctttca atgattttgt gaaaagcaac    240

tttgatgcag cacgcaggtt tttccttgat atagcatctg attgtcctac aagtgatgca    300

gtaaatcata gtctttcctt cataagtgac ggcaatgtgc ttgctttaca tcgtctactc    360

tggaacaatc aggagaaaat tggcagtat ctttccagca acagggatca taaagctgtt    420

ggaagacgac cttttgataa gatggcaaca cttcttgcat acctgggtcc tccagagcac    480

aaacctgtgg cagatacaca ctggtccagc cttaacctta ccagttcaaa gtttgaggaa    540

tttatgacta ggcatcaggt acatgaaaaa gaagaattca aggctttgaa aacgttaagt    600

attttctacc aagctgggac ttccaaagct gggaatccta ttttttatta tgttgcacgg    660

aggttcaaaa ctggtcaaat caatggtgat ttgctgatat accatgtctt actgacttta    720

aagccatatt atgcaaagcc atatgaaatt gtagtggacc ttacccatac cgggcctagc    780

aatcgcttta aaacagactt tctctctaag tggtttgttg tttttcctgg ctttgcttac    840

gacaacgtct ccgcagtcta tatctataac tgtaactcct gggtcaggga gtacaccaag    900

tatcatgagc ggctgctgac tggcctcaaa ggtagcaaaa ggcttgtttt catagactgt    960

cctgggaaac tggctgagca catagagcat gaacaacaga aactacctgc tgccaccttg   1020

gctttagaag aggacctgaa ggtattccac aatgctctca agctagctca caaagacacc   1080

aaagtttcta ttaaagttgg ttctactgct gtccaagtaa cttcagcaga gcgaacaaaa   1140

gtcctagggc aatcagtctt tctaaatgac atttattatg cttcggaaat tgaagaaatc   1200
```

```
tgcctagtag atgagaacca gttcacctta accattgcaa accagggcac gccgctcacc   1260
ttcatgcacc aggagtgtga agccattgtc cagtctatca ttcatatccg gacccgctgg   1320
gaactgtcac agcccgactc tatcccccaa cacaccaaga ttcggccaaa agatgtccct   1380
gggacactgc tcaatatcgc attacttaat ttaggcagtt ctgacccgag tttacggtca   1440
gctgcctata atcttctgtg tgccttaact tgtaccttta atttaaaaat cgagggccag   1500
ttactagaga catcaggttt atgtatccct gccaacaaca ccctctttat tgtctctatt   1560
agtaagacac tggcagccaa tgagccacac ctcacgttag aatttttgga agagtgtatt   1620
tctggattta gcaaatctag tattgaattg aaacaccttt gtttggaata catgactcca   1680
tggctgtcaa atctagttcg tttttgcaag cataatgatg atgccaaacg acaaagagtt   1740
actgctattc ttgacaagct gataacaatg accatcaatg aaaaacagat gtacccatct   1800
attcaagcaa aaatatgggg aagccttggg cagattacag atctgcttga tgttgtacta   1860
gacagtttca tcaaaaccag tgcaacaggt ggcttgggat caataaaagc tgaggtgatg   1920
gcagatactg ctgtagcttt ggcttctgga aatgtgaaat tggtttcaag caaggttatt   1980
ggaaggatgt gcaaaataat tgacaagaca tgcttatctc caactcctac tttagaacaa   2040
catcttatgt gggatgatat tgctatttta gcacgctaca tgctgatgct gtccttcaac   2100
aattcccttg atgtggcagc tcatcttccc tacctcttcc acgttgttac tttcttagta   2160
gccacaggtc cgctctccct tagagcttcc acacatggac tggtcattaa tatcattcac   2220
tctctgtgta cttgttcaca gcttcatttt agtgaagaga ccaagcaagt tttgagactc   2280
agtctgacag agttctcatt acccaaattt tacttgctgt ttggcattag caaagtcaag   2340
tcagctgctg tcattgcctt ccgttccagt taccgggaca ggtcattctc tcctggctcc   2400
tatgagagag agacttttgc tttgacatcc ttggaaacag tcacagaagc tttgttggag   2460
atcatggagg catgcatgag agatattcca acgtgcaagt ggctggacca gtggacagaa   2520
ctagctcaaa gatttgcatt ccaatataat ccatccctgc aaccaagagc tcttgttgtc   2580
tttgggtgta ttagcaaacg agtgtctcat gggcagataa agcagataat ccgtattctt   2640
agcaaggcac ttgagagttg cttaaaagga cctgacactt acaacagtca agttctgata   2700
gaagctacag taatagcact aaccaaatta cagccacttc ttaataagga ctcgcctctg   2760
cacaaagccc tcttttgggt agctgtggct gtgctgcagc ttgatgaggt caacttgtat   2820
tcagcaggta ccgcacttct tgaacaaaac ctgcatactt tagatagtct ccgtatattc   2880
aatgacaaga gtccagagga agtatttatg gcaatccgga atcctctgga gtggcactgc   2940
aagcaaatgg atcattttgt tggactcaat ttcaactcta actttaactt tgcattggtt   3000
ggacaccttt taaaagggta caggcatcct tcacctgcta ttgttgcaag aacagtcaga   3060
attttacata cactactaac tctggttaac aaacacagaa attgtgacaa atttgaagtg   3120
aatacacaga gcgtggccta cttagcagct ttacttacag tgtctgaaga agttcgaagt   3180
cgctgcagcc taaaacatag aaagtcactt cttcttactg atatttcaat ggaaaatgtt   3240
cctatggata catatcccat tcatcatggt gacccttcct ataggacact aaaggagact   3300
cagccatggt cctctcccaa aggttctgaa ggataccttg cagccaccta tccaactgtc   3360
ggccagacca gtccccgagc caggaaatcc atgagcctgg acatggggca accttctcag   3420
gccaacacta agaagttgct tggaacaagg aaaagttttg atcacttgat atcagacaca   3480
aaggctccta aaaggcaaga aatggaatca gggatcacaa caccccccaa aatgaggaga   3540
```

```
gtagcagaaa ctgattatga aatggaaact cagaggattt cctcatcaca acagcaccca   3600

catttacgta aagtttcagt gtctgaatca aatgttctct tggatgaaga agtacttact   3660

gatccgaaga tccaggcgct gcttcttact gttctagcta cactggtaaa atataccaca   3720

gatgagtttg atcaacgaat tctttatgaa tacttagcag aggccagtgt tgtgtttccc   3780

aaagtctttc ctgttgtgca taatttgttg gactctaaga tcaacaccct gttatcattg   3840

tgccaagatc caaatttgtt aaatccaatc catggaattg tgcagagtgt ggtgtaccat   3900

gaagaatccc caccacaata ccaaacatct tacctgcaaa gttttggttt taatggcttg   3960

tggcggtttg caggaccgtt ttcaaagcaa acacaaattc cagactatgc tgagcttatt   4020

gttaagtttc ttgatgcctt gattgacacg tacctgcctg gaattgatga agaaaccagt   4080

gaagaatccc tcctgactcc cacatctcct taccctcctg cactgcagag ccagcttagt   4140

atcactgcca accttaacct ttctaattcc atgacctcac ttgcaacttc ccagcattcc   4200

ccaggaatcg acaaggagaa cgttgaactc tcccctacca ctggccactg taacagtgga   4260

cgaactcgcc acggatccgc aagccaagtg cagaagcaaa gaagcgctgg cagtttcaaa   4320

cgtaatagca ttaagaagat cgtg                                         4344
```

<210> SEQ ID NO 15
<211> LENGTH: 7601
<212> TYPE: DNA
<213> ORGANISM: Artificial Sequence
<220> FEATURE:
<223> OTHER INFORMATION: Synthetic

<400> SEQUENCE: 15

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccaga tctgcaaatt aggaccgaga gtcagtggcc    180

gctcaagagt ctgtgaccat gccccaaatt cagagatggt cccaggagag atggggggaa    240

ctgccaagca atgagtgacc ggttccccct cccccaggtg gttagccagc gtttccctca    300

gaacagcatc ggtgcagtag gaagtgccat gttcctcaga tttatcaatc ctgccattgt    360

ctcaccgtat gaagcaggga ttttagataa aaagccacca cctagaatcg aaaggggctt    420

gaagttaatg tcaaagatac ttcagagtat tgccaatcat gttctcttca caaaagaaga    480

acatatgcgg cctttcaatg attttgtgaa aagcaacttt gatgcagcac gcaggttttt    540

ccttgatata gcatctgatt gtcctacaag tgatgcagta aatcatagtc tttccttcat    600

aagtgacggc aatgtgcttg ctttacatcg tctactctgg aacaatcagg agaaaattgg    660

gcagtatctt tccagcaaca gggatcataa agctgttgga agacgacctt ttgataagat    720

ggcaacactt cttgcatacc tgggtcctcc agagcacaaa cctgtggcag atacacactg    780

gtccagcctt aaccttacca gttcaaagtt tgaggaattt atgactaggc atcaggtaca    840

tgaaaaagaa gaattcaagg ctttgaaaac gttaagtatt ttctaccaag ctgggacttc    900

caaagctggg aatcctattt tttattatgt tgcacggagg ttcaaaactg gtcaaatcaa    960

tggtgatttg ctgatatacc atgtcttact gactttaaag ccatattatg caaagccata   1020

tgaaattgta gtggacctta cccataccgg gcctagcaat cgctttaaaa cagactttct   1080

ctctaagtgg tttgttgttt ttcctggctt tgcttacgac aacgtctccg cagtctatat   1140

ctataactgt aactcctggg tcagggagta caccaagtat catgagcggc tgctgactgg   1200

cctcaaaggt agcaaaaggc ttgttttcat agactgtcct gggaaactgg ctgagcacat   1260
```

```
agagcatgaa caacagaaac tacctgctgc caccttggct ttagaagagg acctgaaggt   1320
attccacaat gctctcaagc tagctcacaa agacaccaaa gtttctatta aagttggttc   1380
tactgctgtc caagtaactt cagcagagcg aacaaaagtc ctagggcaat cagtctttct   1440
aaatgacatt tattatgctt cggaaattga agaaatctgc ctagtagatg agaaccagtt   1500
caccttaacc attgcaaacc agggcacgcc gctcaccttc atgcaccagg agtgtgaagc   1560
cattgtccag tctatcattc atatccggac ccgctgggaa ctgtcacagc ccgactctat   1620
cccccaacac accaagattc ggccaaaaga tgtccctggg acactgctca atatcgcatt   1680
acttaattta ggcagttctg acccgagttt acggtcagct gcctataatc ttctgtgtgc   1740
cttaacttgt acctttaatt taaaaatcga gggccagtta ctagagacat caggtttatg   1800
tatccctgcc aacaacaccc tctttattgt ctctattagt aagacactgg cagccaatga   1860
gccacacctc acgttagaat tttggaaga gtgtatttct ggatttagca aatctagtat   1920
tgaattgaaa cacctttgtt tggaatacat gactccatgg ctgtcaaatc tagttcgttt   1980
ttgcaagcat aatgatgatg ccaaacgaca aagagttact gctattcttg acaagctgat   2040
aacaatgacc atcaatgaaa aacagatgta cccatctatt caagcaaaaa tatggggaag   2100
ccttgggcag attacagatc tgcttgatgt tgtactagac agtttcatca aaaccagtgc   2160
aacaggtggc ttgggatcaa taaaagctga ggtgatggca gatactgctg tagctttggc   2220
ttctggaaat gtgaaattgg tttcaagcaa ggttattgga aggatgtgca aaataattga   2280
caagacatgc ttatctccaa ctcctacttt agaacaacat cttatgtggg atgatattgc   2340
tattttagca cgctacatgc tgatgctgtc cttcaacaat tcccttgatg tggcagctca   2400
tcttccctac ctcttccacg ttgttacttt cttagtagcc acaggtccgc tctcccttag   2460
agcttccaca catggactgg tcattaatat cattcactct ctgtgtactt gttcacagct   2520
tcattttagt gaagagacca agcaagtttt gagactcagt ctgacagagt tctcattacc   2580
caaattttac ttgctgtttg gcattagcaa agtcaagtca gctgctgtca ttgccttccg   2640
ttccagttac cgggacaggt cattctctcc tggctcctat gagagagaga cttttgcttt   2700
gacatccttg gaaacagtca cagaagcttt gttggagatc atggaggcat gcatgagaga   2760
tattccaacg tgcaagtggc tggaccagtg gacagaacta gctcaaagat ttgcattcca   2820
atataatcca tccctgcaac caagagctct tgttgtcttt gggtgtatta gcaaacgagt   2880
gtctcatggg cagataaagc agataatccg tattcttagc aaggcacttg agagttgctt   2940
aaaaggacct gacacttaca acagtcaagt tctgatagaa gctacagtaa tagcactaac   3000
caaattacag ccacttctta ataaggactc gcctctgcac aaagccctct tttgggtagc   3060
tgtggctgtg ctgcagcttg atgaggtcaa cttgtattca gcaggtaccg cacttcttga   3120
acaaaacctg catactttag atagtctccg tatattcaat gacaagagtc cagaggaagt   3180
atttatggca atccggaatc ctctggagtg gcactgcaag caaatggatc attttgttgg   3240
actcaatttc aactctaact ttaactttgc attggttgga caccttttaa aagggtacag   3300
gcatccttca cctgctattg ttgcaagaac agtcagaatt ttacatacac tactaactct   3360
ggttaacaaa cacagaaatt gtgacaaatt tgaagtgaat acacagagcg tggcctactt   3420
agcagcttta cttacagtgt ctgaagaagt tcgaagtcgc tgcagcctaa aacatagaaa   3480
gtcacttctt cttactgata tttcaatgga aaatgttcct atggatacat atcccattca   3540
tcatggtgac ccttcctata ggacactaaa ggagactcag ccatggtcct ctcccaaagg   3600
```

ttctgaagga taccttgcag ccacctatcc aactgtcggc cagaccagtc cccgagccag 3660
gaaatccatg agcctggaca tggggcaacc ttctcaggcc aacactaaga agttgcttgg 3720
aacaaggaaa agttttgatc acttgatatc agacacaaag gctcctaaaa ggcaagaaat 3780
ggaatcaggg atcacaacac cccccaaaat gaggagagta gcagaaactg attatgaaat 3840
ggaaactcag aggatttcct catcacaaca gcacccacat ttacgtaaag tttcagtgtc 3900
tgaatcaaat gttctcttgg atgaagaagt acttactgat ccgaagatcc aggcgctgct 3960
tcttactgtt ctagctacac tggtaaaata taccacagat gagtttgatc aacgaattct 4020
ttatgaatac ttagcagagg ccagtgttgt gtttcccaaa gtctttcctg ttgtgcataa 4080
tttgttggac tctaagatca acaccctgtt atcattgtgc caagatccaa atttgttaaa 4140
tccaatccat ggaattgtgc agagtgtggt gtaccatgaa gaatccccac cacaatacca 4200
aacatcttac ctgcaaagtt ttggttttaa tggcttgtgg cggtttgcag gaccgttttc 4260
aaagcaaaca caaattccag actatgctga gcttattgtt aagtttcttg atgccttgat 4320
tgacacgtac ctgcctggaa ttgatgaaga aaccagtgaa gaatccctcc tgactcccac 4380
atctccttac cctcctgcac tgcagagcca gcttagtatc actgccaacc ttaacctttc 4440
taattccatg acctcacttg caacttccca gcattcccca ggaatcgaca aggagaacgt 4500
tgaactctcc cctaccactg gccactgtaa cagtggacga actcgccacg gatccgcaag 4560
ccaagtgcag aagcaaagaa gcgctggcag tttcaaacgt aatagcatta agaagatcgt 4620
ggagcggccg cttcgagcag acatgataag atacattgat gagtttggac aaaccacaac 4680
tagaatgcag tgaaaaaaat gctttatttg tgaaatttgt gatgctattg ctttatttgt 4740
aaccattata agctgcaata aacaagttaa caacaacaat tgcattcatt ttatgtttca 4800
ggttcagggg gagatgtggg aggtttttta aagcaagtaa aacctctaca aatgtggtaa 4860
aatcgatagg ccgcaggaac ccctagtgat ggagttggcc actccctctc tgcgcgctcg 4920
ctcgctcact gaggccgggc gaccaaaggt cgcccgacgc ccgggcggcc tcagtgagcg 4980
agcgagcgcg cagctgcctg caggacatgt gagcaaaagg ccagcaaaag gccaggaacc 5040
gtaaaaaggc cgcgttgctg gcgtttttcc ataggctccg cccccctgac gagcatcaca 5100
aaaatcgacg ctcaagtcag aggtggcgaa acccgacagg actataaaga taccaggcgt 5160
ttccccctgg aagctccctc gtgcgctctc ctgttccgac cctgccgctt accggatacc 5220
tgtccgcctt tctcccttcg ggaagcgtgg cgctttctca tagctcacgc tgtaggtatc 5280
tcagttcggt gtaggtcgtt cgctccaagc tgggctgtgt gcacgaaccc cccgttcagc 5340
ccgaccgctg cgccttatcc ggtaactatc gtcttgagtc caacccggta agacacgact 5400
tatcgccact ggcagcagcc actggtaaca ggattagcag agcgaggtat gtaggcggtg 5460
ctacagagtt cttgaagtgg tggcctaact acggctacac tagaagaaca gtatttggta 5520
tctgcgctct gctgaagcca gttaccttcg gaaaaagagt tggtagctct tgatccggca 5580
aacaaaccac cgctggtagc ggtggttttt ttgtttgcaa gcagcagatt acgcgcagaa 5640
aaaaaggatc tcaagaagat cctttgatct tttctacggg gtctgacgct cagtggaacg 5700
aaaactcacg ttaagggatt ttggtcatga gattatcaaa aaggatcttc acctagatcc 5760
ttttaaatta aaaatgaagt tttaaatcaa tctaaagtat atatgagtaa acttggtctg 5820
acagttacca atgcttaatc agtgaggcac ctatctcagc gatctgtcta tttcgttcat 5880
ccatagttgc ctgactcccc gtcgtgtaga taactacgat acgggagggc ttaccatctg 5940
gccccagtgc tgcaatgata ccgcgagacc cacgctcacc ggctccagat ttatcagcaa 6000
taaaccagcc agccggaagg gccgagcgca gaagtggtcc tgcaacttta tccgcctcca 6060
tccagtctat taattgttgc cgggaagcta gagtaagtag ttcgccagtt aatagtttgc 6120
gcaacgttgt tgccattgct acaggcatcg tggtgtcacg ctcgtcgttt ggtatggctt 6180
cattcagctc cggttcccaa cgatcaaggc gagttacatg atcccccatg ttgtgcaaaa 6240
aagcggttag ctccttcggt cctccgatcg ttgtcagaag taagttggcc gcagtgttat 6300
cactcatggt tatggcagca ctgcataatt ctcttactgt catgccatcc gtaagatgct 6360
tttctgtgac tggtgagtac tcaaccaagt cattctgaga atagtgtatg cggcgaccga 6420
gttgctcttg cccggcgtca atacgggata ataccgcgcc acatagcaga actttaaaag 6480
tgctcatcat tggaaaacgt tcttcggggc gaaaactctc aaggatctta ccgctgttga 6540
gatccagttc gatgtaaccc actcgtgcac ccaactgatc ttcagcatct tttactttca 6600
ccagcgtttc tgggtgagca aaaacaggaa ggcaaaatgc cgcaaaaaag ggaataaggg 6660
cgacacggaa atgttgaata ctcatactct tcctttttca atattattga agcatttatc 6720
agggttattg tctcatgagc ggatacatat ttgaatgtat ttagaaaaat aaacaaatag 6780
gggttccgcg cacatttccc cgaaaagtgc cacctgacgt ctaagaaacc attattatca 6840
tgacattaac ctataaaaat aggcgtatca cgaggccctt tcgtctcgcg cgtttcggtg 6900
atgacggtga aaacctctga cacatgcagc tcccggagac ggtcacagct tgtctgtaag 6960
cggatgccgg gagcagacaa gcccgtcagg gcgcgtcagc gggtgttggc gggtgtcggg 7020
gctggcttaa ctatgcggca tcagagcaga ttgtactgag agtgcaccat aaaattgtaa 7080
acgttaatat tttgttaaaa ttcgcgttaa atttttgtta aatcagctca ttttttaacc 7140
aataggccga aatcggcaaa atcccttata aatcaaaaga atagcccgag atagggttga 7200
gtgttgttcc agtttggaac aagagtccac tattaaagaa cgtggactcc aacgtcaaag 7260
ggcgaaaaac cgtctatcag ggcgatggcc cactacgtga accatcaccc aaatcaagtt 7320
ttttggggtc gaggtgccgt aaagcactaa atcggaaccc taaagggagc ccccgattta 7380
gagcttgacg gggaaagccg gcgaacgtgg cgagaaagga agggaagaaa gcgaaaggag 7440
cgggcgctaa ggcgctggca agtgtagcgg tcacgctgcg cgtaaccacc acacccgccg 7500
cgcttaatgc gccgctacag ggcgcgtact atggttgctt tgacgtatgc ggtgtgaaat 7560
accgcacaga tgcgtaagga gaaaataccg catcaggcgc c 7601

<210> SEQ ID NO 16
<211> LENGTH: 12373
<212> TYPE: DNA
<213> ORGANISM: Homo Sapiense

<400> SEQUENCE: 16
acttccggtg gggtgtcatg gcggcgtctc ggactgtgat ggctgtgggg agacggcgct 60
agtggggaga gcgaccaaga ggccccctcc cctccccggg tccccttccc ctatccccct 120
ccccccagcc tccttgccaa cgccccctttt ccctctcccc ctcccgctcg gcgctgaccc 180
cccatcccca cccccgtggg aacactggga gcctgcactc cacagaccct ctccttgcct 240
cttccctcac ctcagcctcc gctccccgcc ctcttcccgg cccagggcgc cggcccaccc 300
ttccctccgc cgcccccccgg ccgcggggag gacatggccg cgcacaggcc ggtggaatgg 360
gtccaggccg tggtcagccg cttcgacgag cagcttccaa taaaaacagg acagcagaac 420
acacatacca aagtcagtac tgagcacaac aaggaatgtc taatcaatat ttccaaatac 480

```
aagttttctt tggttataag cggcctcact actattttaa agaatgttaa caatatgaga    540
atatttggag aagctgctga aaaaaattta tatctctctc agttgattat attggataca    600
ctggaaaaat gtcttgctgg gcaaccaaag gacacaatga gattagatga aacgatgctg    660
gtcaaacagt tgctgccaga aatctgccat tttcttcaca cctgtcgtga aggaaaccag    720
catgcagctg aacttcggaa ttctgcctct ggggttttat ttctctcag ctgcaacaac     780
ttcaatgcag tctttagtcg catttctacc aggttacagg aattaactgt ttgttcagaa    840
gacaatgttg atgttcatga tatagaattg ttacagtata tcaatgtgga ttgtgcaaaa    900
ttaaaacgac tcctgaagga aacagcattt aaatttaaag ccctaaagaa ggttgcgcag    960
ttagcagtta taaatagcct ggaaaaggca ttttggaact gggtagaaaa ttatccagat   1020
gaatttacaa aactgtacca gatcccacag actgatatgg ctgaatgtgc agaaaagcta   1080
tttgacttgg tggatggttt tgctgaaagc accaaacgta aagcagcagt ttggccacta   1140
caaatcattc tccttatctt gtgtccagaa ataatccagg atatatccaa agacgtggtt   1200
gatgaaaaca acatgaataa gaagttattt ctggacagtc tacgaaaagc tcttgctggc   1260
catggaggaa gtaggcagct gacagaaagt gctgcaattg cctgtgtcaa actgtgtaaa   1320
gcaagtactt acatcaattg ggaagataac tctgtcattt tcctacttgt tcagtccatg   1380
gtggttgatc ttaagaacct gctttttaat ccaagtaagc cattctcaag aggcagtcag   1440
cctgcagatg tggatctaat gattgactgc cttgtttctt gctttcgtat aagccctcac   1500
aacaaccaac actttaagat ctgcctggct cagaattcac cttctacatt tcactatgtg   1560
ctggtaaatt cactccatcg aatcatcacc aattccgcat tggattggtg gcctaagatt   1620
gatgctgtgt attgtcactc ggttgaactt cgaaatatgt ttggtgaaac acttcataaa   1680
gcagtgcaag gttgtggagc acacccagca atacgaatgg caccgagtct tacatttaaa   1740
gaaaaagtaa caagccttaa atttaaagaa aaacctacag acctggagac aagaagctat   1800
aagtatcttc tcttgtccat ggtgaaacta attcatgcag atccaaagct cttgctttgt   1860
aatccaagaa aacaggggcc cgaaacccaa ggcagtacag cagaattaat tacagggctc   1920
gtccaactgg tccctcagtc acacatgcca gagattgctc aggaagcaat ggaggctctg   1980
ctggttcttc atcagttaga tagcattgat ttgtggaatc ctgatgctcc tgtagaaaca   2040
ttttgggaga ttagctcaca aatgcttttt tacatctgca agaaattaac tagtcatcaa   2100
atgcttagta gcacagaaat tctcaagtgg ttgcgggaaa tattgatctg caggaataaa   2160
tttcttctta aaaataagca ggcagataga agttcctgtc actttctcct tttttacggg   2220
gtaggatgtg atattccttc tagtggaaat accagtcaaa tgtccatgga tcatgaagaa   2280
ttactacgta ctcctggagc ctctctccgg aagggaaaag ggaactcctc tatggatagt   2340
gcagcaggat gcagcggaac ccccccgatt tgccgacaag cccagaccaa actagaagtg   2400
gccctgtaca tgtttctgtg gaaccctgac actgaagctg ttctggttgc catgtcctgt   2460
ttccgccacc tctgtgagga agcagatatc cggtgtgggg tggatgaagt gtcagtgcat   2520
aacctcttgc ccaactataa cacattcatg gagtttgcct ctgtcagcaa tatgatgtca   2580
acaggaagag cagcacttca gaaaagagtg atggcactgc tgaggcgcat tgagcatccc   2640
actgcaggaa acactgaggc ttgggaagat acacatgcaa aatgggaaca agcaacaaag   2700
ctaatcctta actatccaaa agccaaaatg gaagatggcc aggctgctga aagccttcac   2760
aagaccattg ttaagaggcg aatgtcccat gtgagtggag gaggatccat agatttgtct   2820
gacacagact ccctacagga atggatcaac atgactggct tcctttgtgc ccttgggga    2880
```

```
gtgtgcctcc agcagagaag caattctggc ctggcaacct atagcccacc catgggtcca   2940
gtcagtgaac gtaagggttc tatgatttca gtgatgtctt cagagggaaa cgcagataca   3000
cctgtcagca aatttatgga tcggctgttg tccttaatgg tgtgtaacca tgagaaagtg   3060
ggacttcaaa tacggaccaa tgttaaggat ctggtgggtc tagaattgag tcctgctctg   3120
tatccaatgc tatttaacaa attgaagaat accatcagca agtttttga ctcccaagga    3180
caggttttat tgactgatac caatactcaa tttgtagaac aaaccatagc tataatgaag   3240
aacttgctag ataatcatac tgaaggcagc tctgaacatc tagggcaagc tagcattgaa   3300
acaatgatgt taaatctggt caggtatgtt cgtgtgcttg ggaatatggt ccatgcaatt   3360
caaataaaaa cgaaactgtg tcaattagtt gaagtaatga tggcaaggag agatgacctc   3420
tcattttgcc aagagatgaa atttaggaat aagatggtag aatacctgac agactgggtt   3480
atgggaacat caaaccaagc agcagatgat gatgtaaaat gtcttacaag agatttggac   3540
caggcaagca tggaagcagt agtttcactt ctagctggtc tccctctgca gcctgaagaa   3600
ggagatggtg tggaattgat ggaagccaaa tcacagttat ttcttaaata cttcacatta   3660
tttatgaacc ttttgaatga ctgcagtgaa gttgaagatg aaagtgcgca aacaggtggc   3720
aggaaacgtg gcatgtctcg gaggctggca tcactgaggc actgtacggt ccttgcaatg   3780
tcaaacttac tcaatgccaa cgtagacagt ggtctcatgc actccatagg cttaggttac   3840
cacaaggatc tccagacaag agctacattt atggaagttc tgacaaaaat ccttcaacaa   3900
ggcacagaat ttgacacact tgcagaaaca gtattggctg atcggtttga gagattggtg   3960
gaactggtca caatgatggg tgatcaagga gaactcccta tagcgatggc tctggccaat   4020
gtggttcctt gttctcagtg ggatgaacta gctcgagttc tggttactct gtttgattct   4080
cggcatttac tctaccaact gctctggaac atgttttcta aagaagtaga attggcagac   4140
tccatgcaga ctctcttccg aggcaacagc ttggccagta aaataatgac attctgtttc   4200
aaggtatatg gtgctaccta tctacaaaaa ctcctggatc ctttattacg aattgtgatc   4260
acatcctctg attggcaaca tgttagcttt gaagtggatc ctaccaggtt agaaccatca   4320
gagagccttg aggaaaacca gcggaacctc cttcagatga ctgaaaagtt cttccatgcc   4380
atcatcagtt cctcctcaga attcccccct caacttcgaa gtgtgtgcca ctgtttatac   4440
caggcaactt gccactccct actgaataaa gctacagtaa aagaaaaaaa ggaaaacaaa   4500
aaatcagtgg ttagccagcg tttccctcag aacagcatcg gtgcagtagg aagtgccatg   4560
ttcctcagat ttatcaatcc tgccattgtc tcaccgtatg aagcagggat tttagataaa   4620
aagccaccac ctagaatcga aaggggcttg aagttaatgt caaagatact tcagagtatt   4680
gccaatcatg ttctcttcac aaaagaagaa catatgcggc ctttcaatga ttttgtgaaa   4740
agcaactttg atgcagcacg caggtttttc cttgatatag catctgattg tcctacaagt   4800
gatgcagtaa atcatagtct ttccttcata agtgacggca atgtgcttgc tttacatcgt   4860
ctactctgga acaatcagga gaaaattggg cagtatcttt ccagcaacag ggatcataaa   4920
gctgttggaa gacgaccttt tgataagatg gcaacacttc ttgcatacct gggtcctcca   4980
gagcacaaac ctgtggcaga tacacactgg tccagcctta accttaccag ttcaaagttt   5040
gaggaattta tgactaggca tcaggtacat gaaaaagaag aattcaaggc tttgaaaacg   5100
ttaagtattt tctaccaagc tgggacttcc aaagctggga atcctatttt ttattatgtt   5160
gcacggaggt tcaaaactgg tcaaatcaat ggtgatttgc tgatatacca tgtcttactg   5220
```

-continued

```
actttaaagc catattatgc aaagccatat gaaattgtag tggaccttac ccataccggg   5280
cctagcaatc gctttaaaac agactttctc tctaagtggt ttgttgtttt tcctggcttt   5340
gcttacgaca acgtctccgc agtctatatc tataactgta actcctgggt cagggagtac   5400
accaagtatc atgagcggct gctgactggc ctcaaaggta gcaaaaggct tgttttcata   5460
gactgtcctg ggaaactggc tgagcacata gagcatgaac aacagaaact acctgctgcc   5520
accttggctt tagaagagga cctgaaggta ttccacaatg ctctcaagct agctcacaaa   5580
gacaccaaag tttctattaa agttggttct actgctgtcc aagtaacttc agcagagcga   5640
acaaaagtcc tagggcaatc agtctttcta aatgacattt attatgcttc ggaaattgaa   5700
gaaatctgcc tagtagatga gaaccagttc accttaacca ttgcaaacca gggcacgccg   5760
ctcaccttca tgcaccagga gtgtgaagcc attgtccagt ctatcattca tatccggacc   5820
cgctgggaac tgtcacagcc cgactctatc ccccaacaca ccaagattcg gccaaaagat   5880
gtccctggga cactgctcaa tatcgcatta cttaatttag gcagttctga cccgagttta   5940
cggtcagctg cctataatct tctgtgtgcc ttaacttgta cctttaattt aaaaatcgag   6000
ggccagttac tagagacatc aggtttatgt atccctgcca acaacaccct ctttattgtc   6060
tctattagta agacactggc agccaatgag ccacacctca cgttagaatt tttggaagag   6120
tgtatttctg gatttagcaa atctagtatt gaattgaaac acctttgttt ggaatacatg   6180
actccatggc tgtcaaatct agttcgtttt tgcaagcata atgatgatgc caaacgacaa   6240
agagttactg ctattcttga caagctgata acaatgacca tcaatgaaaa acagatgtac   6300
ccatctattc aagcaaaaat atggggaagc cttgggcaga ttacagatct gcttgatgtt   6360
gtactagaca gtttcatcaa aaccagtgca acaggtggct tgggatcaat aaaagctgag   6420
gtgatggcag atactgctgt agctttggct tctggaaatg tgaaattggt ttcaagcaag   6480
gttattggaa ggatgtgcaa aataattgac aagacatgct tatctccaac tcctacttta   6540
gaacaacatc ttatgtggga tgatattgct attttagcac gctacatgct gatgctgtcc   6600
ttcaacaatt cccttgatgt ggcagctcat cttccctacc tcttccacgt tgttactttc   6660
ttagtagcca caggtccgct ctcccttaga gcttccacac atggactggt cattaatatc   6720
attcactctc tgtgtacttg ttcacagctt cattttagtg aagagaccaa gcaagttttg   6780
agactcagtc tgacagagtt ctcattaccc aaattttact tgctgtttgg cattagcaaa   6840
gtcaagtcag ctgctgtcat tgccttccgt tccagttacc gggacaggtc attctctcct   6900
ggctcctatg agagagagac ttttgctttg acatccttgg aaacagtcac agaagctttg   6960
ttggagatca tggaggcatg catgagagat attccaacgt gcaagtggct ggaccagtgg   7020
acagaactag ctcaaagatt tgcattccaa tataatccat ccctgcaacc aagagctctt   7080
gttgtctttg ggtgtattag caaacgagtg tctcatgggc agataaagca gataatccgt   7140
attcttagca aggcacttga gagttgctta aaaggacctg acacttacaa cagtcaagtt   7200
ctgatagaag ctacagtaat agcactaacc aaattacagc cacttcttaa taaggactcg   7260
cctctgcaca aagccctctt ttgggtagct gtggctgtgc tgcagcttga tgaggtcaac   7320
ttgtattcag caggtaccgc acttcttgaa caaaacctgc atactttaga tagtctccgt   7380
atattcaatg acaagagtcc agaggaagta tttatggcaa tccggaatcc tctggagtgg   7440
cactgcaagc aaatggatca ttttgttgga ctcaatttca actctaactt taactttgca   7500
ttggttggac accttttaaa agggtacagg catccttcac ctgctattgt tgcaagaaca   7560
gtcagaattt tacatacact actaactctg gttaacaaac acagaaattg tgacaaattt   7620
```

```
gaagtgaata cacagagcgt ggcctactta gcagctttac ttacagtgtc tgaagaagtt   7680
cgaagtcgct gcagcctaaa acatagaaag tcacttcttc ttactgatat ttcaatggaa   7740
aatgttccta tggatacata tcccattcat catggtgacc cttcctatag gacactaaag   7800
gagactcagc catggtcctc tcccaaaggt tctgaaggat accttgcagc cacctatcca   7860
actgtcggcc agaccagtcc ccgagccagg aaatccatga gcctggacat ggggcaacct   7920
tctcaggcca acactaagaa gttgcttgga acaaggaaaa gttttgatca cttgatatca   7980
gacacaaagg ctcctaaaag gcaagaaatg gaatcaggga tcacaacacc ccccaaaatg   8040
aggagagtag cagaaactga ttatgaaatg gaaactcaga ggatttcctc atcacaacag   8100
cacccacatt tacgtaaagt ttcagtgtct gaatcaaatg ttctcttgga tgaagaagta   8160
cttactgatc cgaagatcca ggcgctgctt cttactgttc tagctacact ggtaaaatat   8220
accacagatg agtttgatca acgaattctt tatgaatact tagcagaggc cagtgttgtg   8280
tttcccaaag tctttcctgt tgtgcataat ttgttggact ctaagatcaa caccctgtta   8340
tcattgtgcc aagatccaaa tttgttaaat ccaatccatg gaattgtgca gagtgtggtg   8400
taccatgaag aatccccacc acaataccaa acatcttacc tgcaaagttt tggttttaat   8460
ggcttgtggc ggtttgcagg accgttttca aagcaaacac aaattccaga ctatgctgag   8520
cttattgtta agtttcttga tgccttgatt gacacgtacc tgcctggaat tgatgaagaa   8580
accagtgaag aatccctcct gactcccaca tctccttacc ctcctgcact gcagagccag   8640
cttagtatca ctgccaacct taacctttct aattccatga cctcacttgc aacttcccag   8700
cattccccag gaatcgacaa ggagaacgtt gaactctccc ctaccactgg ccactgtaac   8760
agtggacgaa ctcgccacgg atccgcaagc caagtgcaga agcaaagaag cgctggcagt   8820
ttcaaacgta atagcattaa gaagatcgtg tgaagcttgc ttgctttctt ttttaaaatc   8880
aacttaacat gggctcttca ctagtgaccc cttccctgtc cttgcccttt ccccccatgt   8940
tgtaatgctg cacttcctgt tttataatga acccatccgg tttgccatgt tgccagatga   9000
tcaactcttc gaagccttgc ctaaatttaa tgctgccttt tctttaactt tttttcttct   9060
acttttggcg tgtatctggt atatgtaagt gttcagaaca actgcaaaga aagtgggagg   9120
tcaggaaact tttaactgag aaatctcaat tgtaagagag gatgaattct tgaatactgc   9180
tactactggc cagtgatgaa agccatttgc acagagctct gccttctgtg gttttccctt   9240
cttcatccta cagagtaaag tgttagtcct atttatacat ttttcaagat acaagtttat   9300
gagagaaata gtattataac cccagtatgt ttaatctttt agctgtggac ttttttttta   9360
accgtacaaa actgaaagaa ccatagaggt caagcctcag tgacttgaca ccataaagcc   9420
acagacaagg tacttggggg ggagggcagg gaaatttcat attttatagt ggattcttaa   9480
gaaatactaa cacttgagta ttagcaataa ttacaggaaa ataagtgcga ccacatatat   9540
cttaacatta ctgaattaaa actatggctt ctaagtcctt atccaaactc agtcatccaa   9600
actagtttat ttttttctcc agttgattat cttttaattt ttaattttgc taaaggtggt   9660
tttttgtgt tttgtttttt gtaaaccaaa actatactaa gtatagtaat tatatatata   9720
tatatatttt ttcccctccc cctcttcttt cctaactaat tctgagcagg gtaatcagtg   9780
aacaaagtgt tgaaaattgt tcccagaagg taattttcat agatgtttgc attagctcca   9840
tagcaaaatg gaatggtacg tgacatttag ggtagctgat atttttattt tgttaaataa   9900
tttccaagaa tagagtatgg tgtatattat aaatttcttt gataagatgt attttgaatg   9960
```

tcttttaatc ttcctcctcc tctccaaaaa aatcagaaac ctctttaaga aaacatgtag 10020
gttatatatg ctagaattgc atttaatcac tgtgaaaaga ctggtcagcc tgcattagta 10080
tgacagtagg ggggctgtta gaattgctgc tatactggtg gtatggatta tcatggcatt 10140
ggaattttca tagtaatgca gatccaattt ctttgtggta cctgcagttt acaaaataat 10200
ttgacttcag tgagcatatt ggtatctgga tgttccaatt tagaactaaa ccatatttat 10260
tacaaaaaga tattaatccc tctactccca ggttcccttt atatgttaag atataatggc 10320
tttgaggggg gaaaaaataa acctagggga gaggggagtt tcctgtagtg ctgtttcatt 10380
agaggatttc agtaaattaa attccacagc taattcaata aataatggta catttaagtg 10440
ttctgatttt aataatatat ttcacattta tccacacagt aacaatgtaa tatgttaatg 10500
taaataaaat tggttttgat actcagaaat aacaagaatt taattttta aatttgttta 10560
cagtcctggg aaaagtaaga attatttgcc aaaataagag gaaagaaaac cttagtatta 10620
ttaatgagtt taccatagaa ttgttggaaa tactgaagac aggtgcaatt tactaaactt 10680
ttgtttttaa actattgtag aggctgcatt agaagaaaat gtttataatg acagagcaac 10740
tatgactata taaaaaagct gaaattagaa ctgtgtttag aaatagatca gtaacccagt 10800
gccaaggatg ccaagctgcc accatggtct tggctctccc acaacccagt gtttctgggg 10860
taagtttcac agtttctagg ccctggaata gcaggcagtg taagcctttg ataactttag 10920
ttcgatgttt ttcttgtttt tgtttgttgg tttggtgcat atgatagtgg gtgttatgct 10980
attttgctct tcccatcaaa ataaagaaac ttccagaggt ttactgttaa aaatactgat 11040
atttccataa acgggtttac caagggtgta gtatttcata ccgcctgaaa tgatcagcat 11100
tggcacaaat caaaattcag ccgcctttga aatgcaaaaa tacctttgac tagtaagtac 11160
atcctaggag tttgaaaact taactaaggt ttaaaattta ccttgtttaa agaacttctg 11220
acttttgagg aaaatctagc tttccaagta actaaaatgt acatgagata aacctctcac 11280
cactatgtgt cccttgagaa atgcaacact tttttagtct tcatacttgt aatctataaa 11340
agaaattctg aagtttagac caagttgccc atttctgcgt aattgacata agttctgtta 11400
aaaatattat aagtaattcg tttcggtttg tagatgtttc ccctgacttg ttaaagagga 11460
aaccaggaac tcagtcatgt ttttgtcctg gataatctac ctgttatgcc agtactccca 11520
tccgaggggc atgcccttag ttgcccagat ggagatgcag ttcagtagat ttggggcaaa 11580
gtggctacag ctctgtcttc cattcactca acacctgttc atgactgagc caggtgccca 11640
ggacacatcc taaacagtca gcttctatcc tgtgtcctag ttggggagac agagtgccag 11700
ccagcaaccc tcccaggttt gtaggtttta ggggttttca gttttgtttg ggttttttgt 11760
tttttgtttt tgtttctaca tccttccccg actcccaggc ataatgaggc atgtcttact 11820
caatgttatg caatggattt aggcaaaaat tcattcttag tgtcagccac acaatttttt 11880
ttaatgcagt atattcacct gtaaatagtt tgtgtaaaat ttgacaaaaa aagtatattt 11940
actatactgt aaatatatgt gatgatatat tgtattattt tgcttttttg taaagcagtt 12000
agttgctgca catggataac aacaaaaatt tgattattct cgtgttagta ttgttaactt 12060
ctttttgcga ctgcgttaca tcatttaaag aaaatgctgt gtattgtaaa cttaaattgt 12120
atatgataac ttactgtcct ttccatccgg gcctaaactt tggcagttcc tttgtctaca 12180
accttgttaa tactgtaaac agttgtacgc cagcaggaaa aatactgccc aacagacaaa 12240
atcgatcatt gtaggggaaa atcatagaaa tccatttcag atctttattg ttcctcaccc 12300
cattttcctc cttgtgtatg tacttccccc accccccttt ttttaagtaa aatgtaaatt 12360

```
caatctgctc taa                                                  12373


<210> SEQ ID NO 17
<211> LENGTH: 2839
<212> TYPE: PRT
<213> ORGANISM: Homo Sapiens

<400> SEQUENCE: 17

Met Ala Ala His Arg Pro Val Glu Trp Val Gln Ala Val Val Ser Arg
1               5                   10                  15

Phe Asp Glu Gln Leu Pro Ile Lys Thr Gly Gln Gln Asn Thr His Thr
            20                  25                  30

Lys Val Ser Thr Glu His Asn Lys Glu Cys Leu Ile Asn Ile Ser Lys
        35                  40                  45

Tyr Lys Phe Ser Leu Val Ile Ser Gly Leu Thr Thr Ile Leu Lys Asn
    50                  55                  60

Val Asn Asn Met Arg Ile Phe Gly Glu Ala Ala Glu Lys Asn Leu Tyr
65                  70                  75                  80

Leu Ser Gln Leu Ile Ile Leu Asp Thr Leu Glu Lys Cys Leu Ala Gly
                85                  90                  95

Gln Pro Lys Asp Thr Met Arg Leu Asp Glu Thr Met Leu Val Lys Gln
            100                 105                 110

Leu Leu Pro Glu Ile Cys His Phe Leu His Thr Cys Arg Glu Gly Asn
        115                 120                 125

Gln His Ala Ala Glu Leu Arg Asn Ser Ala Ser Gly Val Leu Phe Ser
    130                 135                 140

Leu Ser Cys Asn Asn Phe Asn Ala Val Phe Ser Arg Ile Ser Thr Arg
145                 150                 155                 160

Leu Gln Glu Leu Thr Val Cys Ser Glu Asp Asn Val Asp Val His Asp
                165                 170                 175

Ile Glu Leu Leu Gln Tyr Ile Asn Val Asp Cys Ala Lys Leu Lys Arg
            180                 185                 190

Leu Leu Lys Glu Thr Ala Phe Lys Phe Lys Ala Leu Lys Lys Val Ala
        195                 200                 205

Gln Leu Ala Val Ile Asn Ser Leu Glu Lys Ala Phe Trp Asn Trp Val
    210                 215                 220

Glu Asn Tyr Pro Asp Glu Phe Thr Lys Leu Tyr Gln Ile Pro Gln Thr
225                 230                 235                 240

Asp Met Ala Glu Cys Ala Glu Lys Leu Phe Asp Leu Val Asp Gly Phe
                245                 250                 255

Ala Glu Ser Thr Lys Arg Lys Ala Ala Val Trp Pro Leu Gln Ile Ile
            260                 265                 270

Leu Leu Ile Leu Cys Pro Glu Ile Ile Gln Asp Ile Ser Lys Asp Val
        275                 280                 285

Val Asp Glu Asn Asn Met Asn Lys Lys Leu Phe Leu Asp Ser Leu Arg
    290                 295                 300

Lys Ala Leu Ala Gly His Gly Gly Ser Arg Gln Leu Thr Glu Ser Ala
305                 310                 315                 320

Ala Ile Ala Cys Val Lys Leu Cys Lys Ala Ser Thr Tyr Ile Asn Trp
                325                 330                 335

Glu Asp Asn Ser Val Ile Phe Leu Leu Val Gln Ser Met Val Val Asp
            340                 345                 350

Leu Lys Asn Leu Leu Phe Asn Pro Ser Lys Pro Phe Ser Arg Gly Ser
        355                 360                 365
```

```
Gln Pro Ala Asp Val Asp Leu Met Ile Asp Cys Leu Val Ser Cys Phe
    370                 375                 380

Arg Ile Ser Pro His Asn Asn Gln His Phe Lys Ile Cys Leu Ala Gln
385                 390                 395                 400

Asn Ser Pro Ser Thr Phe His Tyr Val Leu Val Asn Ser Leu His Arg
                405                 410                 415

Ile Ile Thr Asn Ser Ala Leu Asp Trp Trp Pro Lys Ile Asp Ala Val
            420                 425                 430

Tyr Cys His Ser Val Glu Leu Arg Asn Met Phe Gly Glu Thr Leu His
        435                 440                 445

Lys Ala Val Gln Gly Cys Gly Ala His Pro Ala Ile Arg Met Ala Pro
    450                 455                 460

Ser Leu Thr Phe Lys Glu Lys Val Thr Ser Leu Lys Phe Lys Glu Lys
465                 470                 475                 480

Pro Thr Asp Leu Glu Thr Arg Ser Tyr Lys Tyr Leu Leu Leu Ser Met
                485                 490                 495

Val Lys Leu Ile His Ala Asp Pro Lys Leu Leu Leu Cys Asn Pro Arg
            500                 505                 510

Lys Gln Gly Pro Glu Thr Gln Gly Ser Thr Ala Glu Leu Ile Thr Gly
        515                 520                 525

Leu Val Gln Leu Val Pro Gln Ser His Met Pro Glu Ile Ala Gln Glu
    530                 535                 540

Ala Met Glu Ala Leu Leu Val Leu His Gln Leu Asp Ser Ile Asp Leu
545                 550                 555                 560

Trp Asn Pro Asp Ala Pro Val Glu Thr Phe Trp Glu Ile Ser Ser Gln
                565                 570                 575

Met Leu Phe Tyr Ile Cys Lys Lys Leu Thr Ser His Gln Met Leu Ser
            580                 585                 590

Ser Thr Glu Ile Leu Lys Trp Leu Arg Glu Ile Leu Ile Cys Arg Asn
        595                 600                 605

Lys Phe Leu Leu Lys Asn Lys Gln Ala Asp Arg Ser Ser Cys His Phe
    610                 615                 620

Leu Leu Phe Tyr Gly Val Gly Cys Asp Ile Pro Ser Ser Gly Asn Thr
625                 630                 635                 640

Ser Gln Met Ser Met Asp His Glu Glu Leu Leu Arg Thr Pro Gly Ala
                645                 650                 655

Ser Leu Arg Lys Gly Lys Gly Asn Ser Ser Met Asp Ser Ala Ala Gly
            660                 665                 670

Cys Ser Gly Thr Pro Pro Ile Cys Arg Gln Ala Gln Thr Lys Leu Glu
        675                 680                 685

Val Ala Leu Tyr Met Phe Leu Trp Asn Pro Asp Thr Glu Ala Val Leu
    690                 695                 700

Val Ala Met Ser Cys Phe Arg His Leu Cys Glu Glu Ala Asp Ile Arg
705                 710                 715                 720

Cys Gly Val Asp Glu Val Ser Val His Asn Leu Leu Pro Asn Tyr Asn
                725                 730                 735

Thr Phe Met Glu Phe Ala Ser Val Ser Asn Met Met Ser Thr Gly Arg
            740                 745                 750

Ala Ala Leu Gln Lys Arg Val Met Ala Leu Leu Arg Arg Ile Glu His
        755                 760                 765

Pro Thr Ala Gly Asn Thr Glu Ala Trp Glu Asp Thr His Ala Lys Trp
    770                 775                 780
```

```
Glu Gln Ala Thr Lys Leu Ile Leu Asn Tyr Pro Lys Ala Lys Met Glu
785                 790                 795                 800

Asp Gly Gln Ala Ala Glu Ser Leu His Lys Thr Ile Val Lys Arg Arg
                805                 810                 815

Met Ser His Val Ser Gly Gly Gly Ser Ile Asp Leu Ser Asp Thr Asp
            820                 825                 830

Ser Leu Gln Glu Trp Ile Asn Met Thr Gly Phe Leu Cys Ala Leu Gly
        835                 840                 845

Gly Val Cys Leu Gln Gln Arg Ser Asn Ser Gly Leu Ala Thr Tyr Ser
    850                 855                 860

Pro Pro Met Gly Pro Val Ser Glu Arg Lys Gly Ser Met Ile Ser Val
865                 870                 875                 880

Met Ser Ser Glu Gly Asn Ala Asp Thr Pro Val Ser Lys Phe Met Asp
                885                 890                 895

Arg Leu Leu Ser Leu Met Val Cys Asn His Glu Lys Val Gly Leu Gln
            900                 905                 910

Ile Arg Thr Asn Val Lys Asp Leu Val Gly Leu Glu Leu Ser Pro Ala
        915                 920                 925

Leu Tyr Pro Met Leu Phe Asn Lys Leu Lys Asn Thr Ile Ser Lys Phe
    930                 935                 940

Phe Asp Ser Gln Gly Gln Val Leu Leu Thr Asp Thr Asn Thr Gln Phe
945                 950                 955                 960

Val Glu Gln Thr Ile Ala Ile Met Lys Asn Leu Leu Asp Asn His Thr
                965                 970                 975

Glu Gly Ser Ser Glu His Leu Gly Gln Ala Ser Ile Glu Thr Met Met
            980                 985                 990

Leu Asn Leu Val Arg Tyr Val Arg  Val Leu Gly Asn Met  Val His Ala
        995                 1000                1005

Ile Gln  Ile Lys Thr Lys Leu  Cys Gln Leu Val Glu  Val Met Met
    1010                1015                1020

Ala Arg  Arg Asp Asp Leu Ser  Phe Cys Gln Glu Met  Lys Phe Arg
    1025                1030                1035

Asn Lys  Met Val Glu Tyr Leu  Thr Asp Trp Val Met  Gly Thr Ser
    1040                1045                1050

Asn Gln  Ala Ala Asp Asp Asp  Val Lys Cys Leu Thr  Arg Asp Leu
    1055                1060                1065

Asp Gln  Ala Ser Met Glu Ala  Val Val Ser Leu Leu  Ala Gly Leu
    1070                1075                1080

Pro Leu  Gln Pro Glu Glu Gly  Asp Gly Val Glu Leu  Met Glu Ala
    1085                1090                1095

Lys Ser  Gln Leu Phe Leu Lys  Tyr Phe Thr Leu Phe  Met Asn Leu
    1100                1105                1110

Leu Asn  Asp Cys Ser Glu Val  Glu Asp Glu Ser Ala  Gln Thr Gly
    1115                1120                1125

Gly Arg  Lys Arg Gly Met Ser  Arg Arg Leu Ala Ser  Leu Arg His
    1130                1135                1140

Cys Thr  Val Leu Ala Met Ser  Asn Leu Leu Asn Ala  Asn Val Asp
    1145                1150                1155

Ser Gly  Leu Met His Ser Ile  Gly Leu Gly Tyr His  Lys Asp Leu
    1160                1165                1170

Gln Thr  Arg Ala Thr Phe Met  Glu Val Leu Thr Lys  Ile Leu Gln
    1175                1180                1185

Gln Gly  Thr Glu Phe Asp Thr  Leu Ala Glu Thr Val  Leu Ala Asp
```

```
    1190                1195                1200

Arg Phe  Glu Arg Leu Val Glu  Leu Val Thr Met Met  Gly Asp Gln
    1205                1210                1215

Gly Glu  Leu Pro Ile Ala Met  Ala Leu Ala Asn Val  Val Pro Cys
    1220                1225                1230

Ser Gln  Trp Asp Glu Leu Ala  Arg Val Leu Val Thr  Leu Phe Asp
    1235                1240                1245

Ser Arg  His Leu Leu Tyr Gln  Leu Leu Trp Asn Met  Phe Ser Lys
    1250                1255                1260

Glu Val  Glu Leu Ala Asp Ser  Met Gln Thr Leu Phe  Arg Gly Asn
    1265                1270                1275

Ser Leu  Ala Ser Lys Ile Met  Thr Phe Cys Phe Lys  Val Tyr Gly
    1280                1285                1290

Ala Thr  Tyr Leu Gln Lys Leu  Leu Asp Pro Leu Leu  Arg Ile Val
    1295                1300                1305

Ile Thr  Ser Ser Asp Trp Gln  His Val Ser Phe Glu  Val Asp Pro
    1310                1315                1320

Thr Arg  Leu Glu Pro Ser Glu  Ser Leu Glu Glu Asn  Gln Arg Asn
    1325                1330                1335

Leu Leu  Gln Met Thr Glu Lys  Phe Phe His Ala Ile  Ile Ser Ser
    1340                1345                1350

Ser Ser  Glu Phe Pro Pro Gln  Leu Arg Ser Val Cys  His Cys Leu
    1355                1360                1365

Tyr Gln  Ala Thr Cys His Ser  Leu Leu Asn Lys Ala  Thr Val Lys
    1370                1375                1380

Glu Lys  Lys Glu Asn Lys Lys  Ser Val Val Ser Gln  Arg Phe Pro
    1385                1390                1395

Gln Asn  Ser Ile Gly Ala Val  Gly Ser Ala Met Phe  Leu Arg Phe
    1400                1405                1410

Ile Asn  Pro Ala Ile Val Ser  Pro Tyr Glu Ala Gly  Ile Leu Asp
    1415                1420                1425

Lys Lys  Pro Pro Pro Arg Ile  Glu Arg Gly Leu Lys  Leu Met Ser
    1430                1435                1440

Lys Ile  Leu Gln Ser Ile Ala  Asn His Val Leu Phe  Thr Lys Glu
    1445                1450                1455

Glu His  Met Arg Pro Phe Asn  Asp Phe Val Lys Ser  Asn Phe Asp
    1460                1465                1470

Ala Ala  Arg Arg Phe Phe Leu  Asp Ile Ala Ser Asp  Cys Pro Thr
    1475                1480                1485

Ser Asp  Ala Val Asn His Ser  Leu Ser Phe Ile Ser  Asp Gly Asn
    1490                1495                1500

Val Leu  Ala Leu His Arg Leu  Leu Trp Asn Asn Gln  Glu Lys Ile
    1505                1510                1515

Gly Gln  Tyr Leu Ser Ser Asn  Arg Asp His Lys Ala  Val Gly Arg
    1520                1525                1530

Arg Pro  Phe Asp Lys Met Ala  Thr Leu Leu Ala Tyr  Leu Gly Pro
    1535                1540                1545

Pro Glu  His Lys Pro Val Ala  Asp Thr His Trp Ser  Ser Leu Asn
    1550                1555                1560

Leu Thr  Ser Ser Lys Phe Glu  Glu Phe Met Thr Arg  His Gln Val
    1565                1570                1575

His Glu  Lys Glu Glu Phe Lys  Ala Leu Lys Thr Leu  Ser Ile Phe
    1580                1585                1590
```

Tyr Gln Ala Gly Thr Ser Lys Ala Gly Asn Pro Ile Phe Tyr Tyr
1595 1600 1605

Val Ala Arg Arg Phe Lys Thr Gly Gln Ile Asn Gly Asp Leu Leu
1610 1615 1620

Ile Tyr His Val Leu Leu Thr Leu Lys Pro Tyr Tyr Ala Lys Pro
1625 1630 1635

Tyr Glu Ile Val Val Asp Leu Thr His Thr Gly Pro Ser Asn Arg
1640 1645 1650

Phe Lys Thr Asp Phe Leu Ser Lys Trp Phe Val Val Phe Pro Gly
1655 1660 1665

Phe Ala Tyr Asp Asn Val Ser Ala Val Tyr Ile Tyr Asn Cys Asn
1670 1675 1680

Ser Trp Val Arg Glu Tyr Thr Lys Tyr His Glu Arg Leu Leu Thr
1685 1690 1695

Gly Leu Lys Gly Ser Lys Arg Leu Val Phe Ile Asp Cys Pro Gly
1700 1705 1710

Lys Leu Ala Glu His Ile Glu His Glu Gln Gln Lys Leu Pro Ala
1715 1720 1725

Ala Thr Leu Ala Leu Glu Glu Asp Leu Lys Val Phe His Asn Ala
1730 1735 1740

Leu Lys Leu Ala His Lys Asp Thr Lys Val Ser Ile Lys Val Gly
1745 1750 1755

Ser Thr Ala Val Gln Val Thr Ser Ala Glu Arg Thr Lys Val Leu
1760 1765 1770

Gly Gln Ser Val Phe Leu Asn Asp Ile Tyr Tyr Ala Ser Glu Ile
1775 1780 1785

Glu Glu Ile Cys Leu Val Asp Glu Asn Gln Phe Thr Leu Thr Ile
1790 1795 1800

Ala Asn Gln Gly Thr Pro Leu Thr Phe Met His Gln Glu Cys Glu
1805 1810 1815

Ala Ile Val Gln Ser Ile Ile His Ile Arg Thr Arg Trp Glu Leu
1820 1825 1830

Ser Gln Pro Asp Ser Ile Pro Gln His Thr Lys Ile Arg Pro Lys
1835 1840 1845

Asp Val Pro Gly Thr Leu Leu Asn Ile Ala Leu Leu Asn Leu Gly
1850 1855 1860

Ser Ser Asp Pro Ser Leu Arg Ser Ala Ala Tyr Asn Leu Leu Cys
1865 1870 1875

Ala Leu Thr Cys Thr Phe Asn Leu Lys Ile Glu Gly Gln Leu Leu
1880 1885 1890

Glu Thr Ser Gly Leu Cys Ile Pro Ala Asn Asn Thr Leu Phe Ile
1895 1900 1905

Val Ser Ile Ser Lys Thr Leu Ala Ala Asn Glu Pro His Leu Thr
1910 1915 1920

Leu Glu Phe Leu Glu Glu Cys Ile Ser Gly Phe Ser Lys Ser Ser
1925 1930 1935

Ile Glu Leu Lys His Leu Cys Leu Glu Tyr Met Thr Pro Trp Leu
1940 1945 1950

Ser Asn Leu Val Arg Phe Cys Lys His Asn Asp Asp Ala Lys Arg
1955 1960 1965

Gln Arg Val Thr Ala Ile Leu Asp Lys Leu Ile Thr Met Thr Ile
1970 1975 1980

```
Asn Glu  Lys Gln Met Tyr Pro  Ser Ile Gln Ala Lys  Ile Trp Gly
    1985                 1990                 1995

Ser Leu  Gly Gln Ile Thr Asp  Leu Leu Asp Val Val  Leu Asp Ser
    2000                 2005                 2010

Phe Ile  Lys Thr Ser Ala Thr  Gly Gly Leu Gly Ser  Ile Lys Ala
    2015                 2020                 2025

Glu Val  Met Ala Asp Thr Ala  Val Ala Leu Ala Ser  Gly Asn Val
    2030                 2035                 2040

Lys Leu  Val Ser Ser Lys Val  Ile Gly Arg Met Cys  Lys Ile Ile
    2045                 2050                 2055

Asp Lys  Thr Cys Leu Ser Pro  Thr Pro Thr Leu Glu  Gln His Leu
    2060                 2065                 2070

Met Trp  Asp Asp Ile Ala Ile  Leu Ala Arg Tyr Met  Leu Met Leu
    2075                 2080                 2085

Ser Phe  Asn Asn Ser Leu Asp  Val Ala Ala His Leu  Pro Tyr Leu
    2090                 2095                 2100

Phe His  Val Val Thr Phe Leu  Val Ala Thr Gly Pro  Leu Ser Leu
    2105                 2110                 2115

Arg Ala  Ser Thr His Gly Leu  Val Ile Asn Ile Ile  His Ser Leu
    2120                 2125                 2130

Cys Thr  Cys Ser Gln Leu His  Phe Ser Glu Glu Thr  Lys Gln Val
    2135                 2140                 2145

Leu Arg  Leu Ser Leu Thr Glu  Phe Ser Leu Pro Lys  Phe Tyr Leu
    2150                 2155                 2160

Leu Phe  Gly Ile Ser Lys Val  Lys Ser Ala Ala Val  Ile Ala Phe
    2165                 2170                 2175

Arg Ser  Ser Tyr Arg Asp Arg  Ser Phe Ser Pro Gly  Ser Tyr Glu
    2180                 2185                 2190

Arg Glu  Thr Phe Ala Leu Thr  Ser Leu Glu Thr Val  Thr Glu Ala
    2195                 2200                 2205

Leu Leu  Glu Ile Met Glu Ala  Cys Met Arg Asp Ile  Pro Thr Cys
    2210                 2215                 2220

Lys Trp  Leu Asp Gln Trp Thr  Glu Leu Ala Gln Arg  Phe Ala Phe
    2225                 2230                 2235

Gln Tyr  Asn Pro Ser Leu Gln  Pro Arg Ala Leu Val  Val Phe Gly
    2240                 2245                 2250

Cys Ile  Ser Lys Arg Val Ser  His Gly Gln Ile Lys  Gln Ile Ile
    2255                 2260                 2265

Arg Ile  Leu Ser Lys Ala Leu  Glu Ser Cys Leu Lys  Gly Pro Asp
    2270                 2275                 2280

Thr Tyr  Asn Ser Gln Val Leu  Ile Glu Ala Thr Val  Ile Ala Leu
    2285                 2290                 2295

Thr Lys  Leu Gln Pro Leu Leu  Asn Lys Asp Ser Pro  Leu His Lys
    2300                 2305                 2310

Ala Leu  Phe Trp Val Ala Val  Ala Val Leu Gln Leu  Asp Glu Val
    2315                 2320                 2325

Asn Leu  Tyr Ser Ala Gly Thr  Ala Leu Leu Glu Gln  Asn Leu His
    2330                 2335                 2340

Thr Leu  Asp Ser Leu Arg Ile  Phe Asn Asp Lys Ser  Pro Glu Glu
    2345                 2350                 2355

Val Phe  Met Ala Ile Arg Asn  Pro Leu Glu Trp His  Cys Lys Gln
    2360                 2365                 2370

Met Asp  His Phe Val Gly Leu  Asn Phe Asn Ser Asn  Phe Asn Phe
```

2375 2380 2385

Ala Leu Val Gly His Leu Leu Lys Gly Tyr Arg His Pro Ser Pro
2390 2395 2400

Ala Ile Val Ala Arg Thr Val Arg Ile Leu His Thr Leu Leu Thr
2405 2410 2415

Leu Val Asn Lys His Arg Asn Cys Asp Lys Phe Glu Val Asn Thr
2420 2425 2430

Gln Ser Val Ala Tyr Leu Ala Ala Leu Leu Thr Val Ser Glu Glu
2435 2440 2445

Val Arg Ser Arg Cys Ser Leu Lys His Arg Lys Ser Leu Leu Leu
2450 2455 2460

Thr Asp Ile Ser Met Glu Asn Val Pro Met Asp Thr Tyr Pro Ile
2465 2470 2475

His His Gly Asp Pro Ser Tyr Arg Thr Leu Lys Glu Thr Gln Pro
2480 2485 2490

Trp Ser Ser Pro Lys Gly Ser Glu Gly Tyr Leu Ala Ala Thr Tyr
2495 2500 2505

Pro Thr Val Gly Gln Thr Ser Pro Arg Ala Arg Lys Ser Met Ser
2510 2515 2520

Leu Asp Met Gly Gln Pro Ser Gln Ala Asn Thr Lys Lys Leu Leu
2525 2530 2535

Gly Thr Arg Lys Ser Phe Asp His Leu Ile Ser Asp Thr Lys Ala
2540 2545 2550

Pro Lys Arg Gln Glu Met Glu Ser Gly Ile Thr Thr Pro Pro Lys
2555 2560 2565

Met Arg Arg Val Ala Glu Thr Asp Tyr Glu Met Glu Thr Gln Arg
2570 2575 2580

Ile Ser Ser Ser Gln Gln His Pro His Leu Arg Lys Val Ser Val
2585 2590 2595

Ser Glu Ser Asn Val Leu Leu Asp Glu Glu Val Leu Thr Asp Pro
2600 2605 2610

Lys Ile Gln Ala Leu Leu Leu Thr Val Leu Ala Thr Leu Val Lys
2615 2620 2625

Tyr Thr Thr Asp Glu Phe Asp Gln Arg Ile Leu Tyr Glu Tyr Leu
2630 2635 2640

Ala Glu Ala Ser Val Val Phe Pro Lys Val Phe Pro Val Val His
2645 2650 2655

Asn Leu Leu Asp Ser Lys Ile Asn Thr Leu Leu Ser Leu Cys Gln
2660 2665 2670

Asp Pro Asn Leu Leu Asn Pro Ile His Gly Ile Val Gln Ser Val
2675 2680 2685

Val Tyr His Glu Glu Ser Pro Pro Gln Tyr Gln Thr Ser Tyr Leu
2690 2695 2700

Gln Ser Phe Gly Phe Asn Gly Leu Trp Arg Phe Ala Gly Pro Phe
2705 2710 2715

Ser Lys Gln Thr Gln Ile Pro Asp Tyr Ala Glu Leu Ile Val Lys
2720 2725 2730

Phe Leu Asp Ala Leu Ile Asp Thr Tyr Leu Pro Gly Ile Asp Glu
2735 2740 2745

Glu Thr Ser Glu Glu Ser Leu Leu Thr Pro Thr Ser Pro Tyr Pro
2750 2755 2760

Pro Ala Leu Gln Ser Gln Leu Ser Ile Thr Ala Asn Leu Asn Leu
2765 2770 2775

Ser Asn Ser Met Thr Ser Leu Ala Thr Ser Gln His Ser Pro Gly
2780 2785 2790

Ile Asp Lys Glu Asn Val Glu Leu Ser Pro Thr Thr Gly His Cys
2795 2800 2805

Asn Ser Gly Arg Thr Arg His Gly Ser Ala Ser Gln Val Gln Lys
2810 2815 2820

Gln Arg Ser Ala Gly Ser Phe Lys Arg Asn Ser Ile Lys Lys Ile
2825 2830 2835

Val

<210> SEQ ID NO 18
<211> LENGTH: 148
<212> TYPE: DNA
<213> ORGANISM: Artificial Sequence
<220> FEATURE:
<223> OTHER INFORMATION: Synthetic

<400> SEQUENCE: 18
gtgggcagca tgtggaacct ggcgagcccc atccccggca agctctcaag ccatgctggt 60
ggggacgact gaatgccagg gcccttcact gggctatttc acccagggac gcttcttgaa 120
ggcacccccc actccaagct caattgaa 148

<210> SEQ ID NO 19
<211> LENGTH: 124
<212> TYPE: DNA
<213> ORGANISM: Artificial Sequence
<220> FEATURE:
<223> OTHER INFORMATION: Synthetic

<400> SEQUENCE: 19
gcaaattagg accgagagtc agtggccgct caagagtctg tgaccatgcc ccaaattcag 60
agatggtccc aggagagatg gggggaactg ccaagcaatg agtgaccggt tccccctccc 120
ccag 124

<210> SEQ ID NO 20
<211> LENGTH: 504
<212> TYPE: PRT
<213> ORGANISM: Artificial Sequence
<220> FEATURE:
<223> OTHER INFORMATION: Synthetic

<400> SEQUENCE: 20

Met Glu Ala Lys Ser Gln Leu Phe Leu Lys Tyr Phe Thr Leu Phe Met
1 5 10 15

Asn Leu Leu Asn Asp Cys Ser Glu Val Glu Asp Glu Ser Ala Gln Thr
20 25 30

Gly Gly Arg Lys Arg Gly Met Ser Arg Arg Leu Ala Ser Leu Arg His
35 40 45

Cys Thr Val Leu Ala Met Ser Asn Leu Leu Asn Ala Asn Val Asp Ser
50 55 60

Gly Leu Met His Ser Ile Gly Leu Gly Tyr His Lys Asp Leu Gln Thr
65 70 75 80

Arg Ala Thr Phe Met Glu Val Leu Thr Lys Ile Leu Gln Gln Gly Thr
85 90 95

Glu Phe Asp Thr Leu Ala Glu Thr Val Leu Ala Asp Arg Phe Glu Arg
100 105 110

Leu Val Glu Leu Val Thr Met Met Gly Asp Gln Gly Glu Leu Pro Ile

```
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
    210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
    290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
    370                 375                 380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu
        435                 440                 445

Ala Tyr Leu Gly Pro Pro Glu His Lys Pro Val Ala Asp Thr His Trp
    450                 455                 460

Ser Ser Leu Asn Leu Thr Ser Ser Lys Phe Glu Glu Phe Met Thr Arg
465                 470                 475                 480

His Gln Val His Glu Lys Glu Glu Phe Lys Ala Leu Lys Thr Leu Tyr
                485                 490                 495

Pro Tyr Asp Val Pro Asp Tyr Ala
            500
```

<210> SEQ ID NO 21
<211> LENGTH: 1512
<212> TYPE: DNA
<213> ORGANISM: Artificial Sequence
<220> FEATURE:
<223> OTHER INFORMATION: Synthetic

<400> SEQUENCE: 21
atggaagcca agagccagct gtttctgaaa tactttaccc tgtttatgaa tctgctgaac 60
gactgtagtg aggtggagga cgagagtgcc cagaccggcg gcaggaagag aggcatgtct 120
aggagactgg ccagcctgag gcactgcaca gtgctggcca tgtccaacct gctgaacgcc 180
aatgtggact ccggcctgat gcactctatc ggcctgggct accacaagga tctgcagacc 240
cgcgccacat tcatggaggt gctgaccaag atcctgcagc agggcaccga gtttgacaca 300
ctggccgaga ccgtgctggc agataggttc gagcgcctgg tggagctggt gacaatgatg 360
ggcgaccagg gagagctgcc tatcgcaatg gcactggcca acgtggtgcc atgcagccag 420
tgggacgagc tggccagggt gctggtgacc ctgtttgatt ccagacacct gctgtaccag 480
ctgctgtgga acatgttctc taaggaggtg gagctggccg acagcatgca gacactgttt 540
aggggcaatt ccctggcctc taagatcatg accttctgtt ttaaggtgta cggcgccaca 600
tatctgcaga agctgctgga tccactgctg agaatcgtga tcaccagctc cgactggcag 660
cacgtgtcct tcgaggtgga tcctacacgg ctggagccaa gcgagtccct ggaggagaac 720
cagcgcaatc tgctgcagat gaccgagaag ttctttcacg ccatcatctc tagctcctct 780
gagtttcccc ctcagctgcg gtccgtgtgc cactgtctgt accaggccac ctgccactct 840
ctgctgaaca aggccacagt gaaggagaag aaggagaata agaagagcgt ggtgtcccag 900
aggttcccac agaacagcat cggagcagtg ggatccgcca tgttcctgag gttcatcaat 960
cccgccatcg tgagccctta tgaggccggc atcctggaca agaagccacc ccctaggatc 1020
gagagaggcc tgaagctgat gagcaagatc ctgcagtcca tcgccaacca cgtgctgttc 1080
accaaggagg agcacatgcg ccccttcaac gactttgtga agtctaattt tgatgccgcc 1140
cggcgcttct ttctggacat cgcctctgat tgtcctacaa gcgacgccgt gaaccactct 1200
ctgagcttca tcagcgatgg caatgtgctg gccctgcacc ggctgctgtg gaacaatcag 1260
gagaagatcg gccagtacct gagctccaac agggaccaca aggcagtggg caggagacct 1320
tttgataaga tggccaccct gctggcatat ctgggaccac cagagcacaa gccagtggca 1380
gacacccact ggtctagcct gaatctgaca tcctctaagt tcgaggagtt tatgacccgg 1440
caccaggtgc acgagaagga ggagtttaag gccctgaaga ccctgtatcc gtatgatgtg 1500
ccggattatg cg 1512

<210> SEQ ID NO 22
<211> LENGTH: 652
<212> TYPE: PRT
<213> ORGANISM: Artificial Sequence
<220> FEATURE:
<223> OTHER INFORMATION: Synthetic

<400> SEQUENCE: 22

Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
    50                  55                  60

-continued

```
Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
    210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
    290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
    370                 375                 380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu
        435                 440                 445

Ala Tyr Leu Gly Pro Pro Glu His Lys Pro Val Ala Asp Thr His Trp
    450                 455                 460

Ser Ser Leu Asn Leu Thr Ser Ser Lys Phe Glu Glu Phe Met Thr Arg
465                 470                 475                 480

His Gln Val His Glu Lys Glu Glu Phe Lys Ala Leu Lys Thr Leu Ser
```

```
                485                 490                 495

Ile Phe Tyr Gln Ala Gly Thr Ser Lys Ala Gly Asn Pro Ile Phe Tyr
            500                 505                 510

Tyr Val Ala Arg Arg Phe Lys Thr Gly Gln Ile Asn Gly Asp Leu Leu
        515                 520                 525

Ile Tyr His Val Leu Leu Thr Leu Lys Pro Tyr Tyr Ala Lys Pro Tyr
    530                 535                 540

Glu Ile Val Val Asp Leu Thr His Thr Gly Pro Ser Asn Arg Phe Lys
545                 550                 555                 560

Thr Asp Phe Leu Ser Lys Trp Phe Val Val Phe Pro Gly Phe Ala Tyr
                565                 570                 575

Asp Asn Val Ser Ala Val Tyr Ile Tyr Asn Cys Asn Ser Trp Val Arg
            580                 585                 590

Glu Tyr Thr Lys Tyr His Glu Arg Leu Leu Thr Gly Leu Lys Gly Ser
        595                 600                 605

Lys Arg Leu Val Phe Ile Asp Cys Pro Gly Lys Leu Ala Glu His Ile
    610                 615                 620

Glu His Glu Gln Gln Lys Leu Pro Ala Ala Thr Leu Ala Leu Glu Glu
625                 630                 635                 640

Asp Leu Lys Tyr Pro Tyr Asp Val Pro Asp Tyr Ala
                645                 650


<210> SEQ ID NO 23
<211> LENGTH: 1956
<212> TYPE: DNA
<213> ORGANISM: Artificial Sequence
<220> FEATURE:
<223> OTHER INFORMATION: Synthetic

<400> SEQUENCE: 23

atggaagcca agagccagct gtttctgaaa tactttaccc tgtttatgaa tctgctgaac      60

gactgtagtg aggtggagga cgagagtgcc cagaccggcg gcaggaagag aggcatgtct     120

aggagactgg ccagcctgag gcactgcaca gtgctggcca tgtccaacct gctgaacgcc     180

aatgtggact ccggcctgat gcactctatc ggcctgggct accacaagga tctgcagacc     240

cgcgccacat tcatggaggt gctgaccaag atcctgcagc agggcaccga gtttgacaca     300

ctggccgaga ccgtgctggc agataggttc gagcgcctgg tggagctggt gacaatgatg     360

ggcgaccagg gagagctgcc tatcgcaatg gcactggcca acgtggtgcc atgcagccag     420

tgggacgagc tggccagggt gctggtgacc ctgtttgatt ccagacacct gctgtaccag     480

ctgctgtgga acatgttctc taaggaggtg gagctggccg acagcatgca gacactgttt     540

aggggcaatt ccctggcctc taagatcatg accttctgtt ttaaggtgta cggcgccaca     600

tatctgcaga agctgctgga tccactgctg agaatcgtga tcaccagctc cgactggcag     660

cacgtgtcct tcgaggtgga tcctacacgg ctggagccaa gcgagtccct ggaggagaac     720

cagcgcaatc tgctgcagat gaccgagaag ttctttcacg ccatcatctc tagctcctct     780

gagtttcccc ctcagctgcg gtccgtgtgc cactgtctgt accaggccac ctgccactct     840

ctgctgaaca aggccacagt gaaggagaag aaggagaata agaagagcgt ggtgtcccag     900

aggttcccac agaacagcat cggagcagtg ggatccgcca tgttcctgag gttcatcaat     960

cccgccatcg tgagccctta tgaggccggc atcctggaca agaagccacc ccctaggatc    1020

gagagaggcc tgaagctgat gagcaagatc ctgcagtcca tcgccaacca cgtgctgttc    1080

accaaggagg agcacatgcg ccccttcaac gactttgtga agtctaattt tgatgccgcc    1140
```

```
cggcgcttct ttctggacat cgcctctgat tgtcctacaa gcgacgccgt gaaccactct   1200

ctgagcttca tcagcgatgg caatgtgctg gccctgcacc ggctgctgtg gaacaatcag   1260

gagaagatcg gccagtacct gagctccaac agggaccaca aggcagtggg caggagacca   1320

tttgataaga tggccacact gctggcctat ctgggaccac cagagcacaa gccagtggca   1380

gacacacact ggtctagcct gaatctgacc tcctctaagt tcgaggagtt tatgacccgg   1440

caccaggtgc acgagaagga ggagtttaag gccctgaaga cactgtctat cttctaccag   1500

gcaggcacca gcaaggcagg aaacccaatc ttttactatg tggcccggcg cttcaagaca   1560

ggccagatca atggcgatct gctgatctac cacgtgctgc tgaccctgaa gccatactat   1620

gccaagccct atgagatcgt ggtggacctg acccacacag gcccctccaa caggtttaag   1680

accgatttcc tgtctaagtg gttcgtggtg tttcctggct tcgcctatga caatgtgagc   1740

gccgtgtaca tctataactg caattcctgg gtgcgggagt acacaaagta tcacgagcgc   1800

ctgctgaccg gcctgaaggg atccaagaga ctggtgttca tcgattgtcc cggcaagctg   1860

gccgagcaca ttgaacacga acagcagaaa ctgcccgccg caaccctggc cctggaagag   1920

gacctgaagt atccgtatga tgtgccggat tatgcg                              1956
```

<210> SEQ ID NO 24
<211> LENGTH: 750
<212> TYPE: PRT
<213> ORGANISM: Artificial Sequence
<220> FEATURE:
<223> OTHER INFORMATION: Synthetic

<400> SEQUENCE: 24

```
Met Glu Ala Lys Ser Gln Leu Phe Leu Lys Tyr Phe Thr Leu Phe Met
1               5                   10                  15

Asn Leu Leu Asn Asp Cys Ser Glu Val Glu Asp Glu Ser Ala Gln Thr
            20                  25                  30

Gly Gly Arg Lys Arg Gly Met Ser Arg Arg Leu Ala Ser Leu Arg His
        35                  40                  45

Cys Thr Val Leu Ala Met Ser Asn Leu Leu Asn Ala Asn Val Asp Ser
    50                  55                  60

Gly Leu Met His Ser Ile Gly Leu Gly Tyr His Lys Asp Leu Gln Thr
65                  70                  75                  80

Arg Ala Thr Phe Met Glu Val Leu Thr Lys Ile Leu Gln Gln Gly Thr
                85                  90                  95

Glu Phe Asp Thr Leu Ala Glu Thr Val Leu Ala Asp Arg Phe Glu Arg
            100                 105                 110

Leu Val Glu Leu Val Thr Met Met Gly Asp Gln Gly Glu Leu Pro Ile
        115                 120                 125

Ala Met Ala Leu Ala Asn Val Val Pro Cys Ser Gln Trp Asp Glu Leu
    130                 135                 140

Ala Arg Val Leu Val Thr Leu Phe Asp Ser Arg His Leu Leu Tyr Gln
145                 150                 155                 160

Leu Leu Trp Asn Met Phe Ser Lys Glu Val Glu Leu Ala Asp Ser Met
                165                 170                 175

Gln Thr Leu Phe Arg Gly Asn Ser Leu Ala Ser Lys Ile Met Thr Phe
            180                 185                 190

Cys Phe Lys Val Tyr Gly Ala Thr Tyr Leu Gln Lys Leu Leu Asp Pro
        195                 200                 205

Leu Leu Arg Ile Val Ile Thr Ser Ser Asp Trp Gln His Val Ser Phe
```

```
    210                 215                 220

Glu Val Asp Pro Thr Arg Leu Glu Pro Ser Glu Ser Leu Glu Glu Asn
225                 230                 235                 240

Gln Arg Asn Leu Leu Gln Met Thr Glu Lys Phe Phe His Ala Ile Ile
                245                 250                 255

Ser Ser Ser Ser Glu Phe Pro Pro Gln Leu Arg Ser Val Cys His Cys
            260                 265                 270

Leu Tyr Gln Ala Thr Cys His Ser Leu Leu Asn Lys Ala Thr Val Lys
        275                 280                 285

Glu Lys Lys Glu Asn Lys Lys Ser Val Val Ser Gln Arg Phe Pro Gln
    290                 295                 300

Asn Ser Ile Gly Ala Val Gly Ser Ala Met Phe Leu Arg Phe Ile Asn
305                 310                 315                 320

Pro Ala Ile Val Ser Pro Tyr Glu Ala Gly Ile Leu Asp Lys Lys Pro
                325                 330                 335

Pro Pro Arg Ile Glu Arg Gly Leu Lys Leu Met Ser Lys Ile Leu Gln
            340                 345                 350

Ser Ile Ala Asn His Val Leu Phe Thr Lys Glu Glu His Met Arg Pro
        355                 360                 365

Phe Asn Asp Phe Val Lys Ser Asn Phe Asp Ala Ala Arg Arg Phe Phe
    370                 375                 380

Leu Asp Ile Ala Ser Asp Cys Pro Thr Ser Asp Ala Val Asn His Ser
385                 390                 395                 400

Leu Ser Phe Ile Ser Asp Gly Asn Val Leu Ala Leu His Arg Leu Leu
                405                 410                 415

Trp Asn Asn Gln Glu Lys Ile Gly Gln Tyr Leu Ser Ser Asn Arg Asp
            420                 425                 430

His Lys Ala Val Gly Arg Arg Pro Phe Asp Lys Met Ala Thr Leu Leu
        435                 440                 445

Ala Tyr Leu Gly Pro Pro Glu His Lys Pro Val Ala Asp Thr His Trp
    450                 455                 460

Ser Ser Leu Asn Leu Thr Ser Ser Lys Phe Glu Glu Phe Met Thr Arg
465                 470                 475                 480

His Gln Val His Glu Lys Glu Glu Phe Lys Ala Leu Lys Thr Leu Ser
                485                 490                 495

Ile Phe Tyr Gln Ala Gly Thr Ser Lys Ala Gly Asn Pro Ile Phe Tyr
            500                 505                 510

Tyr Val Ala Arg Arg Phe Lys Thr Gly Gln Ile Asn Gly Asp Leu Leu
        515                 520                 525

Ile Tyr His Val Leu Leu Thr Leu Lys Pro Tyr Tyr Ala Lys Pro Tyr
    530                 535                 540

Glu Ile Val Val Asp Leu Thr His Thr Gly Pro Ser Asn Arg Phe Lys
545                 550                 555                 560

Thr Asp Phe Leu Ser Lys Trp Phe Val Val Phe Pro Gly Phe Ala Tyr
                565                 570                 575

Asp Asn Val Ser Ala Val Tyr Ile Tyr Asn Cys Asn Ser Trp Val Arg
            580                 585                 590

Glu Tyr Thr Lys Tyr His Glu Arg Leu Leu Thr Gly Leu Lys Gly Ser
        595                 600                 605

Lys Arg Leu Val Phe Ile Asp Cys Pro Gly Lys Leu Ala Glu His Ile
    610                 615                 620

Glu His Glu Gln Gln Lys Leu Pro Ala Ala Thr Leu Ala Leu Glu Glu
625                 630                 635                 640
```

```
Asp Leu Lys Val Phe His Asn Ala Leu Lys Leu Ala His Lys Asp Thr
                645                 650                 655

Lys Val Ser Ile Lys Val Gly Ser Thr Ala Val Gln Val Thr Ser Ala
            660                 665                 670

Glu Arg Thr Lys Val Leu Gly Gln Ser Val Phe Leu Asn Asp Ile Tyr
        675                 680                 685

Tyr Ala Ser Glu Ile Glu Glu Ile Cys Leu Val Asp Glu Asn Gln Phe
    690                 695                 700

Thr Leu Thr Ile Ala Asn Gln Gly Thr Pro Leu Thr Phe Met His Gln
705                 710                 715                 720

Glu Cys Glu Ala Ile Val Gln Ser Ile Ile His Ile Arg Thr Arg Trp
                725                 730                 735

Glu Leu Ser Gln Pro Asp Tyr Pro Tyr Asp Val Pro Asp Tyr
            740                 745                 750
```

<210> SEQ ID NO 25
<211> LENGTH: 2252
<212> TYPE: DNA
<213> ORGANISM: Artificial Sequence
<220> FEATURE:
<223> OTHER INFORMATION: Synthetic

<400> SEQUENCE: 25

```
atggaagcca agagccagct gtttctgaaa tactttaccc tgtttatgaa tctgctgaac      60

gactgtagtg aggtggagga cgagagtgcc cagaccggcg gcaggaagag aggcatgtct     120

aggagactgg ccagcctgag gcactgcaca gtgctggcca tgtccaacct gctgaacgcc     180

aatgtggact ccggcctgat gcactctatc ggcctgggct accacaagga tctgcagacc     240

cgcgccacat tcatggaggt gctgaccaag atcctgcagc agggcaccga gtttgacaca     300

ctggccgaga ccgtgctggc agataggttc gagcgcctgg tggagctggt gacaatgatg     360

ggcgaccagg gagagctgcc tatcgcaatg gcactggcca acgtggtgcc atgcagccag     420

tgggacgagc tggccagggt gctggtgacc ctgtttgatt ccagacacct gctgtaccag     480

ctgctgtgga acatgttctc taaggaggtg gagctggccg acagcatgca gacactgttt     540

aggggcaatt ccctggcctc taagatcatg accttctgtt ttaaggtgta cggcgccaca     600

tatctgcaga agctgctgga tccactgctg agaatcgtga tcaccagctc cgactggcag     660

cacgtgtcct tcgaggtgga tcctacacgg ctggagccaa gcgagtccct ggaggagaac     720

cagcgcaatc tgctgcagat gaccgagaag ttctttcacg ccatcatctc tagctcctct     780

gagtttcccc ctcagctgcg gtccgtgtgc cactgtctgt accaggccac ctgccactct     840

ctgctgaaca aggccacagt gaaggagaag aaggagaata agaagagcgt ggtgtcccag     900

aggttcccac agaacagcat cggagcagtg ggatccgcca tgttcctgag gttcatcaat     960

cccgccatcg tgagccctta tgaggccggc atcctggaca agaagccacc ccctaggatc    1020

gagagaggcc tgaagctgat gagcaagatc ctgcagtcca tcgccaacca cgtgctgttc    1080

accaaggagg agcacatgcg ccccttcaac gactttgtga agtctaattt tgatgccgcc    1140

cggcgcttct ttctggacat cgcctctgat tgtcctacaa gcgacgccgt gaaccactct    1200

ctgagcttca tcagcgatgg caatgtgctg gccctgcacc ggctgctgtg gaacaatcag    1260

gagaagatcg gccagtacct gagctccaac agggaccaca aggcagtggg caggagacct    1320

tttgataaga tggccaccct gctggcatat ctgggaccac cagagcacaa gccagtggca    1380

gacacccact ggtctagcct gaatctgaca tcctctaagt tcgaggagtt tatgacccgg    1440
```

caccaggtgc acgagaagga ggagtttaag gccctgaaga ccctgtccat cttctaccag 1500
gccggcacat ctaaggccgg caaccctatc ttttactatg tggcccggcg cttcaagacc 1560
ggccagatca atggcgatct gctgatctac cacgtgctgc tgacactgaa gccatactat 1620
gccaagccct atgagatcgt ggtggacctg acccacacag gcccaagcaa caggtttaag 1680
accgatttcc tgtccaagtg gttcgtggtg tttcccggct tcgcctatga caacgtgagc 1740
gccgtgtaca tctataactg caatagctgg gtgcgggagt acaccaagta tcacgagcgc 1800
ctgctgacag gcctgaaggg cagcaagaga ctggtgttca tcgattgtcc cggcaagctg 1860
gccgagcaca tcgagcacga gcagcagaag ctgcctgcag ccaccctggc cctggaggag 1920
gacctgaagg tgtttcacaa cgccctgaag ctggcccaca aggatacaaa ggtgtccatc 1980
aaggtcggct ctacagccgt gcaggtgacc tccgccgaga gaacaaaggt gctgggccag 2040
agcgtgttcc tgaatgacat ctactatgcc agcgagatcg aggagatctg cctggtggat 2100
gagaaccagt ttaccctgac aatcgccaat cagggcaccc ccctgacatt catgcaccag 2160
gagtgtgaag caatcgtcca gagcattatt cacattcgca ctcggtggga actgagccag 2220
cctgactatc cgtatgatgt gccggattat gc 2252

<210> SEQ ID NO 26
<211> LENGTH: 1457
<212> TYPE: PRT
<213> ORGANISM: Artificial Sequence
<220> FEATURE:
<223> OTHER INFORMATION: Synthetic

<400> SEQUENCE: 26

Met Val Ser Gln Arg Phe Pro Gln Asn Ser Ile Gly Ala Val Gly Ser
1 5 10 15

Ala Met Phe Leu Arg Phe Ile Asn Pro Ala Ile Val Ser Pro Tyr Glu
20 25 30

Ala Gly Ile Leu Asp Lys Lys Pro Pro Pro Arg Ile Glu Arg Gly Leu
35 40 45

Lys Leu Met Ser Lys Ile Leu Gln Ser Ile Ala Asn His Val Leu Phe
50 55 60

Thr Lys Glu Glu His Met Arg Pro Phe Asn Asp Phe Val Lys Ser Asn
65 70 75 80

Phe Asp Ala Ala Arg Arg Phe Phe Leu Asp Ile Ala Ser Asp Cys Pro
85 90 95

Thr Ser Asp Ala Val Asn His Ser Leu Ser Phe Ile Ser Asp Gly Asn
100 105 110

Val Leu Ala Leu His Arg Leu Leu Trp Asn Asn Gln Glu Lys Ile Gly
115 120 125

Gln Tyr Leu Ser Ser Asn Arg Asp His Lys Ala Val Gly Arg Arg Pro
130 135 140

Phe Asp Lys Met Ala Thr Leu Leu Ala Tyr Leu Gly Pro Pro Glu His
145 150 155 160

Lys Pro Val Ala Asp Thr His Trp Ser Ser Leu Asn Leu Thr Ser Ser
165 170 175

Lys Phe Glu Glu Phe Met Thr Arg His Gln Val His Glu Lys Glu Glu
180 185 190

Phe Lys Ala Leu Lys Thr Leu Ser Ile Phe Tyr Gln Ala Gly Thr Ser
195 200 205

Lys Ala Gly Asn Pro Ile Phe Tyr Tyr Val Ala Arg Arg Phe Lys Thr

```
    210                 215                 220

Gly Gln Ile Asn Gly Asp Leu Leu Ile Tyr His Val Leu Leu Thr Leu
225                 230                 235                 240

Lys Pro Tyr Tyr Ala Lys Pro Tyr Glu Ile Val Val Asp Leu Thr His
                245                 250                 255

Thr Gly Pro Ser Asn Arg Phe Lys Thr Asp Phe Leu Ser Lys Trp Phe
            260                 265                 270

Val Val Phe Pro Gly Phe Ala Tyr Asp Asn Val Ser Met Val Tyr Ile
        275                 280                 285

Tyr Asn Cys Asn Ser Trp Val Arg Glu Tyr Thr Lys Tyr His Glu Arg
    290                 295                 300

Leu Leu Thr Gly Leu Lys Gly Ser Lys Arg Leu Val Phe Ile Asp Cys
305                 310                 315                 320

Pro Gly Lys Leu Ala Glu His Ile Glu His Glu Gln Gln Lys Leu Pro
                325                 330                 335

Ala Ala Thr Leu Ala Leu Glu Glu Asp Leu Lys Val Phe His Asn Ala
            340                 345                 350

Leu Lys Leu Ala His Lys Asp Thr Lys Val Ser Ile Lys Val Gly Ser
        355                 360                 365

Thr Ala Val Gln Val Thr Ser Ala Glu Arg Thr Lys Val Leu Gly Gln
    370                 375                 380

Ser Val Phe Leu Asn Asp Ile Tyr Tyr Ala Ser Glu Ile Glu Glu Ile
385                 390                 395                 400

Cys Leu Val Asp Glu Asn Gln Phe Thr Leu Thr Ile Ala Asn Gln Gly
                405                 410                 415

Thr Pro Leu Thr Phe Met His Gln Glu Cys Glu Ala Ile Val Gln Ser
            420                 425                 430

Ile Ile His Ile Arg Thr Arg Trp Glu Leu Ser Gln Pro Asp Ser Ile
        435                 440                 445

Pro Gln His Thr Lys Ile Arg Pro Lys Asp Val Pro Gly Thr Leu Leu
    450                 455                 460

Asn Ile Ala Leu Leu Asn Leu Gly Ser Ser Asp Pro Ser Leu Arg Ser
465                 470                 475                 480

Ala Ala Tyr Asn Leu Leu Cys Ala Leu Thr Cys Thr Phe Asn Leu Lys
                485                 490                 495

Ile Glu Gly Gln Leu Leu Glu Thr Ser Gly Leu Cys Ile Pro Ala Asn
            500                 505                 510

Asn Thr Leu Phe Ile Val Ser Ile Ser Lys Thr Leu Ala Ala Asn Glu
        515                 520                 525

Pro His Leu Thr Leu Glu Phe Leu Glu Glu Cys Ile Ser Gly Phe Ser
    530                 535                 540

Lys Ser Ser Ile Glu Leu Lys His Leu Cys Leu Glu Tyr Met Thr Pro
545                 550                 555                 560

Trp Leu Ser Asn Leu Val Arg Phe Cys Lys His Asn Asp Asp Ala Lys
                565                 570                 575

Arg Gln Arg Val Thr Ala Ile Leu Asp Lys Leu Ile Thr Met Thr Ile
            580                 585                 590

Asn Glu Lys Gln Met Tyr Pro Ser Ile Gln Ala Lys Ile Trp Gly Ser
        595                 600                 605

Leu Gly Gln Ile Thr Asp Leu Leu Asp Val Val Leu Asp Ser Phe Ile
    610                 615                 620

Lys Thr Ser Ala Thr Gly Gly Leu Gly Ser Ile Lys Ala Glu Val Met
625                 630                 635                 640
```

```
Ala Asp Thr Ala Val Ala Leu Ala Ser Gly Asn Val Lys Leu Val Ser
                645                 650                 655

Ser Lys Val Ile Gly Arg Met Cys Lys Ile Ile Asp Lys Thr Cys Leu
            660                 665                 670

Ser Pro Thr Pro Thr Leu Glu Gln His Leu Met Trp Asp Asp Ile Ala
        675                 680                 685

Ile Leu Ala Arg Tyr Met Leu Met Leu Ser Phe Asn Asn Ser Leu Asp
    690                 695                 700

Val Ala Ala His Leu Pro Tyr Leu Phe His Val Val Thr Phe Leu Val
705                 710                 715                 720

Ala Thr Gly Pro Leu Ser Leu Arg Ala Ser Thr His Gly Leu Val Ile
                725                 730                 735

Asn Ile Ile His Ser Leu Cys Thr Cys Ser Gln Leu His Phe Ser Glu
            740                 745                 750

Glu Thr Lys Gln Val Leu Arg Leu Ser Leu Thr Glu Phe Ser Leu Pro
        755                 760                 765

Lys Phe Tyr Leu Leu Phe Gly Ile Ser Lys Val Lys Ser Ala Ala Val
    770                 775                 780

Ile Ala Phe Arg Ser Ser Tyr Arg Asp Arg Ser Phe Ser Pro Gly Ser
785                 790                 795                 800

Tyr Glu Arg Glu Thr Phe Ala Leu Thr Ser Leu Glu Thr Val Thr Glu
                805                 810                 815

Ala Leu Leu Glu Ile Met Glu Ala Cys Met Arg Asp Ile Pro Thr Cys
            820                 825                 830

Lys Trp Leu Asp Gln Trp Thr Glu Leu Ala Gln Arg Phe Ala Phe Gln
        835                 840                 845

Tyr Asn Pro Ser Leu Gln Pro Arg Ala Leu Val Val Phe Gly Cys Ile
    850                 855                 860

Ser Lys Arg Val Ser His Gly Gln Ile Lys Gln Ile Ile Arg Ile Leu
865                 870                 875                 880

Ser Lys Ala Leu Glu Ser Cys Leu Lys Gly Pro Asp Thr Tyr Asn Ser
                885                 890                 895

Gln Val Leu Ile Glu Ala Thr Val Ile Ala Leu Thr Lys Leu Gln Pro
            900                 905                 910

Leu Leu Asn Lys Asp Ser Pro Leu His Lys Ala Leu Phe Trp Val Ala
        915                 920                 925

Val Ala Val Leu Gln Leu Asp Glu Val Asn Leu Tyr Ser Ala Gly Thr
    930                 935                 940

Ala Leu Leu Glu Gln Asn Leu His Thr Leu Asp Ser Leu Arg Ile Phe
945                 950                 955                 960

Asn Asp Lys Ser Pro Glu Glu Val Phe Met Ala Ile Arg Asn Pro Leu
                965                 970                 975

Glu Trp His Cys Lys Gln Met Asp His Phe Val Gly Leu Asn Phe Asn
            980                 985                 990

Ser Asn Phe Asn Phe Ala Leu Val  Gly His Leu Leu Lys  Gly Tyr Arg
        995                 1000                 1005

His Pro  Ser Pro Ala Ile Val  Ala Arg Thr Val Arg  Ile Leu His
    1010                 1015                 1020

Thr Leu  Leu Thr Leu Val Asn  Lys His Arg Asn Cys  Asp Lys Phe
    1025                 1030                 1035

Glu Val  Asn Thr Gln Ser Val  Ala Tyr Leu Ala Ala  Leu Leu Thr
    1040                 1045                 1050
```

```
Val Ser  Glu Glu Val Arg Ser  Arg Cys Ser Leu Lys  His Arg Lys
    1055                 1060                 1065

Ser Leu  Leu Leu Thr Asp Ile  Ser Met Glu Asn Val  Pro Met Asp
    1070                 1075                 1080

Thr Tyr  Pro Ile His His Gly  Asp Pro Ser Tyr Arg  Thr Leu Lys
    1085                 1090                 1095

Glu Thr  Gln Pro Trp Ser Ser  Pro Lys Gly Ser Glu  Gly Tyr Leu
    1100                 1105                 1110

Ala Ala  Thr Tyr Pro Thr Val  Gly Gln Thr Ser Pro  Arg Ala Arg
    1115                 1120                 1125

Lys Ser  Met Ser Leu Asp Met  Gly Gln Pro Ser Gln  Ala Asn Thr
    1130                 1135                 1140

Lys Lys  Leu Leu Gly Thr Arg  Lys Ser Phe Asp His  Leu Ile Ser
    1145                 1150                 1155

Asp Thr  Lys Ala Pro Lys Arg  Gln Glu Met Glu Ser  Gly Ile Thr
    1160                 1165                 1170

Thr Pro  Pro Lys Met Arg Arg  Val Ala Glu Thr Asp  Tyr Glu Met
    1175                 1180                 1185

Glu Thr  Gln Arg Ile Ser Ser  Ser Gln Gln His Pro  His Leu Arg
    1190                 1195                 1200

Lys Val  Ser Val Ser Glu Ser  Asn Val Leu Leu Asp  Glu Glu Val
    1205                 1210                 1215

Leu Thr  Asp Pro Lys Ile Gln  Ala Leu Leu Leu Thr  Val Leu Ala
    1220                 1225                 1230

Thr Leu  Val Lys Tyr Thr Thr  Asp Glu Phe Asp Gln  Arg Ile Leu
    1235                 1240                 1245

Tyr Glu  Tyr Leu Ala Glu Ala  Ser Val Val Phe Pro  Lys Val Phe
    1250                 1255                 1260

Pro Val  Val His Asn Leu Leu  Asp Ser Lys Ile Asn  Thr Leu Leu
    1265                 1270                 1275

Ser Leu  Cys Gln Asp Pro Asn  Leu Leu Asn Pro Ile  His Gly Ile
    1280                 1285                 1290

Val Gln  Ser Val Val Tyr His  Glu Glu Ser Pro Pro  Gln Tyr Gln
    1295                 1300                 1305

Thr Ser  Tyr Leu Gln Ser Phe  Gly Phe Asn Gly Leu  Trp Arg Phe
    1310                 1315                 1320

Ala Gly  Pro Phe Ser Lys Gln  Thr Gln Ile Pro Asp  Tyr Ala Glu
    1325                 1330                 1335

Leu Ile  Val Lys Phe Leu Asp  Ala Leu Ile Asp Thr  Tyr Leu Pro
    1340                 1345                 1350

Gly Ile  Asp Glu Glu Thr Ser  Glu Glu Ser Leu Leu  Thr Pro Thr
    1355                 1360                 1365

Ser Pro  Tyr Pro Pro Ala Leu  Gln Ser Gln Leu Ser  Ile Thr Ala
    1370                 1375                 1380

Asn Leu  Asn Leu Ser Asn Ser  Met Thr Ser Leu Ala  Thr Ser Gln
    1385                 1390                 1395

His Ser  Pro Gly Ile Asp Lys  Glu Asn Val Glu Leu  Ser Pro Thr
    1400                 1405                 1410

Thr Gly  His Cys Asn Ser Gly  Arg Thr Arg His Gly  Ser Ala Ser
    1415                 1420                 1425

Gln Val  Gln Lys Gln Arg Ser  Ala Gly Ser Phe Lys  Arg Asn Ser
    1430                 1435                 1440

Ile Lys  Lys Ile Val Tyr Pro  Tyr Asp Val Pro Asp  Tyr Ala
```

1445 1450 1455

<210> SEQ ID NO 27
<211> LENGTH: 4372
<212> TYPE: DNA
<213> ORGANISM: Artificial Sequence
<220> FEATURE:
<223> OTHER INFORMATION: Synthetic

<400> SEQUENCE: 27
gtggttagcc agcgtttccc tcagaacagc atcggtgcag taggaagtgc catgttcctc 60
agatttatca atcctgccat tgtctcaccg tatgaagcag ggattttaga taaaaagcca 120
ccacctagaa tcgaaagggg cttgaagtta atgtcaaaga tacttcagag tattgccaat 180
catgttctct tcacaaaaga agaacatatg cggcctttca atgattttgt gaaaagcaac 240
tttgatgcag cacgcaggtt tttccttgat atagcatctg attgtcctac aagtgatgca 300
gtaaatcata gtctttcctt cataagtgac ggcaatgtgc ttgctttaca tcgtctactc 360
tggaacaatc aggagaaaat tggcagtat ctttccagca acagggatca taaagctgtt 420
ggaagacgac cttttgataa gatggcaaca cttcttgcat acctgggtcc tccagagcac 480
aaacctgtgg cagatacaca ctggtccagc cttaacctta ccagttcaaa gtttgaggaa 540
tttatgacta ggcatcaggt acatgaaaaa gaagaattca aggctttgaa aacgttaagt 600
attttctacc aagctgggac ttccaaagct gggaatccta ttttttatta tgttgcacgg 660
aggttcaaaa ctggtcaaat caatggtgat ttgctgatat accatgtctt actgacttta 720
aagccatatt atgcaaagcc atatgaaatt gtagtggacc ttacccatac cgggcctagc 780
aatcgcttta aaacagactt tctctctaag tggtttgttg tttttcctgg ctttgcttac 840
gacaacgtct ccgcagtcta tatctataac tgtaactcct gggtcaggga gtacaccaag 900
tatcatgagc ggctgctgac tggcctcaaa ggtagcaaaa ggcttgtttt catagactgt 960
cctgggaaac tggctgagca catagagcat gaacaacaga aactacctgc tgccaccttg 1020
gctttagaag aggacctgaa ggtattccac aatgctctca agctagctca caaagacacc 1080
aaagtttcta ttaaagttgg ttctactgct gtccaagtaa cttcagcaga gcgaacaaaa 1140
gtcctagggc aatcagtctt tctaaatgac atttattatg cttcggaaat tgaagaaatc 1200
tgcctagtag atgagaacca gttcacctta accattgcaa accagggcac gccgctcacc 1260
ttcatgcacc aggagtgtga agccattgtc cagtctatca ttcatatccg gacccgctgg 1320
gaactgtcac agcccgactc tatcccccaa cacaccaaga ttcggccaaa agatgtccct 1380
gggacactgc tcaatatcgc attacttaat ttaggcagtt ctgacccgag tttacggtca 1440
gctgcctata atcttctgtg tgccttaact tgtaccttta atttaaaaat cgagggccag 1500
ttactagaga catcaggttt atgtatccct gccaacaaca ccctctttat tgtctctatt 1560
agtaagacac tggcagccaa tgagccacac ctcacgttag aatttttgga agagtgtatt 1620
tctggattta gcaaatctag tattgaattg aaacaccttt gtttggaata catgactcca 1680
tggctgtcaa atctagttcg tttttgcaag cataatgatg atgccaaacg acaaagagtt 1740
actgctattc ttgacaagct gataacaatg accatcaatg aaaaacagat gtacccatct 1800
attcaagcaa aaatatgggg aagccttggg cagattacag atctgcttga tgttgtacta 1860
gacagtttca tcaaaaccag tgcaacaggt ggcttgggat caataaaagc tgaggtgatg 1920
gcagatactg ctgtagcttt ggcttctgga aatgtgaaat tggtttcaag caaggttatt 1980
ggaaggatgt gcaaaataat tgacaagaca tgcttatctc caactcctac tttagaacaa 2040

```
catcttatgt gggatgatat tgctatttta gcacgctaca tgctgatgct gtccttcaac   2100
aattcccttg atgtggcagc tcatcttccc tacctcttcc acgttgttac tttcttagta   2160
gccacaggtc cgctctccct tagagcttcc acacatggac tggtcattaa tatcattcac   2220
tctctgtgta cttgttcaca gcttcatttt agtgaagaga ccaagcaagt tttgagactc   2280
agtctgacag agttctcatt acccaaattt tacttgctgt ttggcattag caaagtcaag   2340
tcagctgctg tcattgcctt ccgttccagt taccgggaca ggtcattctc tcctggctcc   2400
tatgagagag agacttttgc tttgacatcc ttggaaacag tcacagaagc tttgttggag   2460
atcatggagg catgcatgag agatattcca acgtgcaagt ggctggacca gtggacagaa   2520
ctagctcaaa gatttgcatt ccaatataat ccatccctgc aaccaagagc tcttgttgtc   2580
tttgggtgta ttagcaaacg agtgtctcat gggcagataa agcagataat ccgtattctt   2640
agcaaggcac ttgagagttg cttaaaagga cctgacactt acaacagtca agttctgata   2700
gaagctacag taatagcact aaccaaatta cagccacttc ttaataagga ctcgcctctg   2760
cacaaagccc tcttttgggt agctgtggct gtgctgcagc ttgatgaggt caacttgtat   2820
tcagcaggta ccgcacttct tgaacaaaac ctgcatactt tagatagtct ccgtatattc   2880
aatgacaaga gtccagagga agtatttatg gcaatccgga atcctctgga gtggcactgc   2940
aagcaaatgg atcattttgt tggactcaat ttcaactcta actttaactt tgcattggtt   3000
ggacaccttt taaaagggta caggcatcct tcacctgcta ttgttgcaag aacagtcaga   3060
attttacata cactactaac tctggttaac aaacacagaa attgtgacaa atttgaagtg   3120
aatacacaga gcgtggccta cttagcagct ttacttacag tgtctgaaga agttcgaagt   3180
cgctgcagcc taaaacatag aaagtcactt cttcttactg atatttcaat ggaaaatgtt   3240
cctatggata catatcccat tcatcatggt gacccttcct ataggacact aaaggagact   3300
cagccatggt cctctcccaa aggttctgaa ggataccttg cagccaccta tccaactgtc   3360
ggccagacca gtccccgagc caggaaatcc atgagcctgg acatggggca accttctcag   3420
gccaacacta agaagttgct tggaacaagg aaaagttttg atcacttgat atcagacaca   3480
aaggctccta aaaggcaaga aatggaatca gggatcacaa cacccccaa aatgaggaga   3540
gtagcagaaa ctgattatga aatggaaact cagaggattt cctcatcaca acagcaccca   3600
catttacgta aagtttcagt gtctgaatca aatgttctct tggatgaaga agtacttact   3660
gatccgaaga tccaggcgct gcttcttact gttctagcta cactggtaaa atataccaca   3720
gatgagtttg atcaacgaat tctttatgaa tacttagcag aggccagtgt tgtgtttccc   3780
aaagtctttc ctgttgtgca taatttgttg gactctaaga tcaacaccct gttatcattg   3840
tgccaagatc caaatttgtt aaatccaatc catggaattg tgcagagtgt ggtgtaccat   3900
gaagaatccc caccacaata ccaaacatct tacctgcaaa gttttggttt taatggcttg   3960
tggcggtttg caggaccgtt ttcaaagcaa acacaaattc cagactatgc tgagcttatt   4020
gttaagtttc ttgatgcctt gattgacacg tacctgcctg gaattgatga agaaaccagt   4080
gaagaatccc tcctgactcc cacatctcct taccctcctg cactgcagag ccagcttagt   4140
atcactgcca accttaacct ttctaattcc atgacctcac ttgcaacttc ccagcattcc   4200
ccaggaatcg acaaggagaa cgttgaactc tcccctacca ctggccactg taacagtgga   4260
cgaactcgcc acggatccgc aagccaagtg cagaagcaaa gaagcgctgg cagtttcaaa   4320
cgtaatagca ttaagaagat cgtgtatccg tatgatgtgc cggattatgc gt           4372
```

<210> SEQ ID NO 28
<211> LENGTH: 6549
<212> TYPE: DNA
<213> ORGANISM: Artificial Sequence
<220> FEATURE:
<223> OTHER INFORMATION: Synthetic

<400> SEQUENCE: 28
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaga tcttcaatat tggccattag ccatattatt 180
cattggttat atagcataaa tcaatattgg ctattggcca ttgcatacgt tgtatctata 240
tcataatatg tacatttata ttggctcatg tccaatatga ccgccatgtt ggcattgatt 300
attgactagt tattaatagt aatcaattac ggggtcatta gttcatagcc catatatgga 360
gttccgcgtt acataactta cggtaaatgg cccgcctggc tgaccgccca acgacccccg 420
cccattgacg tcaataatga cgtatgttcc catagtaacg ccaataggga ctttccattg 480
acgtcaatgg gtggagtatt tacggtaaac tgcccacttg gcagtacatc aagtgtatca 540
tatgccaagt ccgcccccta ttgacgtcaa tgacggtaaa tggcccgcct ggcattatgc 600
ccagtacatg accttacggg actttcctac ttggcagtac atctacgtat tagtcatcgc 660
tattaccatg gtcgaggtga gccccacgtt ctgcttcact ctccccatct cccccccctc 720
cccaccccca attttgtatt tatttatttt ttaattattt tgtgcagcga tgggggcggg 780
gggggggggg gggcgcgcgc caggcggggc ggggcggggc gaggggcggg gcggggcgag 840
gcggagaggt gcggcggcag ccaatcagag cggcgcgctc cgaaagtttc cttttatggc 900
gaggcggcgg cggcggcggc cctataaaaa gcgaagcgcg cggcgggcgg gagtcgctgc 960
gcgctgcctt cgccccgtgc cccgctccgc cgccgcctcg cgccgcccgc cccggctctg 1020
actgaccgcg ttactcccac aggtgagcgg gcgggacggc ccttctcctc cgggctgtaa 1080
ttagcgcttg gtttaatgac ggcttgtttc ttttctgtgg ctgcgtgaaa gccttgaggg 1140
gctccgggag ggccctttgt gcggggggag cggctcgggg ggtgcgtgcg tgtgtgtgtg 1200
cgtggggagc gccgcgtgcg gctccgcgct gcccggcggc tgtgagcgct gcgggcgcgg 1260
cgcggggctt tgtgcgctcc gcagtgtgcg cgaggggagc gcggccgggg gcggtgcccc 1320
gcggtgcggg gggggctgcg aggggaacaa aggctgcgtg cggggtgtgt gcgtgggggg 1380
gtgagcaggg ggtgtgggcg cgtcggtcgg gctgcaaccc cccctgcacc cccctccccg 1440
agttgctgag cacggcccgg cttcgggtgc ggggctccgt acggggcgtg gcgcggggct 1500
cgccgtgccg ggcggggggt ggcggcaggt gggggtgccg ggcggggcgg ggccgcctcg 1560
ggccggggag ggctcggggg aggggcgcgg cggcccccgg agcgccggcg gctgtcgagg 1620
cgcggcgagc cgcagccatt gccttttatg gtaatcgtgc gagagggcgc agggacttcc 1680
tttgtcccaa atctgtgcgg agccgaaatc tgggaggcgc cgccgcaccc cctctagcgg 1740
gcgcggggcg aagcggtgcg gcgccggcag gaaggaaatg ggcggggagg gccttcgtgc 1800
gtcgccgcgc cgccgtcccc ttctccctct ccagcctcgg ggctgtccgc ggggggacgg 1860
ctgccttcgg gggggacggg gcagggcggg gttcggcttc tggcgtgtga ccggcggctc 1920
tagagcctct gctaaccatg ttcatgcctt cttctttttc ctacagctcc tgggcaacgt 1980
gctggttatt gtgctgtctc atcattttgg caaagaattc gatatcaagc ttgccaccat 2040
ggaagccaag agccagctgt ttctgaaata ctttaccctg tttatgaatc tgctgaacga 2100

```
ctgtagtgag gtggaggacg agagtgccca gaccggcggc aggaagagag gcatgtctag   2160
gagactggcc agcctgaggc actgcacagt gctggccatg tccaacctgc tgaacgccaa   2220
tgtggactcc ggcctgatgc actctatcgg cctgggctac cacaaggatc tgcagacccg   2280
cgccacattc atggaggtgc tgaccaagat cctgcagcag ggcaccgagt ttgacacact   2340
ggccgagacc gtgctggcag ataggttcga gcgcctggtg gagctggtga caatgatggg   2400
cgaccaggga gagctgccta tcgcaatggc actggccaac gtggtgccat gcagccagtg   2460
ggacgagctg gccagggtgc tggtgaccct gtttgattcc agacacctgc tgtaccagct   2520
gctgtggaac atgttctcta aggaggtgga gctggccgac agcatgcaga cactgtttag   2580
gggcaattcc ctggcctcta agatcatgac cttctgtttt aaggtgtacg gcgccacata   2640
tctgcagaag ctgctggatc cactgctgag aatcgtgatc accagctccg actggcagca   2700
cgtgtccttc gaggtggatc ctacacggct ggagccaagc gagtccctgg aggagaacca   2760
gcgcaatctg ctgcagatga ccgagaagtt ctttcacgcc atcatctcta gctcctctga   2820
gtttcccccct cagctgcggt ccgtgtgcca ctgtctgtac caggccacct gccactctct   2880
gctgaacaag gccacagtga aggagaagaa ggagaataag aagagcgtgg tgtcccagag   2940
gttcccacag aacagcatcg gagcagtggg atccgccatg ttcctgaggt tcatcaatcc   3000
cgccatcgtg agcccttatg aggccggcat cctggacaag aagccacccc ctaggatcga   3060
gagaggcctg aagctgatga gcaagatcct gcagtccatc gccaaccacg tgctgttcac   3120
caaggaggag cacatgcgcc ccttcaacga ctttgtgaag tctaattttg atgccgcccg   3180
gcgcttcttt ctggacatcg cctctgattg tcctacaagc gacgccgtga accactctct   3240
gagcttcatc agcgatggca atgtgctggc cctgcaccgg ctgctgtgga acaatcagga   3300
gaagatcggc cagtacctga gctccaacag ggaccacaag gcagtgggca ggagaccttt   3360
tgataagatg gccaccctgc tggcatatct gggaccacca gagcacaagc cagtggcaga   3420
cacccactgg tctagcctga atctgacatc ctctaagttc gaggagttta tgacccggca   3480
ccaggtgcac gagaaggagg agtttaaggc cctgaagacc ctgtatccgt atgatgtgcc   3540
ggattatgcg tgatgactcg agtttttttt tgcggccgct tcgagcagac atgataagat   3600
acattgatga gtttggacaa accacaacta gaatgcagtg aaaaaaatgc tttatttgtg   3660
aaatttgtga tgctattgct ttatttgtaa ccattataag ctgcaataaa caagttaaca   3720
acaacaattg cattcatttt atgtttcagg ttcaggggga gatgtgggag gtttttttaaa   3780
gcaagtaaaa cctctacaaa tgtggtaaaa tcgataggcc gcaggaaccc ctagtgatgg   3840
agttggccac tccctctctg cgcgctcgct cgctcactga ggccgggcga ccaaaggtcg   3900
cccgacgccc gggcggcctc agtgagcgag cgagcgcgca gctgcctgca ggacatgtga   3960
gcaaaaggcc agcaaaaggc caggaaccgt aaaaaggccg cgttgctggc gtttttccat   4020
aggctccgcc cccctgacga gcatcacaaa aatcgacgct caagtcagag gtggcgaaac   4080
ccgacaggac tataaagata ccaggcgttt ccccctggaa gctccctcgt gcgctctcct   4140
gttccgaccc tgccgcttac cggatacctg tccgcctttc tcccttcggg aagcgtggcg   4200
ctttctcata gctcacgctg taggtatctc agttcggtgt aggtcgttcg ctccaagctg   4260
ggctgtgtgc acgaaccccc cgttcagccc gaccgctgcg ccttatccgg taactatcgt   4320
cttgagtcca acccggtaag acacgactta tcgccactgg cagcagccac tggtaacagg   4380
attagcagag cgaggtatgt aggcggtgct acagagttct tgaagtggtg gcctaactac   4440
```

```
ggctacacta gaagaacagt atttggtatc tgcgctctgc tgaagccagt taccttcgga   4500
aaaagagttg gtagctcttg atccggcaaa caaaccaccg ctggtagcgg tggttttttt   4560
gtttgcaagc agcagattac gcgcagaaaa aaaggatctc aagaagatcc tttgatcttt   4620
tctacggggt ctgacgctca gtggaacgaa aactcacgtt aagggatttt ggtcatgaga   4680
ttatcaaaaa ggatcttcac ctagatcctt ttaaattaaa aatgaagttt taaatcaatc   4740
taaagtatat atgagtaaac ttggtctgac agttaccaat gcttaatcag tgaggcacct   4800
atctcagcga tctgtctatt tcgttcatcc atagttgcct gactccccgt cgtgtagata   4860
actacgatac gggagggctt accatctggc cccagtgctg caatgatacc gcgagaccca   4920
cgctcaccgg ctccagattt atcagcaata aaccagccag ccggaagggc cgagcgcaga   4980
agtggtcctg caactttatc cgcctccatc cagtctatta attgttgccg ggaagctaga   5040
gtaagtagtt cgccagttaa tagtttgcgc aacgttgttg ccattgctac aggcatcgtg   5100
gtgtcacgct cgtcgtttgg tatggcttca ttcagctccg gttcccaacg atcaaggcga   5160
gttacatgat cccccatgtt gtgcaaaaaa gcggttagct ccttcggtcc tccgatcgtt   5220
gtcagaagta agttggccgc agtgttatca ctcatggtta tggcagcact gcataattct   5280
cttactgtca tgccatccgt aagatgcttt tctgtgactg gtgagtactc aaccaagtca   5340
ttctgagaat agtgtatgcg gcgaccgagt tgctcttgcc cggcgtcaat acgggataat   5400
accgcgccac atagcagaac tttaaaagtg ctcatcattg gaaaacgttc ttcggggcga   5460
aaactctcaa ggatcttacc gctgttgaga tccagttcga tgtaacccac tcgtgcaccc   5520
aactgatctt cagcatcttt tactttcacc agcgtttctg ggtgagcaaa aacaggaagg   5580
caaaatgccg caaaaaaggg aataagggcg acacggaaat gttgaatact catactcttc   5640
ctttttcaat attattgaag catttatcag ggttattgtc tcatgagcgg atacatattt   5700
gaatgtattt agaaaaataa acaaataggg gttccgcgca catttccccg aaaagtgcca   5760
cctgacgtct aagaaaccat tattatcatg acattaacct ataaaaatag gcgtatcacg   5820
aggccctttc gtctcgcgcg tttcggtgat gacggtgaaa acctctgaca catgcagctc   5880
ccggagacgg tcacagcttg tctgtaagcg gatgccggga gcagacaagc ccgtcagggc   5940
gcgtcagcgg gtgttggcgg gtgtcggggc tggcttaact atgcggcatc agagcagatt   6000
gtactgagag tgcaccataa aattgtaaac gttaatattt tgttaaaatt cgcgttaaat   6060
ttttgttaaa tcagctcatt ttttaaccaa taggccgaaa tcggcaaaat cccttataaa   6120
tcaaaagaat agcccgagat agggttgagt gttgttccag tttggaacaa gagtccacta   6180
ttaaagaacg tggactccaa cgtcaaaggg cgaaaaaccg tctatcaggg cgatggccca   6240
ctacgtgaac catcacccaa atcaagtttt ttggggtcga ggtgccgtaa agcactaaat   6300
cggaacccta aagggagccc ccgatttaga gcttgacggg gaaagccggc gaacgtggcg   6360
agaaaggaag ggaagaaagc gaaaggagcg ggcgctaagg cgctggcaag tgtagcggtc   6420
acgctgcgcg taaccaccac acccgccgcg cttaatgcgc cgctacaggg cgcgtactat   6480
ggttgctttg acgtatgcgg tgtgaaatac cgcacagatg cgtaaggaga aaataccgca   6540
tcaggcgcc                                                           6549
```

<210> SEQ ID NO 29
<211> LENGTH: 6993
<212> TYPE: DNA
<213> ORGANISM: Artificial Sequence
<220> FEATURE:
<223> OTHER INFORMATION: Synthetic

<400> SEQUENCE: 29

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccaga tcttcaatat tggccattag ccatattatt    180
cattggttat atagcataaa tcaatattgg ctattggcca ttgcatacgt tgtatctata    240
tcataatatg tacatttata ttggctcatg tccaatatga ccgccatgtt ggcattgatt    300
attgactagt tattaatagt aatcaattac ggggtcatta gttcatagcc catatatgga    360
gttccgcgtt acataactta cggtaaatgg cccgcctggc tgaccgccca acgacccccg    420
cccattgacg tcaataatga cgtatgttcc catagtaacg ccaataggga ctttccattg    480
acgtcaatgg gtggagtatt tacggtaaac tgcccacttg gcagtacatc aagtgtatca    540
tatgccaagt ccgcccccta ttgacgtcaa tgacggtaaa tggcccgcct ggcattatgc    600
ccagtacatg accttacggg actttcctac ttggcagtac atctacgtat tagtcatcgc    660
tattaccatg gtcgaggtga gccccacgtt ctgcttcact ctccccatct cccccccctc    720
cccaccccca attttgtatt tatttatttt ttaattattt tgtgcagcga tgggggcggg    780
gggggggggg gggcgcgcgc caggcggggc ggggcggggc gaggggcggg gcggggcgag    840
gcggagaggt gcggcggcag ccaatcagag cggcgcgctc cgaaagtttc cttttatggc    900
gaggcggcgg cggcggcggc cctataaaaa gcgaagcgcg cggcgggcgg gagtcgctgc    960
gcgctgcctt cgccccgtgc cccgctccgc cgccgcctcg cgccgcccgc cccggctctg   1020
actgaccgcg ttactcccac aggtgagcgg gcgggacggc ccttctcctc cgggctgtaa   1080
ttagcgcttg gtttaatgac ggcttgtttc ttttctgtgg ctgcgtgaaa gccttgaggg   1140
gctccgggag ggccctttgt gcggggggag cggctcgggg ggtgcgtgcg tgtgtgtgtg   1200
cgtggggagc gccgcgtgcg gctccgcgct gcccggcggc tgtgagcgct gcgggcgcgg   1260
cgcggggctt tgtgcgctcc gcagtgtgcg cgaggggagc gcggccgggg gcggtgcccc   1320
gcggtgcggg gggggctgcg aggggaacaa aggctgcgtg cggggtgtgt gcgtgggggg   1380
gtgagcaggg ggtgtgggcg cgtcggtcgg gctgcaaccc cccctgcacc cccctccccg   1440
agttgctgag cacggcccgg cttcgggtgc ggggctccgt acggggcgtg gcgcggggct   1500
cgccgtgccg ggcggggggt ggcggcaggt gggggtgccg ggcggggcgg ggccgcctcg   1560
ggccggggag ggctcggggg aggggcgcgg cggcccccgg agcgccggcg gctgtcgagg   1620
cgcggcgagc cgcagccatt gccttttatg gtaatcgtgc gagagggcgc agggacttcc   1680
tttgtcccaa atctgtgcgg agccgaaatc tgggaggcgc cgccgcaccc cctctagcgg   1740
gcgcggggcg aagcggtgcg gcgccggcag gaaggaaatg ggcggggagg gccttcgtgc   1800
gtcgccgcgc cgccgtcccc ttctccctct ccagcctcgg ggctgtccgc ggggggacgg   1860
ctgccttcgg gggggacggg gcagggcggg gttcggcttc tggcgtgtga ccggcggctc   1920
tagagcctct gctaaccatg ttcatgcctt cttctttttc ctacagctcc tgggcaacgt   1980
gctggttatt gtgctgtctc atcattttgg caaagaattc gatatcaagc ttgccaccat   2040
ggaagccaag agccagctgt ttctgaaata ctttaccctg tttatgaatc tgctgaacga   2100
ctgtagtgag gtggaggacg agagtgccca gaccggcggc aggaagagag gcatgtctag   2160
gagactggcc agcctgaggc actgcacagt gctggccatg tccaacctgc tgaacgccaa   2220
tgtggactcc ggcctgatgc actctatcgg cctgggctac cacaaggatc tgcagacccg   2280
```

cgccacattc atggaggtgc tgaccaagat cctgcagcag ggcaccgagt ttgacacact 2340
ggccgagacc gtgctggcag ataggttcga gcgcctggtg gagctggtga caatgatggg 2400
cgaccaggga gagctgccta tcgcaatggc actggccaac gtggtgccat gcagccagtg 2460
ggacgagctg gccagggtgc tggtgaccct gtttgattcc agacacctgc tgtaccagct 2520
gctgtggaac atgttctcta aggaggtgga gctggccgac agcatgcaga cactgtttag 2580
gggcaattcc ctggcctcta agatcatgac cttctgtttt aaggtgtacg gcgccacata 2640
tctgcagaag ctgctggatc cactgctgag aatcgtgatc accagctccg actggcagca 2700
cgtgtccttc gaggtggatc ctacacggct ggagccaagc gagtccctgg aggagaacca 2760
gcgcaatctg ctgcagatga ccgagaagtt ctttcacgcc atcatctcta gctcctctga 2820
gtttcccccct cagctgcggt ccgtgtgcca ctgtctgtac caggccacct gccactctct 2880
gctgaacaag gccacagtga aggagaagaa ggagaataag aagagcgtgg tgtcccagag 2940
gttcccacag aacagcatcg gagcagtggg atccgccatg ttcctgaggt tcatcaatcc 3000
cgccatcgtg agcccttatg aggccggcat cctggacaag aagccacccc ctaggatcga 3060
gagaggcctg aagctgatga gcaagatcct gcagtccatc gccaaccacg tgctgttcac 3120
caaggaggag cacatgcgcc ccttcaacga ctttgtgaag tctaattttg atgccgcccg 3180
gcgcttcttt ctggacatcg cctctgattg tcctacaagc gacgccgtga accactctct 3240
gagcttcatc agcgatggca atgtgctggc cctgcaccgg ctgctgtgga acaatcagga 3300
gaagatcggc cagtacctga gctccaacag ggaccacaag gcagtgggca ggagaccatt 3360
tgataagatg gccacactgc tggcctatct gggaccacca gagcacaagc cagtggcaga 3420
cacacactgg tctagcctga atctgacctc ctctaagttc gaggagttta tgacccggca 3480
ccaggtgcac gagaaggagg agtttaaggc cctgaagaca ctgtctatct tctaccaggc 3540
aggcaccagc aaggcaggaa acccaatctt ttactatgtg gcccggcgct tcaagacagg 3600
ccagatcaat ggcgatctgc tgatctacca cgtgctgctg accctgaagc catactatgc 3660
caagccctat gagatcgtgg tggacctgac ccacacaggc cctccaaca ggtttaagac 3720
cgatttcctg tctaagtggt tcgtggtgtt tcctggcttc gcctatgaca atgtgagcgc 3780
cgtgtacatc tataactgca attcctgggt gcgggagtac acaaagtatc acgagcgcct 3840
gctgaccggc ctgaagggat ccaagagact ggtgttcatc gattgtcccg gcaagctggc 3900
cgagcacatt gaacacgaac agcagaaact gcccgccgca accctggccc tggaagagga 3960
cctgaagtat ccgtatgatg tgccggatta tgcgtgatga ctcgagtttt tttttgcggc 4020
cgcttcgagc agacatgata agatacattg atgagtttgg acaaaccaca actagaatgc 4080
agtgaaaaaa atgctttatt tgtgaaattt gtgatgctat tgctttattt gtaaccatta 4140
taagctgcaa taaacaagtt aacaacaaca attgcattca ttttatgttt caggttcagg 4200
gggagatgtg ggaggttttt taaagcaagt aaaacctcta caaatgtggt aaaatcgata 4260
ggccgcagga acccctagtg atggagttgg ccactccctc tctgcgcgct cgctcgctca 4320
ctgaggccgg gcgaccaaag gtcgcccgac gcccgggcgg cctcagtgag cgagcgagcg 4380
cgcagctgcc tgcaggacat gtgagcaaaa ggccagcaaa aggccaggaa ccgtaaaaag 4440
gccgcgttgc tggcgttttt ccataggctc cgcccccctg acgagcatca caaaaatcga 4500
cgctcaagtc agaggtggcg aaacccgaca ggactataaa gataccaggc gtttccccct 4560
ggaagctccc tcgtgcgctc tcctgttccg accctgccgc ttaccggata cctgtccgcc 4620
tttctccctt cgggaagcgt ggcgctttct catagctcac gctgtaggta tctcagttcg 4680

```
gtgtaggtcg ttcgctccaa gctgggctgt gtgcacgaac cccccgttca gcccgaccgc   4740
tgcgccttat ccggtaacta tcgtcttgag tccaacccgg taagacacga cttatcgcca   4800
ctggcagcag ccactggtaa caggattagc agagcgaggt atgtaggcgg tgctacagag   4860
ttcttgaagt ggtggcctaa ctacggctac actagaagaa cagtatttgg tatctgcgct   4920
ctgctgaagc cagttacctt cggaaaaaga gttggtagct cttgatccgg caaacaaacc   4980
accgctggta gcggtggttt ttttgtttgc aagcagcaga ttacgcgcag aaaaaaagga   5040
tctcaagaag atcctttgat cttttctacg gggtctgacg ctcagtggaa cgaaaactca   5100
cgttaaggga ttttggtcat gagattatca aaaaggatct tcacctagat ccttttaaat   5160
taaaaatgaa gttttaaatc aatctaaagt atatatgagt aaacttggtc tgacagttac   5220
caatgcttaa tcagtgaggc acctatctca gcgatctgtc tatttcgttc atccatagtt   5280
gcctgactcc ccgtcgtgta gataactacg atacgggagg gcttaccatc tggccccagt   5340
gctgcaatga taccgcgaga cccacgctca ccggctccag atttatcagc aataaaccag   5400
ccagccggaa gggccgagcg cagaagtggt cctgcaactt tatccgcctc catccagtct   5460
attaattgtt gccgggaagc tagagtaagt agttcgccag ttaatagttt gcgcaacgtt   5520
gttgccattg ctacaggcat cgtggtgtca cgctcgtcgt ttggtatggc ttcattcagc   5580
tccggttccc aacgatcaag gcgagttaca tgatccccca tgttgtgcaa aaaagcggtt   5640
agctccttcg gtcctccgat cgttgtcaga agtaagttgg ccgcagtgtt atcactcatg   5700
gttatggcag cactgcataa ttctcttact gtcatgccat ccgtaagatg cttttctgtg   5760
actggtgagt actcaaccaa gtcattctga gaatagtgta tgcggcgacc gagttgctct   5820
tgcccggcgt caatacggga taataccgcg ccacatagca gaactttaaa agtgctcatc   5880
attggaaaac gttcttcggg gcgaaaactc tcaaggatct taccgctgtt gagatccagt   5940
tcgatgtaac ccactcgtgc acccaactga tcttcagcat cttttacttt caccagcgtt   6000
tctgggtgag caaaaacagg aaggcaaaat gccgcaaaaa agggaataag ggcgacacgg   6060
aaatgttgaa tactcatact cttccttttt caatattatt gaagcattta tcagggttat   6120
tgtctcatga gcggatacat atttgaatgt atttagaaaa ataaacaaat aggggttccg   6180
cgcacatttc cccgaaaagt gccacctgac gtctaagaaa ccattattat catgacatta   6240
acctataaaa ataggcgtat cacgaggccc tttcgtctcg cgcgtttcgg tgatgacggt   6300
gaaaacctct gacacatgca gctcccggag acggtcacag cttgtctgta agcggatgcc   6360
gggagcagac aagcccgtca gggcgcgtca gcgggtgttg gcgggtgtcg gggctggctt   6420
aactatgcgg catcagagca gattgtactg agagtgcacc ataaaattgt aaacgttaat   6480
attttgttaa aattcgcgtt aaatttttgt taaatcagct cattttttaa ccaataggcc   6540
gaaatcggca aaatccctta taaatcaaaa gaatagcccg agatagggtt gagtgttgtt   6600
ccagtttgga acaagagtcc actattaaag aacgtggact ccaacgtcaa agggcgaaaa   6660
accgtctatc agggcgatgg cccactacgt gaaccatcac ccaaatcaag ttttttgggg   6720
tcgaggtgcc gtaaagcact aaatcggaac cctaaaggga gcccccgatt tagagcttga   6780
cggggaaagc cggcgaacgt ggcgagaaag gaagggaaga aagcgaaagg agcgggcgct   6840
aaggcgctgg caagtgtagc ggtcacgctg cgcgtaacca ccacacccgc cgcgcttaat   6900
gcgccgctac agggcgcgta ctatggttgc tttgacgtat gcggtgtgaa ataccgcaca   6960
gatgcgtaag gagaaaatac cgcatcaggc gcc                                6993
```

<210> SEQ ID NO 30
<211> LENGTH: 7290
<212> TYPE: DNA
<213> ORGANISM: Artificial Sequence
<220> FEATURE:
<223> OTHER INFORMATION: Synthetic

<400> SEQUENCE: 30
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaga tcttcaatat tggccattag ccatattatt 180
cattggttat atagcataaa tcaatattgg ctattggcca ttgcatacgt tgtatctata 240
tcataatatg tacatttata ttggctcatg tccaatatga ccgccatgtt ggcattgatt 300
attgactagt tattaatagt aatcaattac ggggtcatta gttcatagcc catatatgga 360
gttccgcgtt acataactta cggtaaatgg cccgcctggc tgaccgccca acgacccccg 420
cccattgacg tcaataatga cgtatgttcc catagtaacg ccaataggga ctttccattg 480
acgtcaatgg gtggagtatt tacggtaaac tgcccacttg gcagtacatc aagtgtatca 540
tatgccaagt ccgcccccta ttgacgtcaa tgacggtaaa tggcccgcct ggcattatgc 600
ccagtacatg accttacggg actttcctac ttggcagtac atctacgtat tagtcatcgc 660
tattaccatg gtcgaggtga gccccacgtt ctgcttcact ctccccatct cccccccctc 720
cccaccccca attttgtatt tatttatttt ttaattattt tgtgcagcga tgggggcggg 780
gggggggggg gggcgcgcgc caggcggggc ggggcggggc gaggggcggg gcggggcgag 840
gcggagaggt gcggcggcag ccaatcagag cggcgcgctc cgaaagtttc cttttatggc 900
gaggcggcgg cggcggcggc cctataaaaa gcgaagcgcg cggcgggcgg gagtcgctgc 960
gcgctgcctt cgccccgtgc cccgctccgc cgccgcctcg cgccgcccgc cccggctctg 1020
actgaccgcg ttactcccac aggtgagcgg gcgggacggc ccttctcctc cgggctgtaa 1080
ttagcgcttg gtttaatgac ggcttgtttc ttttctgtgg ctgcgtgaaa gccttgaggg 1140
gctccgggag ggccctttgt gcggggggag cggctcgggg ggtgcgtgcg tgtgtgtgtg 1200
cgtggggagc gccgcgtgcg gctccgcgct gcccggcggc tgtgagcgct gcgggcgcgg 1260
cgcggggctt tgtgcgctcc gcagtgtgcg cgaggggagc gcggccgggg gcggtgcccc 1320
gcggtgcggg gggggctgcg aggggaacaa aggctgcgtg cggggtgtgt gcgtgggggg 1380
gtgagcaggg ggtgtgggcg cgtcggtcgg gctgcaaccc cccctgcacc cccctccccg 1440
agttgctgag cacggcccgg cttcgggtgc ggggctccgt acggggcgtg gcgcggggct 1500
cgccgtgccg ggcggggggt ggcggcaggt gggggtgccg ggcggggcgg ggccgcctcg 1560
ggccggggag ggctcggggg aggggcgcgg cggcccccgg agcgccggcg gctgtcgagg 1620
cgcggcgagc cgcagccatt gccttttatg gtaatcgtgc gagagggcgc agggacttcc 1680
tttgtcccaa atctgtgcgg agccgaaatc tgggaggcgc cgccgcaccc cctctagcgg 1740
gcgcggggcg aagcggtgcg gcgccggcag gaaggaaatg ggcggggagg gccttcgtgc 1800
gtcgccgcgc cgccgtcccc ttctccctct ccagcctcgg ggctgtccgc ggggggacgg 1860
ctgccttcgg gggggacggg gcagggcggg gttcggcttc tggcgtgtga ccggcggctc 1920
tagagcctct gctaaccatg ttcatgcctt cttctttttc ctacagctcc tgggcaacgt 1980
gctggttatt gtgctgtctc atcattttgg caaagaattc gatatcaagc ttgccaccat 2040
ggaagccaag agccagctgt ttctgaaata ctttaccctg tttatgaatc tgctgaacga 2100
ctgtagtgag gtggaggacg agagtgccca gaccggcggc aggaagagag gcatgtctag 2160
gagactggcc agcctgaggc actgcacagt gctggccatg tccaacctgc tgaacgccaa 2220
tgtggactcc ggcctgatgc actctatcgg cctgggctac cacaaggatc tgcagacccg 2280
cgccacattc atggaggtgc tgaccaagat cctgcagcag ggcaccgagt ttgacacact 2340
ggccgagacc gtgctggcag ataggttcga gcgcctggtg gagctggtga caatgatggg 2400
cgaccaggga gagctgccta tcgcaatggc actggccaac gtggtgccat gcagccagtg 2460
ggacgagctg gccagggtgc tggtgaccct gtttgattcc agacacctgc tgtaccagct 2520
gctgtggaac atgttctcta aggaggtgga gctggccgac agcatgcaga cactgtttag 2580
gggcaattcc ctggcctcta agatcatgac cttctgtttt aaggtgtacg gcgccacata 2640
tctgcagaag ctgctggatc cactgctgag aatcgtgatc accagctccg actggcagca 2700
cgtgtccttc gaggtggatc ctacacggct ggagccaagc gagtccctgg aggagaacca 2760
gcgcaatctg ctgcagatga ccgagaagtt ctttcacgcc atcatctcta gctcctctga 2820 gtttcccccct cagctgcggt ccgtgtgcca ctgtctgtac caggccacct gccactctct 2880
gctgaacaag gccacagtga aggagaagaa ggagaataag aagagcgtgg tgtcccagag 2940
gttcccacag aacagcatcg gagcagtggg atccgccatg ttcctgaggt tcatcaatcc 3000
cgccatcgtg agcccttatg aggccggcat cctggacaag aagccacccc ctaggatcga 3060
gagaggcctg aagctgatga gcaagatcct gcagtccatc gccaaccacg tgctgttcac 3120
caaggaggag cacatgcgcc ccttcaacga ctttgtgaag tctaattttg atgccgcccg 3180
gcgcttcttt ctggacatcg cctctgattg tcctacaagc gacgccgtga accactctct 3240
gagcttcatc agcgatggca atgtgctggc cctgcaccgg ctgctgtgga acaatcagga 3300
gaagatcggc cagtacctga gctccaacag ggaccacaag gcagtgggca ggagaccttt 3360
tgataagatg gccaccctgc tggcatatct gggaccacca gagcacaagc cagtggcaga 3420
cacccactgg tctagcctga atctgacatc ctctaagttc gaggagttta tgacccggca 3480
ccaggtgcac gagaaggagg agtttaaggc cctgaagacc ctgtccatct tctaccaggc 3540
cggcacatct aaggccggca accctatctt ttactatgtg gcccggcgct tcaagaccgg 3600
ccagatcaat ggcgatctgc tgatctacca cgtgctgctg acactgaagc catactatgc 3660
caagccctat gagatcgtgg tggacctgac ccacacaggc ccaagcaaca ggtttaagac 3720
cgatttcctg tccaagtggt tcgtggtgtt tcccggcttc gcctatgaca acgtgagcgc 3780
cgtgtacatc tataactgca atagctgggt gcgggagtac accaagtatc acgagcgcct 3840
gctgacaggc ctgaagggca gcaagagact ggtgttcatc gattgtcccg gcaagctggc 3900
cgagcacatc gagcacgagc agcagaagct gcctgcagcc accctggccc tggaggagga 3960
cctgaaggtg tttcacaacg ccctgaagct ggcccacaag gatacaaagg tgtccatcaa 4020
ggtcggctct acagccgtgc aggtgacctc cgccgagaga acaaaggtgc tgggccagag 4080
cgtgttcctg aatgacatct actatgccag cgagatcgag gagatctgcc tggtggatga 4140
gaaccagttt accctgacaa tcgccaatca gggcaccccc ctgacattca tgcaccagga 4200
gtgtgaagca atcgtccaga gcattattca cattcgcact cggtgggaac tgagccagcc 4260
tgactatccg tatgatgtgc cggattatgc gtgatgactc gagttttttt ttgcggccgc 4320
ttcgagcaga catgataaga tacattgatg agtttggaca aaccacaact agaatgcagt 4380
gaaaaaaatg ctttatttgt gaaatttgtg atgctattgc tttatttgta accattataa 4440
gctgcaataa acaagttaac aacaacaatt gcattcattt tatgtttcag gttcaggggg 4500
agatgtggga ggttttttaa agcaagtaaa acctctacaa atgtggtaaa atcgataggc 4560
cgcaggaacc cctagtgatg gagttggcca ctccctctct gcgcgctcgc tcgctcactg 4620
aggccgggcg accaaaggtc gcccgacgcc cgggcggcct cagtgagcga gcgagcgcgc 4680
agctgcctgc aggacatgtg agcaaaaggc cagcaaaagg ccaggaaccg taaaaaggcc 4740
gcgttgctgg cgtttttcca taggctccgc ccccctgacg agcatcacaa aaatcgacgc 4800
tcaagtcaga ggtggcgaaa cccgacagga ctataaagat accaggcgtt tccccctgga 4860
agctccctcg tgcgctctcc tgttccgacc ctgccgctta ccggatacct gtccgccttt 4920
ctcccttcgg gaagcgtggc gctttctcat agctcacgct gtaggtatct cagttcggtg 4980
taggtcgttc gctccaagct gggctgtgtg cacgaacccc ccgttcagcc cgaccgctgc 5040
gccttatccg gtaactatcg tcttgagtcc aacccggtaa gacacgactt atcgccactg 5100
gcagcagcca ctggtaacag gattagcaga gcgaggtatg taggcggtgc tacagagttc 5160
ttgaagtggt ggcctaacta cggctacact agaagaacag tatttggtat ctgcgctctg 5220
ctgaagccag ttaccttcgg aaaaagagtt ggtagctctt gatccggcaa acaaaccacc 5280
gctggtagcg gtggtttttt tgtttgcaag cagcagatta cgcgcagaaa aaaaggatct 5340
caagaagatc ctttgatctt ttctacgggg tctgacgctc agtggaacga aaactcacgt 5400
taagggattt tggtcatgag attatcaaaa aggatcttca cctagatcct tttaaattaa 5460
aaatgaagtt ttaaatcaat ctaaagtata tatgagtaaa cttggtctga cagttaccaa 5520
tgcttaatca gtgaggcacc tatctcagcg atctgtctat ttcgttcatc catagttgcc 5580
tgactccccg tcgtgtagat aactacgata cgggagggct taccatctgg ccccagtgct 5640
gcaatgatac cgcgagaccc acgctcaccg gctccagatt tatcagcaat aaaccagcca 5700
gccggaaggg ccgagcgcag aagtggtcct gcaactttat ccgcctccat ccagtctatt 5760
aattgttgcc gggaagctag agtaagtagt tcgccagtta atagtttgcg caacgttgtt 5820
gccattgcta caggcatcgt ggtgtcacgc tcgtcgtttg gtatggcttc attcagctcc 5880
ggttcccaac gatcaaggcg agttacatga tcccccatgt tgtgcaaaaa agcggttagc 5940
tccttcggtc ctccgatcgt tgtcagaagt aagttggccg cagtgttatc actcatggtt 6000
atggcagcac tgcataattc tcttactgtc atgccatccg taagatgctt ttctgtgact 6060
ggtgagtact caaccaagtc attctgagaa tagtgtatgc ggcgaccgag ttgctcttgc 6120
ccggcgtcaa tacgggataa taccgcgcca catagcagaa ctttaaaagt gctcatcatt 6180
ggaaaacgtt cttcggggcg aaaactctca aggatcttac cgctgttgag atccagttcg 6240
atgtaaccca ctcgtgcacc caactgatct tcagcatctt ttactttcac cagcgtttct 6300
gggtgagcaa aaacaggaag gcaaaatgcc gcaaaaaagg gaataagggc gacacggaaa 6360
tgttgaatac tcatactctt cctttttcaa tattattgaa gcatttatca gggttattgt 6420
ctcatgagcg gatacatatt tgaatgtatt tagaaaaata aacaaatagg ggttccgcgc 6480
acatttcccc gaaaagtgcc acctgacgtc taagaaacca ttattatcat gacattaacc 6540
tataaaaata ggcgtatcac gaggcccttt cgtctcgcgc gtttcggtga tgacggtgaa 6600
aacctctgac acatgcagct cccggagacg gtcacagctt gtctgtaagc ggatgccggg 6660
agcagacaag cccgtcaggg cgcgtcagcg ggtgttggcg ggtgtcgggg ctggcttaac 6720
tatgcggcat cagagcagat tgtactgaga gtgcaccata aaattgtaaa cgttaatatt 6780
ttgttaaaat tcgcgttaaa tttttgttaa atcagctcat tttttaacca ataggccgaa 6840
atcggcaaaa tcccttataa atcaaaagaa tagcccgaga tagggttgag tgttgttcca 6900
gtttggaaca agagtccact attaaagaac gtggactcca acgtcaaagg gcgaaaaacc 6960
gtctatcagg gcgatggccc actacgtgaa ccatcaccca aatcaagttt tttggggtcg 7020
aggtgccgta aagcactaaa tcggaaccct aaagggagcc cccgatttag agcttgacgg 7080
ggaaagccgg cgaacgtggc gagaaaggaa gggaagaaag cgaaaggagc gggcgctaag 7140
gcgctggcaa gtgtagcggt cacgctgcgc gtaaccacca cacccgccgc gcttaatgcg 7200
ccgctacagg gcgcgtacta tggttgcttt gacgtatgcg gtgtgaaata ccgcacagat 7260
gcgtaaggag aaaataccgc atcaggcgcc 7290

<210> SEQ ID NO 31
<211> LENGTH: 7629
<212> TYPE: DNA
<213> ORGANISM: Artificial Sequence
<220> FEATURE:
<223> OTHER INFORMATION: Synthetic

<400> SEQUENCE: 31
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccaga tctgcaaatt aggaccgaga gtcagtggcc 180
gctcaagagt ctgtgaccat gccccaaatt cagagatggt cccaggagag atggggggaa 240
ctgccaagca atgagtgacc ggttccccct cccccaggtg gttagccagc gtttccctca 300
gaacagcatc ggtgcagtag gaagtgccat gttcctcaga tttatcaatc ctgccattgt 360
ctcaccgtat gaagcaggga ttttagataa aaagccacca cctagaatcg aaaggggctt 420
gaagttaatg tcaaagatac ttcagagtat tgccaatcat gttctcttca caaaagaaga 480
acatatgcgg cctttcaatg attttgtgaa aagcaacttt gatgcagcac gcaggttttt 540
ccttgatata gcatctgatt gtcctacaag tgatgcagta aatcatagtc tttccttcat 600
aagtgacggc aatgtgcttg ctttacatcg tctactctgg aacaatcagg agaaaattgg 660
gcagtatctt tccagcaaca gggatcataa agctgttgga agacgacctt ttgataagat 720
ggcaacactt cttgcatacc tgggtcctcc agagcacaaa cctgtggcag atacacactg 780
gtccagcctt aaccttacca gttcaaagtt tgaggaattt atgactaggc atcaggtaca 840
tgaaaaagaa gaattcaagg ctttgaaaac gttaagtatt ttctaccaag ctgggacttc 900
caaagctggg aatcctattt tttattatgt tgcacggagg ttcaaaactg gtcaaatcaa 960
tggtgatttg ctgatatacc atgtcttact gactttaaag ccatattatg caaagccata 1020
tgaaattgta gtggacctta cccataccgg gcctagcaat cgctttaaaa cagactttct 1080
ctctaagtgg tttgttgttt ttcctggctt tgcttacgac aacgtctccg cagtctatat 1140
ctataactgt aactcctggg tcagggagta caccaagtat catgagcggc tgctgactgg 1200
cctcaaaggt agcaaaaggc ttgttttcat agactgtcct gggaaactgg ctgagcacat 1260
agagcatgaa caacagaaac tacctgctgc caccttggct ttagaagagg acctgaaggt 1320
attccacaat gctctcaagc tagctcacaa agacaccaaa gtttctatta aagttggttc 1380
tactgctgtc caagtaactt cagcagagcg aacaaaagtc ctagggcaat cagtctttct 1440
aaatgacatt tattatgctt cggaaattga agaaatctgc ctagtagatg agaaccagtt 1500
caccttaacc attgcaaacc agggcacgcc gctcaccttc atgcaccagg agtgtgaagc 1560
cattgtccag tctatcattc atatccggac ccgctgggaa ctgtcacagc ccgactctat 1620
cccccaacac accaagattc ggccaaaaga tgtccctggg acactgctca atatcgcatt 1680
acttaattta ggcagttctg acccgagttt acggtcagct gcctataatc ttctgtgtgc 1740
cttaacttgt acctttaatt taaaaatcga gggccagtta ctagagacat caggtttatg 1800
tatccctgcc aacaacaccc tctttattgt ctctattagt aagacactgg cagccaatga 1860
gccacacctc acgttagaat ttttggaaga gtgtatttct ggatttagca aatctagtat 1920
tgaattgaaa cacctttgtt tggaatacat gactccatgg ctgtcaaatc tagttcgttt 1980
ttgcaagcat aatgatgatg ccaaacgaca aagagttact gctattcttg acaagctgat 2040
aacaatgacc atcaatgaaa aacagatgta cccatctatt caagcaaaaa tatggggaag 2100
ccttgggcag attacagatc tgcttgatgt tgtactagac agtttcatca aaaccagtgc 2160
aacaggtggc ttgggatcaa taaaagctga ggtgatggca gatactgctg tagctttggc 2220
ttctggaaat gtgaaattgg tttcaagcaa ggttattgga aggatgtgca aaataattga 2280
caagacatgc ttatctccaa ctcctacttt agaacaacat cttatgtggg atgatattgc 2340
tattttagca cgctacatgc tgatgctgtc cttcaacaat tcccttgatg tggcagctca 2400
tcttccctac ctcttccacg ttgttacttt cttagtagcc acaggtccgc tctcccttag 2460
agcttccaca catggactgg tcattaatat cattcactct ctgtgtactt gttcacagct 2520
tcattttagt gaagagacca agcaagtttt gagactcagt ctgacagagt tctcattacc 2580
caaattttac ttgctgtttg gcattagcaa agtcaagtca gctgctgtca ttgccttccg 2640
ttccagttac cgggacaggt cattctctcc tggctcctat gagagagaga cttttgcttt 2700
gacatccttg gaaacagtca cagaagcttt gttggagatc atggaggcat gcatgagaga 2760
tattccaacg tgcaagtggc tggaccagtg gacagaacta gctcaaagat ttgcattcca 2820
atataatcca tccctgcaac caagagctct tgttgtcttt gggtgtatta gcaaacgagt 2880
gtctcatggg cagataaagc agataatccg tattcttagc aaggcacttg agagttgctt 2940
aaaaggacct gacacttaca acagtcaagt tctgatagaa gctacagtaa tagcactaac 3000
caaattacag ccacttctta ataaggactc gcctctgcac aaagccctct tttgggtagc 3060
tgtggctgtg ctgcagcttg atgaggtcaa cttgtattca gcaggtaccg cacttcttga 3120
acaaaacctg catactttag atagtctccg tatattcaat gacaagagtc cagaggaagt 3180
atttatggca atccggaatc ctctggagtg gcactgcaag caaatggatc attttgttgg 3240
actcaatttc aactctaact ttaactttgc attggttgga caccttttaa aagggtacag 3300
gcatccttca cctgctattg ttgcaagaac agtcagaatt ttacatacac tactaactct 3360
ggttaacaaa cacagaaatt gtgacaaatt tgaagtgaat acacagagcg tggcctactt 3420
agcagcttta cttacagtgt ctgaagaagt tcgaagtcgc tgcagcctaa aacatagaaa 3480
gtcacttctt cttactgata tttcaatgga aaatgttcct atggatacat atcccattca 3540
tcatggtgac ccttcctata ggacactaaa ggagactcag ccatggtcct ctcccaaagg 3600
ttctgaagga taccttgcag ccacctatcc aactgtcggc cagaccagtc cccgagccag 3660
gaaatccatg agcctggaca tggggcaacc ttctcaggcc aacactaaga agttgcttgg 3720
aacaaggaaa agttttgatc acttgatatc agacacaaag gctcctaaaa ggcaagaaat 3780
ggaatcaggg atcacaacac cccccaaaat gaggagagta gcagaaactg attatgaaat 3840
ggaaactcag aggatttcct catcacaaca gcacccacat ttacgtaaag tttcagtgtc 3900
tgaatcaaat gttctcttgg atgaagaagt acttactgat ccgaagatcc aggcgctgct 3960

```
tcttactgtt ctagctacac tggtaaaata taccacagat gagtttgatc aacgaattct   4020
ttatgaatac ttagcagagg ccagtgttgt gtttcccaaa gtctttcctg ttgtgcataa   4080
tttgttggac tctaagatca acaccctgtt atcattgtgc caagatccaa atttgttaaa   4140
tccaatccat ggaattgtgc agagtgtggt gtaccatgaa gaatccccac cacaatacca   4200
aacatcttac ctgcaaagtt ttggttttaa tggcttgtgg cggtttgcag gaccgttttc   4260
aaagcaaaca caaattccag actatgctga gcttattgtt aagtttcttg atgccttgat   4320
tgacacgtac ctgcctggaa ttgatgaaga aaccagtgaa gaatccctcc tgactcccac   4380
atctccttac cctcctgcac tgcagagcca gcttagtatc actgccaacc ttaacctttc   4440
taattccatg acctcacttg caacttccca gcattcccca ggaatcgaca aggagaacgt   4500
tgaactctcc cctaccactg gccactgtaa cagtggacga actcgccacg gatccgcaag   4560
ccaagtgcag aagcaaagaa gcgctggcag tttcaaacgt aatagcatta agaagatcgt   4620
gtatccgtat gatgtgccgg attatgcgtg agcggccgct tcgagcagac atgataagat   4680
acattgatga gtttggacaa accacaacta gaatgcagtg aaaaaaatgc tttatttgtg   4740
aaatttgtga tgctattgct ttatttgtaa ccattataag ctgcaataaa caagttaaca   4800
acaacaattg cattcatttt atgtttcagg ttcaggggga gatgtgggag gtttttaaa    4860
gcaagtaaaa cctctacaaa tgtggtaaaa tcgataggcc gcaggaaccc ctagtgatgg   4920
agttggccac tccctctctg cgcgctcgct cgctcactga ggccgggcga ccaaaggtcg   4980
cccgacgccc gggcggcctc agtgagcgag cgagcgcgca gctgcctgca ggacatgtga   5040
gcaaaaggcc agcaaaaggc caggaaccgt aaaaaggccg cgttgctggc gtttttccat   5100
aggctccgcc cccctgacga gcatcacaaa aatcgacgct caagtcagag gtggcgaaac   5160
ccgacaggac tataaagata ccaggcgttt ccccctggaa gctccctcgt gcgctctcct   5220
gttccgaccc tgccgcttac cggatacctg tccgcctttc tcccttcggg aagcgtggcg   5280
ctttctcata gctcacgctg taggtatctc agttcggtgt aggtcgttcg ctccaagctg   5340
ggctgtgtgc acgaaccccc cgttcagccc gaccgctgcg ccttatccgg taactatcgt   5400
cttgagtcca acccggtaag acacgactta tcgccactgg cagcagccac tggtaacagg   5460
attagcagag cgaggtatgt aggcggtgct acagagttct tgaagtggtg gcctaactac   5520
ggctacacta gaagaacagt atttggtatc tgcgctctgc tgaagccagt taccttcgga   5580
aaaagagttg gtagctcttg atccggcaaa caaaccaccg ctggtagcgg tggttttttt   5640
gtttgcaagc agcagattac gcgcagaaaa aaaggatctc aagaagatcc tttgatcttt   5700
tctacggggt ctgacgctca gtggaacgaa aactcacgtt aagggatttt ggtcatgaga   5760
ttatcaaaaa ggatcttcac ctagatcctt ttaaattaaa aatgaagttt taaatcaatc   5820
taaagtatat atgagtaaac ttggtctgac agttaccaat gcttaatcag tgaggcacct   5880
atctcagcga tctgtctatt tcgttcatcc atagttgcct gactccccgt cgtgtagata   5940
actacgatac gggagggctt accatctggc cccagtgctg caatgatacc gcgagaccca   6000
cgctcaccgg ctccagattt atcagcaata aaccagccag ccggaagggc cgagcgcaga   6060
agtggtcctg caactttatc cgcctccatc cagtctatta attgttgccg ggaagctaga   6120
gtaagtagtt cgccagttaa tagtttgcgc aacgttgttg ccattgctac aggcatcgtg   6180
gtgtcacgct cgtcgtttgg tatggcttca ttcagctccg gttcccaacg atcaaggcga   6240
gttacatgat cccccatgtt gtgcaaaaaa gcggttagct ccttcggtcc tccgatcgtt   6300
```

```
gtcagaagta agttggccgc agtgttatca ctcatggtta tggcagcact gcataattct   6360
cttactgtca tgccatccgt aagatgcttt tctgtgactg gtgagtactc aaccaagtca   6420
ttctgagaat agtgtatgcg gcgaccgagt tgctcttgcc cggcgtcaat acgggataat   6480
accgcgccac atagcagaac tttaaaagtg ctcatcattg gaaaacgttc ttcggggcga   6540
aaactctcaa ggatcttacc gctgttgaga tccagttcga tgtaacccac tcgtgcaccc   6600
aactgatctt cagcatcttt tactttcacc agcgtttctg ggtgagcaaa aacaggaagg   6660
caaaatgccg caaaaaaggg aataagggcg acacggaaat gttgaatact catactcttc   6720
ctttttcaat attattgaag catttatcag ggttattgtc tcatgagcgg atacatattt   6780
gaatgtattt agaaaaataa acaaataggg gttccgcgca catttccccg aaaagtgcca   6840
cctgacgtct aagaaaccat tattatcatg acattaacct ataaaaatag gcgtatcacg   6900
aggccctttc gtctcgcgcg tttcggtgat gacggtgaaa acctctgaca catgcagctc   6960
ccggagacgg tcacagcttg tctgtaagcg gatgccggga gcagacaagc ccgtcagggc   7020
gcgtcagcgg gtgttggcgg gtgtcggggc tggcttaact atgcggcatc agagcagatt   7080
gtactgagag tgcaccataa aattgtaaac gttaatattt tgttaaaatt cgcgttaaat   7140
ttttgttaaa tcagctcatt ttttaaccaa taggccgaaa tcggcaaaat cccttataaa   7200
tcaaaagaat agcccgagat agggttgagt gttgttccag tttggaacaa gagtccacta   7260
ttaaagaacg tggactccaa cgtcaaaggg cgaaaaaccg tctatcaggg cgatggccca   7320
ctacgtgaac catcacccaa atcaagtttt ttggggtcga ggtgccgtaa agcactaaat   7380
cggaacccta aagggagccc ccgatttaga gcttgacggg gaaagccggc gaacgtggcg   7440
agaaaggaag ggaagaaagc gaaaggagcg ggcgctaagg cgctggcaag tgtagcggtc   7500
acgctgcgcg taaccaccac acccgccgcg cttaatgcgc cgctacaggg cgcgtactat   7560
ggttgctttg acgtatgcgg tgtgaaatac cgcacagatg cgtaaggaga aaataccgca   7620
tcaggcgcc                                                           7629
```

```
<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gly Cys Met Ser Cys Lys Cys Val Leu Ser
1               5                   10
```